（12）United States Patent
Yuen et al.

(10) Patent No.: US 8,092,994 B2
(45) Date of Patent: *Jan. 10, 2012

(54) HUMAN VIRUS CAUSING RESPIRATORY TRACT INFECTION AND USES THEREOF

(75) Inventors: Kwok Yung Yuen, Hong Kong (CN); Chiu Yat Patrick Woo, Hong Kong (CN); Kar Pui Susanna Lau, Hong Kong (CN); Kwok Hung Chan, Hong Kong (CN); Lit Man Poon, Hong Kong (CN); Joseph Sriyal Malik Peiris, Hong Kong (CN); Yi Guan, Hong Kong (CN)

(73) Assignee: Versitech Limited, Hong Kong (CN)

( * ) Notice: Subject to any disclaimer, the term of this patent is extended or adjusted under 35 U.S.C. 154(b) by 232 days.

This patent is subject to a terminal disclaimer.

(21) Appl. No.: 12/476,019

(22) Filed: Jun. 1, 2009

(65) Prior Publication Data

US 2009/0305282 A1    Dec. 10, 2009

Related U.S. Application Data

(63) Continuation of application No. 10/895,064, filed on Jul. 21, 2004, now Pat. No. 7,553,944.

(51) Int. Cl.
*C12Q 1/68* (2006.01)
(52) U.S. Cl. ........ 435/6; 536/23.1; 536/24.3; 536/24.32
(58) Field of Classification Search ................ None
See application file for complete search history.

(56) References Cited

U.S. PATENT DOCUMENTS

2005/0266397 A1    12/2005 Ecker et al.

FOREIGN PATENT DOCUMENTS

WO    WO2004096842    *    4/2004

OTHER PUBLICATIONS

Weiss, SR et al. "Characterization of Murine Coronavirus RNA by Hybridization with Virusspecific cDNA Probes" J. Gen. Virology; 64:127-133;1983.*

* cited by examiner

*Primary Examiner* — Bo Peng
(74) *Attorney, Agent, or Firm* — Saliwanchik, Lloyd & Eisenschenk

(57) ABSTRACT

The present invention provides the complete genomic sequence of a novel human coronavirus, coined as coronavirus-HKU1 ("CoV-HKU1"), isolated in Hong Kong from a patient who had a recent history of visit to Schenzhen, China. The virus belongs to the order Nidovirales of the family Coronavirdae, being a single-stranded RNA virus of positive polarity. The invention also provides the deduced amino acid sequences of the complete genome of the CoV-HKU1. The nucleotide sequences and deduced amino acid sequences of the CoV-HKU1 are useful in preventing, diagnosing and/or treating the infection by CoV-HKU1. Furthermore, the invention provides immunogenic and vaccine preparations using recombinant and chimeric forms as well as subunits of the CoV-HKU1 based on the nucleotide sequences and deduced amino acid sequences of the CoV-HKU1.

10 Claims, 119 Drawing Sheets

Figure 4:
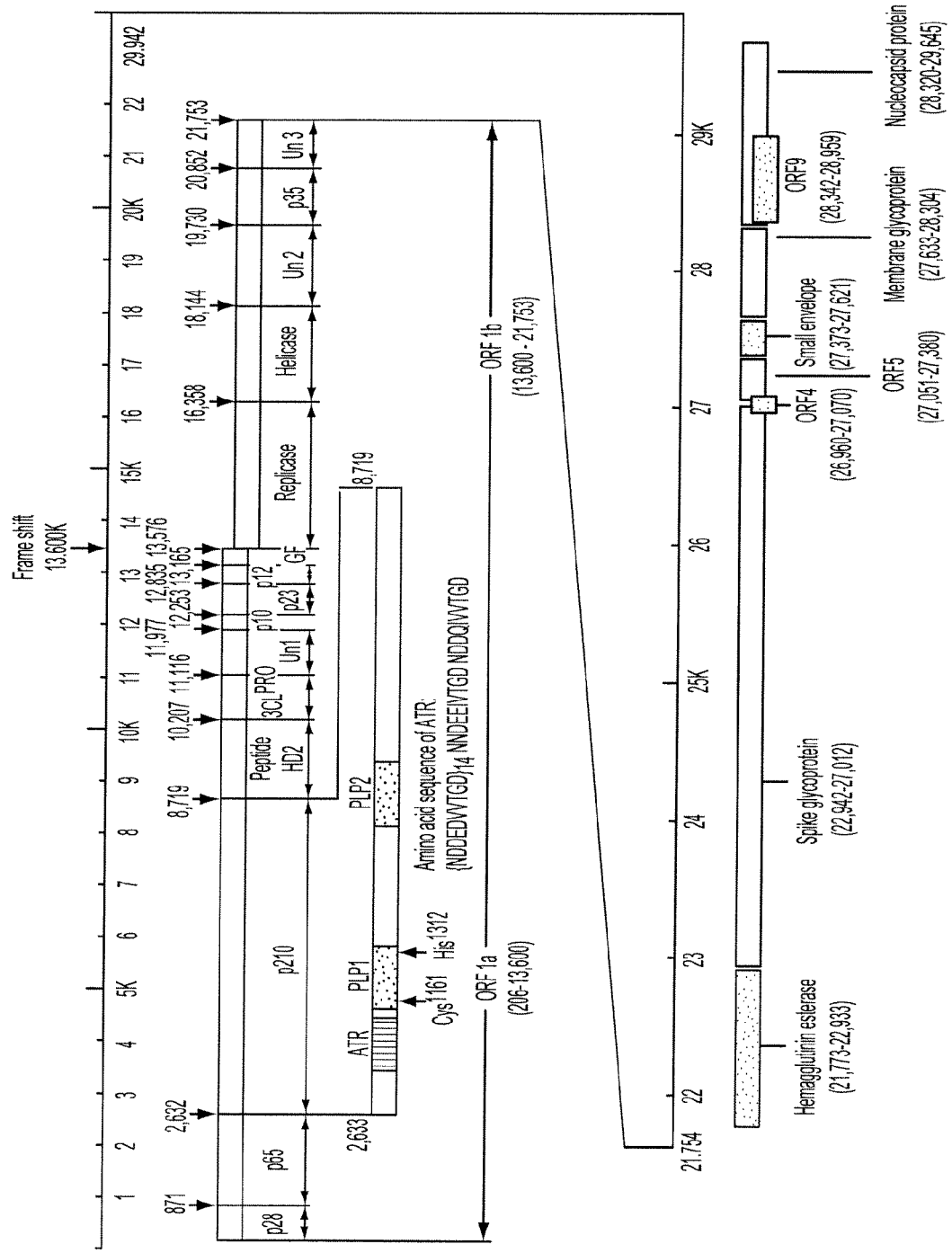

| | | | |
|---|---|---|---|
| SEQ:1 | 1 | TCGTGCTATGCCAAATATTTTGCGTATTGTTAGTAGTTTAGTTTTGGCCCGCAAACAT | 58 |
| SEQ:2 | 1 | R A M P N I L R I V S S L V L A R K H | 19 |
| | 59 | GAATTTTGTTGTTCACATGGTGATAGATTTTATCGCCTTGCGAATGAATGTGCTCAAGTT | 118 |
| | 20 | E F C C S H G D R F Y R L A N E C A Q V | 39 |
| | 119 | TTGAGTGAAATAGTTATGTGTGGCGGTTGCTATTATGTTAAGCCTGGTGGTACTAGCAGT | 178 |
| | 40 | L S E I V M C G G C Y Y V K P G G T S S | 59 |
| | 179 | GGTGATGCAACTACTGCTTTTGCTAATTCTGTTTTTAATATATGTCAGGCTGTTACTGCT | 238 |
| | 60 | G D A T T A F A N S V F N I C Q A V T A | 79 |
| | 239 | AATGTTTGTTCTCTTATGGCCTGTAATGGCCATAAGATTGAAGATTTAAGTATACGCAAT | 298 |
| | 80 | N V C S L M A C N G H K I E D L S I R N | 99 |
| | 299 | TTACAAAAACGCTTATACTCTAATGTTTATCGTACAGATTATGTTGATTATACATTTGTT | 358 |
| | 100 | L Q K R L Y S N V Y R T D Y V D Y T F V | 119 |
| | 359 | AATGAGTATTATGAATTTTTATGTAAGCATTTTAG | 393 |
| | 120 | N E Y Y E F L C K H F | 130 |

FIG. 1

```
SEQ:3    1    GAATAAGAGCGAATTGCGTCCGTACCGTCTATCAGCTTACGATCTCTTGTCAGATCTCAT    60
              E * E R I A S V P S I S L R S L V R S H
              N K S E L R P Y R L S A Y D L L S D L I
              I R A N C V R T V Y Q L T I S C Q I S

61    TAAATCTAAACTTTTTAAACAAGATTCCCTGTTATCCATGCTTGTGAGTGTGGTTTAATC    120
              * I * T F * T R F P V I H A C E C G L I
              K S K L F K Q D S L L S M L V S V V * S
              L N L N F L N K I P C Y P C L * V W F N

121    ATAATCTTGTATTTTACTTTCCACACTTTTCATCTCTCTGCCAGTGACGTGTTGGTTGTC    180
              I I L Y F T F H T F H L S A S D V L V V
              * S C I L L S T L F I S L P V T C W L S
              H N L V F Y F P H F S S L C Q * R V G C

181    CTCAGCGTCCCTCCCATAGGTCGCAATGATTAAAACCAGCAAATACGGTCTCGGCTTCAA    240
              L S V P P I G R N D * N Q Q I R S R L Q
              S A S L P * V A M I K T S K Y G L G F K
              P Q R P S H R S Q * L K P A N T V S A S

241    GTGGGCGCCAGAATTTCGTTGGCTGCTTCCGGATGCAGCGGAGGAGTTGGCTAGTCCTAT    300
              V G A R I S L A A S G C S G G V G * S Y
              W A P E F R W L L P D A A E E L A S P M
              S G R Q N F V G C F R M Q R R S W L V L

301    GAAGTCAGATGAGGGTGGGTTATGCCCCTCTACTGGTCAAGCGATGGAAAGTGTTGGATT    360
              E V R * G W V M P L Y W S S D G K C W I
              K S D E G G L C P S T G Q A M E S V G F
              * S Q M R V G Y A P L L V K R W K V L D

361    CGTTTATGATAATCATGTGAAGATAGATTGTCGCTGCATTCTTGGACAAGAATGGCATGT    420
              R L * * S C E D R L S L H S W T R M A C
              V Y D N H V K I D C R C I L G Q E W H V
              S F M I I M * R * I V A A F L D K N G M

421    GCAGTCAAATCTTATCCGTGATATTTTTGTTCATGAAGATCTACATGTTGTAGAAGTTCT    480
              A V K S Y P * Y F C S * R S T C C R S S
              Q S N L I R D I F V H E D L H V V E V L
              C S Q I L S V I F L F M K I Y M L * K F

481    AACTAAAACAGCCGTAAAGTCCGGTACGGCAATTTTAATTAAATCACCTTTGCATAGCTT    540
              N * N S R K V R Y G N F N * I T F A * L
              T K T A V K S G T A I L I K S P L H S L
              * L K Q P * S P V R Q F * L N H L C I A
```

FIG. 2

```
541  GGGTGGTTTTCCTAAAGGGTATGTTATGGGCTTGTTCCGTTCATACAAGACTAAACGTTA  600
      G  W  F  S  *  R  V  C  Y  G  L  V  P  F  I  Q  D  *  T  L
       G  G  P  P  K  G  Y  V  M  G  L  F  R  S  Y  K  T  K  R  Y
        W  V  V  F  L  K  G  M  L  W  A  C  S  V  H  T  R  L  N  V

601  TGTTGTACATCATCTTTCTATGACTACATCTACTACTAATTTTGGTGAAGATTTTTGGG  660
      C  C  T  S  S  F  Y  D  Y  I  Y  Y  *  F  W  *  R  F  F  G
       V  V  H  H  L  S  M  T  T  S  T  T  N  F  G  E  D  F  L  G
        M  L  Y  I  I  F  L  *  L  H  L  L  L  I  L  V  K  I  F  W

661  TTGGATTGTACCTTTTGGTTTTATGCCATCTTATGTTCACAAATGGTTTCAATTCTGTAG  720
      L  D  C  T  F  W  F  Y  A  I  L  C  S  Q  M  V  S  I  L  *
       W  I  V  P  F  G  F  M  P  S  Y  V  H  K  W  F  Q  F  C  R
        V  G  L  Y  L  L  V  L  C  H  L  M  F  T  N  G  F  N  S  V

721  GTTGTATATTGAAGAGAGTGATTTAATAATTTCAAATTTTAAATTTGATGATTATGATTT  780
      V  V  Y  *  R  E  *  F  N  N  F  K  F  *  I  *  *  L  *  F
       L  Y  I  E  E  S  D  L  I  I  S  N  F  K  F  D  D  Y  D  F
        G  C  I  L  K  R  V  I  *  *  F  Q  I  L  N  L  M  I  M  I

781  TAGTGTAGAAGATGCTTATGCTGAGGTTCATGCTGAGCCTAAAGGTAAATATTCACAAAA  840
      *  C  R  R  C  L  C  *  G  S  C  *  A  *  R  *  I  F  T  K
       S  V  E  D  A  Y  A  E  V  H  A  E  P  K  G  K  Y  S  Q  K
        L  V  *  K  M  L  M  L  R  F  M  L  S  L  K  V  N  I  H  K

841  AGCTTATGCTTTACTTAGACAATATCGTGGTATTAAACCCGTACTTTTTGTAGACCAGTA  900
      S  L  C  F  T  *  T  I  S  W  Y  *  T  R  T  F  C  R  P  V
       A  Y  A  L  L  R  Q  Y  R  G  I  K  P  V  L  F  V  D  Q  Y
        K  L  M  L  Y  L  D  N  I  V  V  L  N  P  Y  F  L  *  T  S

901  TGGTTGTGACTATTCTGGTAAATTAGCAGATTGTCTTCAAGCTTATGGTCATTATTCTTT  960
      W  L  *  L  F  W  *  I  S  R  L  S  S  S  L  W  S  L  F  F
       G  C  D  Y  S  G  K  L  A  D  C  L  Q  A  Y  G  H  Y  S  L
        M  V  V  T  I  L  V  N  *  Q  I  V  F  K  L  M  V  I  I  L

961  GCAAGATATGAGACAAAAGCAGTCTGTATGGCTTGCCAATTGTGACTTTGATATTGTAGT  1020
      A  R  Y  E  T  K  A  V  C  M  A  C  Q  L  *  L  *  Y  C  S
       Q  D  M  R  Q  K  Q  S  V  W  L  A  N  C  D  F  D  I  V  V
        C  K  I  *  D  K  S  S  L  Y  G  L  P  I  V  T  L  I  L  *

1021 GGCTTGGCATGTAGTTCGTGATTCACGATTTGTTATGCGCCTGCAGACTATAGCTACTAT  1080
      G  L  A  C  S  S  *  F  T  I  C  Y  A  P  A  D  Y  S  Y  Y
       A  W  H  V  V  R  D  S  R  F  V  M  R  L  Q  T  I  A  T  I
        W  L  G  M  *  F  V  I  H  D  L  L  C  A  C  R  L  *  L  L
```

FIG. 2 CONT.

```
1081    TTGTGGTATTAAATATGTTGCACAACCTACAGAAGATGTAGTAGATGGAGATGTAGTTAT    1140
          L  W  Y  *  I  C  C  T  T  Y  R  R  C  S  R  W  R  C  S  Y
           C  G  I  K  Y  V  A  Q  P  T  E  D  V  V  D  G  D  V  V  I
         F  V  V  L  N  M  L  H  N  L  Q  K  M  *  *  M  E  M  *  L

1141    ACGTGAACCTGTACATTTATTATCTGCTGATGCAATAGTTTTAAAGCTTCCTAGTTTGAT    1200
          T  *  T  C  T  F  I  I  C  *  C  N  S  F  K  A  S  *  F  D
           R  E  P  V  H  L  L  S  A  D  A  I  V  L  K  L  P  S  L  M
         Y  V  N  L  Y  I  Y  Y  L  L  M  Q  *  F  *  S  F  L  V  *

1201    GAAAGTTATGACTCATATGGATGATTTTTCTATTAAATCTATATATAATGTTGATTTGTG    1260
          E  S  Y  D  S  Y  G  *  F  F  Y  *  I  Y  I  *  C  *  F  V
           K  V  M  T  H  M  D  D  F  S  I  K  S  I  Y  N  V  D  L  C
         *  K  L  *  L  I  W  M  I  F  L  L  N  L  Y  I  M  L  I  C

1261    TGATTGTGGTTTTGTTATGCAGTATGGTTATGTAGATTGTTTTAATGATAATTGTGATTT    1320
          *  L  W  F  C  Y  A  V  W  L  C  R  L  F  *  *  *  L  *  F
           D  C  G  F  V  M  Q  Y  G  Y  V  D  C  F  N  D  N  C  D  F
         V  I  V  V  L  L  C  S  M  V  M  *  I  V  L  M  I  I  V  I

1321    TTATGGTTGGGTTTCAGGTAATATGATGGATGGTTTTTCTTGTCCATTGTGTTGTACAGT    1380
          L  W  L  G  F  R  *  Y  D  G  W  F  F  L  S  I  V  L  Y  S
           Y  G  W  V  S  G  N  M  M  D  G  F  S  C  P  L  C  C  T  V
         F  M  V  G  F  Q  V  I  *  W  M  V  F  L  V  H  C  V  V  Q

1381    TTATGACTCTAGCGAAGTTAAAGCCCAATCATCTGGTGTTATTCCTGAAAATCCTGTGTT    1440
          L  *  L  *  R  S  *  S  P  I  I  W  C  Y  S  *  K  S  C  V
           Y  D  S  S  E  V  K  A  Q  S  S  G  V  I  P  E  N  P  V  L
         F  M  T  L  A  K  L  K  P  N  H  L  V  L  F  L  K  I  L  C

1441    ATTTACTAATAGTACTGATACTGTTAACCATGATTCTTTTAATTTGTATGGTTATTCTGT    1500
          I  Y  *  *  Y  *  Y  C  *  P  *  F  F  *  F  V  W  L  F  C
           F  T  N  S  T  D  T  V  N  H  D  S  F  N  L  Y  G  Y  S  V
         Y  L  L  I  V  L  I  L  L  T  M  I  L  L  I  C  M  V  I  L

1501    CACACCATTTGGTTCTTGTATATATTGGTCGCCGCGTCCTGGATTGTGGATTCCTATAAT    1560
          H  T  I  W  F  L  Y  I  L  V  A  A  S  W  I  V  D  S  Y  N
           T  P  F  G  S  C  I  Y  W  S  P  R  P  G  L  W  I  P  I  I
         S  H  H  L  V  L  V  Y  I  G  R  R  V  L  D  C  G  F  L  *

1561    TAAATCTTCAGTCAAGTCTTATGATGATTTGGTTTATTCAGGTGTAGTAGGTTGTAAATC    1620
          *  I  F  S  Q  V  L  *  *  F  G  L  F  R  C  S  R  L  *  I
           K  S  S  V  K  S  Y  D  D  L  V  Y  S  G  V  V  G  C  K  S
         L  N  L  Q  S  S  L  M  M  I  W  F  I  Q  V  *  *  V  V  N
```

FIG. 2 CONT.

```
1621   TATTGTTAAAGAAACTGCTCTTATTACTCATGCACTTTACTTAGATTATGTTCAATGTAA    1680
         Y  C  *  R  N  C  S  Y  Y  S  C  T  L  L  R  L  C  S  M  *
          I  V  K  E  T  A  L  I  T  H  A  L  Y  L  D  Y  V  Q  C  K
        L  L  L  K  K  L  L  L  L  L  M  H  F  T  *  I  M  F  N  V

1681   GTGTGGTAATCTTGAACAAAATCATATTCTTGGCGTTAATAATTCTTGGTGTAGGCAACT    1740
         V  W  *  S  *  T  K  S  Y  S  W  R  *  *  F  L  V  *  A  T
          C  G  N  L  E  Q  N  H  I  L  G  V  N  N  S  W  C  R  Q  L
        S  V  V  I  L  N  K  I  I  F  L  A  L  I  I  L  G  V  G  N

1741   GTTGCTTAATAGAGGTGATTATAATATGCTTCTAAAAAATATTGACTTGTTTGTTAAGCG    1800
         V  A  *  *  R  *  L  *  Y  A  S  K  K  Y  *  L  V  C  *  A
          L  L  N  R  G  D  Y  N  M  L  L  K  N  I  D  L  F  V  K  R
        C  C  L  I  E  V  I  I  I  C  F  *  K  I  L  T  C  L  L  S

1801   TCGTGCTGATTTTGCTTGCAAGTTTGCAGTTTGTGGAGATGGTTTTGTACCTTTTTTACT    1860
         S  C  *  F  C  L  Q  V  C  S  L  W  R  W  F  C  T  F  F  T
          R  A  D  F  A  C  K  F  A  V  C  G  D  G  F  V  P  F  L  L
        V  V  L  I  L  L  A  S  L  Q  F  V  E  M  V  L  Y  L  F  Y

1861   AGATGGTTTAATTCCCCGTAGTTATTATCTAATTCAGAGTGGTATTTTCTTTACATCTTT    1920
         R  W  F  N  S  P  *  L  L  S  N  S  E  W  Y  F  L  Y  I  F
          D  G  L  I  P  R  S  Y  Y  L  I  Q  S  G  I  F  F  T  S  L
        *  M  V  *  F  P  V  V  I  I  *  F  R  V  V  F  S  L  H  L

1921   GATGTCTCAATTTTCACAAGAAGTTTCTGATATGTGTTTAAAAATGTGTATTTTGTTTAT    1980
         D  V  S  I  F  T  R  S  F  *  Y  V  F  K  N  V  Y  F  V  Y
          M  S  Q  F  S  Q  E  V  S  D  M  C  L  K  M  C  I  L  F  M
        *  C  L  N  F  H  K  K  F  L  I  C  V  *  K  C  V  F  C  L

1981   GGACAGAGTTTCAGTTGCTACATTTTATATAGAGCATTATGTTAATAGGTTGGTTACTCA    2040
         G  Q  S  F  S  C  Y  I  L  Y  R  A  L  C  *  *  V  G  Y  S
          D  R  V  S  V  A  T  F  Y  I  E  H  Y  V  N  R  L  V  T  Q
        W  T  E  F  Q  L  L  H  F  I  *  S  I  M  L  I  G  W  L  L

2041   ATTTAAGTTATTGGGTACTACACTTGTTAATAAAATGGTTAATTGGTTTAATACCATGTT    2100
         I  *  V  I  G  Y  Y  T  C  *  *  N  G  *  L  V  *  Y  H  V
          F  K  L  L  G  T  T  L  V  N  K  M  V  N  W  F  N  T  M  L
        N  L  S  Y  W  V  L  H  L  L  I  K  W  L  I  G  L  I  P  C

2101   AGATGCTAGTGCACCTGCTACAGGCTGGCTTCTTTACCAATTATTGAATGGTCTTTTTGT    2160
         R  C  *  C  T  C  Y  R  L  A  S  L  P  I  I  E  W  S  F  C
          D  A  S  A  P  A  T  G  W  L  L  Y  Q  L  L  N  G  L  F  V
        *  M  L  V  H  L  L  Q  A  G  F  F  T  N  Y  *  M  V  F  L
```

FIG. 2 CONT.

```
2161  AGTATCTCAAGCCAACTTTAATTTTGTTGCTTTAATACCTGATTATGCTAAAATTTTAGT  2220
        S  I  S  S  Q  L  *  F  C  C  F  N  T  *  L  C  *  N  F  S
         V  S  Q  A  N  F  N  F  V  A  L  I  P  D  Y  A  K  I  L  V
       *  Y  L  K  P  T  L  I  L  L  L  *  Y  L  I  M  L  K  F  *

2221  TAATAAATTTTACACTTTTTTTAAGTTATTATTAGAGTGTGTTACAGTTGATGTTTTAAA  2280
        *  *  I  L  H  F  F  *  V  I  I  R  V  C  Y  S  *  C  F  K
          N  K  F  Y  T  F  F  K  L  L  L  E  C  V  T  V  D  V  L  K
        L  I  N  F  T  L  F  L  S  Y  Y  *  S  V  L  Q  L  M  F  *

2281  AGATATGCCTGTTCTTAAAACTATTAATGGTTTAGTTTGTATTGTAGGCAATAAGTTTTA  2340
        R  Y  A  C  S  *  N  Y  *  W  F  S  L  Y  C  R  Q  *  V  L
         D  M  P  V  L  K  T  I  N  G  L  V  C  I  V  G  N  K  F  Y
        K  I  C  L  F  L  K  L  L  M  V  *  F  V  L  *  A  I  S  F

2341  TAACGTTAGTACAGGGTTAATTCCTGGTTTTGTTTTACCATGTAATGCACAGGAACAACA  2400
        *  R  *  Y  R  V  N  S  W  F  C  F  T  M  *  C  T  G  T  T
         N  V  S  T  G  L  I  P  G  F  V  L  P  C  N  A  Q  E  Q  Q
        I  T  L  V  Q  G  *  F  L  V  L  F  Y  H  V  M  H  R  N  N

2401  AATTTATTTTTTGAAGGCGTTGCAGAATCTGTTATAGTAGAAGATGATGTTATTGAGAA  2460
        N  L  F  F  *  R  R  C  R  I  C  Y  S  R  R  *  C  Y  *  E
         I  Y  F  F  E  G  V  A  E  S  V  I  V  E  D  D  V  I  E  N
        K  F  I  F  L  K  A  L  Q  N  L  L  *  *  K  M  M  L  L  R

2461  TGTCAAATCTTCTTTATCATCTTATGAGTATTGTCAACCACCTAAATCTGTAGAAAAAAT  2520
        C  Q  I  F  F  I  I  L  *  V  L  S  T  T  *  I  C  R  K  N
         V  K  S  S  L  S  S  Y  E  Y  C  Q  P  P  K  S  V  E  K  I
        M  S  N  L  L  Y  H  L  M  S  I  V  N  H  L  N  L  *  K  K

2521  TTGTATTATAGATAATATGTACATGGGTAAGTGTGGTGATAAATTTTTCCCTATTGTCAT  2580
        L  Y  Y  R  *  Y  V  H  G  *  V  W  *  *  I  F  P  Y  C  H
         C  I  I  D  N  M  Y  G  K  C  G  D  K  F  F  P  I  V  M
        F  V  L  *  I  I  C  T  W  V  S  V  V  I  N  F  S  L  L  S

2581  GAATGATAAAAATATTTGTCTTTTAGATCAGGCTTGGCGTTTTCCATGTGCAGGTAGAAA  2640
        E  *  *  K  Y  L  S  F  R  S  G  L  A  F  S  M  C  R  *  K
         N  D  K  N  I  C  L  L  D  Q  A  W  R  F  P  C  A  G  R  K
        *  M  I  K  I  F  V  F  *  I  R  L  G  V  F  H  V  Q  V  E

2641  AGTTAATTTTAACGAGAAACCTGTTGTTATGGAGATTCCGTCTTTGATGACAGTTAAGGT  2700
        S  *  F  *  R  E  T  C  C  Y  G  D  S  V  F  D  D  S  *  G
         V  N  F  N  E  K  P  V  V  M  E  I  P  S  L  M  T  V  K  V
        K  L  I  L  T  R  N  L  L  L  W  R  F  R  L  *  *  Q  L  R
```

FIG. 2 CONT.

```
2701   TATGTTTGATTTAGATTCTACTTTTGATGATATTTTAGGTAAAGTTTGTTCAGAATTTGA   2760
        Y  V  *  F  R  F  Y  F  *  *  Y  F  R  *  S  L  F  R  I  *
         M  F  D  L  D  S  T  F  D  D  I  L  G  K  V  C  S  E  F  E
          L  C  L  I  *  I  L  L  M  I  F  *  V  K  F  V  Q  N  L

2761   AGTAGAAAAGGGTGTTACTGTAGATGATTTTGTTGCTGTTGTTTGTGATGCTATAGAGAA   2820
        S  R  K  G  C  Y  C  R  *  F  C  C  C  C  L  *  C  Y  R  E
         V  E  K  G  V  T  V  D  D  F  V  A  V  V  C  D  A  I  E  N
          K  *  K  R  V  L  L  *  M  I  L  L  L  L  F  V  M  L  *  R

2821   TGCTTTAAACTCTTGTAAAGAGCATCCAGTGGTTGGTTATCAAGTTCGTGCATTTTTAAA   2880
        C  F  K  L  L  *  R  A  S  S  G  W  L  S  S  S  C  I  F  K
         A  L  N  S  C  K  E  H  P  V  V  G  Y  Q  V  R  A  F  L  N
          M  L  *  T  L  V  K  S  I  Q  W  L  V  I  K  F  V  H  F  *

2881   TAAACTTAATGAGAATGTTGTTTATTTATTTGATGAGGCTGGTGATGAAGCAATGGCCTC   2940
        *  T  *  *  E  C  C  L  F  I  *  *  G  W  *  *  S  N  G  L
         K  L  N  E  N  V  V  Y  L  F  D  E  A  G  D  E  A  M  A  S
          I  N  L  M  R  M  L  F  I  Y  L  M  R  L  V  M  K  Q  W  P

2941   TCGTATGTATTGTACTTTTGCTATTGAGGATGTTGAAGACGTTATCAGTAGTGAAGCTGT   3000
        S  Y  V  L  Y  F  C  Y  *  G  C  *  R  R  Y  Q  *  *  S  C
         R  M  Y  C  T  F  A  I  E  D  V  E  D  V  I  S  S  E  A  V
          L  V  C  I  V  L  L  L  R  M  L  K  T  L  S  V  V  K  L

3001   CGAAGATACTATTGATGGTGTCGTTGAAGACACTATTAATGACGATGAAGATGTTGTTAC   3060
        R  R  Y  Y  *  W  C  R  *  R  H  Y  *  *  R  *  R  C  C  Y
         E  D  T  I  D  G  V  V  E  D  T  I  N  D  D  E  D  V  V  T
          S  K  I  L  L  M  V  S  L  K  T  L  L  M  T  M  K  M  L  L

3061   TGGTGACAATGACGATGAAGATGTTGTTACTGGTGACAATGACGATGAAGATGTTGTTAC   3120
        W  *  Q  *  R  *  R  C  C  Y  W  *  Q  *  R  *  R  C  C  Y
         G  D  N  D  D  E  D  V  V  T  G  D  N  D  D  E  D  V  V  T
          L  V  T  M  T  M  K  M  L  L  L  V  T  M  T  M  K  M  L  L

3121   TGGTGACAATGACGATGAAGATGTTGTTACTGGTGACAATGACGATGAAGATGTTGTTAC   3180
        W  *  Q  *  R  *  R  C  C  Y  W  *  Q  *  R  *  R  C  C  Y
         G  D  N  D  D  E  D  V  V  T  G  D  N  D  D  E  D  V  V  T
          L  V  T  M  T  M  K  M  L  L  L  V  T  M  T  M  K  M  L  L

3181   TGGTGACAATGACGATGAAGATGTTGTTACTGGTGACAATGACGATGAAGATGTTGTTAC   3240
        W  *  Q  *  R  *  R  C  C  Y  W  *  Q  *  R  *  R  C  C  Y
         G  D  N  D  D  E  D  V  V  T  G  D  N  D  D  E  D  V  V  T
          L  V  T  M  T  M  K  M  L  L  L  V  T  M  T  M  K  M  L  L
```

FIG. 2 CONT.

```
3241    TGGTGACAATGACGATGAAGATGTTGTTACTGGTGACAATGACGATGAAGATGTTGTTAC    3300
        W  *  Q  *  R  *  R  C  C  Y  W  *  Q  *  R  *  R  C  C  Y
         G  D  N  D  D  E  D  V  V  T  G  D  N  D  D  E  D  V  V  T
        L  V  T  M  T  M  K  M  L  L  L  V  T  M  T  M  K  M  L  L

3301    TGGTGACAATGACGATGAAGATGTTGTTACTGGTGACAATGACGATGAAGATGTTGTTAC    3360
        W  *  Q  *  R  *  R  C  C  Y  W  *  Q  *  R  *  R  C  C  Y
         G  D  N  D  D  E  D  V  V  T  G  D  N  D  D  E  D  V  V  T
        L  V  T  M  T  M  K  M  L  L  L  V  T  M  T  M  K  M  L  L

3361    TGGTGACAATGACGATGAAGATGTTGTTACTGGTGACAATGACGATGAAGATGTTGTTAC    3420
        W  *  Q  *  R  *  R  C  C  Y  W  *  Q  *  R  *  R  C  C  Y
         G  D  N  D  D  E  D  V  V  T  G  D  N  D  D  E  D  V  V  T
        L  V  T  M  T  M  K  M  L  L  L  V  T  M  T  M  K  M  L  L

3421    TGGTGACAATGACGATGAAGATGTTGTTACTGGTGACAATAACGATGAAGAGATTGTTAC    3480
        W  *  Q  *  R  *  R  C  C  Y  W  *  Q  *  R  *  R  D  C  Y
         G  D  N  D  D  E  D  V  V  T  G  D  N  N  D  E  E  I  V  T
        L  V  T  M  T  M  K  M  L  L  L  V  T  I  T  M  K  R  L  L

3481    TGGTGACAATGATGACCAAATTGTTGTTACTGGTGATGATGTAGATGATATTGAAAGTAT    3540
        W  *  Q  *  *  P  N  C  C  Y  W  *  *  C  R  *  Y  *  K  Y
         G  D  N  D  D  Q  I  V  V  T  G  D  D  V  D  D  I  E  S  I
        L  V  T  M  M  T  K  L  L  L  V  M  M  *  M  I  L  K  V

3541    TTATGACTTTGATACTTATAAAGCTCTTTTAGTTTTTAATGATGTCTATAATGATGCTTT    3600
        L  *  L  *  Y  L  *  S  S  F  S  F  *  *  C  L  *  *  C  F
         Y  D  F  D  T  Y  K  A  L  L  V  F  N  D  V  Y  N  D  A  L
        F  M  T  L  I  L  I  K  L  F  *  F  L  M  M  S  I  M  M  L

3601    GTTTGTTAGTTATGGTTCTAGTGTTGAAACAGAAACATATTTTAAAGTTAATGGTTTATG    3660
        V  C  *  L  W  F  *  C  *  N  R  N  I  F  *  S  *  W  F  M
         F  V  S  Y  G  S  S  V  E  T  E  T  Y  F  K  V  N  G  L  W
        C  L  L  V  M  V  L  V  L  K  Q  K  H  I  L  K  L  M  V  Y

3661    GTCACCTACTATTACACATACTAATTGTTGGTTGCGTTCTGTGTTACTTGTAATGCAGAA    3720
        V  T  Y  Y  Y  T  Y  *  L  L  V  A  F  C  V  T  C  N  A  E
         S  P  T  I  T  H  T  N  C  W  L  R  S  V  L  L  V  M  Q  K
        G  H  L  L  L  H  I  L  I  V  G  C  V  L  C  Y  L  *  C  R

3721    ATTACCTTTTAAGTTTAAGGATTTAGCTATTGAAAATATGTGGTTATCTTATAAGGTGGG    3780
        I  T  F  *  V  *  G  F  S  Y  *  K  Y  V  V  I  L  *  G  G
         L  P  F  K  F  K  D  L  A  I  E  N  M  W  L  S  Y  K  V  G
        N  Y  L  L  S  L  R  I  *  L  L  K  I  C  G  Y  L  I  R  W
```

FIG. 2 CONT.

```
3781    TTATAATCAAAGTTTTGTTGATTATTTACTGACCACTATTCCTAAAGCTATTGTTTTGCC    3840
         L  *  S  K  F  C  *  L  F  T  D  H  Y  S  *  S  Y  C  F  A
          Y  N  Q  S  F  V  D  Y  L  L  T  T  I  P  K  A  I  V  L  P
           V  I  I  K  V  L  L  I  I  Y  *  P  L  F  L  K  L  L  F  C

3841    TCAAGGTGGTTTTGTAGCTGATTTTGCTTATTGGTTTTTAAACCAGTTTGATATTAATGC    3900
         S  R  W  F  C  S  *  F  C  L  L  V  F  K  P  V  *  Y  *  C
          Q  G  G  F  V  A  D  F  A  Y  W  F  L  N  Q  F  D  I  N  A
           L  K  V  V  L  *  L  I  L  L  I  G  F  *  T  S  L  I  L  M

3901    GTATGCTAATTGGTGTTGTTTAAAATGTGGTTTTTCTTTTGATTTAAATGGTTTGGATGC    3960
         V  C  *  L  V  L  F  K  M  W  F  F  F  *  F  K  W  F  G  C
          Y  A  N  W  C  C  L  K  C  G  F  S  F  D  L  N  G  L  D  A
           R  M  L  I  G  V  V  *  N  V  V  F  L  L  I  *  M  V  W  M

3961    TTTGTTTTTTTATGGAGATATTGTGTCTCATGTTTGTAAGTGTGGACATAATATGACTCT    4020
         F  V  F  L  W  R  Y  C  V  S  C  L  *  V  W  T  *  Y  D  S
          L  F  F  Y  G  D  I  V  S  H  V  C  K  C  G  H  N  M  T  L
           L  C  F  F  M  E  I  L  C  L  M  F  V  S  V  D  I  I  *  L

4021    AATAGCAGCGGACTTACCTTGTACATTACATTTTTCATTATTTGATGACAATTTTTGTGC    4080
         N  S  S  G  L  T  L  Y  I  T  F  F  I  I  *  *  Q  F  L  C
          I  A  A  D  L  P  C  T  L  H  F  S  L  F  D  D  N  F  C  A
           *  *  Q  R  T  Y  L  V  H  Y  I  F  H  Y  L  M  T  I  F  V

4081    TTTTTGCACCCCTAAAAAAATTTTTATTGCTGCATGTGCTGTGGATGTAAACGTTTGTCA    4140
         F  L  H  P  *  K  N  F  Y  C  C  M  C  C  G  C  K  R  L  S
          F  C  T  P  K  K  I  F  I  A  A  C  A  V  D  V  N  V  C  H
           L  F  A  P  L  K  K  F  L  L  H  V  L  W  M  *  T  F  V

4141    TTCTGTAGCTGTTATAGGTGATGAACAAATAGATGGTAAGTTTGTTACTAAATTTAGTGG    4200
         F  C  S  C  Y  R  *  *  T  N  R  W  *  V  C  Y  *  I  *  W
          S  V  A  V  I  G  D  E  Q  I  D  G  K  F  V  T  K  F  S  G
           I  L  *  L  L  *  V  M  N  K  *  M  V  S  L  L  N  L  V

4201    TGATAAATTTGATTTTATAGTAGGTTATGGAATGTCATTTAGTATGTCTTCTTTTGAGTT    4260
         *  *  I  *  F  Y  S  R  L  W  N  V  I  *  Y  V  F  F  *  V
          D  K  F  D  F  I  V  G  Y  G  M  S  F  S  M  S  S  F  E  L
           V  I  N  L  I  L  *  *  V  M  E  C  H  L  V  C  L  L  S

4261    ACCTCAATTGTATGGTTTGTGTATAACACCTAATGTATGTTTTGTTAAAGGTGATATTAT    4320
         T  S  I  V  W  F  V  Y  N  T  *  C  M  F  C  *  R  *  Y  Y
          P  Q  L  Y  G  L  C  I  T  P  N  V  C  F  V  K  G  D  I  I
           Y  L  N  C  M  V  C  V  *  H  L  M  Y  V  L  L  K  V  I  L
```

FIG. 2 CONT.

```
4321    AAATGTTGCTAGACTTGTTAAAGCTGATGTTATTGTTAATCCTGCTAATGGGCATATGCT    4380
         K  C  C  *  T  C  *  S  *  C  Y  C  *  S  C  *  W  A  Y  A
          N  V  A  R  L  V  K  A  D  V  I  V  N  P  A  N  G  H  M  L
        *  M  L  L  D  L  L  K  L  M  L  L  L  I  L  L  M  G  I  C

4381    CCATGGTGGTGGAGTTGCAAAAGCTATAGCTGTAGCTGCAGGTAAAAAATTTTCTAAAGA    4440
         P  W  W  W  S  C  K  S  Y  S  C  S  C  R  *  K  I  F  *  R
          H  G  G  G  V  A  K  A  I  A  V  A  A  G  K  K  F  S  K  E
        S  M  V  V  E  L  Q  K  L  *  L  *  L  Q  V  K  N  F  L  K

4441    AACTGCTGCTATGGTTAAATCTAAAGGTGTTTGCCAAGTAGGAGATTGTTATGTTTCTAC    4500
         N  C  C  Y  G  *  I  *  R  C  L  P  S  R  R  L  L  C  F  Y
          T  A  A  M  V  K  S  K  G  V  C  Q  V  G  D  C  Y  V  S  T
        K  L  L  W  L  N  L  K  V  F  A  K  *  E  I  V  M  F  L

4501    CGGTGGTAAATTATGTAAAACAATTCTTAATATTGTAGGCCCTGATGCTAGACAAGATGG    4560
         R  W  *  I  M  *  N  N  S  *  Y  C  R  P  *  C  *  T  R  W
          G  G  K  L  C  K  T  I  L  N  I  V  G  P  D  A  R  Q  D  G
        P  V  V  N  Y  V  K  Q  F  L  I  L  *  A  L  M  L  D  K  M

4561    AAGACAATCTTATGTTTTGTTAGCACGTGCTTATAAGCATCTTAATAATTATGATTGTTG    4620
         K  T  I  L  C  F  V  S  T  C  L  *  A  S  *  *  L  *  L  L
          R  Q  S  Y  V  L  L  A  R  A  Y  K  H  L  N  N  Y  D  C  C
        E  D  N  L  M  F  C  *  H  V  L  I  S  I  L  I  I  M  I  V

4621    TTTGTCTACTCTCATATCGGCTGGTATATTTAGTGTTCCTGCTGATGTGTCATTAACTTA    4680
         F  V  Y  S  H  I  G  W  Y  I  *  C  S  C  *  C  V  I  N  L
          L  S  T  L  I  S  A  G  I  F  S  V  P  A  D  V  S  L  T  Y
        V  C  L  L  S  Y  R  L  V  Y  L  V  F  L  L  M  C  H  *  L

4681    CCTTCTAGGTGTTGTTGATAAACAAGTTATCCTTGTTAGTAATAATAAAGAAGATTTTGA    4740
         P  S  R  C  C  *  *  T  S  Y  P  C  *  *  *  R  R  F  *
          L  L  G  V  V  D  K  Q  V  I  L  V  S  N  N  K  E  D  F  D
        T  F  *  V  L  L  I  N  K  L  S  L  L  V  I  I  K  K  I  L

4741    TATTATTCAAAAATGTCAAATTACTTCAGTTGTTGGTACTAAAGCATTGGCTGTTAGATT    4800
         Y  Y  S  K  M  S  N  Y  F  S  C  W  Y  *  S  I  G  C  *  I
          I  I  Q  K  C  Q  I  T  S  V  V  G  T  K  A  L  A  V  R  L
        I  L  F  K  N  V  K  L  L  Q  L  L  V  L  K  H  W  L  L  D

4801    AACTGCTAATGTAGGCCGTGTTATTAAATTTGAGACAGATGCATACAAACTTTTTTTGAG    4860
         N  C  *  C  R  P  C  Y  *  I  *  D  R  C  I  Q  T  F  F  E
          T  A  N  V  G  R  V  I  K  F  E  T  D  A  Y  K  L  F  L  S
        *  L  L  M  *  A  V  L  L  N  L  R  Q  M  H  T  N  F  F  *
```

FIG. 2 CONT.

```
4861   TGGTGATGATTGTTTTGTTTCAAATTCTTCTGTTATACAAGAAGTTTTATTGCTTCGTCA   4920
         W  *  *  L  F  C  F  K  F  F  C  Y  T  R  S  F  I  A  S  S
          G  D  D  C  F  V  S  N  S  S  V  I  Q  E  V  L  L  L  R  H
       V  V  M  I  V  L  F  Q  I  L  L  L  Y  K  K  F  Y  C  F  V

4921   TGATATACAATTGAATAATGACGTTCGTGATTATTTGTTGTCTAAGATGACTAGTCTTCC   4980
         *  Y  T  I  E  *  *  R  S  *  L  F  V  V  *  D  D  *  S  S
          D  I  Q  L  N  N  D  V  R  D  Y  L  L  S  K  M  T  S  L  P
       M  I  Y  N  *  I  M  T  F  V  I  I  C  C  L  R  *  L  V  F

4981   TAAAGATTGGCGTCTTATCAATAAATTTGATGTTATTAACGGTGTTAAAACTGTTAAGTA   5040
         *  R  L  A  S  Y  Q  *  I  *  C  Y  *  R  C  *  N  C  *  V
          K  D  W  R  L  I  N  K  F  D  V  I  N  G  V  K  T  V  K  Y
       L  K  I  G  V  L  S  I  N  L  M  L  L  T  V  L  K  L  L  S

5041   TTTTGAGTGTCCTAATTCTATTTATATATGTAGTCAGGGTAAAGACTTTGGTTATGTATG   5100
         F  *  V  S  *  F  Y  L  Y  M  *  S  G  *  R  L  W  L  C  M
          F  E  C  P  N  S  I  Y  I  C  S  Q  G  K  D  F  G  Y  V  C
       I  L  S  V  L  I  L  F  I  Y  V  V  R  V  K  T  L  V  M  Y

5101   TGATGGTTCTTTTTATAAAGCAACTGTTAATCAAGTTTGTGTTTTATTAGCTAAGAAGAT   5160
         *  W  F  F  L  *  S  N  C  *  S  S  L  C  F  I  S  *  E  D
          D  G  S  F  Y  K  A  T  V  N  Q  V  C  V  L  L  A  K  K  I
       V  M  V  L  F  I  K  Q  L  L  I  K  F  V  F  Y  *  L  R  R

5161   AGATGTTTTGCTTACTGTAGATGGTGTTAATTTTAAATCTATTTCTCTTACTGTAGGTGA   5220
         R  C  F  A  Y  C  R  W  C  *  F  *  I  Y  F  S  Y  C  R  *
          D  V  L  L  T  V  D  G  V  N  F  K  S  I  S  L  T  V  G  E
       *  M  F  C  L  L  *  M  V  L  I  L  N  L  F  L  L  L  *  V

5221   AGTTTTTGGTAAAATACTTGGTAATGTTTTCTGTGATGGCATTGATGTTACTAAGTTAAA   5280
         S  F  W  *  N  T  W  *  C  F  L  *  W  H  *  C  Y  *  V  K
          V  F  G  K  I  L  G  N  V  F  C  D  G  I  D  V  T  K  L  K
       K  F  L  V  K  Y  L  V  M  F  S  V  M  A  L  M  L  L  S  *

5281   GTGTAGTGATTTTTATGCCGATAAAATTTTATATCAGTATGAAAATTTGTCTTTAGCTGA   5340
         V  *  *  F  L  C  R  *  N  F  I  S  V  *  K  F  V  F  S  *
          C  S  D  F  Y  A  D  K  I  L  Y  Q  Y  E  N  L  S  L  A  D
       S  V  V  I  F  M  P  I  K  F  Y  I  S  M  K  I  C  L  *  L

5341   TATTTCTGCTGTACAAAGTTCATTTGGGTTTGATCAGCAACAATTGCTTGCTTATTATAA   5400
         Y  F  C  C  T  K  F  I  W  V  *  S  A  T  I  A  C  L  L  *
          I  S  A  V  Q  S  S  F  G  F  D  Q  Q  Q  L  L  A  Y  Y  N
       I  F  L  L  Y  K  V  H  L  G  L  I  S  N  N  C  L  L  I  I
```

FIG. 2 CONT.

```
5401    TTTTTTAACAGTATGTAAATGGTCTGTAGTTGTTAACGGTCCATTTTTTTCTTTTGAACA    5460
          F  F  N  S  M  *  M  V  C  S  C  *  R  S  I  F  F  F  *  T
           F  L  T  V  C  K  W  S  V  V  V  N  G  P  F  F  S  F  E  Q
            I  F  *  Q  Y  V  N  G  L  *  L  L  T  V  H  F  F  L  L  N

5461    GTCTCATAATAATTGTTATGTGAATGTAGCTTGTCTTATGTTGCAGCATATTAATCTTAA    5520
          V  S  *  *  L  L  C  E  C  S  L  S  Y  V  A  A  Y  *  S  *
           S  H  N  N  C  Y  V  N  V  A  C  L  M  L  Q  H  I  N  L  K
            S  L  I  I  I  V  M  *  M  *  L  V  L  C  C  S  I  L  I  L

5521    ATTTAATAAATGGCAGTGGCAGGAAGCATGGTATGAATTTCGTGCTGGCAGACCACATAG    5580
          I  *  *  M  A  V  A  G  S  M  V  *  I  S  C  W  Q  T  T  *
           F  N  K  W  Q  W  Q  E  A  W  Y  E  F  R  A  G  R  P  H  R
            N  L  I  N  G  S  G  R  K  H  G  M  N  F  V  L  A  D  H  I

5581    GTTAGTTGCTCTTGTTTTAGCTAAAGGTCATTTTAAATTTGATGAACCATCAGATGCTAC    5640
          V  S  C  S  C  F  S  *  R  S  F  *  I  *  *  T  I  R  C  Y
           L  V  A  L  V  L  A  K  G  H  F  K  F  D  E  P  S  D  A  T
            G  *  L  L  L  F  *  L  K  V  I  L  N  L  M  N  H  Q  M  L

5641    TGATTTTATTCGTGTTGTTTTGAAACAAGCTGATTTATCAGGTGCAATTTGTGAATTAGA    5700
          *  F  Y  S  C  C  F  E  T  S  *  F  I  R  C  N  L  *  I  R
           D  F  I  R  V  V  L  K  Q  A  D  L  S  G  A  I  C  E  L  E
            L  I  L  F  V  L  F  *  N  K  L  I  Y  Q  V  Q  F  V  N  *

5701    ACTTATTTGTGATTGTGGTATTAAACAAGAAAGTCGTGTTGGTGTTGATGCTGTTATGCA    5760
          T  Y  L  *  L  W  Y  *  T  R  K  S  C  W  C  *  C  C  Y  A
           L  I  C  D  C  G  I  K  Q  E  S  R  V  G  V  D  A  V  M  H
            N  L  F  V  I  V  V  L  N  K  K  V  V  L  V  L  M  L  L  C

5761    TTTTGGTACATTAGCAAAGACTGATCTTTTTAATGGTTATAAGATTGGCTGTAATTGTGC    5820
          F  W  Y  I  S  K  D  *  S  F  *  W  L  *  D  W  L  *  L  C
           F  G  T  L  A  K  T  D  L  F  N  G  Y  K  I  G  C  N  C  A
            I  L  V  H  *  Q  R  L  I  F  L  M  V  I  R  L  A  V  I  V

5821    AGGTAGAATTGTCCATTGTACTAAATTGAATGTACCATTTTTGATTTGTTCTAATACTCC    5880
          R  *  N  C  P  L  Y  *  I  E  C  T  I  F  D  L  F  *  Y  S
           G  R  I  V  H  C  T  K  L  N  V  P  F  L  I  C  S  N  T  P
            Q  V  E  L  S  I  V  L  N  *  M  Y  H  F  *  F  V  L  I  L

5881    TCTGAGTAAGGATTTACCTGATGATGTTGTTGCAGCTAACATGTTTATGGGTGTAGGTGT    5940
          S  E  *  G  F  T  *  *  C  C  C  S  *  H  V  Y  G  C  R  C
           L  S  K  D  L  P  D  D  V  V  A  A  N  M  F  M  G  V  G  V
            L  *  V  R  I  Y  L  M  M  L  L  Q  L  T  C  L  W  V  *  V
```

FIG. 2 CONT.

```
5941  AGGCCATTATACACATTTGAAATGTGGTTCACCTTACCAACATTATGATGCTTGTAGTGT  6000
        R  P  L  Y  T  F  E  M  W  F  T  L  P  T  L  *  C  L  *  C
         G  H  Y  T  H  L  K  C  G  S  P  Y  Q  H  Y  D  A  C  S  V
       *  A  I  I  H  I  *  N  V  V  H  L  T  N  I  M  M  L  V  V

6001  TAAAAAATATACAGGTGTTAGTGGTTGTTTAACTGACTGCTTGTATCTTAAAAATTTAAC  6060
        *  K  I  Y  R  C  *  W  L  F  N  *  L  L  V  S  *  K  F  N
         K  K  Y  T  G  V  S  G  C  L  T  D  C  L  Y  L  K  N  L  T
       L  K  N  I  Q  V  L  V  V  V  *  L  T  A  C  I  L  K  I  *

6061  CCAGACTTTTACATCTATGTTGACTAATTATTTTTTGGATGATGTTGAAATGGTTGCTTA  6120
        P  D  F  Y  I  Y  V  D  *  L  F  F  G  *  C  *  N  G  C  L
         Q  T  F  T  S  M  L  T  N  Y  F  L  D  D  V  E  M  V  A  Y
       P  R  L  L  H  L  C  *  L  I  I  F  W  M  M  L  K  W  L  L

6121  TAACCCTGATCTTTCACAATATTATTGTGATAATGGTAAGTATTATACAAAACCTATTAT  6180
        *  P  *  S  F  T  I  L  L  *  *  W  *  V  L  Y  K  T  Y  Y
         N  P  D  L  S  Q  Y  Y  C  D  N  G  K  Y  Y  T  K  P  I  I
       I  T  L  I  F  H  N  I  I  V  I  M  V  S  I  I  Q  N  L  L

6181  AAAGGCTCAGTTTAAACCATTTGCTAAAGTTGACGGTGTTTATACTAACTTTAAGTTAGT  6240
        K  G  S  V  *  T  I  C  *  S  *  R  C  L  Y  *  L  *  V  S
         K  A  Q  F  K  P  F  A  K  V  D  G  V  Y  T  N  F  K  L  V
       *  R  L  S  L  N  H  L  L  K  L  T  V  F  I  L  T  L  S  *

6241  TGGACATGATATTTGTGCTCAATTGAATGATAAGTTAGGTTTTAATGTAGATTTGCCGTT  6300
        W  T  *  Y  L  C  S  I  E  *  *  V  R  F  *  C  R  F  A  V
         G  H  D  I  C  A  Q  L  N  D  K  L  G  F  N  V  D  L  P  F
       L  D  M  I  F  V  L  N  *  M  I  S  *  V  L  M  *  I  C  R

6301  TGTTGAGTACAAAGTAACAGTCTGGCCTGTAGCTACTGGTGATGTTGTTTTGGCATCTGA  6360
        C  *  V  Q  S  N  S  L  A  C  S  Y  W  *  C  C  F  G  I  *
         V  E  Y  K  V  T  V  W  P  V  A  T  G  D  V  V  L  A  S  D
       L  L  S  T  K  *  Q  S  G  L  *  L  L  V  M  L  F  W  H  L

6361  TGATTTATATGTGAAACGTTATTTTAAAGGATGTGAAACTTTTGGTAAGCCTGTTATTTG  6420
        *  F  I  C  E  T  L  F  *  R  M  *  N  F  W  *  A  C  Y  L
         D  L  Y  V  K  R  Y  F  K  G  C  E  T  F  G  K  P  V  I  W
       M  I  Y  M  *  N  V  I  L  K  D  V  K  L  L  V  S  L  L  F

6421  GTTTTGTCATGATGAAGCATCATTGAATTCTCTTACTTATTTTAATAAACCTAGTTTTAA  6480
        V  L  S  *  *  S  I  I  E  F  S  Y  L  F  *  *  T  *  F  *
         F  C  H  D  E  A  S  L  N  S  L  T  Y  F  N  K  P  S  F  K
       G  F  V  M  M  K  H  H  *  I  L  L  L  I  L  I  N  L  V  L
```

FIG. 2 CONT.

```
6481    ATCTGAAAATAGATATAGTGTTTTGTCTGTTGATTCTGTATCTGAGGAGTCACAAGGTAA    6540
          I  *  K  *  I  *  C  F  V  C  *  F  C  I  *  G  V  T  R  *
           S  E  N  R  Y  S  V  L  S  V  D  S  V  S  E  E  S  Q  G  N
            N  L  K  I  D  I  V  F  C  L  L  I  L  Y  L  R  S  H  K  V

6541    TGTGGTTACTTCTGTTATGGAATCGCAGATTAGTACTAAAGAGGTTAAGTTAAAGGGTGT    6600
          C  G  Y  F  C  Y  G  I  A  D  *  Y  *  R  G  *  V  K  G  C
           V  V  T  S  V  M  E  S  Q  I  S  T  K  E  V  K  L  K  G  V
            M  W  L  L  L  W  N  R  R  L  V  L  K  R  L  S  *  R  V

6601    TAGAAAGACTGTTAAAATAGAAGATGCTATTATTGTTAATGATGAAAATAGTTCTATTAA    6660
          *  K  D  C  *  N  R  R  C  Y  Y  C  *  *  *  K  *  F  Y  *
           R  K  T  V  K  I  E  D  A  I  I  V  N  D  E  N  S  S  I  K
            L  E  R  L  L  K  *  K  M  L  L  L  L  M  M  K  I  V  L  L

6661    GGTTGTTAAAAGTTTATCTTTAGTTGATGTTTGGGATATGTATTTGACAGGTTGTGATTA    6720
          G  C  *  K  F  I  F  S  *  C  L  G  Y  V  F  D  R  L  *  L
           V  V  K  S  L  S  L  V  D  V  W  D  M  Y  L  T  G  C  D  Y
            R  L  L  K  V  Y  L  *  L  M  F  G  I  C  I  *  Q  V  V  I

6721    TGTTGTTTGGGTTGCTAATGAATTGTCACGCCTAGTTAAATCACCAACAGTTAGGGAATA    6780
          C  C  L  G  C  *  *  I  V  T  P  S  *  I  T  N  S  *  G  I
           V  V  W  V  A  N  E  L  S  R  L  V  K  S  P  T  V  R  E  Y
            M  L  F  G  L  L  M  N  C  H  A  *  L  N  H  Q  Q  L  G  N

6781    TATACGATATGGTATTAAACCTATTACTATACCTATAGATTTGTTATGTTTAAGAGATGA    6840
          Y  T  I  W  Y  *  T  Y  Y  Y  T  Y  R  F  V  M  F  K  R  *
           I  R  Y  G  I  K  P  I  T  I  P  I  D  L  L  C  L  R  D  D
            I  Y  D  M  V  L  N  L  L  L  Y  L  *  I  C  Y  V  *  E  M

6841    TAATCAAACTCTTTTAGTTCCTAAAATTTTTAAAGCAAGAGCTATAGAATTTTATGGTTT    6900
          *  S  N  S  F  S  S  *  N  F  *  S  K  S  Y  R  I  L  W  F
           N  Q  T  L  L  V  P  K  I  F  K  A  R  A  I  E  F  Y  G  F
            I  I  K  L  F  *  F  L  K  F  L  K  Q  E  L  *  N  F  M  V

6901    TTTGAAGTGGTTGTTTATTTATGTTTTTAGTTTATTACATTTTACAAATGATAAAACCAT    6960
          F  E  V  V  V  Y  L  C  F  *  F  I  T  F  Y  K  *  *  N  H
           L  K  W  L  F  I  Y  V  F  S  L  L  H  F  T  N  D  K  T  I
            F  *  S  G  C  L  F  M  F  L  V  Y  Y  I  L  Q  M  I  K  P

6961    TTTTTATACTACAGAAATAGCTTCTAAGTTTACTTTTAATTTGTTTTGTTTGGCTCTTAA    7020
          F  L  Y  Y  R  N  S  F  *  V  Y  F  *  F  V  L  F  G  S  *
           F  Y  T  T  E  I  A  S  K  F  T  F  N  L  F  C  L  A  L  K
            F  F  I  L  Q  K  *  L  L  S  L  L  L  I  C  F  V  W  L  L
```

FIG. 2 CONT.

```
7021  AAATGCTTTTCAGACATTTAGATGGAGTATATTTATAAAAGGTTTTCTTGTTGTAGCCAC  7080
       K  C  F  S  D  I  *  M  E  Y  I  Y  K  R  F  S  C  C  S  H
        N  A  F  Q  T  F  R  W  S  I  F  I  K  G  F  L  V  V  A  T
       K  M  L  F  R  H  L  D  G  V  Y  L  *  K  V  F  L  L  *  P

7081  TGTGTTTTGTTTTGGTTTAATTTTTGTATATAAATGTTATTTTTAGTGACTTTTATCT    7140
       C  V  F  V  L  V  *  F  F  V  Y  K  C  Y  F  *  *  L  L  S
        V  F  L  F  W  F  N  F  L  Y  I  N  V  I  F  S  D  F  Y  L
       L  C  F  C  F  G  L  I  F  C  I  *  M  L  F  L  V  T  F  I

7141  TCCTAATATTAGTGTTTTTCCTATTTTTGTGGGAAGAATTGTTATGTGGATAAAGGCTAC  7200
       S  *  Y  *  C  F  S  Y  F  C  G  K  N  C  Y  V  D  K  G  Y
        P  N  I  S  V  F  P  I  F  V  G  R  I  V  M  W  I  K  A  T
       F  L  I  L  V  F  F  L  F  L  W  E  E  L  L  C  G  *  R  L

7201  TTTTGGTTTGGTTACAATTTGTGATTTTTATTCTAAGTTAGGTGTAGGTTTTACAAGTCA  7260
       F  W  F  G  Y  N  L  *  F  L  F  *  V  R  C  R  F  Y  K  S
        F  G  L  V  T  I  C  D  F  Y  S  K  L  G  V  G  F  T  S  H
       L  L  V  W  L  Q  F  V  I  F  I  L  S  *  V  *  V  L  Q  V

7261  TTTTTGTAATGGTAGTTTTATATGTGAATTGTGTCATTCTGGTTTTGATATGTTGGATAC  7320
       F  L  *  W  *  F  Y  M  *  I  V  S  F  W  F  *  Y  V  G  Y
        F  C  N  G  S  F  I  C  E  L  C  H  S  G  F  D  M  L  D  T
       I  F  V  M  V  V  L  Y  V  N  C  V  I  L  V  L  I  C  W  I

7321  ATATGCAGCTATAGATTTTGTTCAGTATGAAGTAGATAGACGTGTTTATTTGATTATGT   7380
       I  C  S  Y  R  F  C  S  V  *  S  R  *  T  C  F  I  *  L  C
        Y  A  A  I  D  F  V  Q  Y  E  V  D  R  R  V  L  F  D  Y  V
       H  M  Q  L  *  I  L  F  S  M  K  *  I  D  V  F  Y  L  I  M

7381  TAGTTTAGTCAAATTAATTGTTGAACTCGTTATTGGTTATTCATTATACACAGTATGGTT  7440
       *  F  S  Q  I  N  C  *  T  R  Y  W  L  F  I  I  H  S  M  V
        S  L  V  K  L  I  V  E  L  V  I  G  Y  S  L  Y  T  V  W  F
       L  V  *  S  N  *  L  L  N  S  L  L  V  I  H  Y  T  Q  Y  G

7441  TTATCCATTATTTTGTCTTATTGGTTTACAATTATTTACTACATGGTTGCCTGATTTGTT  7500
       L  S  I  I  L  S  Y  W  F  T  I  I  Y  Y  M  V  A  *  F  V
        Y  P  L  F  C  L  I  G  L  Q  L  F  T  T  W  L  P  D  L  F
       F  I  H  Y  F  V  L  L  V  Y  N  Y  L  L  H  G  C  L  I  C

7501  TATGTTAGAAACTATGCATTGGTTGATTAGATTTATTGTATTTGTAGCTAATATGTTACC  7560
       Y  V  R  N  Y  A  L  V  D  *  I  Y  C  I  C  S  *  Y  V  T
        M  L  E  T  M  H  W  L  I  R  F  I  V  F  V  A  N  M  L  P
       L  C  *  K  L  C  I  G  *  L  D  L  L  Y  L  *  L  I  C  Y
```

FIG. 2 CONT.

```
7561  TGCTTTTGTCTTGTTGCGGTTTTATATAGTTGTTACTGCTATGTATAAAGTAGTTGGTTT  7620
       C  F  C  L  V  A  V  L  Y  S  C  Y  C  Y  V  *  S  S  W  F
        A  F  V  L  L  R  F  Y  I  V  V  T  A  M  Y  K  V  V  G  F
      L  L  L  S  C  C  G  F  I  *  L  L  L  C  I  K  *  L  V

7621  TATTAGGCATATTGTCTATGGTTGTAATAAAGCTGGTTGTTTATTTTGTTATAAACGAAA  7680
       Y  *  A  Y  C  L  W  L  *  *  S  W  L  F  I  L  L  *  T  K
        I  R  H  I  V  Y  G  C  N  K  A  G  C  L  F  C  Y  K  R  N
      L  L  G  I  L  S  M  V  V  I  K  L  V  V  Y  F  V  I  N  E

7681  TTGTAGTGTTCGTGTTAAGTGTAGTACTATTGTTGGTGGTGTAATTCGTTATTATGATAT  7740
       L  *  C  S  C  *  V  *  Y  Y  C  W  W  C  N  S  L  L  *  Y
        C  S  V  R  V  K  C  S  T  I  V  G  G  V  I  R  Y  Y  D  I
      I  V  V  F  V  L  S  V  V  L  L  L  V  V  *  F  V  I  M  I

7741  TACTGCTAATGGTGGTACTGGTTTTTGTGTTAAACATCAATGGAATTGTTTTAATTGCCA  7800
       Y  C  *  W  W  Y  W  F  L  C  *  T  S  M  E  L  F  *  L  P
        T  A  N  G  G  T  G  F  C  V  K  H  Q  W  N  C  F  N  C  H
      L  L  L  M  V  V  L  V  F  V  L  N  I  N  G  I  V  L  I  A

7801  TTCTTTTAAACCAGGTAACACTTTTATAACTGTAGAAGCTGCTATAGAACTTTCTAAAGA  7860
       F  F  *  T  R  *  H  F  Y  N  C  R  S  C  Y  R  T  F  *  R
        S  F  K  P  G  N  T  F  I  T  V  E  A  A  I  E  L  S  K  E
      I  L  L  N  Q  V  T  L  L  *  L  *  K  L  L  *  N  F  L  K

7861  GCTTAAACGACCTGTAAATCCAACTGATGCTTCACATTATGTAGTTACTGATATTAAGCA  7920
       A  *  T  T  C  K  S  N  *  C  F  T  L  C  S  Y  *  Y  *  A
        L  K  R  P  V  N  P  T  D  A  S  H  Y  V  V  T  D  I  K  Q
      S  L  N  D  L  *  I  Q  L  M  L  H  I  M  *  L  L  I  L  S

7921  AGTTGGTTGTATGATGCGTTTGTTCTATGATAGAGATGGACAGCGTGTTTACGATGATGT  7980
       S  W  L  Y  D  A  F  V  L  *  *  R  W  T  A  C  L  R  *  C
        V  G  C  M  M  R  L  F  Y  D  R  D  G  Q  R  V  Y  D  D  V
      K  L  V  V  *  C  V  C  S  M  I  E  M  D  S  V  F  T  M  M

7981  TGATGCTAGTTTATTTGTAGATATTAATAATCTGTTACATTCTAAAGTTAAAGTTGTTCC  8040
       *  C  *  F  I  C  R  Y  *  *  S  V  T  F  *  S  *  S  C  S
        D  A  S  L  F  V  D  I  N  N  L  L  H  S  K  V  K  V  V  P
      L  M  L  V  Y  L  *  I  L  I  I  C  Y  I  L  K  L  K  L  F

8041  TAATTTGTATGTAGTTGTAGTAGAGAGTGATGCTGATAGAGCTAATTTTCTGAATGCTGT  8100
       *  F  V  C  S  C  S  R  E  *  C  *  *  S  *  F  S  E  C  C
        N  L  Y  V  V  V  E  S  D  A  D  R  A  N  F  L  N  A  V
      L  I  C  M  *  L  *  *  R  V  M  L  I  E  L  I  F  *  M  L
```

FIG. 2 CONT.

```
8101    TGTGTTTTATGCACAATCATTGTATAGGCCTATATTACTTGTAGACAAAAAGTTAATTAC    8160
         C  V  L  C  T  I  I  V  *  A  Y  I  T  C  R  Q  K  V  N  Y
          V  F  Y  A  Q  S  L  Y  R  P  I  L  L  V  D  K  K  L  I  T
        L  C  F  M  H  N  H  C  I  G  L  Y  Y  L  *  T  K  S  *  L

8161    TACAGCTTGTAATGGTATCTCTGTAACCCAGACTATGTTTGATGTTTATGTTGATACTTT    8220
         Y  S  L  *  W  Y  L  C  N  P  D  Y  V  *  C  L  C  *  Y  F
          T  A  C  N  G  I  S  V  T  Q  T  M  F  D  V  Y  V  D  T  F
        L  Q  L  V  M  V  S  L  *  P  R  L  C  L  M  F  M  L  I  L

8221    TATGTCTCATTTTGATGTTGATAGAAAGAGTTTTAATAATTTTGTTAACATTGCTCATGC    8280
         Y  V  S  F  *  C  *  *  K  E  F  *  *  F  C  *  H  C  S  C
          M  S  H  F  D  V  D  R  K  S  F  N  N  F  V  N  I  A  H  A
        L  C  L  I  L  M  L  I  E  R  V  L  I  I  L  L  T  L  L  M

8281    TTCTCTTAGAGAGGGTGTGCAATTAGAAAAGGTTTTAGATACTTTTGTGGGATGTGTACG    8340
         F  S  *  R  G  C  A  I  R  K  G  F  R  Y  F  C  G  M  C  T
          S  L  R  E  G  V  Q  L  E  K  V  L  D  T  F  V  G  C  V  R
        L  L  L  E  R  V  C  N  *  K  R  F  *  I  L  L  W  D  V  Y

8341    TAAATGTTGTTCCATTGATTCAGATGTTGAAACAAGATTTATTACTAAATCTATGATATC    8400
         *  M  L  F  H  *  F  R  C  *  N  K  I  Y  Y  *  I  Y  D  I
          K  C  C  S  I  D  S  D  V  E  T  R  F  I  T  K  S  M  I  S
        V  N  V  V  P  L  I  Q  M  L  K  Q  D  L  L  L  N  L  *  Y

8401    TGCAGTAGCTGCTGGTTTGGAATTTACTGATGAAAATTATAACAATTTGGTACCTACATA    8460
         C  S  S  C  W  F  G  I  Y  *  *  K  L  *  Q  F  G  T  Y  I
          A  V  A  A  G  L  E  F  T  D  E  N  Y  N  N  L  V  P  T  Y
        L  Q  *  L  L  V  W  N  L  L  M  K  I  I  T  I  W  Y  L  H

8461    TTTAAAGAGTGATAATATTGTAGCTGCTGATTTAGGTGTTCTTATACAGAATGGTGCTAA    8520
         F  K  E  *  *  Y  C  S  C  *  F  R  C  S  Y  T  E  W  C  *
          L  K  S  D  N  I  V  A  A  D  L  G  V  L  I  Q  N  G  A  K
        I  *  R  V  I  I  L  *  L  L  I  *  V  F  L  Y  R  M  V  L

8521    GCATGTACAGGGTAATGTTGCTAAGGCAGCTAATATTTCTTGTATATGGTTTATTGATGC    8580
         A  C  T  G  *  C  C  *  G  S  *  Y  F  L  Y  M  V  Y  *  C
          H  V  Q  G  N  V  A  K  A  A  N  I  S  C  I  W  F  I  D  A
        S  M  Y  R  V  M  L  L  R  Q  L  I  F  L  V  Y  G  L  L  M

8581    TTTTAATCAACTTACTGCTGATTTACAGCATAAATTAAAAAAAGCATGTGTTAAAACTGG    8640
         F  *  S  T  Y  C  *  F  T  A  *  I  K  K  S  M  C  *  N  W
          F  N  Q  L  T  A  D  L  Q  H  K  L  K  K  A  C  V  K  T  G
        L  L  I  N  L  L  L  I  Y  S  I  N  *  K  K  H  V  L  K  L
```

FIG. 2 CONT.

```
8641  CTTGAAGTTAAAATTGACTTTTAATAAGCAAGAGGCAAGTGTCCCTATTCTTACAACACC  8700
        L  E  V  K  I  D  F  *  *  A  R  G  K  C  P  Y  S  N  T
         L  K  L  K  L  T  F  N  K  Q  E  A  S  V  P  I  L  T  T  P
       A  *  S  *  N  *  L  L  I  S  K  R  Q  V  S  L  F  L  Q  H

8701  CTTTTCACTTAAAGGAGGTGTTGTATTGAGTAATTTGTTATATATATTATTTTTTGTTAG  8760
        L  F  T  *  R  R  C  C  I  E  *  F  V  I  Y  I  I  F  C  *
         F  S  L  K  G  G  V  V  L  S  N  L  L  Y  I  L  F  F  V  S
       P  F  H  L  K  E  V  L  Y  *  V  I  C  Y  I  Y  Y  F  L  L

8761  TTTAATCTGTTTTATATTATTGTGGGCTTTATTGCCTACATATAGTGTTTATAAGTCTGA  8820
        F  N  L  F  Y  I  I  V  G  F  I  A  Y  I  *  C  L  *  V  *
         L  I  C  F  I  L  L  W  A  L  L  P  T  Y  S  V  Y  K  S  D
       V  *  S  V  L  Y  Y  C  G  L  Y  C  L  H  I  V  F  I  S  L

8821  TATTCATTTGCCTGCTTATGCTAGTTTTAAAGTTATTGATAATGGTGTTGTTAGAGATAT  8880
        Y  S  F  A  C  L  C  *  F  *  S  Y  *  *  W  C  C  *  R  Y
         I  H  L  P  A  Y  A  S  F  K  V  I  D  N  G  V  V  R  D  I
       I  F  I  C  L  L  M  L  V  L  K  L  L  I  M  V  L  L  E  I

8881  TTCAGTTAATGATTTATGTTTTGCTAATAAATTTTTCCAATTTGATCAATGGTATGAGTC  8940
        F  S  *  *  F  M  F  C  *  *  I  F  P  I  *  S  M  V  *  V
         S  V  N  D  L  C  F  A  N  K  F  F  Q  F  D  Q  W  Y  E  S
       F  Q  L  M  I  Y  V  L  L  I  N  F  S  N  L  I  N  G  M  S

8941  CACTTTTGGGTCTGTTTACTATCATAATTCTATGGATTGCCCTATTGTAGTGGCAGTTAT  9000
        H  F  W  V  C  L  L  S  *  F  Y  G  L  P  Y  C  S  G  S  Y
         T  F  G  S  V  Y  Y  H  N  S  M  D  C  P  I  V  V  A  V  M
       P  L  L  G  L  F  T  I  I  I  L  W  I  A  L  L  *  W  Q  L

9001  GGATGAAGATATCGGTTCTACTATGTTTAATGTTCCTACTAAAGTTTTGAGACATGGCTT  9060
        G  *  R  Y  R  F  Y  Y  V  *  C  S  Y  *  S  F  E  T  W  L
         D  E  D  I  G  S  T  M  F  N  V  P  T  K  V  L  R  H  G  F
       W  M  K  I  S  V  L  L  C  L  M  F  L  L  K  F  *  D  M  A

9061  TCATGTTTTACATTTTTTAACTTATGCATTTGCTAGTGATAGTGTTCAGTGCTATACACC  9120
        S  C  F  T  F  F  N  L  C  I  C  *  *  *  C  S  V  L  Y  T
         H  V  L  H  F  L  T  Y  A  F  A  S  D  S  V  Q  C  Y  T  P
       F  M  F  Y  I  F  *  L  M  H  L  L  V  I  V  F  S  A  I  H

9121  ACATATTCAGATTTCTTATAATGATTTTTATGCTAGTGGTTGTGTTTTATCATCTTTGTG  9180
        T  Y  S  D  F  L  *  *  F  L  C  *  W  L  C  F  I  I  F  V
         H  I  Q  I  S  Y  N  D  F  Y  A  S  G  C  V  L  S  S  L  C
       H  I  F  R  F  L  I  M  I  F  M  L  V  V  V  F  Y  H  L  C
```

FIG. 2 CONT.

```
9181  TACTATGTTTAAAAGAGGTGATGGTACACCACATCCTTATTGTTATTCAGATGGTGTTAT  9240
       Y  Y  V  *  K  R  *  W  Y  T  T  S  L  L  L  F  R  W  C  Y
        T  M  F  K  R  G  D  G  T  P  H  P  Y  C  Y  S  D  G  V  M
         V  L  C  L  K  E  V  M  V  H  H  I  L  I  V  I  Q  M  V  L

9241  GAAGAATGCTTCTTTGTATACATCTTTGGTTCCACATACACGTTATAGCCTTGCTAATTC  9300
       E  E  C  F  F  V  Y  I  F  G  S  T  Y  T  L  *  P  C  *  F
        K  N  A  S  L  Y  T  S  L  V  P  H  T  R  Y  S  L  A  N  S
         *  R  M  L  L  C  I  H  L  W  F  H  I  H  V  I  A  L  L  I

9301  TAATGGTTTTATAAGATTTCCTGATGTTATTAGTGAAGGTATTGTACGTATTGTAAGAAC  9360
       *  W  F  Y  K  I  S  *  C  Y  *  *  R  Y  C  T  Y  C  K  N
        N  G  F  I  R  F  P  D  V  I  S  E  G  I  V  R  I  V  R  T
         L  M  V  L  *  D  F  L  M  L  L  V  K  V  L  Y  V  L  *  E

9361  GCGCTCTATGACTTATTGTAGAGTGGGTGCATGTGAATACGCCGAAGAGGGTATATGTTT  9420
       A  L  Y  D  L  L  *  S  G  C  M  *  I  R  R  R  G  Y  M  F
        R  S  M  T  Y  C  R  V  G  A  C  E  Y  A  E  E  G  I  C  F
         R  A  L  *  L  I  V  E  W  V  H  V  N  T  P  K  R  V  Y  V

9421  TAATTTTAATAGTTCCTGGGTTTTGAATAATGATTATTATAGAAGTATGCCTGGAACTTT  9480
       *  F  *  *  F  L  G  F  E  *  *  L  L  *  K  Y  A  W  N  F
        N  F  N  S  S  W  V  L  N  N  D  Y  Y  R  S  M  P  G  T  F
         L  I  L  I  V  P  G  F  *  I  M  I  I  E  V  C  L  E  L

9481  TTGTGGTAGAGATCTTTTTGATTTGTTTTATCAATTTTTTAGTAGTTTAATTCGTCCTAT  9540
       L  W  *  R  S  F  *  F  V  L  S  I  F  *  *  F  N  S  S  Y
        C  G  R  D  L  F  D  L  F  Y  Q  F  F  S  S  L  I  R  P  I
         V  V  E  I  F  L  I  C  F  I  N  F  L  V  V  *  F  V  L

9541  AGATTTCTTTTCTCTTACTGCTAGTTCTATTTTTGGAGCTATATTGGCTATAGTTGTTGT  9600
       R  F  L  F  S  Y  C  *  F  Y  F  W  S  Y  I  G  Y  S  C  C
        D  F  F  S  L  T  A  S  S  I  F  G  A  I  L  A  I  V  V  V
         *  I  S  F  L  L  L  L  V  L  F  L  E  L  Y  W  L  *  L  L

9601  CTTGGTTTTTTATTATTTAATAAAACTTAAGCGTGCTTTTGGAGATTATACTAGTGTTGT  9660
       L  G  F  L  L  F  N  K  T  *  A  C  F  W  R  L  Y  *  C  C
        L  V  F  Y  Y  L  I  K  L  K  R  A  F  G  D  Y  T  S  V  V
         S  W  F  F  I  I  *  *  N  L  S  V  L  L  E  I  I  L  V  L

9661  AGTTATAAATGTTGTTGTTTGGTGTATTAATTTTCTTATGCTTTTGTTTTTCAAGTTTA  9720
       S  Y  K  C  C  C  L  V  Y  *  F  S  Y  A  F  C  F  S  S  L
        V  I  N  V  V  V  W  C  I  N  F  L  M  L  F  V  F  Q  V  Y
         *  L  *  M  L  L  F  G  V  L  I  F  L  C  F  L  F  F  K  F
```

FIG. 2 CONT.

```
9721   TCCTATTTGTGCATGTGTTTATGCTTGTTTTTATTTTTATGTAACATTGTATTTTCCTTC   9780
          S  Y  L  C  M  C  L  C  L  F  L  F  L  C  N  I  V  F  S  F
           P  I  C  A  C  V  Y  A  C  F  Y  F  Y  V  T  L  Y  F  P  S
         I  L  F  V  H  V  F  M  L  V  F  I  F  M  *  H  C  I  F  L

9781   TGAAATTAGTGTAATTATGCATTTGCAATGGATTGTTATGTATGGTGCTATAATGCCTTT   9840
          *  N  *  C  N  Y  A  F  A  M  D  C  Y  V  W  C  Y  N  A  F
           E  I  S  V  I  M  H  L  Q  W  I  V  M  Y  G  A  I  M  P  F
         L  K  L  V  *  L  C  I  C  N  G  L  L  C  M  V  L  *  C  L

9841   TTGGTTTTGTGTCACATATGTAGCTATGGTTATTGCAAACCATGTTTTATGGTTATTTTC   9900
          L  V  L  C  H  I  C  S  Y  G  Y  C  K  P  C  F  M  V  I  F
           W  F  C  V  T  Y  V  A  M  V  I  A  N  H  V  L  W  L  F  S
         F  G  F  V  S  H  M  *  L  W  L  L  Q  T  M  F  Y  G  Y  F

9901   ATATTGTAGGAAAATTGGTGTTAATGTATGTAGTGATAGTACATTTGAAGAAACATCTCT   9960
          I  L  *  E  N  W  C  *  C  M  *  *  *  Y  I  *  R  N  I  S
           Y  C  R  K  I  G  V  N  V  C  S  D  S  T  F  E  E  T  S  L
         H  I  V  G  K  L  V  L  M  Y  V  V  I  V  H  L  K  K  H  L

9961   TACTACTTTTATGATTACTAAAGATTCTTATTGTAGATTAAAGAATTCTGTTTCTGATGT   10020
          Y  Y  F  Y  D  Y  *  R  F  L  L  *  I  K  E  F  C  F  *  C
           T  T  F  M  I  T  K  D  S  Y  C  R  L  K  N  S  V  S  D  V
         L  L  L  L  *  L  L  K  I  L  I  V  D  *  R  I  L  F  L  M

10021  TGCCTACAATAGATATTTGAGTTTGTATAATAAGTATCGTTACTATAGTGGTAAAATGGA   10080
          C  L  Q  *  I  F  E  F  V  *  *  V  S  L  L  *  W  *  N  G
           A  Y  N  R  Y  L  S  L  Y  N  K  Y  R  Y  Y  S  G  K  M  D
         L  P  T  I  D  I  *  V  C  I  I  S  I  V  T  I  V  V  K  W

10081  TACTGCTGCCTATAGAGAAGCGGCGTGTTCTCAGTTAGCTAAAGCTATGGAAACATTTAA   10140
          Y  C  C  L  *  R  S  G  V  F  S  V  S  *  S  Y  G  N  I  *
           T  A  A  Y  R  E  A  A  C  S  Q  L  A  K  A  M  E  T  F  N
         I  L  L  P  I  E  K  R  R  V  L  S  *  L  K  L  W  K  H  L

10141  TCACAATAATGGTAATGATGTCTTATACCAACCTCCTACAGCATCTGTTTCTACATCTTT   10200
          S  Q  *  W  *  *  C  L  I  P  T  S  Y  S  I  C  F  Y  I  F
           H  N  N  G  N  D  V  L  Y  Q  P  P  T  A  S  V  S  T  S  F
         I  T  I  M  V  M  M  S  Y  T  N  L  L  Q  H  L  F  L  H  L

10201  TTTGCAATCAGGTATTGTAAAGATGGTATCTCCTACGTCAAAAATTGAACCTTGTATTGT   10260
          F  A  I  R  Y  C  K  D  G  I  S  Y  V  K  N  *  T  L  Y  C
           L  Q  S  G  I  V  K  M  V  S  P  T  S  K  I  E  P  C  I  V
         F  C  N  Q  V  L  *  R  W  Y  L  L  R  Q  K  L  N  L  V  L
```

FIG. 2 CONT.

```
10261  TAGTGTTACTTATGGTAGTATGACTTTGAATGGTTTATGGTTAGATGACAAAGTTTATTG  10320
         *  C  Y  L  W  *  Y  D  F  E  W  F  M  V  R  *  Q  S  L  L
          S  V  T  Y  G  S  M  T  L  N  G  L  W  L  D  D  K  V  Y  C
       L  V  L  L  M  V  V  *  L  *  M  V  Y  G  *  M  T  K  F  I

10321  TCCTCGTCATGTTATATGTTCATCCTCTAATATGAACGAACCTGATTATTCTGCCTTATT  10380
          S  S  S  C  Y  M  F  I  L  *  Y  E  R  T  *  L  F  C  L  I
           P  R  H  V  I  C  S  S  S  N  M  N  E  P  D  Y  S  A  L  L
       V  L  V  M  L  Y  V  H  P  L  I  *  T  N  L  I  I  L  P  Y

10381  GTGTAGAGTTACTCTAGGTGATTTTACTATAATGTCTGGTCGGATGAGTTTAACAGTTGT  10440
          V  *  S  Y  S  R  *  F  Y  Y  N  V  W  S  D  E  F  N  S  C
           C  R  V  T  L  G  D  F  T  I  M  S  G  R  M  S  L  T  V  V
       C  V  E  L  L  *  V  I  L  L  *  C  L  V  G  *  V  *  Q  L

10441  GTCTTACCAGATGCAGGGCTGTCAACTTGTTTTGACAGTCTCTTTACAAAATCCTTACAC  10500
          V  L  P  D  A  G  L  S  T  C  F  D  S  L  F  T  K  S  L  H
           S  Y  Q  M  Q  G  C  Q  L  V  L  T  V  S  L  Q  N  P  Y  T
       C  L  T  R  C  R  A  V  N  L  F  *  Q  S  L  Y  K  I  L  T

10501  TCCAAAATATACTTTTGGTAATGTTAAACCTGGTGAAACTTTTACTGTTTTAGCTGCGTA  10560
          S  K  I  Y  F  W  *  C  *  T  W  *  N  F  Y  C  F  S  C  V
           P  K  Y  T  F  G  N  V  K  P  G  E  T  F  T  V  L  A  A  Y
       L  Q  N  I  L  L  V  M  L  N  L  V  K  L  L  F  *  L  R

10561  TAATGGCCGACCACAAGGGGCATTTCATGTTACTATGCGTAGTAGTTATACTATTAAAGG  10620
          *  W  P  T  T  R  G  I  S  C  Y  Y  A  *  *  L  Y  Y  *  R
           N  G  R  P  Q  G  A  F  H  V  T  M  R  S  S  Y  T  I  K  G
       I  M  A  D  H  K  G  H  F  M  L  L  C  V  V  V  I  L  L  K

10621  TTCTTTTTTGTGTGGGTCATGTGGATCTGTTGGTTATGTATTAACAGGTGATAGTGTTAA  10680
          F  F  F  V  W  V  M  W  I  C  W  L  C  I  N  R  *  *  C  *
           S  F  L  C  G  S  C  G  S  V  G  Y  V  L  T  G  D  S  V  K
       V  L  F  C  V  G  H  V  D  L  L  V  M  Y  *  Q  V  I  V  L

10681  GTTTGTATATATGCATCAATTAGAGCTCAGTACTGGTTGTCACACTGGCACTGATTTTAC  10740
          V  C  I  Y  A  S  I  R  A  Q  Y  W  L  S  H  W  H  *  F  Y
           F  V  Y  M  H  Q  L  E  L  S  T  G  C  H  T  G  T  D  F  T
       S  L  Y  I  C  I  N  *  S  S  V  L  V  V  T  L  A  L  I  L

10741  TGGTAATTTTTATGGTCCATATAGAGATGCTCAAGTTGTACAGTTGCCAGTTAAGGACTA  10800
          W  *  F  L  W  S  I  *  R  C  S  S  C  T  V  A  S  *  G  L
           G  N  F  Y  G  P  Y  R  D  A  Q  V  V  Q  L  P  V  K  D  Y
       L  V  I  F  M  V  H  I  E  M  L  K  L  Y  S  C  Q  L  R  T
```

FIG. 2 CONT.

```
10801   CGTCCAGACTGTTAATGTTATTGCTTGGCTCTATGCAGCTATACTTAATAATTGTGCTTG   10860
         R  P  D  C  *  C  Y  C  L  A  L  C  S  Y  T  *  *  L  C  L
          V  Q  T  V  N  V  I  A  W  L  Y  A  A  I  L  N  N  C  A  W
           T  S  R  L  L  M  L  L  L  G  S  M  Q  L  Y  L  I  I  V  L

10861   GTTTGTACAAAATGATGTTTGTTCTACTGAAGATTTTAATGTTTGGGCTATGGCAAATGG   10920
         V  C  T  K  *  C  L  F  Y  *  R  F  *  C  L  G  Y  G  K  W
          F  V  Q  N  D  V  C  S  T  E  D  F  N  V  W  A  M  A  N  G
           G  L  Y  K  M  M  F  V  L  L  K  I  L  M  F  G  L  W  Q  M

10921   TTTTAGCCAAGTAAAAGCAGATCTTGTCTTAGATGCTTTGGCTTCAATGACAGGTGTTTC   10980
         F  *  P  S  K  S  R  S  C  L  R  C  F  G  F  N  D  R  C  F
          F  S  Q  V  K  A  D  L  V  L  D  A  L  A  S  M  T  G  V  S
           V  L  A  K  *  K  Q  I  L  S  *  M  L  W  L  Q  *  Q  V  F

10981   TATTGAAACTTTATTGGCTGCTATTAAGCGTCTATATATGGATTTCAAGGTCGTCAAAT   11040
         Y  *  N  F  I  G  C  Y  *  A  S  I  Y  G  I  S  R  S  S  N
          I  E  T  L  L  A  A  I  K  R  L  Y  M  G  F  Q  G  R  Q  I
           L  L  K  L  Y  W  L  L  L  S  V  Y  I  W  D  F  K  V  V  K

11041   ACTAGGAAGTTGTACTTTTGAAGATGAATTGGCACCTTCTGACGTTTATCAACAATTGGC   11100
         T  R  K  L  Y  F  *  R  *  I  G  T  F  *  R  L  S  T  I  G
          L  G  S  C  T  F  E  D  E  L  A  P  S  D  V  Y  Q  Q  L  A
           Y  *  E  V  V  L  L  K  M  N  W  H  L  L  T  F  I  N  N  W

11101   TGGTGTTAAATTGCAATCTAAAACAAAAAGATTTATTAAAGAAACAATTTATTGGATTTT   11160
         W  C  *  I  A  I  *  N  K  K  I  Y  *  R  N  N  L  L  D  F
          G  V  K  L  Q  S  K  T  K  R  F  I  K  E  T  I  Y  W  I  L
           L  V  L  N  C  N  L  K  Q  K  D  L  L  K  K  Q  F  I  G  F

11161   GATATCTACATTTTTGTTTAGTTGTATAATTTCTGCATTTGTTAAATGGACTATATTTAT   11220
         D  I  Y  I  F  V  *  L  Y  N  F  C  I  C  *  M  D  Y  I  Y
          I  S  T  F  L  F  S  C  I  I  S  A  F  V  K  W  T  I  F  M
           *  Y  L  H  F  C  L  V  V  *  F  L  H  L  L  N  G  L  Y  L

11221   GTATATTAATACACATATGATTGGTGTTACATTATGTGTACTTTGTTTTGTTAGTTTTAT   11280
         V  Y  *  Y  T  Y  D  W  C  Y  I  M  C  T  L  F  C  *  F  Y
          Y  I  N  T  H  M  I  G  V  T  L  C  V  L  C  F  V  S  F  M
           C  I  L  I  H  I  *  L  V  L  H  Y  V  V  F  V  L  L  V  L

11281   GATGTTACTAGTTAAACATAAGCATTTTTATTTGACTATGTATATAATTCCTGTACTCTG   11340
         D  V  T  S  *  T  *  A  F  L  F  D  Y  V  Y  N  S  C  T  L
          M  L  L  V  K  H  K  H  F  Y  L  T  M  Y  I  I  P  V  L  C
           *  C  Y  *  L  N  I  S  I  F  I  *  L  C  I  *  F  L  Y  S
```

FIG. 2 CONT.

```
11341  TACCTTGTTTTATGTAAATTATTTAGTTGTTTATAAGGAAGGTTTTAGAGGTTTTACTTA  11400
          Y  L  V  L  C  K  L  F  S  C  L  *  G  R  F  *  R  F  Y  L
           T  L  F  Y  V  N  Y  L  V  V  Y  K  E  G  F  R  G  F  T  Y
            V  P  C  F  M  *  I  I  *  L  F  I  R  K  V  L  E  V  L  L

11401  TGTCTGGCTCTCATATTTTGTTCCTGCTGTGAATTTTACTTATGTTTATGAAGTATTTTA  11460
          C  L  A  L  I  F  C  S  C  C  E  F  Y  L  C  L  *  S  I  L
           V  W  L  S  Y  F  V  P  A  V  N  F  T  Y  V  V  Y  E  V  F  Y
            M  S  G  S  H  I  L  F  L  L  *  I  L  L  M  F  M  K  Y  F

11461  TGGTTGTATTTTATGTGTTTTTGCTATTTTTATAACTATGCATAGTATTAATCATGACAT  11520
          W  L  Y  F  M  C  F  C  Y  F  Y  N  Y  A  *  Y  *  S  *  H
           G  C  I  L  C  V  F  A  I  F  I  T  M  H  S  I  N  H  D  I
            M  V  V  F  Y  V  F  L  L  F  L  *  L  C  I  V  L  I  M  T

11521  TTTTTCTTTGATGTTTTTGGTTGGTAGAATAGTTACTTTAATTTCTATGTGGTATTTTGG  11580
          F  F  F  D  V  F  G  W  *  N  S  Y  F  N  F  Y  V  V  F  W
           F  S  L  M  F  L  V  G  R  I  V  T  L  I  S  M  W  Y  F  G
            F  F  L  *  C  F  W  L  V  E  *  L  L  *  F  L  C  G  I  L

11581  GTCGAATTTAGAAGAGGATGTTTTGTTATTTATTACAGCCTTTTTAGGTACTTATACATG  11640
          V  E  F  R  R  G  C  F  V  I  Y  Y  S  L  F  R  Y  L  Y  M
           S  N  L  E  E  D  V  L  L  F  I  T  A  F  L  G  T  Y  T  W
            G  R  I  *  K  R  M  F  C  Y  L  L  Q  P  F  *  V  L  I  H

11641  GACCACTATTTTGTCATTAGCTATAGCAAAAATTGTTGCTAATTGGTTGTCTGTTAATAT  11700
          D  H  Y  F  V  I  S  Y  S  K  N  C  C  *  L  V  V  C  *  Y
           T  T  I  L  S  L  A  I  A  K  I  V  A  N  W  L  S  V  N  I
            G  P  L  F  C  H  *  L  *  Q  K  L  L  L  I  G  C  L  L  I

11701  ATTTTATTTTACAGATGTACCTTATATTAAATTGATTCTCTTGAGTTACTTATTTATAGG  11760
          I  L  F  Y  R  C  T  L  Y  *  I  D  S  L  E  L  L  I  Y  R
           F  Y  F  T  D  V  P  Y  I  K  L  I  L  L  S  Y  L  F  I  G
            Y  F  I  L  Q  M  Y  L  I  L  N  *  F  S  *  V  T  Y  L  *

11761  GTATATTTTATCTTGTTATTGGGGATTTTTCTCTCTTTTAAACAGTGTTTTTAGAATGCC  11820
          V  Y  F  I  L  L  L  G  I  F  L  S  F  K  Q  C  F  *  N  A
           Y  I  L  S  C  Y  W  G  F  F  S  L  L  N  S  V  F  R  M  P
            G  I  F  Y  L  V  I  G  D  F  S  L  F  *  T  V  F  L  E  C

11821  TATGGGTGTTTATAATTATAAAATTTCTGTTCAAGAATTGCGTTATATGAATGCTAATGG  11880
          Y  G  C  L  *  L  *  N  F  C  S  R  I  A  L  Y  E  C  *  W
           M  G  V  Y  N  Y  K  I  S  V  Q  E  L  R  Y  M  N  A  N  G
            L  W  V  F  I  I  K  F  L  F  K  N  C  V  I  *  M  L  M
```

FIG. 2 CONT.

```
11881  CTTACGTCCACCTCGTAATAGTTTTGAGGCTATTTTGTTAAATTTAAAACTGCTTGGAAT  11940
         L  T  S  T  S  *  *  F  *  G  Y  F  V  K  F  K  T  A  W  N
          L  R  P  P  R  N  S  F  E  A  I  L  L  N  L  K  L  L  G  I
           A  Y  V  H  L  V  I  V  L  R  L  F  C  *  I  *  N  C  L  E

11941  AGGTGGCGTGCCAGTTATTGAAGTCTCCCAAATTCAATCAAAATTGACTGATGTGAAATG  12000
         R  W  R  A  S  Y  *  S  L  P  N  S  I  K  I  D  *  C  E  M
          G  G  V  P  V  I  E  V  S  Q  I  Q  S  K  L  T  D  V  K  C
           *  V  A  C  Q  L  L  K  S  P  K  F  N  Q  N  *  L  M  *  N

12001  TGCTAATGTTGTTTTGTTAAATTGTTTACAGCATTTGCATGTTGCTTCTAATTCTAAGTT  12060
         C  *  C  C  F  V  K  L  F  T  A  F  A  C  C  F  *  F  *  V
          A  N  V  V  L  L  N  C  L  Q  H  L  H  V  A  S  N  S  K  L
           V  L  M  L  F  C  *  I  V  Y  S  I  C  M  L  L  I  L  S

12061  GTGGCAGTATTGTAGTGTTTTACATAATGAAATACTATCTACTTCAGATTTGAGTGTAGC  12120
         V  A  V  L  *  C  F  T  *  *  N  T  I  Y  F  R  F  E  C  S
          W  Q  Y  C  S  V  L  H  N  E  I  L  S  T  S  D  L  S  V  A
           C  G  S  I  V  V  F  Y  I  M  K  Y  Y  L  L  Q  I  *  V  *

12121  TTTTGATAAGCTTGCTCAATTATTGATTGTTTTATTCGCCAATCCTGCTGCAGTTGATAC  12180
         F  *  *  A  C  S  I  I  D  C  F  I  R  Q  S  C  C  S  *  Y
          F  D  K  L  A  Q  L  L  I  V  L  F  A  N  P  A  A  V  D  T
           L  L  I  S  L  L  N  Y  *  L  F  Y  S  P  I  L  L  Q  L  I

12181  TAAGTGTCTTGCAAGTATAGATGAAGTTAGCGATGATTATGTTCAAGATAGTACCGTTTT  12240
         *  V  S  C  K  Y  R  *  S  *  R  *  L  C  S  R  *  Y  R  F
          K  C  L  A  S  I  D  E  V  S  D  D  Y  V  Q  D  S  T  V  L
           L  S  V  L  Q  V  *  M  K  L  A  M  I  M  F  K  I  V  P  F

12241  GCAGGCTTTGCAAAGTGAGTTTGTAAATATGGCTAGTTTTGTTGAATATGAAGTCGCAAA  12300
         A  G  F  A  K  *  V  C  K  Y  G  *  F  C  *  I  *  S  R  K
          Q  A  L  Q  S  E  F  V  N  M  A  S  F  V  E  Y  E  V  A  K
           C  R  L  C  K  V  S  L  *  I  W  L  V  L  L  N  M  K  S  Q

12301  GAAAAATTTGGCTGATGCTAAAAATAGTGGTTCTGTTAATCAACAACAGATAAAACAGTT  12360
         E  K  F  G  *  C  *  K  *  W  F  C  *  S  T  T  D  K  T  V
          K  N  L  A  D  A  K  N  S  G  S  V  N  Q  Q  Q  I  K  Q  L
           R  K  I  W  L  M  L  K  I  V  V  L  L  I  N  N  R  *  N  S

12361  AGAAAAGCATGTAATATAGCTAAGTCTGTGTATGAACGTGATAAAGCTGTAGCTCGCAA  12420
         R  K  S  M  *  Y  S  *  V  C  V  *  T  *  *  S  C  S  S  Q
          E  K  A  C  N  I  A  K  S  V  Y  E  R  D  K  A  V  A  R  K
           *  K  K  H  V  I  *  L  S  L  C  M  N  V  I  K  L  *  L  A
```

FIG. 2 CONT.

```
12421  ACTTGAACGTATGGCAGACCTAGCACTTACTAACATGTATAAAGAGGCTCGGATTAATGA  12480
        T  *  T  Y  G  R  P  S  T  Y  *  H  V  *  R  G  S  D  *  *
         L  E  R  M  A  D  L  A  L  T  N  M  Y  K  E  A  R  I  N  D
          N  L  N  V  W  Q  T  *  H  L  L  T  C  I  K  R  L  G  L  M

12481  TAAGAAGAGTAAAGTTGTTTCCGCTTTGCAGACAATGCTTTTTAGCATGGTTCGTAAATT  12540
        *  E  E  *  S  C  F  R  F  A  D  N  A  F  *  H  G  S  *  I
         K  K  S  K  V  V  S  A  L  Q  T  M  L  F  S  M  V  R  K  L
          I  R  R  V  K  L  F  P  L  C  R  Q  C  F  L  A  W  F  V  N

12541  GGATAATCAGGCTTTAAATTCTATTCTGGATAATGCTGTTAAAGGTTGTGTACCTTTGAG  12600
        G  *  S  G  F  K  F  Y  S  G  *  C  C  *  R  L  C  T  F  E
         D  N  Q  A  L  N  S  I  L  D  N  A  V  K  G  C  V  P  L  S
          W  I  I  R  L  *  I  L  F  W  I  M  L  L  K  V  V  Y  L  *

12601  TGCTATTCCAGCATTGGCTGCTAATACTTTAACTATAGTAATACCAGATAAACAAGTTTT  12660
        C  Y  S  S  I  G  C  *  Y  F  N  Y  S  N  T  R  *  T  S  F
         A  I  P  A  L  A  A  N  T  L  T  I  V  I  P  D  K  Q  V  F
          V  L  F  Q  H  W  L  L  I  L  *  L  *  *  Y  Q  I  N  K  F

12661  TGATAAAGTTGTTGATAATGTTTATGTTACATATGCTGGTAGTGTATGGCATATACAGAC  12720
        *  *  S  C  *  *  C  L  C  Y  I  C  W  *  C  M  A  Y  T  D
         D  K  V  V  D  N  V  Y  V  T  Y  A  G  S  V  W  H  I  Q  T
          L  I  K  L  L  I  M  F  M  L  H  M  L  V  V  Y  G  I  Y  R

12721  TGTTCAAGATGCTGATGGTATTAATAAACAGTTAACTGATATTAGTGTTGATTCTAATTG  12780
        C  S  R  C  *  W  Y  *  *  T  V  N  *  Y  *  C  *  F  *  L
         V  Q  D  A  D  G  I  N  K  Q  L  T  D  I  S  V  D  S  N  W
          L  F  K  M  L  M  V  L  I  N  S  *  L  I  L  V  L  I  L  I

12781  GCCTCTTGTTATCATTGCGAACAGGTATAATGAAGTTGCTAATGCTGTTATGCAGAATAA  12840
        A  S  C  Y  H  C  E  Q  V  *  *  S  C  *  C  C  Y  A  E  *
         P  L  V  I  I  A  N  R  Y  N  E  V  A  N  A  V  M  Q  N  N
          G  L  L  L  S  L  R  T  G  I  M  K  L  L  M  L  L  C  R  I

12841  TGAGTTGATGCCTCATAAAATTAAAAATACAAGTTGTTAATAGTGGTTCTGATATGAATTG  12900
        *  V  D  A  S  *  I  K  N  T  S  C  *  *  W  F  *  Y  E  L
         E  L  M  P  H  K  L  K  I  Q  V  V  N  S  G  S  D  M  N  C
          M  S  *  C  L  I  N  *  K  Y  K  L  L  I  V  V  L  I  *  I

12901  TAATATTCCTACTCAATGTTATTATAATAATGGTAGTAGTGGTAGAATAGTTTATGCTGT  12960
        *  Y  S  Y  S  M  L  L  *  *  W  *  *  W  *  N  S  L  C  C
         N  I  P  T  Q  C  Y  Y  N  N  G  S  S  G  R  I  V  Y  A  V
          V  I  F  L  L  N  V  I  I  I  M  V  V  V  E  *  F  M  L
```

FIG. 2 CONT.

```
12961  TCTTAGTGATGTTGATGGTCTTAAGTATACTAAGATAATGAAAGATGATGGAAATTGTGT  13020
         S  *  *  C  *  W  S  *  V  Y  *  D  N  E  R  *  W  K  L  C
          L  S  D  V  D  G  L  K  Y  T  K  I  M  K  D  D  G  N  C  V
           F  L  V  M  L  M  V  L  S  I  L  R  *  *  K  M  M  E  I  V

13021  TGTTTTAGAGCTTGATCCTCCTTGTAAATTTTCTATACAAGATGTTAAGGGACTTAAAAT  13080
         C  F  R  A  *  S  S  L  *  I  F  Y  T  R  C  *  G  T  *  N
          V  L  E  L  D  P  P  C  K  F  S  I  Q  D  V  K  G  L  K  I
           L  F  *  S  L  I  L  L  V  N  F  L  Y  K  M  L  R  D  L  K

13081  TAAGTATCTTTATTTTATTAAAGGATGTAACACTTTAGCTAGAGGGTGGGTTGTTGGTAC  13140
         *  V  S  L  F  Y  *  R  M  *  H  F  S  *  R  V  G  C  W  Y
          K  Y  L  Y  F  I  K  G  C  N  T  L  A  R  G  W  V  V  G  T
           L  S  I  F  I  L  L  K  D  V  T  L  *  L  E  G  G  L  L  V

13141  TTTATCTTCAACAATTAGATTGCAGGCTGGTGTTGCTACTGAGTATGCAGCTAATTCTTC  13200
         F  I  F  N  N  *  I  A  G  W  C  C  Y  *  V  C  S  *  F  F
          L  S  S  T  I  R  L  Q  A  G  V  A  T  E  Y  A  A  N  S  S
           L  Y  L  Q  Q  L  D  C  R  L  V  L  L  S  M  Q  L  I  L

13201  TATACTTTCATTATGTGCATTTTCTGTAGATCCTAAGAAAACTTATTTAGATTATATACA  13260
         Y  T  F  I  M  C  I  F  C  R  S  *  E  N  L  F  R  L  Y  T
          I  L  S  L  C  A  F  S  V  D  P  K  K  T  Y  L  D  Y  I  Q
           L  Y  F  H  Y  V  H  F  L  *  I  L  R  K  L  I  *  I  I  Y

13261  ACAAGGTGGTGTACCTATAATTAATTGTGTTAAAATGCTCTGTGATCATGCTGGTACTGG  13320
         T  R  W  C  T  Y  N  *  L  C  *  N  A  L  *  S  C  W  Y  W
          Q  G  G  V  P  I  I  N  C  V  K  M  L  C  D  H  A  G  T  G
           N  K  V  V  Y  L  *  L  I  V  L  K  C  S  V  I  M  L  V  L

13321  TATGGCCATTACTATTAAACCTGAGGCTACTATTAACCAAGATTCTTATGGTGGTGCCTC  13380
         Y  G  H  Y  Y  *  T  *  G  Y  Y  *  P  R  F  L  W  W  C  L
          M  A  I  T  I  K  P  E  A  T  I  N  Q  D  S  Y  G  G  A  S
           V  W  P  L  L  L  N  L  R  L  L  L  T  K  I  L  M  V  V  P

13381  AGTTTGTATTTATTGCCGTGCACGTGTAGAGCATCCAGATGTAGATGGTATATGTAAATT  13440
         S  L  Y  L  L  P  C  T  C  R  A  S  R  C  R  W  Y  M  *  I
          V  C  I  Y  C  R  A  R  V  E  H  P  D  V  D  G  I  C  K  L
           Q  F  V  F  I  A  V  H  V  *  S  I  Q  M  *  M  V  Y  V  N

13441  ACGTGGTAAATTTGTACAAGTCCCTTTGGGTATAAAAGATCCTATTCTTTATGTGTTAAC  13500
         T  W  *  I  C  T  S  P  F  G  Y  K  R  S  Y  S  L  C  V  N
          R  G  K  F  V  Q  V  P  L  G  I  K  D  P  I  L  Y  V  L  T
           Y  V  V  N  L  Y  K  S  L  W  V  *  K  I  L  F  F  M  C  *
```

FIG. 2 CONT.

```
13501  ACATGATGTTTGTCAAGTCTGTGGTTTTTGGAGAGATGGCAGTTGTTCCTGTGTAGGTTC  13560
        T * C L S S L W F L E R W Q L F L C R F
         H D V C Q V C G F W R D G S C S C V G S
          H M M F V K S V V F G E M A V V P V * V

13561  AAGTGTCGCTGTTCAATCTAAAGATTTAAATTTTTTAAACGGGTTCGGGGTACTAGTGTG  13620
        K C R C S I * R F K F F K R V R G T S V
         S V A V Q S K D L N F L N G F G V L V *
          Q V S L F N L K I * I F * T G S G Y * C

13621  AATGCCCGGCTAGTACCCTGTGCTAGTGGTTTATCTACTGATGTTCAATTAAGGGCATTT  13680
        N A R L V P C A S G L S T D V Q L R A F
         M P G * Y P V L V V Y L L M F N * G H L
          E C P A S T L C * W F I Y * C S I K G I

13681  GACATTTGTAATACCAATAGAGCTGGTATAGGTTTATATTATAAAGTGAATTGTTGCCGT  13740
        D I C N T N R A G I G L Y Y K V N C C R
         T F V I P I E L V * V Y I I K * I V A V
          * H L * Y Q * S W Y R F I L * S E L L P

13741  TTTCAGCGTATAGATGACGACGGTAATAAATTGGATAAGTTCTTTGTTGTCAAAAGAACT  13800
        F Q R I D D D G N K L D K F F V V K R T
         F S V * M T T V I N W I S S L L S K E L
          F S A Y R * R R * * I G * V L C C Q K N

13801  AATTTAGAAGTTTATAATAAAGAGAAAACTTATTATGAGTTGACTAAAAGTTGTGGTGTT  13860
        N L E V Y N K E K T Y Y E L T K S C G V
         I * K F I I K R K L I M S * L K V V V L
          * F R S L * * R E N L L * V D * K L W C

13861  GTGGCTGAACATGATTTCTTTACATTTGATATTGATGGTAGTCGCGTGCCACATATAGTT  13920
        V A E H D F F T F D I D G S R V P H I V
         W L N M I S L H L I L M V V A C H I * F
          C G * T * F L Y I * Y * W * S R A T Y S

13921  CGTAGGAATCTTTCAAAGTATACTATGTTAGATCTTTGCTATGCATTGCGTCATTTTGAT  13980
        R R N L S K Y T M L D L C Y A L R H F D
         V G I F Q S I L C * I F A M H C V I L I
          S * E S F K V Y Y V R S L L C I A S F *

13981  CGTAATGATTGTTCAATATTGTGTGAAATTCTTTGTGAGTATGCTGATTGTAAAGAATCC  14040
        R N D C S I L C E I L C E Y A D C K E S
         V M I V Q Y C V K F F V S M L I V K N P
          S * * L F N I V * N S L * V C * L * R I
```

FIG. 2 CONT.

```
14041  TACTTTTCTAAGAAAGATTGGTATGATTTTGTTGAAAATCCTGATATTATTAATATATAT  14100
          Y  F  S  K  K  D  W  Y  D  F  V  E  N  P  D  I  I  N  I  Y
         T  F  L  R  K  I  G  M  I  L  L  K  I  L  I  L  L  I  Y  I
        L  L  F  *  E  R  L  V  *  F  C  *  K  S  *  Y  Y  *  Y  I

14101  AAAAAATTAGGCCCTATTTTTAATAGAGCTTTACTTAATACTGTCATTTTTGCAGACACC  14160
          K  K  L  G  P  I  F  N  R  A  L  L  N  T  V  I  F  A  D  T
         K  N  *  A  L  F  L  I  E  L  Y  L  I  L  S  F  L  Q  T  P
        *  K  I  R  P  Y  F  *  *  S  F  T  *  Y  C  H  F  C  R  H

14161  TTAGTTGAAGTAGGTTTAGTTGGTGTTTTAACTTTAGATAACCAAGATTTGTATGGTCAA  14220
          L  V  E  V  G  L  V  G  V  L  T  L  D  N  Q  D  L  Y  G  Q
         *  L  K  *  V  *  L  V  F  *  L  *  I  T  K  I  C  M  V  N
        L  S  *  S  R  F  S  W  C  F  N  F  R  *  P  R  F  V  W  S

14221  TGGTATGATTTTGGTGATTTTATACAAACAGCCCCAGGGTTTGGTGTGGCAGTTGCAGAT  14280
          W  Y  D  F  G  D  F  I  Q  T  A  P  G  F  G  V  A  V  A  D
         G  M  I  L  V  I  L  Y  K  Q  P  Q  G  L  V  W  Q  L  Q  I
        M  V  *  F  W  *  F  Y  T  N  S  P  R  V  W  C  G  S  C  R

14281  TCTTACTATTCTTATATGATGCCTATGTTGACTATGTGTCATGTATTAGATTGTGAATTA  14340
          S  Y  Y  S  Y  M  M  P  M  L  T  M  C  H  V  L  D  C  E  L
         L  T  I  L  I  *  C  L  C  *  L  C  V  M  Y  *  I  V  N  Y
        F  L  L  F  L  Y  D  A  Y  V  D  Y  V  S  C  I  R  L  *  I

14341  TTTGTTAATGATAGTTATAGACAATTCGATCTTGTACAGTATGATTTTACTGATTACAAG  14400
          F  V  N  D  S  Y  R  Q  F  D  L  V  Q  Y  D  F  T  D  Y  K
         L  L  M  I  V  I  D  N  S  I  L  Y  S  M  I  L  L  I  T  S
        I  C  *  *  *  L  *  T  I  R  S  C  T  V  *  F  Y  *  L  Q

14401  TTAGAGTTGTTTAATAAGTATTTTAAGTATTGGGGTATGAAGTATCATCCTAATACTGTG  14460
          L  E  L  F  N  K  Y  F  K  Y  W  G  M  K  Y  H  P  N  T  V
         *  S  C  L  I  S  I  L  S  I  G  V  *  S  I  I  L  I  L  W
        V  R  V  V  *  *  V  F  *  V  L  G  Y  E  V  S  S  *  Y  C

14461  GATTGTGATAATGATAGGTGTATTATTCATTGTGCTAATTTTAATATACTATTTAGTATG  14520
          D  C  D  N  D  R  C  I  I  H  C  A  N  F  N  I  L  F  S  M
         I  V  I  M  I  G  V  L  F  I  V  L  I  L  I  Y  Y  L  V  W
        G  L  *  *  *  V  Y  Y  S  L  C  *  F  *  Y  T  I  *  Y

14521  GTTTTACCTAATACTTGTTTTGGTCCCCTTGTTAGACAAATTTTTGTAGATGGTGTACCG  14580
          V  L  P  N  T  C  F  G  P  L  V  R  Q  I  F  V  D  G  V  P
         F  Y  L  I  L  V  L  V  P  L  L  D  K  F  L  *  M  V  Y  R
        G  F  T  *  Y  L  F  W  S  P  C  *  T  N  F  C  R  W  C  T
```

FIG. 2 CONT.

```
14581  TTTGTTGTTTCTATTGGTTACCATTACAAAGAGTTAGGTGTAGTTATGAACTTAGATGTT  14640
         F  V  V  S  I  G  Y  H  Y  K  E  L  G  V  V  M  N  L  D  V
          L  L  F  L  L  V  T  I  T  K  S  *  V  *  L  *  T  *  M  L
       V  C  C  F  Y  W  L  P  L  Q  R  V  R  C  S  Y  E  L  R  C

14641  GACACACACCGTTATCGTTTGTCTCTTAAAGATTTACTTCTTTATGCAGCAGATCCTGCT  14700
         D  T  H  R  Y  R  L  S  L  K  D  L  L  L  Y  A  A  D  P  A
          T  H  T  V  I  V  C  L  L  K  I  Y  F  F  M  Q  Q  I  L  L
       *  H  T  P  L  S  F  V  S  *  R  F  T  S  L  C  S  R  S  C

14701  ATGCACGTTGCATCTGCTAGTGCTCTGCTTGATTTACGAACTTGTTGTTTTAGTGTAGCT  14760
         M  H  V  A  S  A  S  A  L  L  D  L  R  T  C  C  F  S  V  A
          C  T  L  H  L  L  V  L  C  L  I  Y  E  L  V  V  L  V  *  L
       Y  A  R  C  I  C  *  C  S  A  *  F  T  N  L  L  F  *  C  S

14761  GCCATTACAAGTGGTATAAAATTTCAAACTGTAAAACCAGGTAACTTTAACCAAGACTTT  14820
         A  I  T  S  G  I  K  F  Q  T  V  K  P  G  N  F  N  Q  D  F
          P  L  Q  V  V  *  N  F  K  L  *  N  Q  V  T  L  T  K  T  F
       C  H  Y  K  W  Y  K  I  S  N  C  K  T  R  *  L  *  P  R  L

14821  TACGAGTTTGTTAAAAGTAAAGGCTTGTTTAAAGAGGGTAGTACAGTTGATTTGAAACAT  14880
         Y  E  F  V  K  S  K  G  L  F  K  E  G  S  T  V  D  L  K  H
          T  S  L  L  K  V  K  A  C  L  K  R  V  V  Q  L  I  *  N  I
       L  R  V  C  *  K  *  R  L  V  *  R  G  *  Y  S  *  F  E  T

14881  TTTTTCTTTACTCAAGATGGTAATGCTGCAATTACTGATTATAATTATTATAAGTATAAT  14940
         F  F  F  T  Q  D  G  N  A  A  I  T  D  Y  N  Y  Y  K  Y  N
          F  S  L  L  K  M  V  M  L  Q  L  L  I  I  I  I  S  I  I
       F  F  L  Y  S  R  W  *  C  C  N  Y  *  L  *  L  L  *  V  *

14941  TTACCTACTATGGTTGATATTAAGCAGTTATTGTTTGTATTAGAAGTTGTTTATAAATAT  15000
         L  P  T  M  V  D  I  K  Q  L  L  F  V  L  E  V  V  Y  K  Y
          Y  L  L  W  L  I  L  S  S  Y  C  L  Y  *  K  L  F  I  N  I
       F  T  Y  Y  G  *  Y  *  A  V  I  V  C  I  R  S  C  L  *  I

15001  TTTGAAATTTATGATGGTGGTTGTATACCAGCATCACAAGTTATTGTTAATAATTATGAT  15060
         F  E  I  Y  D  G  G  C  I  P  A  S  Q  V  I  V  N  N  Y  D
          L  K  F  M  M  V  V  V  Y  Q  H  H  K  L  L  L  I  I  M  I
       F  *  N  L  *  W  W  L  Y  T  S  I  T  S  Y  C  *  *  L  *

15061  AAAAGTGCTGGTTATCCATTTAATAAATTTGGTAAAGCCAGACTTTATTATGAGGCATTA  15120
         K  S  A  G  Y  P  F  N  K  F  G  K  A  R  L  Y  Y  E  A  L
          K  V  L  V  I  H  L  I  N  L  V  K  P  D  F  I  M  R  H  Y
       *  K  C  W  L  S  I  *  *  I  W  *  S  Q  T  L  L  *  G  I
```

FIG. 2 CONT.

```
15121   TCATTTGAGGAACAGAATGAAATTTATGCATATACTAAACGTAATGTTCTGCCCACCTTA   15180
          S  F  E  E  Q  N  E  I  Y  A  Y  T  K  R  N  V  L  P  T  L
           H  L  R  N  R  M  K  F  M  H  I  L  N  V  M  F  C  P  P  *
            I  I  *  G  T  E  *  N  L  C  I  Y  *  T  *  C  S  A  H  L

15181   ACTCAAATGAATTTAAAATATGCTATCAGTGCTAAGAATAGAGCTCGCACTGTAGCAGGT   15240
          T  Q  M  N  L  K  Y  A  I  S  A  K  N  R  A  R  T  V  A  G
           L  K  *  I  *  N  M  L  S  V  L  R  I  E  L  A  L  *  Q  V
            N  S  N  E  F  K  I  C  Y  Q  C  *  E  *  S  S  H  C  S  R

15241   GTTTCTATTCTTAGTACTATGACAGGCCGAATGTTCCATCAAAAATGTTTGAAGAGTATA   15300
          V  S  I  L  S  T  M  T  G  R  M  F  H  Q  K  C  L  K  S  I
           F  L  F  L  V  L  *  Q  A  E  C  S  I  K  N  V  *  R  V  *
            C  F  Y  S  *  Y  Y  D  R  P  N  V  P  S  K  M  F  E  E  Y

15301   GCAGCTACCCGAGGTGTTCCTGTTGTTATAGGAACCACTAAATTTTATGGTGGTTGGGAC   15360
          A  A  T  R  G  V  P  V  V  I  G  T  T  K  F  Y  G  G  W  D
           Q  L  P  E  V  F  L  L  L  *  E  P  L  N  F  M  V  V  G  T
            S  S  Y  P  R  C  S  C  C  Y  R  N  H  *  I  L  W  W  L  G

15361   GATATGTTACGTCATCTTATAAAGGATGTTGACAACCCTGTTCTTATGGGTTGGGATTAT   15420
          D  M  L  R  H  L  I  K  D  V  D  N  P  V  L  M  G  W  D  Y
           I  C  Y  V  I  L  *  R  M  L  T  T  L  F  L  W  V  G  I  I
            R  Y  V  T  S  S  Y  K  G  C  *  Q  P  C  S  Y  G  L  G  L

15421   CCTAAATGTGATCGTGCTATGCCAAATATTTTGCGTATTGTTAGTAGTTTAGTTTTGGCC   15480
          P  K  C  D  R  A  M  P  N  I  L  R  I  V  S  S  L  V  L  A
           L  N  V  I  V  L  C  Q  I  F  C  V  L  L  V  V  *  F  W  P
            S  *  M  *  S  C  Y  A  K  Y  F  A  Y  C  *  *  F  S  F  G

15481   CGCAAACATGAATTTTGTTGTTCACATGGTGATAGATTTTATCGCCTTGCGAATGAATGT   15540
          R  K  H  E  F  C  C  S  H  G  D  R  F  Y  R  L  A  N  E  C
           A  N  M  N  F  V  V  H  M  V  I  D  F  I  A  L  R  M  N  V
            P  Q  T  *  I  L  L  F  T  W  *  *  I  L  S  P  C  E  *  M

15541   GCTCAAGTTTTGAGTGAAATAGTTATGTGTGGCGGTTGCTATTATGTTAAGCCTGGTGGT   15600
          A  Q  V  L  S  E  I  V  M  C  G  G  C  Y  Y  V  K  P  G  G
           L  K  F  *  V  K  *  L  C  V  A  V  A  I  M  L  S  L  V  V
            C  S  S  F  E  *  N  S  Y  V  W  R  L  L  L  C  *  A  W  W

15601   ACTAGCAGTGGTGATGCAACTACTGCTTTTGCTAATTCTGTTTTTAATATATGTCAGGCT   15660
          T  S  S  G  D  A  T  T  A  F  A  N  S  V  F  N  I  C  Q  A
           L  A  V  V  M  Q  L  L  L  L  L  I  L  F  L  I  Y  V  R  L
            Y  *  Q  W  *  C  N  Y  C  F  C  *  F  C  F  *  Y  M  S  G
```

FIG. 2 CONT.

```
15661  GTTACTGCTAATGTTTGTTCTCTTATGGCCTGTAATGGCCATAAGATTGAAGATTTAAGT  15720
         V  T  A  N  V  C  S  L  M  A  C  N  G  H  K  I  E  D  L  S
          L  L  L  M  F  V  L  L  W  P  V  M  A  I  R  L  K  I  *  V
           C  Y  C  *  C  L  F  S  Y  G  L  *  W  P  *  D  *  R  F  K

15721  ATACGCAATTTACAAAAACGCTTATACTCTAATGTTTATCGTACAGATTATGTTGATTAT  15780
         I  R  N  L  Q  K  R  L  Y  S  N  V  Y  R  T  D  Y  V  D  Y
          Y  A  I  Y  K  N  A  Y  T  L  M  F  I  V  Q  I  M  L  I  I
           Y  T  Q  F  T  K  T  L  I  L  *  C  L  S  Y  R  L  C  *  L

15781  ACATTTGTTAATGAGTATTATGAATTTTATGTAAGCATTTTAGTATGATGATTTTGAGT  15840
         T  F  V  N  E  Y  Y  E  F  L  C  K  H  F  S  M  M  I  L  S
          H  L  L  M  S  I  M  N  F  Y  V  S  I  L  V  *  *  F  *  V
           Y  I  C  *  *  V  L  *  I  F  M  *  A  F  *  Y  D  D  F  E

15841  GATGATGGTGTTGTCTGTTATAACTCTGATTATGCTAGTAAGGGTTATATAGCTAATATA  15900
         D  D  G  V  V  C  Y  N  S  D  Y  A  S  K  G  Y  I  A  N  I
          M  M  V  L  S  V  I  T  L  I  M  L  V  R  V  I  *  L  I  *
           *  *  W  C  C  L  L  *  L  *  L  C  *  *  G  L  Y  S  *  Y

15901  AGTGTTTTTCAACAAGTTTTGTACTATCAGAATAATGTCTTTATGTCTGAATCTAAATGT  15960
         S  V  F  Q  Q  V  L  Y  Y  Q  N  N  V  F  M  S  E  S  K  C
          V  F  F  N  K  F  C  T  I  R  I  M  S  L  C  L  N  L  N  V
           K  C  F  S  T  S  F  V  L  S  E  *  C  L  Y  V  *  I  *  M

15961  TGGGTTGAAAATGATATTACTAATGGTCCTCATGAATTTTGTTCCCAACATACTATGTTA  16020
         W  V  E  N  D  I  T  N  G  P  H  E  F  C  S  Q  H  T  M  L
          G  L  K  M  I  L  L  M  V  L  M  N  F  V  P  N  I  L  C  *
           L  G  *  K  *  Y  Y  *  W  S  S  *  I  L  F  P  T  Y  Y  V

16021  GTTAAGATAGATGGTGATTATGTTTATTTACCATATCCAGATCCTTCTAGAATTTTAGGA  16080
         V  K  I  D  G  D  Y  V  Y  L  P  Y  P  D  P  S  R  I  L  G
          L  R  *  M  V  I  M  F  I  Y  H  I  Q  I  L  L  E  F  *  E
           S  *  D  R  W  *  L  C  L  F  T  I  S  R  S  F  *  N  F  R

16081  GCTGGTTGTTTTGTTGATGATTTATTGAAGACTGACAGTGTTCTTTTGATAGAGCGCTTT  16140
         A  G  C  F  V  D  D  L  L  K  T  D  S  V  L  L  I  E  R  F
          L  V  V  L  L  M  I  Y  *  R  L  T  V  F  F  *  *  S  A  L
           S  W  L  F  C  *  *  F  I  E  D  *  Q  C  S  F  D  R  A  L

16141  GTAAGTCTAGCTATAGATGCTTACCCTTTAGTACATCATGAAAATGAAGAATACCAAAAA  16200
         V  S  L  A  I  D  A  Y  P  L  V  H  H  E  N  E  E  Y  Q  K
          *  V  *  L  *  M  L  T  L  *  Y  I  M  K  M  K  N  T  K  K
           C  K  S  S  Y  R  C  L  P  F  S  T  S  *  K  *  R  I  P  K
```

FIG. 2 CONT.

```
16201  GTCTTTCGTGTATATTTAGAATATATAAAAAAACTGTATAATGATCTTGGTACTCAGATC  16260
        V  F  R  V  Y  L  E  Y  I  K  K  L  Y  N  D  L  G  T  Q  I
         S  F  V  Y  I  *  N  I  *  K  N  C  I  M  I  L  V  L  R  S
       S  L  S  C  I  F  R  I  Y  K  K  T  V  *  *  S  W  Y  S  D

16261  TTAGATAGTTATAGTGTTATTTTAAGTACTTGTGATGGTTTAAAGTTTACTGAAGAATCA  16320
        L  D  S  Y  S  V  I  L  S  T  C  D  G  L  K  F  T  E  E  S
         *  I  V  I  V  L  F  *  V  L  V  M  V  *  S  L  L  K  N  H
       L  R  *  L  *  C  Y  F  K  Y  L  *  W  F  K  V  Y  *  R  I

16321  TTTTACAAGAATATGTATTTAAAAAGTGCCGTGATGCAGAGTGTAGGTGCATGCGTTGTT  16380
        F  Y  K  N  M  Y  L  K  S  A  V  M  Q  S  V  G  A  C  V  V
         F  T  R  I  C  I  *  K  V  P  *  C  R  V  *  V  H  A  L  F
       I  L  Q  E  Y  V  F  K  K  C  R  D  A  E  C  R  C  M  R  C

16381  TGTTCATCACAAACTTCTTTGCGTTGTGGCAGTTGTATACGTAAGCCTTTGTTATGTTGT  16440
        C  S  S  Q  T  S  L  R  C  G  S  C  I  R  K  P  L  L  C  C
         V  H  H  K  L  L  C  V  V  A  V  V  Y  V  S  L  C  Y  V  V
       L  F  I  T  N  F  F  A  L  W  Q  L  Y  T  *  A  F  V  M  L

16441  AAATGTTGTTATGACCATGTTATGGCAACTAATCATAAATATGTTTTGAGTGTCTCACCT  16500
        K  C  C  Y  D  H  V  M  A  T  N  H  K  Y  V  L  S  V  S  P
         N  V  V  M  T  M  L  W  Q  L  I  I  N  M  F  *  V  S  H  L
       *  M  L  L  *  P  C  Y  G  N  *  S  *  I  C  F  E  C  L  T

16501  TACGTTTGTAATGCACCTAACTGTGATGTGAGTGATGTCACCAAATTATATTTGGGCGGT  16560
        Y  V  C  N  A  P  N  C  D  V  S  D  V  T  K  L  Y  L  G  G
         T  F  V  M  H  L  T  V  M  *  V  M  S  P  N  Y  I  W  A  V
       L  R  L  *  C  T  *  L  *  C  E  *  C  H  Q  I  I  F  G  R

16561  ATGTCTTACTATTGTGAAAACCATAAACCCCATTATTCATTTAAGTTAGTTATGAATGGT  16620
        M  S  Y  Y  C  E  N  H  K  P  H  Y  S  F  K  L  V  M  N  G
         C  L  T  I  V  K  T  I  N  P  I  I  H  L  S  *  L  *  M  V
       Y  V  L  L  *  K  P  *  T  P  L  F  I  *  V  S  Y  E  W

16621  ATGGTCTTTGGTTTGTATAAACAATCTTGCACGGGTTCACCTTATATAGATGATTTTAAT  16680
        M  V  F  G  L  Y  K  Q  S  C  T  G  S  P  Y  I  D  D  F  N
         W  S  L  V  C  I  N  N  L  A  R  V  H  L  I  *  M  I  L  I
       Y  G  L  W  F  V  *  T  I  L  H  G  F  T  L  Y  R  *  F  *

16681  AAGATAGCTAGTTGTAAATGGACAGAAGTTGATGATTATGTTCTGGCAAATGAGTGTATT  16740
        K  I  A  S  C  K  W  T  E  V  D  D  Y  V  L  A  N  E  C  I
         R  *  L  V  V  N  G  Q  K  L  M  I  M  F  W  Q  M  S  V  L
       *  D  S  *  L  *  M  D  R  S  *  *  L  C  S  G  K  *  V  Y
```

FIG. 2 CONT.

```
16741   GAACGTTTAAAGTTATTTGCTGCAGAAACTCAAAAGGCAACTGAAGAGGCTTTTAAACAA   16800
          E  R  L  K  L  F  A  A  E  T  Q  K  A  T  E  E  A  F  K  Q
           N  V  *  S  Y  L  L  Q  K  L  K  R  Q  L  K  R  L  L  N  K
         *  T  F  K  V  I  C  C  R  N  S  K  G  N  *  R  G  F  *  T

16801   AGCTATGCTTCTGCTACCATTCAAGAGATTGTTAGTGATAGAGAAGTTATTTTGTGTTGG   16860
          S  Y  A  S  A  T  I  Q  E  I  V  S  D  R  E  V  I  L  C  W
           A  M  L  L  P  F  K  R  L  L  V  I  E  K  L  F  C  V  G
         K  L  C  F  C  Y  H  S  R  D  C  *  *  *  R  S  Y  F  V  L

16861   GAGACAGGTAAAGTTAAACCACCACTTAATAAAAATTATGTTTTCACAGGCTACCATTTT   16920
          E  T  G  K  V  K  P  P  L  N  K  N  Y  V  F  T  G  Y  H  F
           R  Q  V  K  L  N  H  H  L  I  K  I  M  F  S  Q  A  T  I  L
         G  D  R  *  S  *  T  T  T  *  *  K  L  C  F  H  R  L  P  F

16921   ACTAGTACTGGTAAGACAGTTTTAGGTGAGTATGTTTTTGATAAAAGTGAATTAACTAAC   16980
          T  S  T  G  K  T  V  L  G  E  Y  V  F  D  K  S  E  L  T  N
           L  V  L  V  R  Q  F  *  V  S  M  F  L  I  K  V  N  *  L  T
         Y  *  Y  W  *  D  S  F  R  *  V  C  F  *  *  K  *  I  N  *

16981   GGTGTGTATTACCGCGCTACAACTACTTATAAACTTTCTATAGGTGATGTTTTTGTTTTA   17040
          G  V  Y  Y  R  A  T  T  T  Y  K  L  S  I  G  D  V  F  V  L
           V  C  I  T  A  L  Q  L  L  I  N  F  L  *  V  M  F  L  F  *
         R  C  V  L  P  R  Y  N  Y  L  *  T  F  Y  R  *  C  F  C  F

17041   ACATCACATTCTGTAGCTAGTTTAAGTGCACCTACACTTGTCCCACAAGAGAACTATGCT   17100
          T  S  H  S  V  A  S  L  S  A  P  T  L  V  P  Q  E  N  Y  A
           H  H  I  L  *  L  V  *  V  H  L  H  L  S  H  K  R  T  M  L
         N  I  T  F  C  S  *  F  K  C  T  Y  T  C  P  T  R  E  L  C

17101   AGTATAAGATTTTCTAGTGTTTATAGTGTTCCATTGGTGTTTCAAAATAATGTTGCTAAT   17160
          S  I  R  F  S  S  V  Y  S  V  P  L  V  F  Q  N  N  V  A  N
           V  *  D  F  L  V  F  I  V  F  H  W  C  F  K  I  M  L  L  I
         *  Y  K  I  F  *  C  L  *  C  S  I  G  V  S  K  *  C  C  *

17161   TATCAGCACATTGGAATGAAACGTTATTGCACTGTTCAAGGTCCCCCTGGTACGGGAAAG   17220
          Y  Q  H  I  G  M  K  R  Y  C  T  V  Q  G  P  P  G  T  G  K
           I  S  T  L  E  *  N  V  I  A  L  F  K  V  P  L  V  R  E  S
         L  S  A  H  W  N  E  T  L  L  H  C  S  R  S  P  W  Y  G  K

17221   TCTCATCTTGCTATAGGTCTAGCTGTTTATTACTACACAGCACGTGTAGTTTATACTGCT   17280
          S  H  L  A  I  G  L  A  V  Y  Y  Y  T  A  R  V  V  Y  T  A
           L  I  L  L  *  V  *  L  F  I  T  T  Q  H  V  *  F  I  L  L
         V  S  S  C  Y  R  S  S  C  L  L  L  H  S  T  C  S  L  Y  C
```

FIG. 2 CONT.

```
17281  GCTAGTCATGCTGCTGTAGATGCATTGTGTGAAAAAGCTTATAAGTTTTTAAATATTAAC  17340
         A  S  H  A  A  V  D  A  L  C  E  K  A  Y  K  F  L  N  I  N
        L  V  M  L  L  *  M  H  C  V  K  K  L  I  S  F  *  I  L  T
       C  *  S  C  C  C  R  C  I  V  *  K  S  L  *  V  F  K  Y  *

17341  GATTGTACACGTATTATTCCTGCTAAAGTTCGTGTAGATTGTTATGATAAGTTTAAAATT  17400
         D  C  T  R  I  I  P  A  K  V  R  V  D  C  Y  D  K  F  K  I
        I  V  H  V  L  F  L  L  K  F  V  *  I  V  M  I  S  L  K  L
       R  L  Y  T  Y  Y  S  C  *  S  S  C  R  L  L  *  *  V  *  N

17401  AATGATACCACTTGTAAGTATGTTTTTACCACAATAAATGCATTACCAGAGTTGGTTACA  17460
         N  D  T  T  C  K  Y  V  F  T  T  I  N  A  L  P  E  L  V  T
        M  I  P  L  V  S  M  F  L  P  Q  *  M  H  Y  Q  S  W  L  Q
       *  *  Y  H  L  *  V  C  F  Y  H  N  K  C  I  T  R  V  G  Y

17461  GATATTGTTGTTGTTGATGAAGTTAGTATGCTTACTAATTATGAATTGTCTGTTATAAAT  17520
         D  I  V  V  V  D  E  V  S  M  L  T  N  Y  E  L  S  V  I  N
        I  L  L  L  L  M  K  L  V  C  L  L  I  M  N  C  L  L  *  M
       R  Y  C  C  C  *  *  S  *  Y  A  Y  *  L  *  I  V  C  Y  K

17521  GCTCGTATTAAAGCTAAACATTATGTATATATTGGAGATCCTGCTCAATTACCTGCACCA  17580
         A  R  I  K  A  K  H  Y  V  V  Y  I  G  D  P  A  Q  L  P  A  P
        L  V  L  K  N  I  M  Y  I  L  E  I  L  L  N  Y  L  H  H
       C  S  Y  *  S  *  T  L  C  I  Y  W  R  S  C  S  I  T  C  T

17581  CGTGTGCTGTTGAGCAAGGGTTCTTTAGAACCTAGGCACTTCAATTCTATTACTAAAATA  17640
         R  V  L  L  S  K  G  S  L  E  P  R  H  F  N  S  I  T  K  I
        V  C  C  *  A  R  V  L  *  N  L  G  T  S  I  L  L  L  K  *
       T  C  A  V  E  Q  G  F  F  R  T  *  A  L  Q  F  Y  Y  *  N

17641  ATGTGTTGTTTAGGTCCTGATATCTTTTTGGGAAATTGTTATAGGTGTCCTAAAGAAATT  17700
         M  C  C  L  G  P  D  I  F  L  G  N  C  Y  R  C  P  K  E  I
        C  V  V  *  V  L  I  S  F  W  E  I  V  I  G  V  L  K  K  L
       N  V  L  F  R  S  *  Y  L  F  G  K  L  L  *  V  S  *  R  N

17701  GTAGAAACTGTTTCAGCATTGGTTTATGATAATAAACTCAAGGCTAAAAATGATAATAGT  17760
         V  E  T  V  S  A  L  V  Y  D  N  K  L  K  A  K  N  D  N  S
        *  K  L  F  Q  H  W  F  M  I  I  N  S  R  L  K  M  I  I  V
       C  R  N  C  F  S  I  G  L  *  *  *  T  Q  G  *  K  *  *  *

17761  TCATTATGTTTTAAAGTATATTTTAAGGGACAGACAACACATGAGAGTTCAAGTGCTGTA  17820
         S  L  C  F  K  V  Y  F  K  G  Q  T  T  H  E  S  S  S  A  V
        H  Y  V  L  K  Y  I  L  R  D  R  Q  H  M  R  V  Q  V  L  *
       F  I  M  F  *  S  I  F  *  G  T  D  N  T  *  E  F  K  C  C
```

FIG. 2 CONT.

```
17821  AATATTCAACAGATATATCTAATTAGTAAATTTTTAAAAGCTAATCCAGTTTGGAATAGT  17880
         N  I  Q  Q  I  Y  L  I  S  K  F  L  K  A  N  P  V  W  N  S
          I  F  N  R  Y  I  *  L  V  N  F  *  K  L  I  Q  F  G  I  V
       K  Y  S  T  D  I  S  N  *  *  I  F  K  S  *  S  S  L  E  *

17881  GCTGTTTTTATTAGTCCTTATAATAGTCAGAATTATGTTGCTAAGCGTGTTTTAGGTGTT  17940
         A  V  F  I  S  P  Y  N  S  Q  N  Y  V  A  K  R  V  L  G  V
          L  F  L  L  V  L  I  I  V  R  I  M  L  L  S  V  F  *  V  F
       C  C  F  Y  *  S  L  *  *  S  E  L  C  C  *  A  C  F  R  C

17941  CAAACACAAACTGTAGATTCTGCTCAAGGTTCGGAATATGATTATGTTATATATTCACAA  18000
         Q  T  Q  T  V  D  S  A  Q  G  S  E  Y  D  Y  V  I  Y  S  Q
          K  H  K  L  *  I  L  L  K  V  R  N  M  I  M  L  Y  I  H  K
       S  N  T  N  C  R  F  C  S  R  F  G  I  *  L  C  Y  I  F  T

18001  ACAGCAGAAACAGCCCATTCTGTTAATGTTAATCGATTTAATGTTGCCATAACTAGAGCC  18060
         T  A  E  T  A  H  S  V  N  V  N  R  F  N  V  A  I  T  R  A
          Q  Q  K  Q  P  I  L  L  M  L  I  D  L  M  L  P  *  L  E  P
       N  S  R  N  S  P  F  C  *  C  *  S  I  *  C  C  H  N  *  S

18061  AAGAAGGGCATTTTTTGTGTTATGAGTAATATGCAATTATTTGAATCTCTTAATTTTATT  18120
         K  K  G  I  F  C  V  M  S  N  M  Q  L  F  E  S  L  N  F  I
          R  R  A  F  F  V  L  *  V  I  C  N  Y  L  N  L  L  I  L  L
       Q  E  G  H  F  L  C  Y  E  *  Y  A  I  I  *  I  S  *  F  Y

18121  ACTCTACCTTTAGATAAAATTCAAAATCAAACTTTACCTCGTTTGCATTGCACAACTAAT  18180
         T  L  P  L  D  K  I  Q  N  Q  T  L  P  R  L  H  C  T  T  N
          L  Y  L  *  I  K  F  K  I  K  L  Y  L  V  C  I  A  Q  L  I
       Y  S  T  F  R  *  N  S  K  S  N  F  T  S  F  A  L  H  N  *

18181  CTTTTTAAAGATTGTAGTAAAAGTTGCTTAGGTTATCATCCAGCGCATGCCCCCTCATTT  18240
         L  F  K  D  C  S  K  S  C  L  G  Y  H  P  A  H  A  P  S  F
          F  L  K  I  V  V  K  V  A  *  V  I  I  Q  R  M  P  P  H  F
       S  F  *  R  L  *  *  K  L  L  R  L  S  S  S  A  C  P  L  I

18241  TTAGCAGTTGATGATAAATATAAGGTTAATGAAAATTTGGCTGTAAATTTAAATATTTGT  18300
         L  A  V  D  D  K  Y  K  V  N  E  N  L  A  V  N  L  N  I  C
          *  Q  L  M  I  N  I  R  L  M  K  I  W  L  *  I  *  I  F  V
       F  S  S  *  *  *  I  *  G  *  *  K  F  G  C  K  F  K  Y  L

18301  GAACCTGTTTTAACATATTCTCGTTAATATCTCTTATGGGTTTTAAATTAGATTTGACT  18360
         E  P  V  L  T  Y  S  R  L  I  S  L  M  G  F  K  L  D  L  T
          N  L  F  *  H  I  L  V  *  Y  L  L  W  V  L  N  *  I  *  L
       *  T  C  F  N  I  F  S  F  N  I  S  Y  G  F  *  I  R  F  D
```

FIG. 2 CONT.

```
18361  CTTGATGGTTATTCTAAATTGTTTATTACTAAAGATGAAGCCATTAAACGTGTTAGAGGT  18420
         L  D  G  Y  S  K  L  F  I  T  K  D  E  A  I  K  R  V  R  G
          L  M  V  I  L  N  C  L  L  L  K  M  K  P  L  N  V  L  E  V
           S  *  W  L  F  *  I  V  Y  Y  *  R  *  S  H  *  T  C  *  R

18421  TGGGTTGGTTTTGATGTTGAGGGCGCTCATGCTACTCGCGAAAACATTGGAACAAACTTT  18480
         W  V  G  F  D  V  E  G  A  H  A  T  R  E  N  I  G  T  N  F
          G  L  V  L  M  L  R  A  L  M  L  L  A  K  T  L  E  Q  T  F
           L  G  W  F  *  C  *  G  R  S  C  Y  S  R  K  H  W  N  K  L

18481  CCACTGCAAATAGGTTTTTCAACTGGTGTGGATTTTGTAGTTGAAGCTACTGGCTTATTT  18540
         P  L  Q  I  G  F  S  T  G  V  D  F  V  V  E  A  T  G  L  F
          H  C  K  *  V  F  Q  L  V  W  I  L  *  L  K  L  L  A  Y  L
           S  T  A  N  R  F  F  N  W  C  G  F  C  S  *  S  Y  W  L  I

18541  GCTGAGAGAGATTGTTATACTTTTAAAAAAACTGTAGCTAAAGCTCCTCCTGGTGAAAAA  18600
         A  E  R  D  C  Y  T  F  K  K  T  V  A  K  A  P  P  G  E  K
          L  R  E  I  V  I  L  L  K  K  L  *  L  K  L  L  L  V  K  N
           C  *  E  R  L  L  Y  F  *  K  N  C  S  *  S  S  S  W  *  K

18601  TTTAAACATTTAATACCCCTTATGTCAAAAGGTCAAAAGTGGGATATTGTTAGAATTAGA  18660
         F  K  H  L  I  P  L  M  S  K  G  Q  K  W  D  I  V  R  I  R
          L  N  I  *  Y  P  L  C  Q  K  V  K  S  G  I  L  L  E  L  E
           I  *  T  F  N  T  P  Y  V  K  R  S  K  V  G  Y  C  *  N  *

18661  ATTGTTCAAATGTTATCTGATTATCTTTTAGACCTTTCTGATAGTGTAGTATTTATTACT  18720
         I  V  Q  M  L  S  D  Y  L  L  D  L  S  D  S  V  V  F  I  T
          L  F  K  C  Y  L  I  I  F  *  T  F  L  I  V  *  Y  L  L  L
           N  C  S  N  V  I  *  L  S  F  R  P  F  *  *  C  S  I  Y  Y

18721  TGGTCTGCCAGTTTTGAACTTACTTGTTTAAGGTATTTTGCTAAATTAGGCAGAGAGCTT  18780
         W  S  A  S  F  E  L  T  C  L  R  Y  F  A  K  L  G  R  E  L
          G  L  P  V  L  N  L  L  V  *  G  I  L  L  N  *  A  E  S  L
           L  V  C  Q  F  *  T  Y  L  F  K  V  F  C  *  I  R  Q  R  A

18781  AATTGTAATGTGTGTTCTAATCGTGCTACATGCTACAATTCTAGAACTGGTTATTATGGT  18840
         N  C  N  V  C  S  N  R  A  T  C  Y  N  S  R  T  G  Y  Y  G
          I  V  M  C  V  L  I  V  L  H  A  T  I  L  E  L  V  I  M  V
           *  L  *  C  V  F  *  S  C  Y  M  L  Q  F  *  N  W  L  L  W

18841  TGTTGGCGCCATAGTTATACTTGTGATTATGTGTATAATCCACTTATTGTAGATATACAA  18900
         C  W  R  H  S  Y  T  C  D  Y  V  V  N  P  L  I  V  D  I  Q
          V  G  A  I  V  I  L  V  I  M  C  I  I  H  L  L  *  I  Y  N
           L  L  A  P  *  L  Y  L  *  L  C  V  *  S  T  Y  C  R  Y  T
```

FIG. 2 CONT.

```
18901  CAGTGGGGTTATACAGGTTCTTTAACTAGTAATCACGATATAATTTGTAATGTACATAAA  18960
        Q  W  G  Y  T  G  S  L  T  S  N  H  D  I  I  C  N  V  H  K
         S  G  V  I  Q  V  L  *  L  V  I  T  I  *  F  V  M  Y  I  K
        T  V  G  L  Y  R  F  F  N  *  *  S  R  Y  N  L  *  C  T  *

18961  GGTGCACATGTTGCGTCAGCTGATGCAATTATGACTCGTTGTTTAGCAATCTATGATTGT  19020
        G  A  H  V  A  S  A  D  A  I  M  T  R  C  L  A  I  Y  D  C
         V  H  M  L  R  Q  L  M  Q  L  *  L  V  V  *  Q  S  M  I  V
        R  C  T  C  C  V  S  *  C  N  Y  D  S  L  F  S  N  L  *  L

19021  TTTTGTAAATCTGTTAATTGGAATTTAGAGTATCCAATAATTTCTAATGAGGTCAGTATA  19080
        F  C  K  S  V  N  W  N  L  E  Y  P  I  I  S  N  E  V  S  I
         F  V  N  L  L  I  G  I  *  S  I  Q  *  F  L  M  R  S  V  *
        F  L  *  I  C  *  L  E  F  R  V  S  N  N  F  *  *  G  Q  Y

19081  AATACATCTTGTAGGTTATTGCAGCGTGTCATGCTTAAAGCTGCCATGCTATGTAATAGA  19140
        N  T  S  C  R  L  L  Q  R  V  M  L  K  A  A  M  L  C  N  R
         I  H  L  V  G  Y  C  S  V  S  C  L  K  L  P  C  Y  V  I  D
        K  Y  I  L  *  V  I  A  A  C  H  A  *  S  C  H  A  M  *  *

19141  TACAACTTATGTTATGACATAGGCAATCCTAAAGGTTTAGCTTGTGTCAAAGATTATGAA  19200
        Y  N  L  C  Y  D  I  G  N  P  K  G  L  A  C  V  K  D  Y  E
         T  T  Y  V  M  T  *  A  I  L  K  V  *  L  V  S  K  I  M  N
        I  Q  L  M  L  *  H  R  Q  S  *  R  F  S  L  C  Q  R  L  *

19201  TTTAAATTTTATGATGCTTTTCCTGTAGCCAAGTCTGTTAAACAGTTATTTTATGTCTAT  19260
        F  K  F  Y  D  A  F  P  V  A  K  S  V  K  Q  L  F  Y  V  Y
         L  N  F  M  M  L  F  L  *  P  S  L  L  N  S  Y  F  M  S  M
        I  *  I  L  *  C  F  S  C  S  Q  V  C  *  T  V  I  L  C  L

19261  GATGTGCATAAAGATAATTTTAAAGATGGTTTATGTATGTTTTGGAATTGTAATGTTGAT  19320
        D  V  H  K  D  N  F  K  D  G  L  C  M  F  W  N  C  N  V  D
         M  C  I  K  I  I  L  K  M  V  Y  V  C  F  G  I  V  M  L  I
        *  C  A  *  R  *  F  *  R  W  F  M  Y  V  L  E  L  *  C  *

19321  AAATATCCATCTAATTCAATTGTTTGTAGATTTGACACTCGAGTGTTAAATAAATTAAAC  19380
        K  Y  P  S  N  S  I  V  C  R  F  D  T  R  V  L  N  K  L  N
         N  I  H  L  I  Q  L  F  V  D  L  T  L  E  C  *  I  N  *  T
        *  I  S  I  *  F  N  C  L  *  I  *  H  S  S  V  K  *  I  K

19381  CTTCCTGGATGTAATGGTGGTAGTTTGTATGTTAATAAACATGCATTCCATACTAATCCT  19440
        L  P  G  C  N  G  G  S  L  Y  V  N  K  H  A  F  H  T  N  P
         F  L  D  V  M  V  V  V  C  M  L  I  N  M  H  S  I  L  I  L
        P  S  W  M  *  W  W  *  F  V  C  *  *  T  C  I  P  Y  *  S
```

FIG. 2 CONT.

```
19441   TTTACTAGAACTGTTTTGAAAATCTTAAGCCTATGCCTTTTTTCTATTATTCAGATACG   19500
          F  T  R  T  V  F  E  N  L  K  P  M  P  F  F  Y  Y  S  D  T
           L  L  E  L  F  L  K  I  L  S  L  C  L  F  S  I  I  Q  I  R
         F  Y  *  N  C  F  *  K  S  *  A  Y  A  F  F  L  L  F  R  Y

19501   CCTTGTGTGTACGTAGATGGTTTAGAATCTAAACAAGTTGATTACGTTCCTTTAAGAAGC   19560
          P  C  V  Y  V  D  G  L  E  S  K  Q  V  D  Y  V  P  L  R  S
           L  V  C  T  *  M  V  *  N  L  N  K  L  I  T  F  L  *  E  A
         A  L  C  V  R  R  W  F  R  I  *  T  S  *  L  R  S  F  K  K

19561   GCCACTTGTATCACACGGTGTAATCTAGGTGGAGCTGTTTGTTCAAAGCATGCTGAAGAA   19620
          A  T  C  I  T  R  C  N  L  G  G  A  V  C  S  K  H  A  E  E
           P  L  V  S  H  G  V  I  *  V  E  L  F  V  Q  S  M  L  K  N
         R  H  L  Y  H  T  V  *  S  R  W  S  C  L  F  K  A  C  *  R

19621   TATTGTAACTACCTTGAGTCTTATAATATAGTTACTACAGCAGGCTTTACTTTTTGGGTT   19680
          Y  C  N  Y  L  E  S  Y  N  I  V  T  T  A  G  F  T  F  W  V
           I  V  T  T  L  S  L  I  I  *  L  L  Q  Q  A  L  L  F  G  F
         I  L  *  L  P  *  V  L  *  Y  S  Y  Y  S  R  L  Y  F  L  G

19681   TATAAGAATTTTGATTTTTATAATTTATGGAACACTTTTACTACGTTACAGAGTTTAGAA   19740
          Y  K  N  F  D  F  Y  N  L  W  N  T  F  T  T  L  Q  S  L  E
           I  R  I  L  I  F  I  I  Y  G  T  L  L  L  R  Y  R  V  *  K
         L  *  E  F  *  F  L  *  F  M  E  H  F  Y  Y  V  T  E  F  R

19741   AACGTAATATATAACTTGGTTAATGTTGGTCATTATGATGGACGTACAGGTGAATTACCT   19800
          N  V  I  Y  N  L  V  N  V  G  H  Y  D  G  R  T  G  E  L  P
           T  *  Y  I  T  W  L  M  L  V  I  M  M  D  V  Q  V  N  Y  L
         K  R  N  I  *  L  G  *  C  W  S  L  *  W  T  Y  R  *  I  T

19801   TGTGCTATTATGAATGACAAAGTTGTTGTTAAGATTAATAATGTAGATACTGTTATTTTT   19860
          C  A  I  M  N  D  K  V  V  V  K  I  N  N  V  D  T  V  I  F
           V  L  L  *  M  T  K  L  L  L  R  L  I  M  *  I  L  L  F  L
         L  C  Y  Y  E  *  Q  S  C  C  *  D  *  *  C  R  Y  C  Y  F

19861   AAAAATAATACATCATTTCCTACTAATATAGCTGTTGAATTGTTTACAAAACGTAGTATC   19920
          K  N  N  T  S  F  P  T  N  I  A  V  E  L  F  T  K  R  S  I
           K  I  I  H  H  F  L  L  I  *  L  L  N  C  L  Q  N  V  V  S
         *  K  *  Y  I  I  S  Y  *  Y  S  C  *  I  V  Y  K  T  *  Y

19921   CGGCACCACCCTGAACTTAAGATTCTTAGAAATTTGAACATTGATATTTGTTGGAAGCAT   19980
          R  H  H  P  E  L  K  I  L  R  N  L  N  I  D  I  C  W  K  H
           G  T  T  L  N  L  R  F  L  E  I  *  T  L  I  F  V  G  S  M
         P  A  P  P  *  T  *  D  S  *  K  F  E  H  *  Y  L  L  E  A
```

FIG. 2 CONT.

```
19981  GTCCTGTGGGATTATGTTAAAGATAGTTTGTTTTGTAGTTCCACTTATGGTGTTTGTAAA  20040
         V  L  W  D  Y  V  K  D  S  L  F  C  S  S  T  Y  G  V  C  K
          S  C  G  I  M  L  K  I  V  C  F  V  V  P  L  M  V  F  V  N
       C  P  V  G  L  C  *  R  *  F  V  L  *  F  H  L  W  C  L  *

20041  TACACAGATTTGAAGTTCATCGAAAATTTGAATATACTTTTTGATGGTCGTGACACTGGC  20100
         Y  T  D  L  K  F  I  E  N  L  N  I  L  F  D  G  R  D  T  G
          T  Q  I  *  S  S  S  K  I  *  I  Y  F  L  M  V  V  T  L  A
       I  H  R  F  E  V  H  R  K  F  E  Y  T  F  *  W  S  *  H  W

20101  GCTTTAGAAGCTTTTAGAAAAGCAAGAAATGGTGTTTTTATTAGTACTGAAAAATTAAGT  20160
         A  L  E  A  F  R  K  A  R  N  G  V  F  I  S  T  E  K  L  S
          L  *  K  L  L  E  K  Q  E  M  V  F  L  L  V  L  K  N  *  V
       R  F  R  S  F  *  K  S  K  K  W  C  F  Y  *  Y  *  K  I  K

20161  AGGTTATCAATGATTAAAGGTCCGCAACGAGCTGATTTAAATGGTGTGATTGTGGATAAA  20220
         R  L  S  M  I  K  G  P  Q  R  A  D  L  N  G  V  I  V  D  K
          G  Y  Q  *  L  K  V  R  N  E  L  I  *  M  V  *  L  W  I  K
       *  V  I  N  D  *  R  S  A  T  S  *  F  K  W  C  D  C  G  *

20221  GTTGGAGAACTCAAAGTTGAGTTTTGGTTCGCTATGAGAAAAGATGGTGACGATGTTATC  20280
         V  G  E  L  K  V  E  F  W  F  A  M  R  K  D  G  D  D  V  I
          L  E  N  S  K  L  S  F  G  S  L  *  E  K  M  V  T  M  L  S
       S  W  R  T  Q  S  *  V  L  V  R  Y  E  K  R  W  *  R  C  Y

20281  TTCAGCCGAACAGACAGCCTATGCTCAAGCCATTACTGGAGCCCACAAGGTAATCTAGGT  20340
         F  S  R  T  D  S  L  C  S  S  H  Y  W  S  P  Q  G  N  L  G
          S  A  E  Q  T  A  Y  A  Q  A  I  T  G  A  H  K  V  I  *  V
       L  Q  P  N  R  Q  P  M  L  K  P  L  L  E  P  T  R  *  S  R

20341  GGTAATTGCGCGGGTAATGTCATTGGTAATGATGCTCTAACACGTTTTACTATCTTTACT  20400
         G  N  C  A  G  N  V  I  G  N  D  A  L  T  R  F  T  I  F  T
          V  I  A  R  V  M  S  L  V  M  M  L  *  H  V  L  L  S  L  L
       W  *  L  R  G  *  C  H  W  *  *  C  S  N  T  F  Y  Y  L  Y

20401  CAGAGTCGTGTATTGTCAAGTTTTGAACCTCGCTCAGATTTAGAACGGGATTTTATTGAT  20460
         Q  S  R  V  L  S  S  F  E  P  R  S  D  L  E  R  D  F  I  D
          R  V  V  Y  C  Q  V  L  N  L  A  Q  I  *  N  G  I  L  L  I
       S  E  S  C  I  V  K  F  *  T  S  L  R  F  R  T  G  F  Y  *

20461  ATGGATGATAATCTGTTTATTGCTAAATATGGTTTAGAAGACTATGCATTTGATCATATA  20520
         M  D  D  N  L  F  I  A  K  Y  G  L  E  D  Y  A  F  D  H  I
          W  M  I  I  C  L  L  L  N  M  V  *  K  T  M  H  L  I  I  *
       Y  G  *  *  S  V  Y  C  *  I  W  F  R  R  L  C  I  *  S  Y
```

FIG. 2 CONT.

```
20521   GTTTATGGTAGTTTTAACCATAAAGTTATAGGAGGTTTGCATTTGCTTATAGGCTTATTT   20580
         V  Y  G  S  F  N  H  K  V  I  G  G  L  H  L  L  I  G  L  F
          F  M  V  V  L  T  I  K  L  *  E  V  C  I  C  L  *  A  Y  F
        S  L  W  *  F  *  P  *  S  Y  R  R  F  A  F  A  Y  R  L  I

20581   CGTAGGAAAAAAAAATCTAATTTGTTAATTCAAGAGTTTTTACAGTATGATTCTAGTATT   20640
         R  R  K  K  K  S  N  L  L  I  Q  E  F  L  Q  Y  D  S  S  I
          V  G  K  K  N  L  I  C  *  F  K  S  F  Y  S  M  I  L  V  F
        S  *  E  K  K  I  *  F  V  N  S  R  V  F  T  V  *  F  *  Y

20641   CATTCATATTTTATTACTGATCAGGAGTGTGGTAGTAGTAAGAGTGTTTGTACAGTTATT   20700
         H  S  Y  F  I  T  D  Q  E  C  G  S  S  K  S  V  C  T  V  I
          I  H  I  L  L  L  I  R  S  V  V  V  V  R  V  F  V  Q  L  L
        S  F  I  F  Y  Y  *  S  G  V  W  *  *  *  E  C  L  Y  S  Y

20701   GATTTATTATTAGATGATTTTGTTTCTATTGTTAAGTCATTAAATTTGAGTTGTGTTAGT   20760
         D  L  L  L  D  D  F  V  S  I  V  K  S  L  N  L  S  C  V  S
          I  Y  Y  *  M  I  L  F  L  L  S  H  *  I  *  V  V  L  V
        *  F  I  I  R  *  F  C  F  Y  C  *  V  I  K  F  E  L  C  *

20761   AAAGTTGTTAATATTAATGTTGATTTTAAGGATTTTCAATTTATGTTGTGGTGTAATGAT   20820
         K  V  V  N  I  N  V  D  F  K  D  F  Q  F  M  L  W  C  N  D
          K  L  L  I  L  M  L  I  L  R  I  F  N  L  C  C  G  V  M  I
        *  S  C  *  Y  *  C  *  F  *  G  F  S  I  Y  V  V  *  *

20821   AATAAAATTATGACTTTTTATCCTAAAATGCAAGCCACTAATGATTGGAAACCTGGCTAT   20880
         N  K  I  M  T  F  Y  P  K  M  Q  A  T  N  D  W  K  P  G  Y
          I  K  L  *  L  F  I  L  K  C  K  P  L  M  I  G  N  L  A  I
        *  *  N  Y  D  F  L  S  *  N  A  S  H  *  *  L  E  T  W  L

20881   TCTATGCCTGTTTTGTATAAGTATTTGAATGTTCCATTAGAGAGAGTCTCTTTATGGAAT   20940
         S  M  P  V  L  Y  K  Y  L  N  V  P  L  E  R  V  S  L  W  N
          L  C  L  F  C  I  S  I  *  M  F  H  *  R  E  S  L  Y  G  I
        F  Y  A  C  F  V  *  V  F  E  C  S  I  R  E  S  L  F  M  E

20941   TATGGTAAACCTATTAATTTGCCTACAGGCTGTATGATGAATGTTGCTAAGTACACTCAA   21000
         Y  G  K  P  I  N  L  P  T  G  C  M  M  N  V  A  K  Y  T  Q
          M  V  N  L  L  I  C  L  Q  A  V  *  *  M  L  L  S  T  L  N
        L  W  *  T  Y  *  F  A  Y  R  L  Y  D  E  C  C  *  V  H  S

21001   TTATGTCAGTATTTGAATACTACAACATTAGCTGTTCCTGTTAATATGCGTGTTTTACAT   21060
         L  C  Q  Y  L  N  T  T  T  L  A  V  P  V  N  M  R  V  L  H
          Y  V  S  I  *  I  L  Q  H  *  L  F  L  L  I  C  V  F  Y  I
        I  M  S  V  F  E  Y  Y  N  I  S  C  S  C  *  Y  A  C  F  T
```

FIG. 2 CONT.

```
21061  TTAGGTGCAGGGTCTGATAAAGAAGTAGCTCCAGGTTCTGCTGTTTTAAGACAGTGGTTA  21120
         L  G  A  G  S  D  K  E  V  A  P  G  S  A  V  L  R  Q  W  L
        *  V  Q  G  L  I  K  K  *  L  Q  V  L  L  F  *  D  S  G  Y
       F  R  C  R  V  *  *  R  S  S  S  R  F  C  C  F  K  T  V  V

21121  CCATCTGGTAGTATTCTTGTAGATAATGATTTAAACCCATTTGTTAGCGATAGTTTAGTT  21180
         P  S  G  S  I  L  V  D  N  D  L  N  P  F  V  S  D  S  L  V
        H  L  V  V  F  L  *  I  M  I  *  T  H  L  L  A  I  V  *  L
       T  I  W  *  Y  S  C  R  *  *  F  K  P  I  C  *  R  *  F  S

21181  ACTTATTTTGGAGATTGTATGACTTTACCATTTGATTGTCATTGGGATTTGATAATATCT  21240
         T  Y  F  G  D  C  M  T  L  P  F  D  C  H  W  D  L  I  I  S
        L  I  L  E  I  V  *  L  Y  H  L  I  V  I  G  I  *  *  Y  L
       Y  L  F  W  R  L  Y  D  F  T  I  *  L  S  L  G  F  D  N  I

21241  GATATGTATGATCCTCTTACTAAAAATATTGGTGATTATAATGTGAGTAAGGATGGGTTT  21300
         D  M  Y  D  P  L  T  K  N  I  G  D  Y  N  V  S  K  D  G  F
        I  C  M  I  L  L  L  K  I  L  V  I  I  M  *  V  R  M  G  F
       *  Y  V  *  S  S  Y  *  K  Y  W  *  L  *  C  E  *  G  W  V

21301  TTTACTTACATTTGTCATTTAATTCGTGATAAATTATCTTTGGGTGGTAGTGTAGCTATA  21360
         F  T  Y  I  C  H  L  I  R  D  K  L  S  L  G  G  S  V  A  I
        L  L  T  F  V  I  *  F  V  I  N  Y  L  W  V  V  V  *  L  *
       F  Y  L  H  L  S  F  N  S  *  *  I  I  F  G  W  *  C  S  Y

21361  AAAATTACAGAGTTTTCTTGGAATGCTGATTTATATAAATTAATGAGTTGTTTTGCATTT  21420
         K  I  T  E  F  S  W  N  A  D  L  Y  K  L  M  S  C  F  A  F
        K  L  Q  S  F  L  G  M  L  I  Y  I  N  *  *  V  V  L  H  F
       K  N  Y  R  V  F  L  E  C  *  F  I  *  I  N  E  L  F  C  I

21421  TGGACAGTTTTTTGTACTAATGTAAATGCTTCTTCTAGTGAAGGGTTTTTAATAGGTATA  21480
         W  T  V  F  C  T  N  V  N  A  S  S  S  E  G  F  L  I  G  I
        G  Q  F  F  V  L  M  *  M  L  L  L  V  K  G  F  *  *  V  *
       L  D  S  F  L  Y  *  C  K  C  F  F  *  *  R  V  F  N  R  Y

21481  AATTACCTGGGTAAATCTTCTTTTGAAATAGATGGCAATGTTATGCATGCTAACTATTTG  21540
         N  Y  L  G  K  S  S  F  E  I  D  G  N  V  M  H  A  N  Y  L
        I  T  W  V  N  L  L  L  K  *  M  A  M  L  C  M  L  T  I  C
       K  L  P  G  *  I  F  F  *  N  R  W  Q  C  Y  A  C  *  L  F

21541  TTTTGGAGAAATAGTACAACATGGAATGGCGGTGCTTATAGTTTATTTGATATGACTAAA  21600
         F  W  R  N  S  T  T  W  N  G  G  A  Y  S  L  F  D  M  T  K
        F  G  E  I  V  Q  H  G  M  A  V  L  I  V  Y  L  I  *  L  N
       V  L  E  K  *  Y  N  M  E  W  R  C  L  *  F  I  *  Y  D  *
```

FIG. 2 CONT.

```
21601  TTTTCTTTGAAATTGGCTGGCACTGCTGTTGTTAATTTAAGACCAGATCAATTAAATGAT  21660
        F  S  L  K  L  A  G  T  A  V  V  N  L  R  P  D  Q  L  N  D
         F  L  *  N  W  L  A  L  L  L  L  I  *  D  Q  I  N  *  M  I
          I  F  F  E  I  G  W  H  C  C  C  *  F  K  T  R  S  I  K  *

21661  TTAGTTTATTCTCTTATTGAAAGAGGTAAATTATTAGTTCGCGATACGCGTAAAGAGATT  21720
        L  V  Y  S  L  I  E  R  G  K  L  L  V  R  D  T  R  K  E  I
         *  F  I  L  L  L  K  E  V  N  Y  *  F  A  I  R  V  K  R  F
          F  S  L  F  S  Y  *  K  R  *  I  I  S  S  R  Y  A  *  R  D

21721  TTTGTTGGTGATAGTCTTGTAAATACTTGTTAGATCTCATTAAATCTAAACTATGTTAAT  21780
        F  V  G  D  S  L  V  N  T  C  *  I  S  L  N  L  N  Y  V  N
         L  L  V  I  V  L  *  I  L  V  R  S  H  *  I  *  T  M  L  I
          F  C  W  *  *  S  C  K  Y  L  L  D  L  I  K  S  K  L  C  *

21781  TATTTTTTATTTTTTATTTCTGTTATGGTTTTAATGAACCTCTTAATGTTGTGTCTCA    21840
        Y  F  F  I  F  L  F  L  L  W  F  *  *  T  S  *  C  C  V  S
         I  F  L  F  F  Y  F  C  Y  G  F  N  E  P  L  N  V  V  S  H
          L  F  F  Y  F  F  I  S  V  M  V  L  M  N  L  L  M  L  C  L

21841  TTTAAACCATGACTGGTTTTTATTTGGTGATAGTCGTTCTGATTGTAACCATATTAATAA  21900
        F  K  P  *  L  V  F  I  W  *  *  S  F  *  L  *  P  Y  *  *
         L  N  H  D  W  F  L  F  G  D  S  R  S  D  C  N  H  I  N  N
          I  *  T  M  T  G  F  Y  L  V  I  V  V  L  I  V  T  I  L  I

21901  TTTAAAAATTAAAAATTTTGATTATTTGGATATTCACCCTAGTTTGTGCAACAATGGTAA  21960
        F  K  N  *  K  F  *  L  F  G  Y  S  P  *  F  V  Q  Q  W  *
         L  K  I  K  N  F  D  Y  L  D  I  H  P  S  L  C  N  N  G  K
          I  *  K  L  K  I  L  I  I  W  I  F  T  L  V  C  A  T  M  V

21961  GATTTCATCTAGTGCCGGTGATTCTATTTTTAAGAGTTTTCATTTCACTCGATTTTATAA  22020
        D  F  I  *  C  R  *  F  Y  F  *  E  F  S  F  H  S  I  L  *
         I  S  S  S  A  G  D  S  I  F  K  S  F  H  F  T  R  F  Y  N
          R  F  H  L  V  P  V  I  L  F  L  R  V  F  I  S  L  D  F  I

22021  TTACACTGGCGAAGGTGATCAAATTATTTTTTATGAGGGTGTTAATTTTAATCCTTATCA  22080
        L  H  W  R  R  *  S  N  Y  F  L  *  G  C  *  F  *  S  L  S
         Y  T  G  E  G  D  Q  I  I  F  Y  E  G  V  N  F  N  P  Y  H
          I  T  L  A  K  V  I  K  L  F  F  M  R  V  L  I  L  I  L  I

22081  TAGATTTAAGTGTTTTCCTAATGGTAGTAATGATGTATGGCTTCTTAACAAGGTAAGATT  22140
        *  I  *  V  F  S  *  W  *  *  *  C  M  A  S  *  Q  G  K  I
         R  F  K  C  F  P  N  G  S  N  D  V  W  L  L  N  K  V  R  F
          I  D  L  S  V  F  L  M  V  V  M  M  Y  G  F  L  T  R  *  D
```

FIG. 2 CONT.

```
22141  TTATCGTGCCTTATATTCTAATATGGCCTTTTTTCGTTATCTTACTTTTGTTGATATTCC  22200
       L  S  C  L  I  F  *  Y  G  L  F  S  L  S  Y  F  C  *  Y  S
        Y  R  A  L  Y  S  N  M  A  F  F  R  Y  L  T  F  V  D  I  P
         F  I  V  P  Y  I  L  I  W  P  F  F  V  I  L  L  L  I  F

22201  TTATAATGTTTCTCTTTCTAAGTTTAATTCTTGTAAAAGTGATATTTTATCACTTAACAA  22260
       L  *  C  F  S  F  *  V  *  F  L  *  K  *  Y  F  I  T  *  Q
        Y  N  V  S  L  S  K  F  N  S  C  K  S  D  I  L  S  L  N  N
         L  I  M  F  L  F  L  S  L  I  L  V  K  V  I  F  Y  H  L  T

22261  TCCTATTTTTATTAATTATTCTAAGGAAGTTTATTTTACTTTATTAGGTTGTTCTCTTTA  22320
       S  Y  F  Y  *  L  F  *  G  S  L  F  Y  F  I  R  L  F  S  L
        P  I  F  I  N  Y  S  K  E  V  Y  F  T  L  L  G  C  S  L  Y
         I  L  F  L  L  I  I  L  R  K  F  I  L  L  Y  *  V  V  L  F

22321  TTTAGTACCGCTTTGCCTTTTTAAATCTAACTTTAGTCAGTACTATTATAACATAGATAC  22380
       F  S  T  A  L  P  F  *  I  *  L  *  S  V  L  L  *  H  R  Y
        L  V  P  L  C  L  F  K  S  N  F  S  Q  Y  Y  Y  N  I  D  T
         I  *  Y  R  F  A  F  L  N  L  T  L  V  S  T  I  I  T  *  I

22381  TGGCTCTGTTTATGGTTTTTCTAATGTTGTTTATCCTGATTTAGACTGTATTTATATTTC  22440
       W  L  C  L  W  F  F  *  C  C  L  S  *  F  R  L  Y  L  Y  F
        G  S  V  Y  G  F  S  N  V  V  Y  P  D  L  D  C  I  Y  I  S
         L  A  L  F  M  V  F  L  M  L  F  I  L  I  *  T  V  F  I  F

22441  TCTTAAACCAGGTTCTTATAAAGTTTCCACCACTGCACCTTTTTTATCCTTACCTACTAA  22500
       S  *  T  R  F  L  *  S  F  H  H  C  T  F  F  I  L  T  Y  *
        L  K  P  G  S  Y  K  V  S  T  T  A  P  F  L  S  L  P  T  K
         L  L  N  Q  V  L  I  K  F  P  P  L  H  L  F  Y  P  Y  L  L

22501  AGCTCTCTGTTTTGATAAATCTAAACAATTTGTACCTGTACAGGTTGTTGATTCTAGATG  22560
       S  S  L  F  *  *  I  *  T  I  C  T  C  T  G  C  *  F  *  M
        A  L  C  F  D  K  S  K  Q  F  V  P  V  Q  V  V  D  S  R  W
         K  L  S  V  L  I  N  L  N  N  L  Y  L  Y  R  L  L  I  L  D

22561  GAACAACGAGCGTGCCTCAGATATTTCTTTATCTGTTGCATGTCAATTGCCATATTGTTA  22620
       E  Q  R  A  C  L  R  Y  F  F  I  C  C  M  S  I  A  I  L  L
        N  N  E  R  A  S  D  I  S  L  S  V  A  C  Q  L  P  Y  C  Y
         G  T  T  S  V  P  Q  I  F  L  Y  L  L  H  V  N  C  H  I  V

22621  TTTTCGCAATTCTTCTGCTAATTATGTTGGCAAGTATGATATTAACCACGGTGATAGTGG  22680
       F  S  Q  F  F  C  *  L  C  W  Q  V  *  Y  *  P  R  *  *  W
        F  R  N  S  S  A  N  Y  V  G  K  Y  D  I  N  H  G  D  S  G
         I  F  A  I  L  L  L  I  M  L  A  S  M  I  L  T  T  V  I  V
```

FIG. 2 CONT.

```
22681  TTTTATTTCTATTTTATCTGGTCTTTTATATAATGTTTCTTGTATTTCATATTATGGTGT  22740
         F Y F Y F I W S F I * C F L Y F I L W C
          F I S I L S G L L Y N V S C I S Y Y G V
        V L F L F Y L V F Y I M F L V F H I M V

22741  ATTTTTATATGATAATTTTACATCCATTTGGCCCTATTATTCTTTTGGTAGGTGTCCTAC  22800
         I F I * * F Y I H L A L L F F W * V S Y
          F L Y D N F T S I W P Y Y S F G R C P T
        Y F Y M I I L H P F G P I I L L V G V L

22801  ATCTTCTATTATTAAACATCCAATTTGTGTTTATGATTTTTGCCTATTATTTTACAAGG  22860
         I F Y Y * T S N L C L * F F A Y Y F T R
          S S I I K H P I C V Y D F L P I I L Q G
        H L L L N I Q F V F M I F C L L F Y K

22861  TATTTTATTATGTTTAGCTTTACTTTTTGTTGTTTTCTATTATTTTTGTTATATAACGA  22920
         Y F I M F S F T F C C F S I I F V I * R
          I L L C L A L L F V V F L L F L L Y N D
        V F Y Y V * L Y F L L F F Y Y F C Y I T

22921  TAAATCTCATTAAATCTAAACATGTTATTAATTATTTTTATTTTGCCTACAACATTAGCT  22980
         * I S L N L N M L L I I F I L P T T L A
          K S H * I * T C Y * L F L F C L Q H * L
        I N L I K S K H V I N Y F Y F A Y N I S

22981  GTTATAGGTGATTTTAATTGTACTAATTTTGCTATTAATGATTTAAACACCACAGTTCCT  23040
         V I G D F N C T N F A I N D L N T T V P
          L * V I L I V L I L L M I * T P Q F L
        C Y R * F * L Y * F C Y * * F K H H S S

23041  CGCATAAGTGAGTATGTTGTGGATGTTTCTTATGGTTTGGGTACATATTATATACTTGAT  23100
         R I S E Y V V D V S Y G L G T Y Y I L D
          A * V S M L W M F L M V W V H I I Y L I
        S H K * V C C G C F L W F G Y I L Y T *

23101  CGTGTTTATTTAAATACTACTATATTATTTACTGGTTATTTCCCTAAATCTGGTGCCAAT  23160
         R V Y L N T T I L F T G Y F P K S G A N
          V F I * I L L Y Y L L V I S L N L V P I
        S C L F K Y Y Y I I Y W L F P * I W C Q

23161  TTTAGGGATCTATCTTTAAAAGGTACTACATATTTGAGTACTCTTTGGTATCAGAAACCC  23220
         F R D L S L K G T T Y L S T L W Y Q K P
          L G I Y L * K V L H I * V L F G I R N P
        F * G S I F K R Y Y I F E Y S L V S E T
```

FIG. 2 CONT.

```
23221  TTTTTATCTGATTTTAATAATGGTATTTTTTCTAGAGTTAAGAATACTAAGTTGTATGTT  23280
         F  L  S  D  F  N  N  G  I  F  S  R  V  K  N  T  K  L  Y  V
          F  Y  L  I  L  I  M  V  F  F  L  E  L  R  I  L  S  C  M  L
        L  F  I  *  F  *  *  W  Y  F  F  *  S  *  E  Y  *  V  V  C

23281  AATAAAACTTTGTATAGTGAGTTTAGTACTATAGTTATAGGTAGTGTTTTTATTAACAAC  23340
         N  K  T  L  Y  S  E  F  S  T  I  V  I  G  S  V  F  I  N  N
          I  K  L  C  I  V  S  L  V  L  *  L  *  V  V  F  L  L  T  T
        *  *  N  F  V  *  *  V  *  Y  Y  S  Y  R  *  C  F  Y  *  Q

23341  TCTTATACTATTGTTGTTCAACCTCATAATGGTGTTTTGGAGATTACAGCTTGTCAATAC  23400
         S  Y  T  I  V  V  Q  P  H  N  G  V  L  E  I  T  A  C  Q  Y
          L  I  L  L  L  F  N  L  I  M  V  F  W  R  L  Q  L  V  N  T
        L  L  Y  Y  C  C  S  T  S  *  W  C  F  G  D  Y  S  L  S  I

23401  ACTATGTGTGAGTATCCTCATACTATTTGTAAATCTAAAGGTAGTTCTCGTAATGAATCT  23460
         T  M  C  E  Y  P  H  T  I  C  K  S  K  G  S  S  R  N  E  S
          L  C  V  S  I  L  I  L  F  V  N  L  K  V  V  L  V  M  N  L
        H  Y  V  *  V  S  S  Y  Y  L  *  I  *  R  *  F  S  *  *  I

23461  TGGCATTTTGATAAATCTGAACCTTTGTGTCTGTTCAAGAAAAATTTTACTTATAATGTT  23520
         W  H  F  D  K  S  E  P  L  C  L  F  K  K  N  F  T  Y  N  V
          G  I  L  I  N  L  N  L  C  V  C  S  R  K  I  L  L  I  M  F
        L  A  F  *  *  I  *  T  F  V  S  V  Q  E  K  F  Y  L  *  C

23521  TCTACAGATTGGTTGTATTTTCATTTTTATCAAGAACGTGGCACTTTTTATGCTTATTAT  23580
         S  T  D  W  L  Y  F  H  F  Y  Q  E  R  G  T  F  Y  A  Y  Y
          L  Q  I  G  C  I  F  I  F  I  K  N  V  A  L  F  M  L  I  M
        F  Y  R  L  V  V  F  S  F  L  S  R  T  W  H  F  L  C  L  L

23581  GCTGATTCTGGCATGCCTACTACTTTTTTATTTAGTTTGTATCTTGGTACTCTTTTATCT  23640
         A  D  S  G  M  P  T  T  F  L  F  S  L  Y  L  G  T  L  L  S
          L  I  L  A  C  L  L  L  F  Y  L  V  C  I  L  V  L  F  Y  L
        C  *  F  W  H  A  Y  Y  F  F  I  *  F  V  S  W  Y  S  F  I

23641  CATTATTATGTTTTGCCTTTGACTTGTAATGCTATATCTTCTAATACTGATAATGAGACT  23700
         H  Y  Y  V  L  P  L  T  C  N  A  I  S  S  N  T  D  N  E  T
          I  I  M  F  C  L  *  L  V  M  L  Y  L  L  I  L  I  M  R  L
        S  L  L  C  F  A  F  D  L  *  C  Y  I  F  *  Y  *  *  *  D

23701  TTACAATATTGGGTCACACCTTTGTCTAAACGCCAATATCTTCTTAAATTTGACAACCGT  23760
         L  Q  Y  W  V  T  P  L  S  K  R  Q  Y  L  L  K  F  D  N  R
          Y  N  I  G  S  H  L  C  L  N  A  N  I  F  L  N  L  T  T  V
        F  T  I  L  G  H  T  F  V  *  T  P  I  S  S  *  I  *  Q  P
```

FIG. 2 CONT.

```
23761  GGTGTTATTACTAATGCTGTTGATTGTTCTAGTAGTTTCTTTAGCGAGATTCAATGTAAA  23820
         G  V  I  T  N  A  V  D  C  S  S  S  F  F  S  E  I  Q  C  K
          V  L  L  L  M  L  L  I  V  L  V  V  S  L  A  R  F  N  V  K
           W  C  Y  Y  *  C  C  *  L  F  *  *  F  L  *  R  D  S  M  *

23821  ACTAAATCTTTATTACCTAATACTGGTGTTTATGACTTATCTGGTTTTACTGTTAAGCCT  23880
         T  K  S  L  L  P  N  T  G  V  Y  D  L  S  G  F  T  V  K  P
          L  N  L  Y  Y  L  I  L  V  F  M  T  Y  L  V  L  L  L  S  L
           N  *  I  F  I  T  *  Y  W  C  L  *  L  I  W  F  Y  C  *  A

23881  GTTGCAACTGTACATCGTCGTATTCCTGATTTACCTGATTGTGACATTGATAAATGGCTT  23940
         V  A  T  V  H  R  R  I  P  D  L  P  D  C  D  I  D  K  W  L
          L  Q  L  Y  I  V  V  F  L  I  Y  L  I  V  T  L  I  N  G  L
           C  C  N  C  T  S  S  Y  S  *  F  T  *  L  *  H  *  *  M  A

23941  AACAATTTTAATGTACCCTCACCTCTTAATTGGGAACGTAAAATTTTTTCTAATTGCAAC  24000
         N  N  F  N  V  P  S  P  L  N  W  E  R  K  I  F  S  N  C  N
          T  I  L  M  Y  P  H  L  L  I  G  N  V  K  F  F  L  I  A  T
           *  Q  F  *  C  T  L  T  S  *  L  G  T  *  N  F  F  *  L  Q

24001  TTTAATTTGAGTACTTTGCTTCGTTTAGTTCATACTGATTCTTTTTCTTGTAATAATTTT  24060
         F  N  L  S  T  L  L  R  L  V  H  T  D  S  F  S  C  N  N  F
          L  I  *  V  L  C  F  V  *  F  I  L  I  L  F  L  V  I  I  L
           L  *  F  E  Y  F  A  S  F  S  S  Y  *  F  F  F  L  *  *  F

24061  GATGAATCTAAGATATATGGTAGTTGTTTTAAGAGTATTGTTTTAGATAAATTTGCCATA  24120
         D  E  S  K  I  Y  G  S  C  F  K  S  I  V  L  D  K  F  A  I
          M  N  L  R  Y  M  V  V  V  L  R  V  L  F  *  I  N  L  P  Y
           *  *  I  *  D  I  W  *  L  F  *  E  Y  C  F  R  *  I  C  H

24121  CCCAACTCCAGACGATCTGATTTGCAGTTGGGCAGTTCTGGTTTTCTGCAATCTTCTAAT  24180
         P  N  S  R  R  S  D  L  Q  L  G  S  S  G  F  L  Q  S  S  N
          P  T  P  D  D  L  I  C  S  W  A  V  L  V  F  C  N  L  L  I
           T  Q  L  Q  T  I  *  F  A  V  G  Q  F  W  F  S  A  I  F  *

24181  TATAAAATTGACACTACTTCTAGTTCTTGTCAATTGTATTATAGTTTGCCTGCAATTAAT  24240
         Y  K  I  D  T  T  S  S  S  C  Q  L  Y  Y  S  L  P  A  I  N
          I  K  L  T  L  L  V  L  V  N  C  I  I  V  C  L  Q  L  M
           L  *  N  *  H  Y  F  *  F  L  S  I  V  L  *  F  A  C  N  *

24241  GTTACTATTAATAATTATAATCCTTCTTCTTGGAATAGAAGGTATGGTTTTAATAATTTT  24300
         V  T  I  N  N  Y  N  P  S  S  W  N  R  R  Y  G  F  N  N  F
          L  L  L  I  I  I  I  L  L  L  G  I  E  G  M  V  L  I  I  L
           C  Y  Y  *  *  L  *  S  F  F  L  E  *  K  V  W  F  *  *  F
```

FIG. 2 CONT.

```
24301  AATTTGAGCTCTCATAGTGTTGTTTACTCACGTTATTGTTTTCTGTTAATAATACTTTT  24360
          N  L  S  S  H  S  V  V  Y  S  R  Y  C  F  S  V  N  N  T  F
         I  *  A  L  I  V  L  F  T  H  V  I  V  F  L  L  I  L  F
        *  F  E  L  S  *  C  C  L  L  T  L  L  F  F  C  *  *  Y  F

24361  TGTCCTTGTGCTAAACCTTCTTTTGCTTCAAGTTGCAAGAGTCATAAACCACCTTCTGCT  24420
          C  P  C  A  K  P  S  F  A  S  S  C  K  S  H  K  P  P  S  A
         V  L  V  L  N  L  L  L  Q  V  A  R  V  I  N  H  L  L
        L  S  L  C  *  T  F  F  C  F  K  L  Q  E  S  *  T  T  F  C

24421  TCCTGTCCTATTGGTACTAATTATCGTTCTTGTGAGAGTACTACTGTACTCGACCACACT  24480
          S  C  P  I  G  T  N  Y  R  S  C  E  S  T  T  V  L  D  H  T
         P  V  L  L  V  L  I  I  V  L  V  R  V  L  L  Y  S  T  T  L
        F  L  S  Y  W  Y  *  L  S  F  L  *  E  Y  Y  C  T  R  P  H

24481  GACTGGTGTAGGTGTTCTTGTTTACCTGATCCTATAACTGCTTATGACCCTAGGTCTTGT  24540
          D  W  C  R  C  S  C  L  P  D  P  I  T  A  Y  D  P  R  S  C
         T  G  V  G  V  L  V  Y  L  I  L  *  L  L  M  T  L  G  L  V
        *  L  V  *  V  F  L  F  T  *  S  Y  N  C  L  *  P  *  V  L

24541  TCTCAAAAAAAGTCTCTGGTTGGTGTTGGTGAACATTGTGCAGGGTTCGGTGTTGATGAA  24600
          S  Q  K  K  S  L  V  G  V  G  E  H  C  A  G  F  G  V  D  E
         L  K  K  S  L  W  L  V  L  V  N  I  V  Q  G  S  V  L  M  K
        F  S  K  K  V  S  G  W  C  W  *  T  L  C  R  V  R  C  *  *

24601  GAAAAGTGTGGTGTATTGGATGGATCATATAATGTTTCTTGTCTTTGTAGTACTGATGCC  24660
          E  K  C  G  V  L  D  G  S  Y  N  V  S  C  L  C  S  T  D  A
         K  S  V  V  Y  W  M  D  H  I  M  F  L  V  F  V  V  L  M  P
        R  K  V  W  C  I  G  W  I  I  *  C  F  L  S  L  *  Y  *  C

24661  TTTCTAGGTTGGTCTTATGACACTTGCGTCAGTAACAACCGTTGTAATATTTTTTCTAAT  24720
          F  L  G  W  S  Y  D  T  C  V  S  N  N  R  C  N  I  F  S  N
         F  *  V  G  L  M  T  L  A  S  V  T  T  V  V  I  F  F  L  I
        L  S  R  L  V  L  *  H  L  R  Q  *  Q  P  L  *  Y  F  F  *

24721  TTTATTTTAAATGGTATCAATAGTGGTACCACTTGTTCTAATGATTTATTGCAGCCTAAT  24780
          F  I  L  N  G  I  N  S  G  T  T  C  S  N  D  L  L  Q  P  N
         L  F  *  M  V  S  I  V  V  P  L  V  L  M  I  Y  C  S  L  I
        F  Y  F  K  W  Y  Q  *  W  Y  H  L  F  *  *  F  I  A  A  *

24781  ACTGAAGTTTTTACTGATGTTTGTGTTGATTACGACCTTTATGGTATTACAGGACAAGGT  24840
          T  E  V  F  T  D  V  C  V  D  Y  D  L  Y  G  I  T  G  Q  G
         L  K  F  L  L  M  F  V  L  I  T  T  F  M  V  L  Q  D  K  V
        Y  *  S  F  Y  *  C  L  C  *  L  R  P  L  W  Y  Y  R  T  R
```

FIG. 2 CONT.

```
24841  ATTTTTAAAGAAGTTTCTGCTGTTTATTATAATAGTTGGCAAAATCTTTTGTATGATTCT  24900
        I  F  K  E  V  S  A  V  Y  Y  N  S  W  Q  N  L  L  Y  D  S
         F  L  K  K  F  L  L  F  I  I  I  V  G  K  I  F  C  M  I  L
        Y  F  *  R  S  F  C  C  L  L  *  *  L  A  K  S  F  V  *  F

24901  AATGGCAACATTATTGGTTTTAAAGATTTTGTTACTAATAAAACATATAATATTTTCCCT  24960
        N  G  N  I  I  G  F  K  D  F  V  T  N  K  T  Y  N  I  F  P
         M  A  T  L  L  V  L  K  I  L  L  L  I  K  H  I  I  F  S  L
        *  W  Q  H  Y  W  F  *  R  F  C  Y  *  *  N  I  *  Y  F  P

24961  TGTTATGCAGGAAGAGTTTCTGCTGCTTTTCATCAAAATGCTTCCTCTTTGGCTTTACTT  25020
        C  Y  A  G  R  V  S  A  A  F  H  Q  N  A  S  S  L  A  L  L
         V  M  Q  E  E  F  L  L  L  F  I  K  M  L  P  L  W  L  Y  F
        L  L  C  R  K  S  F  C  C  F  S  S  K  C  F  L  G  F  T

25021  TATCGTAATTTAAAATGTAGCTATGTTTTGAATAATATTTCTTTAACTACTCAGCCATAT  25080
        Y  R  N  L  K  C  S  Y  V  L  N  N  I  S  L  T  T  Q  P  Y
         I  V  I  *  N  V  A  M  F  *  I  I  F  L  *  L  L  S  H  I
        L  S  *  F  K  M  *  L  C  F  E  *  Y  F  F  N  Y  S  A  I

25081  TTTGATAGTTATCTTGGTTGCGTTTTTAATGCTGATAATTTAACTGATTATTCTGTTTCT  25140
        F  D  S  Y  L  G  C  V  F  N  A  D  N  L  T  D  Y  S  V  S
         L  I  V  I  L  V  A  F  L  M  L  I  I  *  L  I  I  L  F  L
        F  *  *  L  S  W  L  R  F  *  C  *  *  F  N  *  L  F  C  F

25141  TCTTGTGCTCTTCGCATGGGTAGTGGTTTTTGTGTTGATTATAACTCACCTTCTTCTTCC  25200
        S  C  A  L  R  M  G  S  G  F  C  V  D  Y  N  S  P  S  S  S
         L  V  L  F  A  W  V  V  V  F  V  L  I  I  T  H  L  L  L  P
        F  L  C  S  S  H  G  *  W  F  L  C  *  L  *  L  T  F  F  F

25201  TCTTCGCGTCGTAAACGTAGAAGTATTTCTGCTTCTTATCGTTTTGTTACTTTTGAACCC  25260
        S  S  R  R  K  R  R  S  I  S  A  S  Y  R  F  V  T  F  E  P
         L  R  V  V  N  V  E  V  F  L  L  L  I  V  L  L  L  N  P
        L  F  A  S  *  T  *  K  Y  F  C  F  L  S  F  C  Y  F  *  T

25261  TTTAATGTCAGTTTTGTTAATGACAGTATTGAGTCTGTGGGTGGTCTTTATGAGATCAAA  25320
        F  N  V  S  F  V  N  D  S  I  E  S  V  G  G  L  Y  E  I  K
         L  M  S  V  L  L  M  T  V  L  S  L  W  V  V  F  M  R  S  K
        L  *  C  Q  F  C  *  *  Q  Y  *  V  C  G  W  S  L  *  D  Q

25321  ATTCCCACTAACTTTACTATAGTTGGTCAAGAGGAATTTATTCAAACTAATTCTCCTAAA  25380
        I  P  T  N  F  T  I  V  G  Q  E  E  F  I  Q  T  N  S  P  K
         F  P  L  T  L  L  *  L  V  K  R  N  L  F  K  L  I  L  L  K
        N  S  H  *  L  Y  Y  S  W  S  R  G  I  Y  S  N  *  F  S  *
```

FIG. 2 CONT.

```
25381  GTTACTATTGATTGTTCTTTATTTGTCTGTTCTAATTATGCAGCTTGCCATGACTTATTG  25440
         V  T  I  D  C  S  L  F  V  C  S  N  Y  A  A  C  H  D  L  L
          L  L  L  I  V  L  Y  L  S  V  L  I  M  Q  L  A  M  T  Y  C
        S  Y  Y  *  L  F  F  I  C  L  F  *  L  C  S  L  P  *  L  I

25441  TCAGAGTATGGCACTTTTTGTGATAATATTAATAGTATTTTAGATGAAGTTAATGGTTTA  25500
         S  E  Y  G  T  F  C  D  N  I  N  S  I  L  D  E  V  N  G  L
          Q  S  M  A  L  F  V  I  I  L  I  V  F  *  M  K  L  M  V  Y
        V  R  V  W  H  F  L  *  *  Y  *  *  Y  F  R  *  S  *  W  F

25501  CTTGATACTACTCAATTGCATGTAGCTGATACTCTTATGCAAGGTGTCACACTTAGCTCC  25560
         L  D  T  T  Q  L  H  V  A  D  T  L  M  Q  G  V  T  L  S  S
          L  I  L  L  N  C  M  *  L  I  L  L  C  K  V  S  H  L  A  P
        T  *  Y  Y  S  I  A  C  S  *  Y  S  Y  A  R  C  H  T  *  L

25561  AATCTTAATACTAATTTGCATTTTGATGTTGATAATATTAATTTTAAATCCCTAGTTGGA  25620
         N  L  N  T  N  L  H  F  D  V  D  N  I  N  F  K  S  L  V  G
          I  L  I  L  I  C  I  L  M  L  I  I  L  I  L  N  P  *  L  D
        Q  S  *  Y  *  F  A  F  *  C  *  *  Y  *  F  *  I  P  S  W

25621  TGTTTAGGTCCACACTGCGGTTCTTCTTCTCGTTCTTTTTTTGAAGATTTATTGTTTGAC  25680
         C  L  G  P  H  C  G  S  S  S  R  S  F  F  E  D  L  L  F  D
          V  *  V  H  T  A  V  L  L  L  V  L  F  L  K  I  Y  C  L  T
        M  F  R  S  T  L  R  F  F  F  S  F  F  F  *  R  F  I  V  *

25681  AAAGTTAAACTTTCAGATGTTGGTTTTGTTGAAGCTTATAACAATTGTACTGGTGGTAGT  25740
         K  V  K  L  S  D  V  G  F  V  E  A  Y  N  N  C  T  G  G  S
          K  L  N  F  Q  M  L  V  L  L  K  L  I  T  I  V  L  V  V  V
        Q  S  *  T  F  R  C  W  F  C  *  S  L  *  Q  L  Y  W  W  *

25741  GAAATTAGAGATCTTCTTTGTGTACAATCCTTTAATGGTATTAAAGTTTTGCCTCCTATT  25800
         E  I  R  D  L  L  C  V  Q  S  F  N  G  I  K  V  L  P  P  I
          K  L  E  I  F  F  V  Y  N  P  L  M  V  L  K  F  C  L  L  F
        *  N  *  R  S  S  L  C  T  I  L  *  W  Y  *  S  F  A  S  Y

25801  TTGTCTGAATCTCAAATTTCTGGTTACACCACAGCCGCTACTGTTGCTGCTATGTTTCCA  25860
         L  S  E  S  Q  I  S  G  Y  T  T  A  A  T  V  A  A  M  F  P
          C  L  N  L  K  F  L  V  T  P  Q  P  L  L  L  L  L  C  F  H
        F  V  *  I  S  N  F  W  L  H  H  S  R  Y  C  C  C  Y  V  S

25861  CCATGGTCAGCAGCAGCTGGCATACCATTTTCTCTTAATGTACAATATAGAATTAATGGT  25920
         P  W  S  A  A  A  G  I  P  F  S  L  N  V  Q  Y  R  I  N  G
          H  G  Q  Q  Q  L  A  Y  H  F  L  L  M  Y  N  I  E  L  M  V
        T  M  V  S  S  S  W  H  T  I  F  S  *  C  T  I  *  N  *  W
```

FIG. 2 CONT.

```
25921   TTGGGTGTTACTATGGATGTTCTTAATAAAAATCAAAAGTTGATAGCTACTGCTTTTAAT   25980
         L  G  V  T  M  D  V  L  N  K  N  Q  K  L  I  A  T  A  F  N
          W  V  L  L  W  M  F  L  I  K  I  K  S  *  *  L  L  L  L  I
        F  G  C  Y  Y  G  C  S  *  *  K  S  K  V  D  S  Y  C  F  *

25981   AATGCTCTTCTTTCTATTCAGAATGGTTTTAGTGCTACCAACTCTGCACTTGCTAAAATA   26040
         N  A  L  L  S  I  Q  N  G  F  S  A  T  N  S  A  L  A  K  I
          M  L  F  F  L  P  R  M  V  L  V  L  P  T  L  H  L  L  K  Y
        *  C  S  S  F  Y  S  E  W  F  *  C  Y  Q  L  C  T  C  *  N

26041   CAAAGTGTTGTTAATTCTAATGCTCAAGCACTTAATAGTTTGTTACAGCAATTATTTAAT   26100
         Q  S  V  V  N  S  N  A  Q  A  L  N  S  L  L  Q  Q  L  F  N
          K  V  L  L  I  L  M  L  K  H  L  I  V  C  Y  S  N  Y  L  I
        T  K  C  C  *  F  *  C  S  S  T  *  *  F  V  T  A  I  I  *

26101   AAATTTGGTGCAATTAGTTCTTCTTTACAAGAAATTTTATCTCGTCTCGATGCTTTAGAG   26160
         K  F  G  A  I  S  S  S  L  Q  E  I  L  S  R  L  D  A  L  E
          N  L  V  Q  L  V  L  L  Y  K  K  F  Y  L  V  S  M  L  *  R
        *  I  W  C  N  *  F  F  F  T  R  N  F  I  S  S  R  C  F  R

26161   GCTCAGGTTCAGATTGATAGGCTTATTAATGGTCGTTTAACTGCTTTAAATGCTTATGTC   26220
         A  Q  V  Q  I  D  R  L  I  N  G  R  L  T  A  L  N  A  Y  V
          L  R  F  R  L  I  G  L  L  M  V  V  *  L  L  *  M  L  M  S
        G  S  G  S  D  *  *  A  Y  *  W  S  F  N  C  F  K  C  L  C

26221   TCTCAACAGCTTAGTGATATTTCTCTTGTAAAATTTGGTGCTGCTTTAGCTATGGAGAAG   26280
         S  Q  Q  L  S  D  I  S  L  V  K  F  G  A  A  L  A  M  E  K
          L  N  S  L  V  I  F  L  L  *  N  L  V  L  L  *  L  W  R  R
        L  S  T  A  *  *  Y  P  S  C  K  I  W  C  C  F  S  Y  G  E

26281   GTTAATGAGTGTGTTAAAAGTCAATCTCCTCGTATTAATTTTTGTGGTAATGGTAATCAT   26340
         V  N  E  C  V  K  S  Q  S  P  R  I  N  F  C  G  N  G  N  H
          L  M  S  V  L  K  V  N  L  L  V  L  I  F  V  V  M  V  I  I
        G  *  *  V  C  *  K  S  I  S  S  Y  *  F  L  W  *  W  *  S

26341   ATTTTGTCATTAGTTCAAAATGCTCCTTATGGTTTGTTGTTTATGCATTTTAGTTATAAA   26400
         I  L  S  L  V  Q  N  A  P  Y  G  L  L  F  M  H  F  S  Y  K
          F  C  H  *  F  K  M  L  L  M  V  C  C  L  C  I  L  V  I  N
        Y  F  V  I  S  S  K  C  S  L  W  F  V  V  Y  A  F  *  L  *

26401   CCTATTTCTTTTAAAACTGTTTTAGTAAGTCCTGGTTTGTGTATATCAGGTGATGTAGGT   26460
         P  I  S  F  K  T  V  L  V  S  P  G  L  C  I  S  G  D  V  G
          L  F  L  L  K  L  F  *  *  V  L  V  C  V  Y  Q  V  M  *  V
        T  Y  F  F  *  N  C  F  S  K  S  W  F  V  Y  I  R  *  C  R
```

FIG. 2 CONT.

```
26461   ATTGCACCTAAACAAGGGTATTTTATTAAACATAATGATCATTGGATGTTCACTGGTAGT   26520
          I  A  P  K  Q  G  Y  F  I  K  H  N  D  H  W  M  F  T  G  S
           L  H  L  N  K  G  I  L  L  N  I  M  I  I  G  C  S  L  V  V
            Y  C  T  *  T  R  V  F  Y  *  T  *  *  S  L  D  V  H  W  *

26521   TCTTACTATTATCCTGAACCAATTTCAGATAAAAATGTTGTTTTTATGAATACTTGTTCT   26580
          S  Y  Y  Y  P  E  P  I  S  D  K  N  V  V  F  M  N  T  C  S
           L  T  I  I  L  N  Q  F  Q  I  K  M  L  F  L  *  I  L  V  L
            F  L  L  S  *  T  N  F  R  *  K  C  C  F  Y  E  Y  L  F

26581   GTTAATTTTACTAAAGCGCCTCTTGTTTATTTGAATCATTCTGTACCAAAATTGTCTGAT   26640
          V  N  F  T  K  A  P  L  V  Y  L  N  H  S  V  P  K  L  S  D
           L  I  L  L  K  R  L  L  F  I  *  I  I  L  Y  Q  N  C  L  I
            C  *  F  Y  *  S  A  S  C  L  F  E  S  F  C  T  K  I  V  *

26641   TTTGAATCTGAGTTATCTCATTGGTTTAAAAATCAAACATCCATTGCGCCTAATTTGACT   26700
          F  E  S  E  L  S  H  W  F  K  N  Q  T  S  I  A  P  N  L  T
           L  N  L  S  Y  L  I  G  L  K  I  K  H  P  L  R  L  I  *  L
            F  *  I  *  V  I  S  L  V  *  K  S  N  I  H  C  A  *  F  D

26701   TTAAATCTTCATACTATTAATGCTACTTTTTTAGATTTGTATTATGAGATGAATCTTATT   26760
          L  N  L  H  T  I  N  A  T  F  L  D  L  Y  Y  E  M  N  L  I
           *  I  F  I  L  L  M  L  L  F  *  I  C  I  M  R  *  I  L  F
            F  K  S  S  Y  Y  *  C  Y  F  F  R  F  V  L  *  D  E  S  Y

26761   CAAGAGTCTATTAAGTCTTTGAATAATAGTTATATCAATCTTAAAGATATAGGTACATAT   26820
          Q  E  S  I  K  S  L  N  N  S  Y  I  N  L  K  D  I  G  T  Y
           K  S  L  L  S  L  *  I  I  V  I  S  I  L  K  I  *  V  H  M
            S  R  V  Y  *  V  F  E  *  *  L  Y  Q  S  *  R  Y  R  Y  I

26821   GAAATGTATGTAAAATGGCCTTGGTATGTTTGGCTACTAATTTCTTTTTCATTTATAATA   26880
          E  M  Y  V  K  W  P  W  Y  V  W  L  L  I  S  F  S  F  I  I
           K  C  M  *  N  G  L  G  M  F  G  Y  *  F  L  F  H  L  *  Y
            *  N  V  C  K  M  A  L  V  C  L  A  T  N  F  F  F  I  Y  N

26881   TTCCTTGTATTGCTCTTTTTTATATGTTGTTGTACTGGTTGTGGTTCTGCATGTTTTAGT   26940
          F  L  V  L  L  F  F  I  C  C  C  T  G  C  G  S  A  C  F  S
           S  L  Y  C  S  F  L  Y  V  V  V  L  V  V  V  L  H  V  L  V
            I  P  C  I  A  L  F  Y  M  L  L  Y  W  L  W  F  C  M  F  *

26941   AAATGTCATAATTGTTGTGATGAGTATGGTGGTCATCATGATTTTGTTATCAAAACATCT   27000
          K  C  H  N  C  C  D  E  Y  G  G  H  H  D  F  V  I  K  T  S
           N  V  I  I  V  V  M  S  M  V  V  I  M  I  L  L  S  K  H  L
            *  M  S  *  L  L  *  *  V  W  W  S  S  *  F  C  Y  Q  N  I
```

FIG. 2 CONT.

```
27001  CATGATGATTAGAATCTCTTGTCAGATCTCATTAAATCTAAACTTTATTTATGGACGTTT  27060
        H  D  D  *  N  L  L  S  D  L  I  K  S  K  L  Y  L  W  T  F
         M  M  I  R  I  S  C  Q  I  S  L  N  L  N  F  I  Y  G  R  L
        S  *  *  L  E  S  L  V  R  S  H  *  I  *  T  L  F  M  D  V

27061  GGAGACCTAGCTACACACATTCTCTTGTTATTAGAGAATTTGGTGTTACAAACCTTGAAG  27120
        G  D  L  A  T  H  I  L  L  L  E  N  L  V  L  Q  T  L  K
         E  T  *  L  H  T  F  S  C  Y  *  R  I  W  C  Y  K  P  *  R
        W  R  P  S  Y  T  H  S  L  V  I  R  E  F  G  V  T  N  L  E

27121  ATTTGTGTCTAAAGTATAATTACTGTCAACCTATTGTTGGTTACTGTATTGTACCTTTAA  27180
        I  C  V  *  S  I  I  T  V  N  L  L  L  V  T  V  L  Y  L  *
         F  V  S  K  V  *  L  L  S  T  Y  C  W  L  L  Y  C  T  F  K
        D  L  C  L  K  Y  N  Y  C  Q  P  I  V  G  Y  C  I  V  P  L

27181  ATGTTTGGTGTCGCAAGTTTGGCAAATTTGCTTCTCACTTTACATTACGTAGTCACGATA  27240
        M  F  G  V  A  S  L  A  N  L  L  L  T  L  H  Y  V  V  T  I
         C  L  V  S  Q  V  W  Q  I  C  F  S  L  Y  I  T  *  S  R  Y
        N  V  W  C  R  K  F  G  K  F  A  S  H  F  T  L  R  S  H  D

27241  TTTCCCATAGTAATAATTTTGGTGTTGTAACTAGTTTTACTACTTATGGTAATACTGTTT  27300
        F  P  I  V  I  I  L  V  L  *  L  V  L  L  M  V  I  L  F
         F  P  *  *  *  F  W  C  C  N  *  F  Y  Y  L  W  *  Y  C  F
        I  S  H  S  N  N  F  G  V  V  T  S  F  T  T  Y  G  N  T  V

27301  CTGAGGCTGTGTCTAGATTAGTTGAATCAGCTTCTGAATTTATTGTTTGGCGTGCAGAGG  27360
        L  R  L  C  L  D  *  L  N  Q  L  L  N  L  L  F  G  V  Q  R
         *  G  C  V  *  I  S  *  I  S  F  *  I  Y  C  L  A  C  R  G
        S  E  A  V  S  R  L  V  E  S  A  S  E  F  I  V  W  R  A  E

27361  CACTTAATAAGTATGGTTGATTTATTTTTCAATGATACTGCTTGGTACATAGGACAGATT  27420
        H  L  I  S  M  V  D  L  F  F  N  D  T  A  W  Y  I  G  Q  I
         T  *  *  V  W  L  I  Y  F  S  M  I  L  L  G  T  *  D  R  F
        A  L  N  K  Y  G  *  F  I  F  Q  *  Y  C  L  V  H  R  T  D

27421  TTAGTTTTAGTTTTATTTTGTCTTATTTCTTTAATCTTTGTTGTTGCTTTTTTAGCAACT  27480
        L  V  L  V  L  F  C  L  I  S  L  I  F  V  V  A  F  L  A  T
         *  F  *  F  Y  F  V  L  F  L  *  S  L  L  L  L  F  *  Q  L
        F  S  F  S  F  I  L  S  Y  F  F  N  L  C  C  C  F  F  S  N

27481  ATTAAGCTTTGTATGCAACTTTGTGGTTTTTGTAATTTCTTTATTATTTCACCTTCGGCT  27540
        I  K  L  C  M  Q  L  C  G  F  C  N  F  F  I  I  S  P  S  A
         L  S  F  V  C  N  F  V  V  F  V  I  S  L  L  F  H  L  R  L
        Y  *  A  L  Y  A  T  L  W  F  L  *  F  L  Y  Y  F  T  F  G
```

FIG. 2 CONT.

```
27541  TACGTTTATAAAAGAGGTATGCAGTTGTATAAGTCTTATAGTGAACAAGTTATACCACCC  27600
          Y  V  Y  K  R  G  M  Q  L  Y  K  S  Y  S  E  Q  V  I  P  P
         T  F  I  K  E  V  C  S  C  I  S  L  I  V  N  K  L  Y  H  P
       L  R  L  *  K  R  Y  A  V  V  *  V  L  *  *  T  S  Y  T  T

27601  ACTTCAGATTATTTAATCTAAATCTAAACATTATGAATAAATCTTTTCTTCCTCAATTTA  27660
          T  S  D  Y  L  I  *  I  *  T  L  *  I  N  L  F  F  L  N  L
         L  Q  I  I  *  S  K  S  K  H  Y  E  *  I  F  S  S  S  I  Y
       H  F  R  L  F  N  L  N  L  N  I  M  N  K  S  F  L  P  Q  F

27661  CTTCTGATCAAGCTGTTACATTCTTAAAAGAATGGAATTTCTCTTTGGGTGTAATACTAC  27720
          L  L  I  K  L  L  H  S  *  K  N  G  I  S  L  W  V  *  Y  Y
         F  *  S  S  C  Y  I  L  K  R  M  E  F  L  F  G  C  N  T  T
       T  S  D  Q  A  V  T  F  L  K  E  W  N  F  S  L  G  V  I  L

27721  TTTTTATTACTATCATATTGCAGTTCGGTTATACGAGCCGTAGTATGTTTGTTTATCTTA  27780
          F  L  L  L  S  Y  C  S  S  V  I  R  A  V  V  C  L  F  I  L
         F  Y  Y  Y  H  I  A  V  R  L  Y  E  P  *  Y  V  C  L  S  Y
       L  F  I  T  I  I  L  Q  F  G  Y  T  S  R  S  M  F  V  Y  L

27781  TCAAGATGATTATTCTTTGGCTTATGTGGCCATTGACTATCACCTTGACTATATTTAATT  27840
          S  R  *  L  F  F  G  L  C  G  H  *  L  S  P  *  L  Y  L  I
         Q  D  D  Y  S  L  A  Y  V  A  I  D  Y  H  L  D  Y  I  *  L
       I  K  M  I  I  L  W  L  M  W  P  L  T  I  T  L  T  I  F  N

27841  GTTTTTATGCTTTGAATAATGCTTTCTTGCATTTTCTATAGTGTTACTATTATTTCTA   27900
          V  F  M  L  *  I  M  L  F  L  H  F  L  *  C  L  L  L  F  L
         F  L  C  F  E  *  C  F  S  C  I  F  Y  S  V  Y  Y  Y  F  Y
       C  F  Y  A  L  N  N  A  F  L  A  F  S  I  V  F  T  I  I  S

27901  TTGTTATATGGATTCTTTATTTTGTTAATAGTATTCGGCTTTTTATTAGAACTGGCAGTT  27960
          L  L  Y  G  F  F  I  L  L  I  V  F  G  F  L  L  E  L  A  V
         C  Y  M  D  S  L  F  C  *  *  Y  S  A  F  Y  *  N  W  Q  L
       I  V  I  W  I  L  Y  F  V  N  S  I  R  L  F  I  R  T  G  S

27961  GGTGGAGTTTTAATCCAGAGACCAATAATCTTATGTGTATTGATATGAAAGGCAAGATGT  28020
          G  G  V  L  I  Q  R  P  I  I  L  C  V  L  I  *  K  A  R  C
         V  E  F  *  S  R  D  Q  *  S  Y  V  Y  *  Y  E  R  Q  D  V
       W  W  S  F  N  P  E  T  N  N  L  M  C  I  D  M  K  G  K  M

28021  TTGTTAGGCCAGTTATTGAGGACTATCACACATTAACTGCTACTGTTATTCGTGGTCATC  28080
          L  L  G  Q  L  L  R  T  I  T  H  *  L  L  L  L  F  V  V  I
         C  *  A  S  Y  *  G  L  S  H  I  N  C  Y  C  Y  S  W  S  S
       F  V  R  P  V  I  E  D  Y  H  T  L  T  A  T  V  I  R  G  H
```

FIG. 2 CONT.

```
28081  TTTATATACAGGGTGTCAAACTTGGCACTGGTTATACTCTTTCAGATTTGCCCGTATATG  28140
        F  I  Y  R  V  S  N  L  A  L  V  I  L  F  Q  I  C  P  Y  M
         L  Y  T  G  C  Q  T  W  H  W  L  Y  S  F  R  F  A  R  I  C
          L  Y  I  Q  G  V  K  L  G  T  G  Y  T  L  S  D  L  P  V  Y

28141  TTACTGTAGCTAAGGTGCAAGTACTTTGTACCTATAAACGTGCCTTTTTAGATAAGTTAG  28200
        L  L  *  L  R  C  K  Y  F  V  P  I  N  V  P  F  *  I  S  *
         Y  C  S  *  G  A  S  T  L  Y  L  *  T  C  L  F  R  *  V  R
          V  T  V  A  K  V  Q  V  L  C  T  Y  K  R  A  F  L  D  K  L

28201  ATGTTAATAGTGGTTTTGCTGTTTTTGTTAAGTCTAAAGTTGGTAACTATCGTTTACCGT  28260
        M  L  I  V  V  L  L  F  L  L  S  L  K  L  V  T  I  V  Y  R
         C  *  *  W  F  C  C  F  C  *  V  *  S  W  *  L  S  F  T  V
          D  V  N  S  G  F  A  V  F  V  K  S  K  V  G  N  Y  R  L  P

28261  CTAGTAAACCTAGTGGTATGGATACTGCCTTGTTAAGAGCTTAAATCTAAACTATTAGGA  28320
        L  V  N  L  V  V  W  I  L  P  C  *  E  L  K  S  K  L  L  G
         *  *  T  *  W  Y  G  Y  C  L  V  K  S  L  N  L  N  Y  *  D
          S  S  K  P  S  G  M  D  T  A  L  L  R  A  *  I  *  T  I  R

28321  TGTCTTATACTCCCGGTCATTATGCTGGAAGTAGAAGCTCCTCTGGAAATCGTTCAGGAA  28380
        C  L  I  L  P  V  I  M  L  E  V  E  A  P  L  E  I  V  Q  E
         V  L  Y  S  R  S  L  C  W  K  *  K  L  L  W  K  S  F  R  N
          M  S  Y  T  P  G  H  Y  A  G  S  R  S  S  S  G  N  R  S  G

28381  TCCTCAAGAAAACTTCTTGGGCTGACCAATCTGAGCGAAATTACCAAACCTTTAATAGAG  28440
        S  S  R  K  L  L  G  L  T  N  L  S  E  I  T  K  P  L  I  E
         P  Q  E  N  F  L  G  *  P  I  *  A  K  L  P  N  L  *  *  R
          I  L  K  K  T  S  W  A  D  Q  S  E  R  N  Y  Q  T  F  N  R

28441  GCAGAAAAACCCAACCTAAATTCACTGTGTCTACTCAACCACAAGGAAATACTATCCCAC  28500
        A  E  K  P  N  L  N  S  L  C  L  L  N  H  K  E  I  L  S  H
         Q  K  N  P  T  *  I  H  C  V  Y  S  T  T  R  K  Y  Y  P  T
          G  R  K  T  Q  P  K  F  T  V  S  T  Q  P  Q  G  N  T  I  P

28501  ATTATTCCTGGTTCTCCGGGATCACTCAATTTCAAAAGGTAGAGACTTTAAATTTTCAG  28560
        I  I  P  G  S  P  G  S  L  N  F  K  K  V  E  T  L  N  F  Q
         L  F  L  V  L  R  D  H  S  I  S  K  R  *  R  L  *  I  F  R
          H  Y  S  W  F  S  G  I  T  Q  F  Q  K  G  R  D  F  K  F  S

28561  ATGGTCAAGGAGTTCCCATTGCTTTCGGAGTACCCCCTTCTGAAGCAAAAGGATATTGGT  28620
        M  V  K  E  F  P  L  L  S  E  Y  P  L  L  K  Q  K  D  I  G
         W  S  R  S  S  H  C  F  R  S  T  P  F  *  S  K  R  I  L  V
          D  G  Q  G  V  P  I  A  F  G  V  P  P  S  E  A  K  G  Y  W
```

FIG. 2 CONT.

```
28621  ATAGACACAGCCGGCGTTCTTTTAAAACAGCTGATGGTCAACAAAAGCAGTTGTTACCGA  28680
        I  D  T  A  G  V  L  L  K  Q  L  M  V  N  K  S  S  C  Y  R
         *  T  Q  P  A  F  F  *  N  S  *  W  S  T  K  A  V  V  T  E
          Y  R  H  S  R  R  S  F  K  T  A  D  G  Q  Q  K  Q  L  L  P

28681  GATGGTATTTCTACTATCTCGGTACCGGCCCATATGCCAATGCATCCTATGGTGAATCCC  28740
        D  G  I  S  T  I  S  V  P  A  H  M  P  M  H  P  M  V  N  P
         M  V  F  L  L  S  R  Y  R  P  I  C  Q  C  I  L  W  *  I  P
          R  W  Y  F  Y  Y  L  G  T  G  P  Y  A  N  A  S  Y  G  E  S

28741  TCGAAGGGGTCTTCTGGGTTGCTAATCACCAAGCTGACACTTCTACTCCCTCCGATGTTT  28800
        S  K  G  S  S  G  L  L  I  T  K  L  T  L  L  P  P  M  F
         R  R  G  L  L  G  C  *  S  P  S  *  H  F  Y  S  L  R  C  F
          L  E  G  V  F  W  V  A  N  H  Q  A  D  T  S  T  P  S  D  V

28801  CGTCAAGGGATCCTACTACTCAAGAAGCTATCCCTACTAGGTTTCCGCCTGGTACGATTT  28860
        R  Q  G  I  L  L  L  K  K  L  S  L  L  G  F  R  L  V  R  F
         V  K  G  S  Y  Y  S  R  S  Y  P  Y  *  V  S  A  W  Y  D  F
          S  S  R  D  P  T  T  Q  E  A  I  P  T  R  F  P  P  G  T  I

28861  TGCCTCAAGGCTATTATGTTGAAGGCTCAGGAAGGTCTGCTTCTAATAGTCGACCAGGTT  28920
        C  L  K  A  I  M  L  K  A  Q  E  G  L  L  L  I  V  D  Q  V
         A  S  R  L  L  C  *  R  L  R  K  V  C  F  *  *  S  T  R  F
          L  P  Q  G  Y  Y  V  E  G  S  G  R  S  A  S  N  S  R  P  G

28921  CACGTTCTCAATCACGTGGACCCAATAATCGTTCATTAAGTAGAAGTAATTCTAATTTTA  28980
        H  V  L  N  H  V  D  P  I  I  V  H  *  V  E  V  I  L  I  L
         T  F  S  I  T  W  T  Q  *  S  F  I  K  *  K  *  F  *  F  *
          S  R  S  Q  S  R  G  P  N  N  R  S  L  S  R  S  N  S  N  F

28981  GACATTCAGATTCTATAGTAAAACCTGATATGGCTGATGAGATCGCTAATCTTGTTTTAG  29040
        D  I  Q  I  L  *  *  N  L  I  W  L  M  R  S  L  I  L  F  *
         T  F  R  F  Y  S  K  T  *  Y  G  *  *  D  R  *  S  C  F  S
          R  H  S  D  S  I  V  K  P  D  M  A  D  E  I  A  N  L  V  L

29041  CCAAGCTTGGTAAAGATTCTAAACCTCAGCAAGTCACTAAGCAAAATGCCAAGGAAATCA  29100
        P  S  L  V  K  I  L  N  L  S  K  S  L  S  K  M  P  R  K  S
         Q  A  W  *  R  F  *  T  S  A  S  H  *  A  K  C  Q  G  N  Q
          A  K  L  G  K  D  S  K  P  Q  Q  V  T  K  Q  N  A  K  E  I

29101  GGCATAAAATTTTAACAAAACCTCGCCAAAAGCGAACTCCTAATAAACATTGTAATGTTC  29160
        G  I  K  F  *  Q  N  L  A  K  S  E  L  L  I  N  I  V  M  F
         A  *  N  F  N  K  T  S  P  K  A  N  S  *  *  T  L  *  C  S
          R  H  K  I  L  T  K  P  R  Q  K  R  T  P  N  K  H  C  N  V
```

FIG. 2 CONT.

```
29161  AACAGTGTTTTGGTAAAAGAGGACCTTCTCAAAATTTTGGTAATGCTGAAATGTTAAAGC  29220
        N  S  V  L  V  K  E  D  L  L  K  I  L  V  M  L  K  C  *  S
         T  V  F  W  *  K  R  T  F  S  K  F  W  *  C  *  N  V  K  A
          Q  Q  C  F  G  K  R  G  P  S  Q  N  F  G  N  A  E  M  L  K

29221  TTGGTACTAATGATCCTCAGTTTCCTATTCTTGCAGAATTAGCTCCTACACCAGGTGCTT  29280
        L  V  L  M  I  L  S  F  L  F  L  Q  N  *  L  L  H  Q  V  L
         W  Y  *  *  S  S  V  S  Y  S  C  R  I  S  S  Y  T  R  C  F
          L  G  T  N  D  P  Q  F  P  I  L  A  E  L  A  P  T  P  G  A

29281  TTTTCTTTGGTTCTAAATTAGACTTGGTTAAAAGAGATTCCGAGGCTGACTCACCTGTTA  29340
        F  S  L  V  L  N  *  T  W  L  K  E  I  P  R  L  T  H  L  L
         F  L  W  F  *  I  R  L  G  *  K  R  F  R  G  *  L  T  C  *
          F  F  F  G  S  K  L  D  L  V  K  R  D  S  E  A  D  S  P  V

29341  AAGATGTTTTTGAACTTCATTATTCTGGTTCTATTAGGTTTGATAGTACTTTACCAGGCT  29400
        K  M  F  L  N  F  I  I  L  V  L  L  G  L  I  V  L  Y  Q  A
         R  C  F  *  T  S  L  F  W  F  Y  *  V  *  *  Y  F  T  R  L
          K  D  V  F  E  L  H  Y  S  G  S  I  R  F  D  S  T  L  P  G

29401  TTGAGACAATTATGAAAGTTCTTGAAGAGAATTTAAATGCTTACGTTAATTCTAATCAGA  29460
        L  R  Q  L  *  K  F  L  K  R  I  *  M  L  T  L  I  L  I  R
         *  D  N  Y  E  S  S  *  R  E  F  K  C  L  R  *  F  *  S  E
          F  E  T  I  M  K  V  L  E  E  N  L  N  A  Y  V  N  S  N  Q

29461  ACACTGATTCTGATTCGTTGAGTTCTAAACCTCAGCGTAAAAGAGGTGTTAAACAATTAC  29520
        T  L  I  L  I  R  *  V  L  N  L  S  V  K  E  V  L  N  N  Y
         H  *  F  *  F  V  E  F  *  T  S  A  *  K  R  C  *  T  I  T
          N  T  D  S  D  S  L  S  S  K  P  Q  R  K  R  G  V  K  Q  L

29521  CAGAACAGTTTGACTCTCTTAATTTAAGTGCTGGTACTCAGCACATTTCAAATGATTTTA  29580
        Q  N  S  L  T  L  L  I  *  V  L  V  L  S  T  F  Q  M  I  L
         R  T  V  *  L  S  *  F  K  C  W  Y  S  A  H  F  K  *  F  Y
          P  E  Q  F  D  S  L  N  L  S  A  G  T  Q  H  I  S  N  D  F

29581  CTCCTGAGGATCATAGTTTACTTGCTACTCTTGATGATCCTTATGTAGAAGACTCTGTTG  29640
        L  L  R  I  I  V  Y  L  L  L  M  I  L  M  *  K  T  L  L
         S  *  G  S  *  F  T  C  Y  S  *  *  S  L  C  R  R  L  C  C
          T  P  E  D  H  S  L  L  A  T  L  D  D  P  Y  V  E  D  S  V

29641  CTTAATGAGAATGAATCCTAATTCGACACTAGGTGGTAACCCCTCGCTATTATTCGGAAT  29700
        L  N  E  N  E  S  *  F  D  T  R  W  *  P  L  A  I  I  R  N
         L  M  R  M  N  P  N  S  T  L  G  G  N  P  S  L  L  F  G  I
          A  *  *  E  *  I  L  I  R  H  *  V  V  T  P  R  Y  Y  S  E
```

FIG. 2 CONT.

```
29701  AGGACACTCTCTATCAGAATGAATTCTTGCTGTAATAACAGATAGAGTAGGTTGTTACAG  29760
         R  T  L  S  I  R  M  N  S  C  C  N  N  R  *  S  R  L  L  Q
          G  H  S  L  S  E  *  I  L  A  V  I  T  D  R  V  G  C  Y  R
        *  D  T  L  Y  Q  N  E  F  L  L  *  *  Q  I  E  *  V  V  T

29761  ACTATATATTAATTAGTAGAAATTTTATATTTAGACATTTGATTGTTAGAGTAGTTATAA  29820
         T  I  Y  *  L  V  E  I  L  Y  L  D  I  *  L  L  E  *  L  *
          L  Y  I  N  *  *  K  F  Y  I  *  T  F  D  C  *  S  S  Y  K
        D  Y  I  L  I  S  R  N  F  I  F  R  H  L  I  V  R  V  V  I

29821  GGTTTAGCTGTAGTATAAACGCCTCCGGGAAGAGCTATCAATTGTAGTGTTTAATATATA  29880
         G  L  A  V  V  *  T  P  P  G  R  A  I  N  C  S  V  *  Y  I
          V  *  L  *  Y  K  R  L  R  E  E  L  S  I  V  V  F  N  I  Y
        R  F  S  C  S  I  N  A  S  G  K  S  Y  Q  L  *  C  L  I  Y

29881  TATTAGTATATGATTGAAATTAATTATAGCCTTTTGGAGGAATTACAAAAAAAAAAAAAA  29940
         Y  *  Y  M  I  E  I  N  Y  S  L  L  E  E  L  Q  K  K  K  K
          I  S  I  *  L  K  L  I  I  A  F  W  R  N  Y  K  K  K  K  K
        I  L  V  Y  D  *  N  *  L  *  P  F  G  G  I  T  K  K  K  K

29941  AA                                                            29942

K
```

FIG. 2 CONT.

```
SEQ:   1   CTTATTCTCGCTTAACGCAGGCATGGCAGATAGTCGAATGCTAGAGAACAGTCTAGAGTA   60
             Y  S  R  I  A  D  T  G  D  I  L  K  R  D  R  T  L  D  *
            I  L  A  F  Q  T  R  V  T  *  *  S  V  I  E  Q  *  I  E
          F  L  L  S  N  R  G  Y  R  R  D  A  *  S  R  K  D  S  R  M

61   ATTTAGATTTGAAAAATTTGTTCTAAGGGACAATAGGTACGAACACTCACACCAAATTAG  120
             *  I  *  V  K  *  V  L  N  G  T  I  W  Q  S  H  P  K  I
            N  F  R  F  K  K  F  L  I  G  Q  *  G  H  K  H  T  N  L
          L  D  L  S  K  L  C  S  E  R  N  D  M  S  T  L  T  T  *  D

121   TATTAGAACATAAAATGAAAGGTGTGAAAAGTAGAGAGACGGTCACTGCACAACCAACAG  180
             M  I  K  Y  K  V  V  K  W  V  K  *  R  E  A  L  S  T  N  T  T
            *  L  R  T  N  *  K  G  C  K  E  D  R  Q  W  H  R  T  P  Q
          Y  D  Q  I  K  S  E  V  S  K  M  E  R  G  T  V  H  Q  N  D

181   GAGTCGCAGGGAGGGTATCCAGCGTTACTAATTTTGGTCGTTTATGCCAGAGCCGAAGTT  240
             R  L  T  G  G  M  P  R  L  S  *  F  W  C  I  R  D  R  S  *
            G  *  R  G  E  W  L  D  C  H  N  F  G  A  F  V  T  E  A  E
          E  A  D  R  G  Y  T  A  I  I  L  V  L  L  Y  P  R  P  K  L

241   CACCCGCGGTCTTAAAGCAACCGACGAAGGCCTACGTCGCCTCCTCAACCGATCAGGATA  300
             T  P  A  L  I  E  N  A  A  E  P  H  L  P  P  T  P  *  D  *
            L  P  R  W  F  K  T  P  Q  K  R  I  C  R  L  L  Q  S  T  R
          H  A  G  S  N  R  Q  S  S  G  S  A  A  S  S  N  A  L  G  I

301   CTTCAGTCTACTCCCACCCAATACGGGGAGATGACCAGTTCGCTACCTTTCACAACCTAA  360
             S  T  L  H  P  H  T  I  G  R  *  Q  D  L  S  P  F  H  Q  I
            H  L  *  I  L  T  P  *  A  G  R  S  T  L  R  H  F  T  N  S
          F  D  S  S  P  P  N  H  G  E  V  P  *  A  I  S  L  T  P  N

361   GCAAATACTATTAGTACACTTCTATCTAACAGCGACGTAAGAACCTGTTCTTACCGTACA  420
             R  K  H  Y  D  H  S  S  L  N  D  S  C  E  Q  V  L  I  A  H
            E  N  I  I  I  M  H  L  Y  I  T  A  A  N  K  S  L  F  P  M
          T  *  S  L  *  T  F  I  S  Q  R  Q  M  R  P  C  S  H  C  T

421   CGTCAGTTTAGAATAGGCACTATAAAAACAAGTACTTCTAGATGTACAACATCTTCAAGA  480
             A  T  L  D  *  G  H  Y  K  Q  E  H  L  D  V  H  Q  L  L  E
            H  L  *  I  K  D  T  I  N  K  N  M  F  I  *  M  N  Y  F  N
          C  D  F  R  I  R  S  I  K  T  *  S  S  R  C  T  T  S  T  R

481   TTGATTTTGTCGGCATTTCAGGCCATGCCGTTAAAATTAATTTAGTGGAAACGTATCGAA  540
             L  *  F  L  R  L  T  R  Y  P  L  K  L  *  I  V  K  A  Y  S
            *  S  F  C  G  Y  L  G  T  R  C  N  *  N  F  *  R  Q  M  A
          V  L  V  A  T  F  D  P  V  A  I  K  I  L  D  G  K  C  L  K
```

FIG. 3

```
541  CCCACCAAAAGGATTTCCCATACAATACCCGAACAAGGCAAGTATGTTCTGATTTGCAAT  600
       P  H  N  E  *  L  T  H  *  P  S  T  G  N  M  C  S  *  V  N
      Q  T  T  K  R  F  P  I  N  H  A  Q  E  T  *  V  L  S  F  T
       P  P  K  G  L  P  Y  T  I  P  K  N  R  E  Y  L  V  L  R  *

601  ACAACATGTAGTAGAAAGATACTGATGTAGATGATGATTAAAACCACTTCTAAAAAACCC  660
       H  Q  V  D  D  K  *  S  *  M  *  *  *  N  Q  H  L  N  K  P
      I  N  Y  M  M  K  R  H  S  C  R  S  S  I  K  T  F  I  K  Q
       T  T  C  *  R  E  I  V  V  D  V  V  L  K  P  S  S  K  K  P

661  AACCTAACATGGAAAACCAAAATACGGTAGAATACAAGTGTTTACCAAAGTTAAGACATC  720
       N  S  Q  V  K  Q  N  *  A  M  K  H  E  C  I  T  E  I  R  Y
      T  P  N  Y  R  K  T  K  H  W  R  I  N  V  F  P  K  L  E  T
       Q  I  T  G  K  P  K  I  G  D  *  T  *  L  H  N  *  N  Q  L

721  CAACATATAACTTCTCTCACTAAATTATTAAAGTTTAAAATTTAAACTACTAATACTAAA  780
       T  T  Y  Q  L  S  H  N  L  L  K  L  N  *  I  Q  H  N  H  N
      P  Q  I  N  F  L  T  I  *  Y  N  *  I  K  F  K  I  I  I  I
       N  Y  I  S  S  L  S  K  I  I  E  F  K  L  N  S  S  *  S  K

781  ATCACATCTTCTACGAATACGACTCCAAGTACGACTCGGATTTCCATTTATAAGTGTTTT  840
       *  H  L  L  H  K  H  Q  P  E  H  Q  A  *  L  Y  I  N  V  F
      K  T  Y  F  I  S  I  S  L  N  M  S  L  R  F  T  F  I  *  L
       L  T  S  S  A  *  A  S  T  *  A  S  G  L  P  L  Y  E  C  F

841  TCGAATACGAAATGAATCTGTTATAGCACCATAATTTGGGCATGAAAAACATCTGGTCAT  900
       L  K  H  K  V  *  V  I  D  H  Y  *  V  R  V  K  Q  L  G  T
      F  S  I  S  *  K  S  L  I  T  T  N  F  G  Y  K  K  Y  V  L
       A  *  A  K  S  L  C  Y  R  P  I  L  G  T  S  K  T  S  W  Y

901  ACCAACACTGATAAGACCATTTAATCGTCTAACAGAAGTTCGAATACCAGTAATAAGAAA  960
       H  N  H  S  N  Q  Y  I  L  L  N  D  E  L  K  H  D  N  N  K
      I  T  T  V  I  R  T  F  *  C  I  T  K  L  S  I  T  M  I  R
       P  Q  S  *  E  P  L  N  A  S  Q  R  *  A  *  P  *  *  E  K

961  CGTTCTATACTCTGTTTTCGTCAGACATACCGAACGGTTAACACTGAAACTATAACATCA  1020
       A  L  Y  S  V  F  A  T  Q  I  A  Q  W  N  H  S  Q  Y  Q  L
      Q  L  I  H  S  L  L  L  R  Y  P  K  G  I  T  V  K  I  N  Y
       C  S  I  L  C  F  C  D  T  H  S  A  L  Q  S  K  S  I  T  T

1021 CCGAACCGTACATCAAGCACTAAGTGCTAAACAATACGCGGACGTCTGATATCGATGATA  1080
       P  K  A  H  L  E  H  N  V  I  Q  *  A  G  A  S  *  L  *  *
      H  S  P  M  Y  N  T  I  *  S  K  N  H  A  Q  L  S  Y  S  S
       A  Q  C  T  T  R  S  E  R  N  T  I  R  R  C  V  I  A  V  ]
```

FIG. 3 CONT'D

```
1081  AACACCATAATTTATACAACGTGTTGGATGTCTTCTACATCATCTACCTCTACATCAATA  1140
       K  H  Y  *  I  H  Q  V  V  *  L  L  H  L  L  H  L  *
        N  T  T  N  F  I  N  C  L  R  C  F  I  Y  Y  I  S  I  Y  N
         Q  P  I  L  Y  T  A  C  G  V  S  S  T  T  S  P  S  T  T  I

1141  TGCACTTGGACATGTAAATAATAGACGACTACGTTATCAAAATTTCGAAGGATCAAACTA  1200
       V  H  V  Q  V  N  I  I  Q  Q  H  L  L  K  L  A  E  *  N  S
        Y  T  F  R  Y  M  *  *  R  S  I  C  Y  N  *  L  K  R  T  Q
         R  S  G  T  C  K  N  D  A  S  A  I  T  K  F  S  G  L  K  I

1201  CTTTCAATACTGAGTATACCTACTAAAAAGATAATTTAGATATATATTACAACTAAACAC  1260
       S  L  *  S  E  Y  P  H  N  K  *  *  I  *  I  Y  H  Q  N  T
        H  F  N  H  S  M  H  I  I  K  R  N  F  R  Y  I  I  N  I  Q
         F  T  I  V  *  I  S  S  K  E  I  L  D  I  Y  L  T  S  K  H

1261  ACTAACACCAAAACAATACGTCATACCAATACATCTAACAAAATTACTATTAACACTAAA  1320
       H  N  H  N  Q  *  A  T  H  N  H  L  N  N  *  H  Y  N  H  N
        T  I  T  T  K  N  H  L  I  T  I  Y  I  T  K  I  I  I  T  I
         S  Q  P  K  T  I  C  Y  P  *  T  S  Q  K  L  S  L  Q  S  K

1321  AATACCAACCCAAAGTCCATTATACTACCTACCAAAAAGAACAGGTAACACAACATGTCA  1380
       K  H  N  P  K  L  Y  Y  S  P  H  N  K  K  D  M  T  N  Y  L
        K  I  T  P  N  *  T  I  H  H  I  T  K  R  T  W  Q  T  T  C
         *  P  Q  T  E  P  L  I  I  S  P  K  E  Q  G  N  H  Q  V  T

1381  AATACTGAGATCGCTTCAATTTCGGGTTAGTAGACCACAATAAGGACTTTTAGGACACAA  1440
       K  H  S  *  R  L  *  L  G  I  M  Q  H  *  E  Q  F  D  Q  T
        N  I  V  R  A  F  N  F  G  L  *  R  T  N  N  R  F  I  R  H
         *  S  E  L  S  T  L  A  W  D  D  P  T  I  G  S  F  G  T  N

1441  TAAATGATTATCATGACTATGACAATTGGTACTAAGAAAATTAAACATACCAATAAGACA  1500
       I  *  *  Y  Y  Q  Y  Q  *  G  H  N  K  *  N  T  H  N  N  Q
        *  K  S  I  T  S  I  S  N  V  M  I  R  K  I  Q  I  T  I  R
         N  V  L  L  V  S  V  T  L  W  S  E  K  L  K  Y  P  *  E  T

1501  GTGTGGTAAACCAAGAACATATATAACCAGCGGCGCAGGACCTAACACCTAAGGATATTA  1560
       *  V  M  Q  N  K  Y  I  N  T  A  A  D  Q  I  T  S  E  *  L
        D  C  W  K  T  R  T  Y  I  P  R  R  T  R  S  Q  P  N  R  Y
         V  G  N  P  E  Q  I  Y  Q  D  G  R  G  P  N  H  I  G  I  I

1561  ATTTAGAAGTCAGTTCAGAATACTACTAAACCAAATAAGTCCACATCATCCAACATTTAG  1620
       *  I  K  L  *  T  K  H  H  N  P  K  N  L  H  L  L  N  Y  I
        N  F  R  *  D  L  R  I  I  I  Q  N  I  *  T  Y  Y  T  T  F
         L  D  E  T  L  D  *  S  S  K  T  *  E  P  T  T  P  Q  L  D
```

FIG. 3 CONT'D

```
1621  ATAACAATTTCTTTGACGAGAATAATGAGTACGTGAAATGAATCTAATACAAGTTACATT   1680
       *  Q  *  L  F  Q  E  *  *  E  H  V  K  S  L  N  H  E  I  Y
         R  N  N  F  F  S  S  K  N  S  M  C  K  V  *  I  I  N  L  T
           I  T  L  S  V  A  R  I  V  *  A  S  *  K  S  *  T  *  H  L

1681  CACACCATTAGAACTTGTTTTAGTATAAGAACCGCAATTATTAAGAACCACATCCGTTGA   1740
       T  H  Y  D  Q  V  F  D  Y  E  Q  R  *  Y  N  K  T  Y  A  V
         L  T  T  I  K  F  L  I  M  N  K  A  N  I  I  R  P  T  P  L
           H  P  L  R  S  C  F  *  I  R  P  T  L  L  E  Q  H  L  C  S

1741  CAACGAATTATCTCCACTAATATTATACGAAGATTTTTTATAACTGAACAAACAATTCGC   1800
       T  A  *  Y  L  H  N  Y  Y  A  E  L  F  Y  Q  S  T  Q  *  A
         Q  Q  K  I  S  T  I  I  I  H  K  *  F  I  N  V  Q  K  N  L
           N  S  L  L  P  S  *  L  I  S  R  F  F  I  S  K  N  T  L  R

1801  AGCACGACTAAAACGAACGTTCAAACGTCAAACACCTCTACCAAAACATGGAAAAAATGA   1860
       D  H  Q  N  Q  K  C  T  Q  L  K  H  L  H  N  Q  V  K  K  V
         T  T  S  I  K  S  A  L  K  C  N  T  S  I  T  K  Y  R  K  *
           R  A  S  K  A  Q  L  N  A  T  Q  P  S  P  K  T  G  K  K  S

1861  TCTACCAAATTAAGGGGCATCAATAATAGATTAAGTCTCACCATAAAAGAAATGTAGAAA   1920
       L  H  N  L  E  G  Y  N  N  D  L  E  S  H  Y  K  R  *  M  K
         *  I  T  *  N  G  T  T  I  I  *  N  L  T  T  N  E  K  C  R
           S  P  K  I  G  R  L  *  *  R  I  *  L  P  I  K  K  V  D  K

1921  CTACAGAGTTAAAAGTGTTCTTCAAAGACTATACACAAATTTTTACACATAAAACAAATA   1980
       S  T  E  I  K  V  L  L  K  Q  Y  T  N  L  F  T  Y  K  T  *
         Q  H  R  L  K  *  L  F  N  R  I  H  T  *  F  H  T  N  Q  K
           I  D  *  N  E  C  S  T  E  S  I  H  K  F  I  H  I  K  N  I

1981  CCTGTCTCAAAGTCAACGATGTAAAATATATCTCGTAATACAATTATCCAACCAATGAGT   2040
       P  C  L  K  L  Q  *  M  K  Y  L  A  N  H  *  Y  T  P  *  E
         H  V  S  N  *  N  S  C  K  I  Y  L  M  I  N  I  P  Q  N  S
           S  L  T  E  T  A  V  N  *  I  S  C  *  T  L  L  N  T  V  *

2041  TAAATTCAATAACCCATGATGTGAACAATTATTTTACCAATTAACCAAATTATGGTACAA   2100
       I  *  T  I  P  Y  *  V  Q  *  Y  F  P  *  N  T  *  Y  W  T
         L  K  L  *  Q  T  S  C  K  N  I  F  H  N  I  P  K  I  G  H
           N  L  N  N  P  V  V  S  T  L  L  I  T  L  Q  N  L  V  M  N

2101  TCTACGATCACGTGGACGATGTCCGACCGAAGAAATGGTTAATAACTTACCAGAAAAACA   2160
       L  H  *  H  V  Q  *  L  S  A  E  K  G  I  I  S  H  D  K  Q
         *  I  S  T  C  R  S  C  A  P  K  K  V  L  *  Q  I  T  K  K
           S  A  L  A  G  A  V  P  Q  S  R  *  W  N  N  F  P  R  K  T
```

FIG. 3 CONT'D

```
2161  TCATAGAGTTCGGTTGAAATTAAAACAACGAAATTATGGACTAATACGATTTTAAAATCA  2220
        L  I  E  L  W  S  *  N  Q  Q  K  L  V  Q  N  H  *  F  K  L
       Y  Y  R  L  G  V  K  I  K  N  S  *  Y  R  I  I  S  F  N  *
         T  D  *  A  L  K  L  K  T  A  K  I  G  S  *  A  L  I  K  T

2221  ATTATTTAAAATGTGAAAAAAATTCAATAATAATCTCACACAATGTCAACTACAAAATTT  2280
        *  Y  I  K  C  K  K  *  T  I  L  T  H  *  L  Q  H  K  L
       N  I  F  K  V  S  K  K  L  *  *  *  L  T  N  C  N  I  N  *
         L  L  N  *  V  K  K  L  N  N  N  S  H  T  V  T  S  T  K  F

2281  TCTATACGGACAAGAATTTTGATAATTACCAAATCAAACATAACATCCGTTATTCAAAAT  2340
        L  Y  A  Q  E  *  F  *  *  H  N  L  K  Y  Q  L  C  Y  T  K
       F  I  H  R  N  K  F  S  N  I  T  *  N  T  N  Y  A  I  L  K
         S  I  G  T  R  L  V  I  L  P  K  T  Q  I  T  P  L  L  N  *

2341  ATTGCAATCATGTCCCAATTAAGGACCAAAACAAAATGGTACATTACGTGTCCTTGTTGT  2400
        Y  R  *  Y  L  T  L  E  Q  N  Q  K  V  M  Y  H  V  P  V  V
       I  V  N  T  C  P  *  N  R  T  K  N  *  W  T  I  C  L  F  L
         L  T  L  V  P  N  I  G  P  K  T  K  G  H  L  A  C  S  C  C

2401  TTAAATAAAAAAACTTCCGCAACGTCTTAGACAATATCATCTTCTACTACAATAACTCTT  2460
        F  K  N  K  Q  L  R  Q  L  I  Q  *  L  L  L  H  H  *  Q  S
       L  N  I  K  K  F  A  N  C  F  R  N  Y  Y  F  I  I  N  N  L
         I  *  K  K  S  P  T  A  S  D  T  I  T  S  S  S  T  I  S  F

2461  ACAGTTTAGAAGAAATAGTAGAATACTCATAACAGTTGGTGGATTTAGACATCTTTTTTA  2520
        H  *  I  K  K  I  M  K  H  T  N  D  V  V  *  I  Q  L  F  F
       I  D  F  R  R  *  *  R  I  L  I  T  L  W  R  F  Y  F  F
         T  L  D  E  K  D  D  *  S  Y  Q  *  G  G  L  D  T  S  F  I

2521  AACATAATATCTATTATACATGTACCCATTCACACCACTATTTAAAAAGGGATAACAGTA  2580
        K  Y  *  L  Y  Y  T  C  P  Y  T  H  H  Y  I  K  G  *  Q  *
       N  T  N  Y  I  I  H  V  H  T  L  T  T  I  F  K  E  R  N  D
         Q  I  I  S  L  I  Y  M  P  L  H  P  S  L  N  K  G  I  T  M

2581  CTTACTATTTTTATAAACAGAAAATCTAGTCCGAACCGCAAAAGGTACACGTCCATCTTT  2640
        S  H  Y  F  Y  K  D  K  L  D  P  K  A  N  E  M  H  L  Y  F
       H  I  I  F  I  N  T  K  *  I  L  S  P  T  K  W  T  C  T  S
         F  S  L  F  I  Q  R  K  S  *  A  Q  R  K  G  H  A  P  L  F

2641  TCAATTAAAATTGCTCTTTGGACAACAATACCTCTAAGGCAGAAACTACTGTCAATTCCA  2700
        L  *  N  *  R  S  V  Q  Q  *  P  S  E  T  K  S  S  L  *  P
       F  N  I  K  V  L  F  R  N  N  H  L  N  R  R  Q  H  C  N  L
         T  L  K  L  S  F  G  T  T  I  S  I  G  D  K  I  V  T  L  T
```

FIG. 3 CONT'D

```
2701  ATACAAACTAAATCTAAGATGAAAACTACTATAAAATCCATTTCAAACAAGTCTTAAACT  2760
       *  T  Q  N  L  N  *  K  Q  H  Y  K  L  Y  L  K  N  L  I  Q
         N  H  K  I  *  I  R  S  K  I  I  N  *  T  F  N  T  *  F  K
            I  N  S  K  S  E  V  K  S  S  I  K  P  L  T  Q  E  S  N  S

2761  TCATCTTTTCCCACAATGACATCTACTAAAACAACGACAACAAACACTACGATATCTCTT  2820
       L  L  F  P  H  *  Q  L  H  N  Q  Q  Q  K  H  H  *  L  S
         F  Y  F  L  T  N  S  Y  I  I  K  N  S  N  N  T  I  S  Y  L
            T  S  F  P  T  V  T  S  S  K  T  A  T  T  Q  S  A  I  S  F

2821  ACGAAATTTGAGAACATTTCTCGTAGGTCACCAACCAATAGTTCAAGCACGTAAAAATTT  2880
       H  K  L  S  K  Y  L  A  D  L  P  Q  N  D  L  E  H  M  K  L
         I  S  *  V  R  T  F  L  M  W  H  N  T  I  L  N  T  C  K  *
            A  K  F  E  Q  L  S  C  G  T  T  P  *  *  T  R  A  N  K  F

2881  ATTTGAATTACTCTTACAACAAATAAATAAACTACTCCGACCACTACTTCGTTACCGGAG  2940
       Y  V  *  H  S  H  Q  K  N  I  Q  H  P  Q  H  H  L  L  P  R
         I  F  K  I  L  I  N  N  I  *  K  I  L  S  T  I  F  C  H  G
            L  S  L  S  F  T  T  *  K  N  S  S  A  P  S  S  A  I  A  E

2941  AGCATACATAACATGAAAACGATAACTCCTACAACTTCTGCAATAGTCATCACTTCGACA  3000
       E  Y  T  N  Y  K  Q  *  Q  P  H  Q  L  R  *  *  Y  H  L  Q
         R  T  H  I  T  S  K  S  N  L  I  N  F  V  N  D  T  T  F  S
            R  I  Y  Q  V  K  A  I  S  S  T  S  S  T  I  L  L  S  A  T

3001  GCTTCTATGATAACTACCACAGCAACTTCTGTGATAATTACTGCTACTTCTACAACAATG  3060
       R  L  Y  *  Q  H  H  R  Q  L  C  *  *  H  R  H  L  H  Q  *
         D  F  I  S  N  I  T  D  N  F  V  S  N  I  V  I  F  I  N  N
            S  S  V  I  S  P  T  T  S  S  V  I  L  S  S  S  T  T  V

3061  ACCACTGTTACTGCTACTTCTACAACAATGACCACTGTTACTGCTACTTCTACAACAATG  3120
       Q  H  C  H  R  H  L  H  Q  *  Q  H  C  H  R  H  L  H  Q  *
         S  T  V  I  V  I  F  I  N  N  S  T  V  I  V  I  F  I  N  N
            P  S  L  S  S  S  S  T  T  V  P  S  L  S  S  S  S  T  T  V

3121  ACCACTGTTACTGCTACTTCTACAACAATGACCACTGTTACTGCTACTTCTACAACAATG  3180
       Q  H  C  H  R  H  L  H  Q  *  Q  H  C  H  R  H  L  H  Q  *
         S  T  V  I  V  I  F  I  N  N  S  T  V  I  V  I  F  I  N  N
            P  S  L  S  S  S  S  T  T  V  P  S  L  S  S  S  S  T  T  V

3181  ACCACTGTTACTGCTACTTCTACAACAATGACCACTGTTACTGCTACTTCTACAACAATG  3240
       Q  H  C  H  R  H  L  H  Q  *  Q  H  C  H  R  H  L  H  Q  *
         S  T  V  I  V  I  F  I  N  N  S  T  V  I  V  I  F  I  N  N
            P  S  L  S  S  S  S  T  T  V  P  S  L  S  S  S  S  T  T  V
```

FIG. 3 CONT'D

```
3241  ACCACTGTTACTGCTACTTCTACAACAATGACCACTGTTACTGCTACTTCTACAACAATG  3300
        Q  H  C  R  H  L  H  Q  *  Q  H  C  R  H  L  H  Q  *
       S  T  V  I  V  I  F  I  N  N  S  T  V  I  V  I  F  I  N  N
          P  S  L  S  S  S  S  T  T  V  P  S  L  S  S  S  S  T  T  V

3301  ACCACTGTTACTGCTACTTCTACAACAATGACCACTGTTACTGCTACTTCTACAACAATG  3360
        Q  H  C  R  H  L  H  Q  *  Q  H  C  R  H  L  H  Q  *
       S  T  V  I  V  I  F  I  N  N  S  T  V  I  V  I  F  I  N  N
          P  S  L  S  S  S  S  T  T  V  P  S  L  S  S  S  S  T  T  V

3361  ACCACTGTTACTGCTACTTCTACAACAATGACCACTGTTACTGCTACTTCTACAACAATG  3420
        Q  H  C  R  H  L  H  Q  *  Q  H  C  R  H  L  H  Q  *
       S  T  V  I  V  I  F  I  N  N  S  T  V  I  V  I  F  I  N  N
          P  S  L  S  S  S  S  T  T  V  P  S  L  S  S  S  S  T  T  V

3421  ACCACTGTTACTGCTACTTCTACAACAATGACCACTGTTATTGCTACTTCTCTAACAATG  3480
        Q  H  C  R  H  L  H  Q  *  Q  H  C  Y  R  H  L  S  Q  *
       S  T  V  I  V  I  F  I  N  N  S  T  V  I  V  I  F  L  N  N
          P  S  L  S  S  S  S  T  T  V  P  S  L  L  S  S  S  I  T  V

3481  ACCACTGTTACTACTGGTTTAACAACAATGACCACTACTACATCTACTATAACTTTCATA  3540
        Q  H  C  H  H  G  F  Q  Q  *  Q  H  H  H  L  H  Y  Q  F  Y
       S  T  V  I  I  V  L  N  N  N  S  T  I  I  Y  I  I  N  F  T
          P  S  L  S  S  W  I  T  T  V  P  S  S  T  S  S  I  S  L  I

3541  AATACTGAAACTATGAATATTTCGAGAAAATCAAAAATTACTACAGATATTACTACGAAA  3600
        K  H  S  Q  Y  K  Y  L  E  K  L  K  *  H  H  R  Y  H  H  K
       N  I  V  K  I  S  I  F  S  K  *  N  K  I  I  D  I  I  S
          *  S  K  S  V  *  L  A  R  K  T  K  L  S  T  *  L  S  A  K

3601  CAAACAATCAATACCAAGATCACAACTTTGTCTTTGTATAAAATTTCAATTACCAAATAC  3660
        T  Q  *  N  H  N  *  H  Q  F  L  F  M  N  *  L  *  H  N  I
       Q  K  N  T  I  T  R  T  N  F  C  F  C  I  K  F  N  I  T  *
          N  T  L  *  P  E  L  T  S  V  S  V  Y  K  L  T  L  P  K  H

3661  CAGTGGATGATAATGTGTATGATTAACAACCAACGCAAGACACAATGAACATTACGTCTT  3720
        T  V  *  *  *  V  Y  *  N  N  T  A  N  Q  T  V  Q  L  A  S
       P  *  R  S  N  C  M  S  I  T  P  Q  T  R  H  *  K  Y  H  L
          D  G  V  I  V  C  V  L  Q  Q  N  R  E  T  N  S  T  I  C  F

3721  TAATGGAAAATTCAAATTCCTAAATCGATAACTTTTATACACCAATAGAATATTCCACCC  3780
        I  V  K  *  T  *  P  N  L  *  Q  F  Y  T  T  I  K  Y  P  P
       F  *  R  K  L  K  L  I  *  S  N  F  I  H  P  *  R  I  L  H
          N  G  K  L  N  L  S  K  A  I  S  F  I  H  N  D  *  L  T  P
```

FIG. 3 CONT'D

```
3781  AATATTAGTTTCAAAACAACTAATAAATGACTGGTGATAAGGATTTCGATAACAAAACGG  3840
       N  Y  D  F  N  Q  Q  N  N  V  S  W  *  E  *  L  *  Q  K  A
        T  I  I  L  T  K  N  I  I  *  Q  G  S  N  R  F  S  N  N  Q
         *  L  *  L  K  T  S  *  K  S  V  V  I  G  L  A  I  T  K  G

3841  AGTTCCACCAAAACATCGACTAAAACGAATAACCAAAAATTTGGTCAAACTATAATTACG  3900
       E  L  H  N  Q  L  Q  N  Q  K  N  T  K  L  G  T  Q  Y  *  H
        R  L  T  T  K  Y  S  I  K  S  I  P  K  *  V  L  K  I  N  I
         *  P  P  K  T  A  S  K  A  *  Q  N  K  F  W  N  S  I  L  A

3901  CATACGATTAACCACAACAAATTTTACACCAAAAAGAAAACTAAATTTACCAAACCTACG  3960
       T  H  *  N  T  N  N  L  I  H  N  K  K  Q  N  L  H  N  P  H
        R  I  S  I  P  T  T  *  F  T  T  K  R  K  I  *  I  T  Q  I
         Y  A  L  Q  H  Q  K  F  H  P  K  E  K  S  K  F  P  K  S  A

3961  AAACAAAAAAATACCTCTATAACACAGAGTACAAACATTCACACCTGTATTATACTGAGA  4020
       K  T  K  K  H  L  Y  Q  T  E  H  K  Y  T  H  V  Y  Y  S  E
        S  Q  K  K  I  S  I  N  H  R  M  N  T  L  T  S  M  I  H  S
         K  N  K  *  P  S  I  T  D  *  T  Q  L  H  P  C  L  I  V  R

4021  TTATCGTCGCCTGAATGGAACATGTAATGTAAAAAGTAATAAACTACTGTTAAAAACACG  4080
       L  L  L  P  S  V  K  Y  M  V  N  K  M  I  Q  H  C  N  K  H
        *  Y  C  R  V  *  R  T  C  *  M  K  *  *  K  I  V  I  K  T
         I  A  A  S  K  G  Q  V  N  C  K  E  N  N  S  S  L  K  Q  A

4081  AAAAACGTGGGGATTTTTTTAAAAATAACGACGTACACGACACCTACATTTGCAAACAGT  4140
       K  K  C  G  *  F  F  K  *  Q  Q  M  H  Q  P  H  L  R  K  D
        S  K  A  G  R  F  F  N  K  N  S  C  T  S  H  I  Y  V  N  T
         K  Q  V  G  L  F  I  K  I  A  A  H  A  T  S  T  F  T  Q  *

4141  AAGACATCGACAATATCCACTACTTGTTTATCTACCATTCAAACAATGATTTAAATCACC  4200
       N  Q  L  Q  *  L  H  H  V  F  L  H  Y  T  Q  *  *  I  *  H
        M  R  Y  S  N  Y  T  I  F  L  Y  I  T  L  K  N  S  F  K  T
         E  T  A  T  I  P  S  S  C  I  S  P  L  N  T  V  L  N  L  P

4201  ACTATTTAAACTAAAATATCATCCAATACCTTACAGTAAATCATACAGAAGAAAACTCAA  4260
       H  Y  I  Q  N  *  L  L  N  H  F  T  M  *  Y  T  K  K  Q  T
        T  I  F  K  I  K  Y  Y  T  I  S  H  *  K  T  H  R  R  K  L
         S  L  N  S  K  I  T  P  *  P  I  D  N  L  I  D  E  K  S  N

4261  TGGAGTTAACATACCAAACACATATTGTGGATTACATACAAAACAATTTCCACTATAATA  4320
       V  E  I  T  H  N  T  Y  L  V  *  H  I  N  Q  *  L  H  Y  *
        *  R  L  Q  I  T  Q  T  Y  C  R  I  Y  T  K  N  F  T  I  N
         G  *  N  Y  P  K  H  I  V  G  L  T  H  K  T  L  P  S  I  I
```

FIG. 3 CONT'D

```
4321  TTTACAACGATCTGAACAATTTCGACTACAATAACAATTAGGACGATTACCCGTATACGA  4380
       L  H  Q  *  V  Q  *  L  Q  H  *  Q  *  D  Q  *  H  A  Y  A
        Y  I  N  S  S  K  N  F  S  I  N  N  N  I  R  S  I  P  M  H
         F  T  A  L  S  T  L  A  S  T  I  T  L  G  A  L  P  C  I  S

4381  GGTACCACCACCTCAACGTTTTCGATATCGACATCGACGTCCATTTTTTAAAAGATTTCT  4440
        G  H  H  H  L  Q  L  L  *  L  Q  L  Q  L  Y  F  I  K  *  L
         E  M  T  T  S  N  C  F  S  Y  S  Y  S  C  T  F  F  K  R  F
          W  P  P  P  T  A  F  A  I  A  T  A  A  P  L  F  N  E  L  S

4441  TTGACGACGATACCAATTTAGATTTCCACAAACGGTTCATCCTCTAACAATACAAAGATG  4500
        F  Q  Q  *  P  *  I  *  L  H  K  G  L  L  N  N  H  K  *
         F  S  S  S  H  N  F  R  F  T  N  A  L  Y  S  I  T  I  N  R
          V  A  A  I  T  L  D  L  P  T  Q  W  T  P  S  Q  *  T  E  V

4501  GCCACCATTTAATACATTTTGTTAAGAATTATAACATCCGGGACTACGATCTGTTCTACC  4560
        R  H  Y  I  I  Y  F  L  E  *  Y  Q  L  G  Q  H  *  V  L  H
         G  T  T  F  *  T  F  C  N  K  I  N  Y  A  R  I  S  S  L  I
          P  P  L  N  H  L  V  I  R  L  I  T  P  G  S  A  L  C  S  P

4561  TTCTGTTAGAATACAAAACAATCGTGCACGAATATTCGTAGAATTATTAATACTAACAAC  4620
        F  V  I  K  H  K  T  L  V  H  K  Y  A  D  *  Y  N  H  N  N
         S  S  L  R  I  N  Q  *  C  T  S  I  L  M  K  I  I  I  I  T
          L  C  D  *  T  K  N  A  R  A  *  L  C  R  L  L  *  S  Q  Q

4621  AAACAGATGAGAGTATAGCCGACCATATAAATCACAAGGACGACTACACAGTAATTGAAT  4680
        N  T  *  E  *  I  P  Q  Y  I  *  H  E  Q  Q  H  T  M  L  K
         T  Q  R  S  E  Y  R  S  T  Y  K  T  N  R  S  I  H  *  *  S
          K  D  V  R  M  D  A  P  I  N  L  T  G  A  S  T  D  N  V  *

4681  GGAAGATCCACAACAACTATTTGTTCAATAGGAACAATCATTATTATTTCTTCTAAAACT  4740
        G  E  L  H  Q  Q  Y  V  L  *  G  Q  *  Y  Y  Y  L  L  N  Q
         V  K  *  T  N  N  I  F  L  N  D  K  N  T  I  I  F  F  I  K
          R  R  P  T  T  S  L  C  T  I  R  T  L  L  L  S  S  K  S

4741  ATAATAAGTTTTTACAGTTTAATGAAGTCAACAACCATGATTTCGTAACCGACAATCTAA  4800
        Y  *  E  F  I  D  F  *  K  L  Q  Q  Y  *  L  M  P  Q  *  I
         I  N  N  L  F  T  L  N  S  *  N  N  T  S  F  C  Q  S  N  S
          I  I  *  F  H  *  I  V  E  T  T  P  V  L  A  N  A  T  L  N

4801  TTGACGATTACATCCGGCACAATAATTTAAACTCTGTCTACGTATGTTTGAAAAAAACTC  4860
        L  Q  *  H  L  G  H  *  *  I  Q  S  L  H  M  C  V  K  K  S
         *  S  S  I  Y  A  T  N  N  F  K  L  C  I  C  V  F  K  K  Q
          V  A  L  T  P  R  T  I  L  N  S  V  S  A  Y  L  S  K  K  L
```

FIG. 3 CONT'D

```
4861  ACCACTACTAACAAAACAAAGTTTAAGAAGACAATATGTTCTTCAAAATAACGAAGCAGT  4920
        H  H  H  N  N  Q  K  L  N  K  Q  *  V  L  L  K  I  A  E  D
       T  T  I  I  T  K  N  *  I  R  R  N  Y  L  F  N  *  Q  K  T
         P  S  S  Q  K  T  E  F  E  E  T  I  C  S  T  K  N  S  R  *

4921  ACTATATGTTAACTTATTACTGCAAGCACTAATAAACAACAGATTCTACTGATCAGAAGG  4980
        H  Y  V  I  S  Y  H  R  E  H  N  N  T  T  *  S  S  *  D  E
       M  I  Y  L  Q  I  I  V  N  T  I  I  Q  Q  R  L  H  S  T  K
         S  I  C  N  F  L  S  T  R  S  *  K  N  D  L  I  V  L  R  G

4981  ATTTCTAACCGCAGAATAGTTATTTAAACTACAATAATTGCCACAATTTTGACAATTCAT  5040
        *  L  N  A  D  *  *  Y  I  Q  H  *  *  R  H  *  F  Q  *  T
       R  F  I  P  T  K  D  I  F  K  I  N  N  V  T  N  F  S  N  L
         L  S  Q  R  R  I  L  L  N  S  T  I  L  P  T  L  V  T  L  Y

5041  AAAACTCACAGGATTAAGATAAATATATACATCAGTCCCATTTCTGAAACCAATACATAC  5100
        N  Q  T  D  *  N  *  K  Y  I  Y  D  P  Y  L  S  Q  N  H  I
       I  K  L  T  R  I  R  N  I  Y  T  T  L  T  F  V  K  T  I  Y
         K  S  H  G  L  E  I  *  I  H  L  *  P  L  S  K  P  *  T  H

5101  ACTACCAAGAAAAATATTTCGTTGACAATTAGTTCAAACACAAAATAATCGATTCTTCTA  5160
        H  H  N  K  K  Y  L  L  Q  *  D  L  K  H  K  I  L  *  S  S
       T  I  T  R  K  I  F  C  S  N  I  L  N  T  N  *  *  S  L  L
         S  P  E  K  *  L  A  V  T  L  *  T  Q  T  K  N  A  L  F  I

5161  TCTACAAAACGAATGACATCTACCACAATTAAAATTTAGATAAAGAGAATGACATCCACT  5220
        L  H  K  A  *  Q  L  H  H  *  N  *  I  *  K  E  *  Q  L  H
       Y  I  N  Q  K  S  Y  I  T  N  I  K  F  R  N  R  K  S  Y  T
         S  T  K  S  V  T  S  P  T  L  K  L  D  I  E  R  V  T  P  S

5221  TCAAAACCATTTTATGAACCATTACAAAAGACACTACCGTAACTACAATGATTCAATTT  5280
        L  K  Q  Y  F  V  Q  Y  H  K  R  H  H  C  Q  H  *  *  T  L
       F  N  K  T  F  Y  K  T  I  N  E  T  I  A  N  I  N  S  L  *
         T  K  P  L  I  S  P  L  T  K  Q  S  P  M  S  T  V  L  N  F

5281  CACATCACTAAAAATACGGCTATTTTAAAATATAGTCATACTTTTAAACAGAAATCGACT  5340
        T  Y  H  N  K  H  R  Y  F  K  I  D  T  H  F  N  T  K  L  Q
       L  T  T  I  K  I  G  I  F  N  *  I  L  I  F  I  Q  R  *  S
         H  L  S  K  *  A  S  L  I  K  Y  *  Y  S  F  K  D  K  A  S

5341  ATAAAGACGACATGTTTCAAGTAAACCCAAACTAGTCGTTGTTAACGAACGAATAATATT  5400
        Y  K  Q  Q  V  F  N  M  Q  T  Q  D  A  V  I  A  Q  K  N  Y
       I  N  R  S  Y  L  T  *  K  P  K  I  L  L  L  Q  K  S  I  I
         I  E  A  T  C  L  E  N  P  N  S  *  C  C  N  S  A  *  *  L
```

FIG. 3 CONT'D

```
5401  AAAAAATTGTCATACATTTACCAGACATCAACAATTGCCAGGTAAAAAAGAAAACTTGT  5460
        N  K  L  L  I  Y  I  T  Q  L  Q  *  R  D  M  K  K  Q  V
       I  K  *  C  Y  T  F  P  R  Y  N  N  V  T  W  K  K  R  K  F
         K  K  V  T  H  L  H  D  T  T  T  L  P  G  N  K  E  K  S  C

5461  CAGAGTATTATTAACAATACACTTACATCGAACAGAATACAACGTCGTATAATTAGAATT  5520
        T  E  Y  Y  N  N  H  S  H  L  K  D  *  T  A  A  Y  *  D  *
       L  R  M  I  I  T  I  H  I  Y  S  T  K  H  Q  L  M  N  I  K
         D  *  L  L  Q  *  T  F  T  A  Q  R  I  N  C  C  I  L  R  L

5521  TAAATTATTTACCGTCACCGTCCTTCGTACCATACTTAAAGCACGACCGTCTGGTGTATC  5580
        I  *  Y  I  A  T  A  P  L  M  T  H  I  E  H  Q  C  V  V  Y
       F  K  I  F  P  L  P  L  F  C  P  I  F  K  T  S  A  S  W  M
         N  L  L  H  C  H  C  S  A  H  Y  S  N  R  A  P  L  G  C  L

5581  CAATCAACGAGAACAAAATCGATTTCCAGTAAAATTTAAACTACTTGGTAGTCTACGATG  5640
        T  L  Q  E  Q  K  L  *  L  D  N  *  I  Q  H  V  M  L  H  *
       P  *  N  S  K  N  *  S  F  T  M  K  F  K  I  F  W  *  I  S
         N  T  A  R  T  K  A  L  P  *  K  L  N  S  S  G  D  S  A  V

5641  ACTAAAATAAGCACAACAAAACTTTGTTCGACTAAATAGTCCACGTTAAACACTTAATCT  5700
        Q  N  *  E  H  Q  K  S  V  L  Q  N  I  L  H  L  K  H  I  L
       S  I  K  N  T  N  N  Q  F  L  S  I  *  *  T  C  N  T  F  *
         S  K  I  R  T  T  K  F  C  A  S  K  D  P  A  I  Q  S  N  S

5701  TGAATAAACACTAACACCATAATTTGTTCTTTCAGCACAACCACAACTACGACAATACGT  5760
        V  *  K  H  N  H  Y  *  V  L  F  D  H  Q  H  Q  *  A
       F  K  N  T  I  T  T  N  F  L  F  T  T  N  T  N  I  S  N  H
         S  I  Q  S  Q  P  I  L  C  S  L  R  T  P  T  S  A  T  I  C

5761  AAAACCATGTAATCGTTTCTGACTAGAAAAATTACCAATATTCTAACCGACATTAACACG  5820
        N  Q  Y  M  L  L  S  Q  D  K  *  H  N  Y  S  Q  S  Y  N  H
       M  K  T  C  *  C  L  S  I  K  K  I  T  I  L  N  A  T  I  T
         K  P  V  N  A  F  V  S  R  K  L  P  *  L  I  P  Q  L  Q  A

5821  TCCATCTTAACAGGTAACATGATTTAACTTACATGGTAAAAACTAAACAAGATTATGAGG  5880
        L  Y  F  Q  G  N  Y  *  I  S  H  V  M  K  S  K  N  *  Y  E
       C  T  S  N  D  M  T  S  F  Q  I  Y  W  K  Q  N  T  R  I  S
         P  L  I  T  W  Q  V  L  N  F  T  G  N  K  I  Q  E  L  V  G

5881  AGACTCATTCCTAAATGGACTACTACAACAACGTCGATTGTACAAATACCCACATCCACA  5940
        E  S  Y  P  N  V  Q  H  H  Q  Q  L  *  C  T  *  P  H  L  H
       R  Q  T  L  I  *  R  I  I  N  N  C  S  V  H  K  H  T  Y  T
         R  L  L  S  K  G  S  S  T  T  A  A  L  M  N  I  P  T  P  T
```

FIG. 3 CONT'D

```
5941  TCCGGTAATATGTGTAAACTTTACACCAAGTGGAATGGTTGTAATACTACGAACATCACA  6000
        L  G  N  Y  V  N  S  I  H  N  V  K  G  V  N  H  H  K  Y  H
       Y  A  M  I  C  M  Q  F  T  T  *  R  V  L  M  I  I  S  T  T
        P  W  *  V  C  K  F  H  P  E  G  *  W  C  *  S  A  Q  L  T

6001  ATTTTTTATATGTCCACAATCACCAACAAATTGACTGACGAACATAGAATTTTTAAATTG  6060
        *  F  I  Y  L  H  *  H  N  N  L  Q  S  S  T  D  *  F  N  L
       N  F  F  I  C  T  N  T  T  T  *  S  V  A  Q  I  K  F  I  *
        L  F  Y  V  P  T  L  P  Q  K  V  S  Q  K  Y  R  L  F  K  V

6061  GGTCTGAAAATGTAGATACAACTGATTAATAAAAAACCTACTACAACTTTACCAACGAAT  6120
        G  S  K  *  M  *  T  S  *  N  N  K  P  H  H  Q  F  P  Q  K
       G  L  S  K  C  R  H  Q  S  I  I  K  Q  I  I  N  F  H  N  S
        W  V  K  V  D  I  N  V  L  *  K  K  S  S  T  S  I  T  A  *

6121  ATTGGGACTAGAAAGTGTTATAATAACACTATTACCATTCATAATATGTTTTGGATAATA  6180
        Y  G  Q  D  K  V  I  N  N  H  Y  H  Y  T  N  Y  L  V  *  *
       I  V  R  I  K  *  L  I  I  T  I  I  T  L  I  I  C  F  R  N
        L  G  S  R  E  C  Y  *  Q  S  L  P  L  Y  *  V  F  G  I  I

6181  TTTCCGAGTCAAATTTGGTAAACGATTTCAACTGCCACAAATATGATTGAAATTCAATCA  6240
        L  P  E  T  *  V  M  Q  *  L  Q  R  H  K  Y  *  S  *  T  L
       Y  L  S  L  K  F  W  K  S  F  N  V  T  N  I  S  V  K  L  *
        F  A  *  N  L  G  N  A  L  T  S  P  T  *  V  L  K  L  N  T

6241  ACCTGTACTATAAACACGAGTTAACTTACTATTCAATCCAAAATTACATCTAAACGGCAA  6300
        Q  V  H  Y  K  H  E  I  S  H  Y  T  L  N  *  H  L  N  A  T
       N  S  M  I  N  T  S  L  Q  I  I  L  *  T  K  I  Y  I  Q  R
        P  C  S  I  Q  A  *  N  F  S  L  N  P  K  L  T  S  K  G  N

6301  ACAACTCATGTTTCATTGTCAGACCGGACATCGATGACCACTACAACAAAACCGTAGACT  6360
        Q  Q  T  C  L  L  R  Q  L  *  Q  H  H  Q  K  P  M  Q
       K  N  L  V  F  Y  C  D  P  R  Y  S  S  T  I  N  N  Q  C  R
        T  S  Y  L  T  V  T  Q  G  T  A  V  P  S  T  T  K  A  D  S

6361  ACTAAATATACACTTTGCAATAAAATTTCCTACACTTTGAAAACCATTCGGACAATAAAC  6420
        H  N  I  H  S  V  N  N  *  L  I  H  F  K  Q  Y  A  Q  *  K
       I  I  *  I  H  F  T  I  K  F  S  T  F  S  K  T  L  R  N  N
        S  K  Y  T  F  R  *  K  L  P  H  S  V  K  P  L  G  T  I  Q

6421  CAAAACAGTACTACTTCGTAGTAACTTAAGAGAATGAATAAAATTATTTGGATCAAAATT  6480
        T  K  D  H  H  L  M  M  S  N  E  *  K  N  *  Y  V  *  N  *
       P  K  T  M  I  F  C  *  Q  I  R  K  S  I  K  I  F  R  T  K
        N  Q  *  S  S  A  D  N  F  E  R  V  *  K  L  L  G  L  K  L
```

FIG. 3 CONT'D

```
6481  TAGACTTTTATCTATATCACAAAACAGACAACTAAGACATAGACTCCTCAGTGTTCCATT  6540
         I  Q  F  Y  I  Y  H  K  T  Q  Q  N  Q  I  Q  P  T  V  L  Y
        F  R  F  I  S  I  T  N  Q  R  N  I  R  Y  R  L  L  *  L  T
          D  S  F  L  Y  L  T  K  D  T  S  E  T  D  S  S  D  C  P  L

6541  ACACCAATGAAGACAATACCTTAGCGTCTAATCATGATTTCTCCAATTCAATTTCCCACA  6600
         H  P  *  K  Q  *  P  I  A  S  *  Y  *  L  P  *  T  L  P  H
        I  H  N  S  R  N  H  F  R  L  N  T  S  F  L  N  L  *  L  T
          T  T  V  E  T  I  S  D  C  I  L  V  L  S  T  L  N  F  P  T

6601  ATCTTTCTGACAATTTTATCTTCTACGATAATAACAATTACTACTTTTATCAAGATAATT  6660
         *  F  S  Q  *  F  L  L  H  *  *  Q  *  H  H  F  Y  N  *  *
        N  S  L  S  N  F  Y  F  I  S  N  N  N  I  I  F  I  T  R  N
          L  F  V  T  L  I  S  S  A  I  I  T  L  S  S  F  L  E  I  L

6661  CCAACAATTTTCAAATAGAAATCAACTACAAACCCTATACATAAACTGTCCAACACTAAT  6720
         P  Q  *  F  N  I  K  L  Q  H  K  P  Y  T  N  S  L  N  H  N
        L  N  N  F  T  *  R  *  N  I  N  P  I  H  I  Q  C  T  T  I
          T  T  L  L  K  D  K  T  S  T  Q  S  I  Y  K  V  P  Q  S  *

6721  ACAACAAACCCAACGATTACTTAACAGTGCGGATCAATTTAGTGGTTGTCAATCCCTTAT  6780
         H  Q  K  P  Q  *  H  I  T  V  G  L  *  I  V  L  L  *  P  I
        I  N  N  P  N  S  I  F  Q  *  A  *  N  F  *  W  C  N  P  F
          T  T  Q  T  A  L  S  N  D  R  R  T  L  D  G  V  T  L  S  Y

6781  ATATGCTATACCATAATTTGGATAATGATATGGATATCTAAACAATACAAATTCTCTACT  6840
         Y  V  I  H  Y  *  V  *  *  *  V  *  L  N  T  I  N  L  L  H
        I  Y  S  I  T  N  F  R  N  S  Y  R  Y  I  Q  *  T  *  S  I
          I  R  Y  P  I  L  G  I  V  I  G  I  S  K  N  H  K  L  S  S

6841  ATTAGTTTGAGAAAATCAAGGATTTTAAAAATTTCGTTCTCGATATCTTAAAATACCAAA  6900
         Y  D  F  E  K  L  E  *  F  K  *  L  L  L  *  L  I  K  H  N
        I  I  L  S  K  *  N  R  F  N  K  F  C  S  S  Y  F  K  I  T
          L  *  V  R  K  T  G  L  I  K  L  A  L  A  I  S  N  *  P  K

6901  AAACTTCACCAACAAATAAATACAAAAATCAAATAATGTAAAATGTTTACTATTTTGGTA  6960
         K  S  T  T  T  *  K  H  K  *  N  I  V  N  *  L  H  Y  F  W
        K  Q  L  P  Q  K  N  I  N  K  T  *  *  M  K  C  I  I  F  G
          K  F  H  N  N  I  *  T  K  L  K  N  C  K  V  F  S  L  V  M

6961  AAAAATATGATGTCTTTATCGAAGATTCAAATGAAAATTAAACAAAACAAACCGAGAATT  7020
         K  K  Y  *  L  F  L  K  *  T  *  K  *  N  T  K  N  P  E  *
        N  K  I  S  C  F  Y  S  R  L  K  S  K  I  Q  K  T  Q  S  K
          K  *  V  V  S  I  A  E  L  N  V  K  L  K  N  Q  K  A  R  L
```

FIG. 3 CONT'D

```
7021  TTTACGAAAAGTCTGTAAATCTACCTCATATAAATATTTTCCAAAAGAACAACATCGGTG  7080
         F  H  K  E  S  M  *  I  S  Y  I  *  L  L  N  E  Q  Q  L  W
        F  I  S  K  L  C  K  S  P  T  Y  K  Y  F  T  K  K  N  Y  G
       F  A  K  *  V  N  L  H  L  I  N  I  F  P  K  R  T  T  A  V

7081  ACACAAAAACAAAACCAAATTAAAAAACATATATTTACAATAAAAATCACTGAAAATAGA  7140
         Q  T  K  T  K  T  *  N  K  T  Y  L  H  *  K  *  H  S  K  D
        S  H  K  Q  K  P  K  I  K  Q  I  Y  I  N  N  K  T  V  K  I
       T  N  K  N  Q  N  L  K  K  Y  I  F  T  I  K  L  S  K  *  R

7141  AGGATTATAATCACAAAAAGGATAAAAACACCCTTCTTAACAATACACCTATTTCCGATG  7200
         E  *  Y  *  H  K  E  *  K  Q  P  F  F  Q  *  T  S  L  P  *
        K  R  I  N  T  N  K  R  N  K  H  S  S  N  N  H  P  Y  L  S
       G  L  I  L  T  K  G  I  K  T  P  L  I  T  I  H  I  F  A  V

7201  AAAACCAAACCAATGTTAAACACTAAAAATAAGATTCAATCCACATCCAAAATGTTCAGT  7260
         K  Q  N  P  *  L  K  H  N  K  N  *  T  L  H  L  N  *  L  D
        S  K  T  Q  N  C  N  T  I  K  I  R  L  *  T  Y  T  K  C  T
       K  P  K  T  V  I  Q  S  K  *  E  L  N  P  T  P  K  V  L  *

7261  AAAAACATTACCATCAAAATATACACTTAACACAGTAAGACCAAAACTATACAACCTATG  7320
         N  K  Y  H  Y  N  *  I  H  I  T  D  N  Q  N  Q  Y  T  P  Y
        M  K  T  I  T  T  K  Y  T  F  Q  T  M  R  T  K  I  H  Q  I
       K  Q  L  P  L  K  I  H  S  N  H  *  E  P  K  S  I  N  S  V

7321  TATACGTCGATATCTAAAACAAGTCATACTTCATCTATCTGCACAAAATAAACTAATACA  7380
         M  H  L  *  L  N  Q  E  T  H  L  L  Y  V  H  K  I  Q  N  H
        C  I  C  S  Y  I  K  N  L  I  F  Y  I  S  T  N  *  K  I  I
       Y  A  A  I  S  K  T  *  Y  S  T  S  L  R  T  K  N  S  *  T

7381  ATCAAATCAGTTTAATTAACAACTTGAGCAATAACCAATAAGTAATATGTGTCATACCAA  7440
         *  N  L  *  I  L  Q  Q  V  R  *  Q  N  N  M  I  C  L  I  T
        N  T  *  D  F  *  N  N  F  E  N  N  T  I  *  *  V  C  Y  P
       L  K  T  L  N  I  T  S  S  T  I  P  *  E  N  Y  V  T  H  N

7441  AATAGGTAATAAAACAGAATAACCAAATGTTAATAAATGATGTACCAACGGACTAAACAA  7500
         K  D  M  I  K  D  *  Q  N  V  I  I  *  *  M  T  A  Q  N  T
        K  I  W  *  K  T  K  N  T  *  L  *  K  S  C  P  Q  R  I  Q
       *  G  N  N  Q  R  I  P  K  C  N  N  V  V  H  N  G  S  K  N

7501  ATACAATCTTTGATACGTAACCAACTAATCTAAATAACATAAACATCGATTATACAATGG  7560
         *  T  L  F  *  A  N  T  S  *  I  *  Q  I  Q  L  *  Y  T  V
        K  H  *  F  S  H  M  P  Q  N  S  K  N  Y  K  Y  S  I  H  *
       I  N  S  V  I  C  Q  N  I  L  N  I  T  N  T  A  L  I  N  G
```

FIG. 3 CONT'D

```
7561  ACGAAAACAGAACAACGCCAAAATATATCAACAATGACGATACATATTTCATCAACCAAA  7620
         Q  K  Q  R  T  A  T  K  Y  L  Q  *  Q  *  T  Y  L  L  Q  N
        R  S  K  D  Q  Q  P  K  I  Y  N  N  S  S  H  I  F  Y  N  T
          A  K  T  K  N  R  N  *  I  T  T  V  A  I  Y  L  T  T  P  K

7621  ATAATCCGTATAACAGATACCAACATTATTTCGACCAACAAATAAAACAATATTTGCTTT  7680
         *  *  A  Y  Q  R  H  N  Y  Y  L  Q  N  N  I  K  N  Y  V  F
        K  N  P  M  N  D  I  T  T  I  F  S  T  T  *  K  T  I  F  S
          I  L  C  I  T  *  P  Q  L  L  A  P  Q  K  N  Q  *  L  R  F

7681  AACATCACAAGCACAATTCACATCATGATAACAACCACCACATTAAGCAATAATACTATA  7740
         N  Y  H  E  H  *  T  Y  Y  *  Q  Q  H  H  L  E  N  N  H  Y
        I  T  T  N  T  N  L  T  T  S  N  N  T  T  Y  N  T  I  I  I
          Q  L  T  R  T  L  H  L  V  I  T  P  P  T  I  R  *  *  S  I

7741  ATGACGATTACCACCATGACCAAAAACACAATTTGTAGTTACCTTAACAAAATTAACGGT  7800
         *  Q  *  H  H  Y  Q  N  K  H  *  V  D  I  S  N  N  *  N  G
        N  S  S  I  T  T  S  T  K  T  N  F  M  L  P  I  T  K  I  A
          V  A  L  P  P  V  P  K  Q  T  L  C  *  H  F  Q  K  L  Q  W

7801  AAGAAAATTTGGTCCATTGTGAAAATATTGACATCTTCGACGATATCTTGAAAGATTTCT  7860
         N  K  *  V  L  Y  C  K  *  L  Q  L  L  Q  *  L  V  K  *  L
        M  R  K  F  W  T  V  S  K  Y  S  Y  F  S  S  Y  F  K  R  F
          E  K  L  G  P  L  V  K  I  V  T  S  A  A  I  S  S  E  L  S

7861  CGAATTTGCTGGACATTTAGGTTGACTACGAAGTGTAATACATCAATGACTATAATTCGT  7920
         A  *  V  V  Q  L  D  L  Q  H  K  V  N  H  L  *  Q  Y  *  A
        L  K  F  S  R  Y  I  W  S  I  S  *  M  I  Y  N  S  I  N  L
          S  L  R  G  T  F  G  V  S  A  E  C  *  T  T  V  S  I  L  C

7921  TCAACCAACATACTACGCAAACAAGATACTATCTCTACCTGTCGCACAAATGCTACTACA  7980
         L  Q  N  Y  S  A  N  T  R  H  Y  L  H  V  A  H  K  R  H  H
        L  N  T  T  H  H  T  Q  E  I  I  S  I  S  L  T  N  V  I  I
          T  P  Q  I  I  R  K  N  *  S  L  S  P  C  R  T  *  S  S  T

7981  ACTACGATCAAATAAACATCTATAATTATTAGACAATGTAAGATTTCAATTTCAACAAGG  8040
         Q  H  *  N  I  Q  L  Y  *  Y  D  T  V  N  *  L  *  L  Q  E
        N  I  S  T  *  K  Y  I  N  I  I  Q  *  M  R  F  N  F  N  N
          S  A  L  K  N  T  S  I  L  L  R  N  C  E  L  T  L  T  T  G

8041  ATTAAACATACATCAACATCATCTCTCACTACGACTATCTCGATTAAAAGACTTACGACA  8100
         *  N  T  H  L  Q  L  L  S  H  H  Q  Y  L  *  N  E  S  H  Q
        R  I  Q  I  Y  N  Y  Y  L  T  I  S  I  S  S  I  K  Q  I  S
          L  K  Y  T  T  T  T  S  L  S  A  S  L  A  L  K  R  F  A  T
```

FIG. 3 CONT'D

```
8101  ACACAAAATACGTGTTAGTAACATATCCGGATATAATGAACATCTGTTTTTCAATTAATG  8160
         Q  T  K  H  V  I  M  T  Y  A  *  I  V  Q  L  C  F  T  L  *
       N  H  K  I  C  L  *  Q  I  P  R  Y  *  K  Y  V  F  L  *  N
         T  N  *  A  C  D  N  Y  L  G  I  N  S  T  S  L  F  N  I  V

8161  ATGTCGAACATTACCATAGAGACATTGGGTCTGATACAAACTACAAATACAACTATGAAA  8220
         *  L  K  Y  H  Y  R  Q  L  G  S  *  T  Q  H  K  H  Q  Y  K
       S  C  S  T  I  T  D  R  Y  G  L  S  H  K  I  N  I  N  I  S
         V  A  Q  L  P  I  E  T  V  W  V  I  N  S  T  *  T  S  V  K

8221  ATACAGAGTAAAACTACAACTATCTTTCTCAAAATTATTAAAACAATTGTAACGAGTACG  8280
         *  T  E  N  Q  H  Q  Y  F  S  N  *  Y  N  Q  *  C  Q  E  H
       K  H  R  M  K  I  N  I  S  L  T  K  I  I  K  N  V  N  S  M
         I  D  *  K  S  T  S  L  F  L  K  L  L  K  T  L  M  A  *  A

8281  AAGAGAATCTCTCCCACACGTTAATCTTTTCCAAAATCTATGAAAACACCCTACACATGC  8340
         K  E  *  L  P  H  A  I  L  F  P  K  L  Y  K  Q  P  I  H  V
       S  R  K  S  L  T  H  L  *  F  L  N  *  I  S  K  H  S  T  Y
         E  R  L  S  P  T  C  N  S  F  T  K  S  V  K  T  P  H  T  R

8341  ATTTACAACAAGGTAACTAAGTCTACAACTTTGTTCTAAATAATGATTTAGATACTATAG  8400
         Y  I  N  N  W  Q  N  L  H  Q  F  L  I  *  *  *  I  *  S  I
       T  F  T  T  G  N  I  *  I  N  F  C  S  K  N  S  F  R  H  Y
         L  H  Q  E  M  S  E  S  T  S  V  L  N  I  V  L  D  I  I  D

8401  ACGTCATCGACGACCAAACCTTAAATGACTACTTTTAATATTGTTAAACCATGGATGTAT  8460
         Q  L  L  Q  Q  N  P  I  *  Q  H  F  N  Y  C  N  P  V  *  M
       R  C  Y  S  S  T  Q  F  K  S  I  F  I  I  V  I  Q  Y  R  C
         A  T  A  A  P  K  S  N  V  S  S  F  *  L  L  K  T  G  V  Y

8461  AAATTTCTCACTATTATAACATCGACGACTAAATCCACAAGAATATGTCTTACCACGATT  8520
         N  L  S  H  Y  Y  Q  L  Q  Q  N  L  H  E  *  V  S  H  H  *
       I  *  L  T  I  I  N  Y  S  S  I  *  T  N  K  Y  L  I  T  S
         K  F  L  S  L  I  T  A  A  S  K  P  T  R  I  C  F  P  A  L

8521  CGTACATGTCCCATTACAACGATTCCGTCGATTATAAAGAACATATACCAAATAACTACG  8580
         A  H  V  P  Y  H  Q  *  P  L  *  Y  K  K  Y  I  T  *  Q  H
       L  M  Y  L  T  I  N  S  L  C  S  I  N  R  T  Y  P  K  N  I
         C  T  C  P  L  T  A  L  A  A  L  I  E  Q  I  H  N  I  S  A

8581  AAAATTAGTTGAATGACGACTAAATGTCGTATTTAATTTTTTTCGTACACAATTTTGACC  8640
         K  *  D  V  *  Q  Q  N  V  A  Y  I  L  F  L  M  H  *  F  Q
       S  K  I  L  K  S  S  I  *  L  M  F  *  F  F  C  T  N  F  S
         K  L  *  S  V  A  S  K  C  C  L  N  F  F  A  H  T  L  V  P
```

FIG. 3 CONT'D

```
8641  GAACTTCAATTTTAACTGAAAATTATTCGTTCTCCGTTCACAGGGATAAGAATGTTGTGG  8700
        S  S  T  L  I  S  K  *  Y  A  L  P  L  H  G  *  E  *  L  V
       A  Q  L  *  F  Q  S  K  I  L  L  L  C  T  D  R  N  K  C  C
         K  F  N  F  N  V  K  L  L  C  S  A  L  T  G  I  R  V  V  G

8701  GAAAAGTGAATTTCCTCCACAACATAACTCATTAAACAATATATATAATAAAAAACAATC  8760
        R  K  V  *  L  L  H  Q  I  S  Y  N  T  I  Y  I  I  K  Q  *
       G  K  *  K  F  S  T  N  Y  Q  T  I  Q  *  I  Y  *  K  K  N
         K  E  S  L  P  P  T  T  N  L  L  K  N  Y  I  N  N  K  T  L

8761  AAATTAGACAAAATATAATAACACCCGAAATAACGGATGTATATCACAAATATTCAGACT  8820
        N  L  R  N  *  I  I  T  P  K  I  A  *  M  Y  H  K  Y  T  Q
       T  *  D  T  K  Y  *  Q  P  S  *  Q  R  C  I  T  N  I  L  R
         K  I  Q  K  I  N  N  H  A  K  N  G  V  Y  L  T  *  L  D  S

8821  ATAAGTAAACGGACGAATACGATCAAAATTTCAATAACTATTACCACAACAATCTCTATA  8880
        Y  E  N  A  Q  K  H  *  N  *  L  *  Q  Y  H  H  Q  *  L  Y
       I  N  M  Q  R  S  I  S  T  K  F  N  N  I  I  T  N  N  S  I
         I  *  K  G  A  *  A  L  K  L  T  I  S  L  P  T  T  L  S  I

8881  AAGTCAATTACTAAATACAAAACGATTATTTAAAAAGGTTAAACTAGTTACCATACTCAG  8940
        K  L  *  H  N  I  N  Q  *  Y  I  K  G  I  Q  D  I  T  H  T
       N  *  N  I  I  *  T  K  S  I  F  K  E  L  K  I  L  P  I  L
         E  T  L  S  K  H  K  A  L  L  N  K  W  N  S  *  H  Y  S  D

8941  GTGAAAACCCAGACAAATGATAGTATTAAGATACCTAACGGGATAACATCACCGTCAATA  9000
        W  K  Q  T  Q  K  S  D  Y  N  *  P  N  G  *  Q  L  P  L  *
       G  S  K  P  R  N  V  I  M  I  R  H  I  A  R  N  Y  H  C  N
         V  K  P  D  T  *  *  *  L  E  I  S  Q  G  I  T  T  A  T  I

9001  CCTACTTCTATAGCCAAGATGATACAAATTACAAGGATGATTTCAAAACTCTGTACCGAA  9060
        P  H  L  Y  R  N  *  *  T  *  H  E  *  *  L  K  S  V  H  S
       H  I  F  I  D  T  R  S  H  K  I  N  R  S  F  N  Q  S  M  A
         S  S  S  I  P  E  V  I  N  L  T  G  V  L  T  K  L  C  P  K

9061  AGTACAAAATGTAAAAAATTGAATACGTAAACGATCACTATCACAAGTCACGATATGTGG  9120
        E  H  K  V  N  K  L  K  H  M  Q  *  H  Y  H  E  T  S  Y  V
       K  M  N  *  M  K  *  S  I  C  K  S  T  I  T  N  L  A  I  C
         *  T  K  C  K  K  V  *  A  N  A  L  S  L  T  *  H  *  V  G

9121  TGTATAAGTCTAAAGAATATTACTAAAAATACGATCACCAACACAAAATAGTAGAAACAC  9180
        V  Y  E  S  K  K  Y  H  N  K  H  *  H  N  H  K  I  M  K  T
       W  M  N  L  N  R  I  I  I  K  I  S  T  T  T  N  *  *  R  Q
         C  I  *  I  E  *  L  S  K  *  A  L  P  Q  T  K  D  D  K  H
```

FIG. 3 CONT'D

```
9181  ATGATACAAATTTTCTCCACTACCATGTGGTGTAGGAATAACAATAAGTCTACCACAATA  9240
       Y * T * F L H H Y V V D K N N N L H H *
       T S H K F S T I T C W M R I T I * I T N
        V I N L L P S P V G C G * Q * E S P T I

9241  CTTCTTACGAAGAAACATATGTAGAAACCAAGGTGTATGTGCAATATCGGAACGATTAAG  9300
       S S H K K T Y M K P E V Y V N Y G Q * N
       H L I S R Q I C R Q N W M C T I A K S I
        F F A E K Y V D K T G C V R * L R A L E

9301  ATTACCAAAATATTCTAAAGGACTACAATAATCACTTCCATAACATGCATAACATTCTTG  9360
       * H N * L I E Q H * * H L Y Q V Y Q L F
       R I T K Y S K R I N N T F T N Y T N Y S
        L P K I L N G S T I L S P I T R I T L V

9361  CGCGAGATACTGAATAACATCTCACCCACGTACACTTATGCGGCTTCTCCCATATACAAA  9420
       A S * S K N Y L P H M H I R R L P Y I N
       R A R H S I T S H T C T F V G F L T Y T
        R E I V * Q L T P A H S Y A S S P I H K

9421  ATTAAAATTATCAAGGACCCAAAACTTATTACTAATAATATCTTCATACGGACCTTGAAA  9480
       * N * Y N R P K S Y H N N Y F Y A Q F K
       K I K I T G P N Q I I I I S T H R S S
        L K L L E Q T K F L S * * L L I G P V K

9481  AACACCATCTCTAGAAAAACTAAACAAAATAGTTAAAAAATCATCAAATTAAGCAGGATA  9540
       K H Y L D K Q N T K D I K * Y N L E D *
       K T T S I K K I Q K I L K K T T * N T R
        Q P L S R K S K N * * N K L L K I R G I

9541  TCTAAAGAAAAGAGAATGACGATCAAGATAAAAACCTCGATATAACCGATATCAACAACA  9600
       L N R K E * Q * N * K Q L * I P * L Q Q
       Y I E K R K S S T R N K S S Y Q S Y N N
        S K K E R V A L E I K P A I N A I T T T

9601  GAACCAAAAAATAATAAATTATTTTGAATTCGCACGAAAACCTCTAATATGATCACAACA  9660
       R P K K N N L L V * A H K Q L N Y * H Q
       D Q N K I I * Y F K L T S K S I I S T N
        K T K * * K I F S L R A K P S * V L T T

9661  TCAATATTTACAACAACAAACCACATAATTAAAAGAATACGAAAAACAAAAAGTTCAAAT  9720
       L * L H Q Q K T Y * N E * A K Q K E L K
       Y N Y I N N P T N I K K H K K N K L N
        T I F T T T Q H I L K R I S K T K * T *
```

FIG. 3 CONT'D

```
9721  AGGATAAACACGTACACAAATACGAACAAAAATAAAAATACATTGTAACATAAAAGGAAG  9780
         D  *  K  H  M  H  K  H  K  N  K  N  K  H  L  M  T  N  E  K
        I  R  N  T  C  T  N  I  S  T  K  I  K  I  Y  C  Q  I  K  R
          G  I  Q  A  H  T  *  A  Q  K  *  K  *  T  V  N  Y  K  G  E

9781  ACTTTAATCACATTAATACGTAAACGTTACCTAACAATACATACCACGATATTACGGAAA  9840
         Q  F  *  H  L  *  A  N  A  I  S  Q  *  T  H  H  *  L  A  K
        R  F  N  T  Y  N  H  M  Q  L  P  N  N  H  I  T  S  Y  H  R
          S  I  L  T  I  I  C  K  C  H  I  T  I  Y  P  A  I  I  G  K

9841  AACCAAAACACAGTGTATACATCGATACCAATAACGTTTGGTACAAAATACCAATAAAAG  9900
         K  T  K  H  *  M  H  L  *  P  *  Q  L  G  H  K  I  T  I  K
        K  P  K  T  D  C  I  Y  S  H  N  N  C  V  M  N  *  P  *  K
          Q  N  Q  T  V  Y  T  A  I  T  I  A  F  W  T  K  H  N  N  E

9901  TATAACATCCTTTTAACCACAATTACATACATCACTATCATGTAAACTTCTTTGTAGAGA  9960
         M  N  Y  S  F  Q  H  *  H  I  Y  H  Y  Y  M  Q  L  F  M  E
        *  I  T  P  F  N  T  N  I  Y  T  T  I  T  C  K  F  F  C  R
          Y  Q  L  F  I  P  T  L  T  H  L  S  L  V  N  S  S  V  D  R

9961  ATGATGAAAATACTAATGATTTCTAAGAATAACATCTAATTTCTTAAGACAAAGACTACA  10020
         *  *  K  *  S  *  *  L  N  K  N  Y  I  L  S  N  Q  K  Q  H
        K  S  S  K  H  N  S  F  I  R  I  T  S  *  L  I  R  N  R  I
          V  V  K  I  I  V  L  S  E  *  Q  L  N  F  F  E  T  E  S  T

10021 ACGGATGTTATCTATAAACTCAAACATATTATTCATAGCAATGATATCACCATTTTACCT  10080
         Q  R  C  Y  I  N  S  N  T  Y  Y  T  D  N  S  Y  H  Y  F  P
        N  G  V  I  S  I  Q  T  Q  I  I  L  I  T  V  I  T  T  F  H
          A  *  L  L  Y  K  L  K  Y  L  L  Y  R  *  *  L  P  L  I  S

10081 ATGACGACGGATATCTCTTCGCCGCACAAGAGTCAATCGATTTCGATACCTTTGTAAATT  10140
         Y  Q  Q  R  Y  L  L  P  T  N  E  T  L  *  L  *  P  F  M  *
        I  S  S  G  I  S  F  R  R  T  R  L  *  S  F  S  H  F  C  K
          V  A  A  *  L  S  A  A  H  E  *  N  A  L  A  I  S  V  N  L

10141 AGTGTTATTACCATTACTACAGAATATGGTTGGAGGATGTCGTAGACAAAGATGTAGAAA  10200
         D  C  Y  H  Y  H  H  R  I  G  V  E  *  L  M  Q  K  *  M  K
        I  V  I  I  T  I  I  D  *  V  L  R  R  C  C  R  N  R  C  R
          *  L  L  P  L  S  T  K  Y  W  G  G  V  A  D  T  E  V  D  K

10201 AAACGTTAGTCCATAACATTTCTACCATAGAGGATGCAGTTTTAACTTGGAACATAACA  10260
         K  A  I  L  Y  Q  L  S  P  I  E  *  T  L  F  Q  V  K  Y  Q
        K  Q  L  *  T  N  Y  L  H  Y  R  R  R  *  F  N  F  R  T  N
          K  C  D  P  I  T  F  I  T  D  G  V  D  F  I  S  G  Q  I  T
```

FIG. 3 CONT'D

```
10261  ATCACAATGAATACCATCATACTGAAACTTACCAAATACCAATCTACTGTTTCAAATAAC  10320
         *  H  *  K  H  Y  Y  S  K  S  H  N  I  T  L  H  C  L  K  N
          N  T  N  S  I  T  T  H  S  Q  I  T  *  P  *  I  V  F  N  I
           L  T  V  *  P  L  I  V  K  F  P  K  H  N  S  S  L  T  *  Q

10321  AGGAGCAGTACAATATACAAGTAGGAGATTATACTTGCTTGGACTAATAAGACGGAATAA  10380
         D  E  D  H  *  I  N  M  R  *  Y  S  R  V  Q  N  N  Q  R  I
          T  R  T  M  N  Y  T  *  G  R  I  H  V  F  R  I  I  R  G  *
           G  R  *  T  I  H  E  D  E  L  I  F  S  G  S  *  E  A  K  N

10381  CACATCTCAATGAGATCCACTAAAATGATATTACAGACCAGCCTACTCAAATTGTCAACA  10440
         T  Y  L  *  E  L  H  N  *  *  L  T  Q  D  S  S  N  L  L  Q
          Q  T  S  N  S  *  T  I  K  S  Y  H  R  T  P  H  T  *  C  N
           H  L  T  V  R  P  S  K  V  I  I  D  P  R  I  L  K  V  T  T

10441  CAGAATGGTCTACGTCCCGACAGTTGAACAAAACTGTCAGAGAAATGTTTTAGGAATGTG  10500
         T  K  G  S  A  P  S  D  V  Q  K  S  L  R  K  V  F  D  K  C
          H  R  V  L  H  A  T  L  K  N  Q  C  D  R  *  L  I  R  V
           D  *  W  I  C  P  Q  *  S  T  K  V  T  E  K  C  F  G  *  V

10501  AGGTTTTATATGAAAACCATTACAATTTGGACCACTTTGAAAATGACAAAATCGACGCAT  10560
         E  L  I  Y  K  Q  Y  H  *  V  Q  H  F  K  *  Q  K  L  Q  T
          S  W  F  I  S  K  T  I  N  F  R  T  F  S  K  S  N  *  S  R
           G  F  Y  V  K  P  L  T  L  G  P  S  V  K  V  T  K  A  A  Y

10561  ATTACCGGCTGGTGTTCCCCGTAAAGTACAATGATACGCATCATCAATATGATAATTTCC  10620
         Y  H  G  V  V  L  P  M  E  H  *  *  A  Y  Y  N  Y  *  *  L
          I  I  A  S  W  L  P  C  K  M  N  S  H  T  T  T  I  S  N  F
           L  P  R  G  C  P  A  N  *  T  V  I  R  L  L  *  V  I  L  P

10621  AAGAAAAAACACACCCAGTACACCTAGACAACCAATACATAATTGTCCACTATCACAATT  10680
         N  K  K  T  H  T  M  H  I  Q  Q  N  H  I  L  L  H  Y  H  *
          T  R  K  Q  T  P  *  T  S  R  N  T  I  Y  *  C  T  I  T  N
           E  K  K  H  P  D  H  P  D  T  P  *  T  N  V  P  S  L  T  L

10681  CAAACATATATACGTAGTTAATCTCGAGTCATGACCAACAGTGTGACCGTGACTAAAATG  10740
         T  Q  I  Y  A  D  I  L  A  *  Y  Q  N  D  C  Q  C  Q  N  *
          L  K  Y  I  H  M  L  *  L  E  T  S  T  T  V  S  A  S  I  K
           N  T  Y  I  C  *  N  S  S  L  V  P  Q  *  V  P  V  S  K  V

10741  ACCATTAAAAATACCAGGTATATCTCTACGAGTTCAACATGTCAACGGTCAATTCCTGAT  10800
         Q  Y  N  K  H  D  M  Y  L  H  E  L  Q  V  T  A  L  *  P  S
          S  T  I  K  I  T  W  I  S  I  S  L  N  Y  L  Q  W  N  L  V
           P  L  K  *  P  G  Y  L  S  A  *  T  T  C  N  G  T  L  S  *
```

FIG. 3 CONT'D

```
10801  GCAGGTCTGACAATTACAATAACGAACCGAGATACGTCGATATGAATTATTAACACGAAC  10860
         R  G  S  Q  *  H  *  Q  K  A  R  H  L  *  V  *  Y  N  H  K
        V  D  L  S  N  I  N  N  S  P  E  I  C  S  Y  K  I  I  T  S
          T  W  V  T  L  T  I  A  Q  S  *  A  A  I  S  L  L  Q  A  Q

10861  CAAACATGTTTTACTACAAACAAGATGACTTCTAAAATTACAAACCCGATACCGTTTACC  10920
         T  Q  V  F  H  H  K  N  *  Q  L  N  *  H  K  P  *  P  L  H
        P  K  Y  L  I  I  N  T  R  S  F  I  K  I  N  P  S  H  C  I
          N  T  C  F  S  T  Q  E  V  S  S  K  L  T  Q  A  I  A  F  P

10921  AAAATCGGTTCATTTTCGTCTAGAACAGAATCTACGAAACCGAAGTTACTGTCCACAAAG  10980
         N  *  G  L  L  L  D  Q  R  L  H  K  P  K  L  S  L  H  K
        T  K  A  L  Y  F  C  I  K  D  *  I  S  Q  S  *  H  C  T  N
          K  L  W  T  F  A  S  R  T  K  S  A  K  A  E  I  V  P  T  E

10981  ATAACTTTGAAATAACCGACGATAATTCGCAGATATATACCCTAAAGTTCCAGCAGTTTA  11040
         *  Q  F  K  I  P  Q  *  *  A  D  I  Y  P  I  E  L  D  D  F
        R  N  F  S  *  Q  S  S  N  L  T  *  I  H  S  K  L  T  T  L
          I  S  V  K  N  A  A  I  L  R  R  Y  I  P  N  *  P  R  *  I

11041  TGATCCTTCAACATGAAAACTTCTACTTAACCGTGGAAGACTGCAAATAGTTGTTAACCG  11100
         V  L  F  N  Y  K  Q  L  H  I  P  V  K  Q  R  K  D  V  I  P
        Y  *  S  T  T  S  K  F  I  F  Q  C  R  R  V  N  I  L  L  Q
          S  P  L  Q  V  K  S  S  S  N  A  G  E  S  T  *  *  C  N  A

11101  ACCACAATTTAACGTTAGATTTTGTTTTTCTAAATAATTTCTTTGTTAAATAACCTAAAA  11160
         Q  H  *  I  A  I  *  F  L  F  I  *  *  L  F  L  K  N  S  K
        S  T  N  F  Q  L  R  F  C  F  S  K  N  F  F  C  N  I  P  N
          P  T  L  N  C  D  L  V  F  L  N  I  L  S  V  I  *  Q  I  K

11161  CTATAGATGTAAAAACAAATCAACATATTAAAGACGTAAACAATTTACCTGATATAAATA  11220
         S  I  *  M  K  T  *  N  Y  L  K  Q  M  Q  *  I  S  *  I  *
        Q  Y  R  C  K  Q  K  T  T  Y  N  R  C  K  N  F  P  S  Y  K
          I  D  V  N  K  N  L  Q  I  I  E  A  N  T  L  H  V  I  N  I

11221  CATATAATTATGTGTATACTAACCACAATGTAATACACATGAAACAAAACAATCAAAATA  11280
         T  Y  *  Y  V  Y  S  Q  H  *  M  I  H  V  K  N  Q  *  N  *
        H  I  N  I  C  M  H  N  T  N  C  *  T  Y  K  T  K  N  T  K
          Y  I  L  V  C  I  I  P  T  V  N  H  T  S  Q  K  T  L  K  I

11281  CTACAATGATCAATTTGTATTCGTAAAAATAAACTGATACATATATTAAGGACATGAGAC  11340
         S  T  V  L  *  V  Y  A  N  K  N  S  *  T  Y  L  E  Q  V  R
        H  H  *  *  N  F  M  L  M  K  I  Q  S  H  I  Y  N  R  Y  E
          I  N  S  T  L  C  L  C  K  *  K  V  I  Y  I  I  G  T  S  Q
```

FIG. 3 CONT'D

```
11341  ATGGAACAAAATACATTTAATAAATCAACAAATATTCCTTCCAAAATCTCCAAAATGAAT  11400
          Y  R  T  K  H  L  N  N  L  Q  K  Y  P  L  N  *  L  N  *  K
         T  G  Q  K  I  Y  I  I  *  N  N  I  L  F  T  K  S  T  K  S
        V  K  N  *  T  F  *  K  T  T  *  L  S  P  K  L  P  K  V  *

11401  ACAGACCGAGAGTATAAAACAAGGACGACACTTAAAATGAATACAAATACTTCATAAAAT  11460
          H  R  A  R  M  N  Q  E  Q  Q  S  N  *  K  H  K  H  L  I  K
         I  D  P  E  *  I  K  N  R  S  H  I  K  S  I  N  I  F  Y  K
        T  Q  S  E  Y  K  T  G  A  T  F  K  V  *  T  *  S  T  N  *

11461  ACCAACATAAAATACACAAAAACGATAAAAATATTGATACGTATCATAATTAGTACTGTA  11520
          H  N  Y  K  I  H  K  Q  *  K  *  L  *  A  Y  Y  *  D  H  C
         I  T  T  N  *  T  N  K  S  N  K  Y  S  H  M  T  N  I  M  V
        P  Q  I  K  H  T  K  A  I  K  I  V  I  C  L  I  L  *  S  M

11521  AAAAGAAACTACAAAAACCAACCATCTTATCAATGAAATTAAAGATACACCATAAAACC  11580
          K  K  K  S  T  K  P  Q  Y  F  L  *  K  L  K  *  T  T  N  Q
         N  K  R  Q  H  K  Q  N  T  S  Y  N  S  *  N  R  H  P  I  K
        K  E  K  I  N  K  T  P  L  I  T  V  K  I  E  I  H  Y  K  P

11581  CAGCTTAAATCTTCTCCTACAAAACAATAAATAATGTCGGAAAAATCCATGAATATGTAC  11640
          T  S  N  L  L  P  H  K  T  I  *  *  L  R  K  L  Y  K  Y  M
         P  R  I  *  F  L  I  N  Q  *  K  N  C  G  K  *  T  S  I  C
        D  F  K  S  S  S  T  K  N  N  I  V  A  K  K  P  V  *  V  H

11641  CTGGTGATAAAACAGTAATCGATATCGTTTTTAACAACGATTAACCAACAGACAATTATA  11700
          S  W  *  K  T  M  L  *  L  L  F  Q  Q  *  N  T  T  Q  *  Y
         P  G  S  N  Q  *  *  S  Y  C  F  N  N  S  I  P  Q  R  N  I
        V  V  I  K  D  N  A  I  A  F  I  T  A  L  Q  N  D  T  L  I

11701  TAAAATAAAATGTCTACATGGAATATAATTTAACTAAGAGAACTCAATGAATAAATATCC  11760
          I  K  N  *  L  H  V  K  Y  *  I  S  E  R  S  N  S  I  *  L
         Y  K  I  K  C  I  Y  R  I  N  F  Q  N  E  Q  T  V  *  K  Y
        N  *  K  V  S  T  G  *  I  L  N  I  R  K  L  *  K  N  I  P

11761  CATATAAAATAGAACAATAACCCCTAAAAGAGAGAAAATTTGTCACAAAAATCTTACGG  11820
          T  Y  K  I  K  N  N  P  I  K  R  E  K  L  C  H  K  *  F  A
         P  I  N  *  R  T  I  P  S  K  E  R  K  *  V  T  N  K  S  H
        Y  I  K  D  Q  *  Q  P  N  K  E  R  K  F  L  T  K  L  I  G

11821  ATACCCACAAATATTAATATTTTAAAGACAAGTTCTTAACGCAATATACTTACGATTACC  11880
          *  P  H  K  Y  N  Y  F  K  Q  E  L  I  A  N  Y  S  H  *  H
         R  H  T  N  I  I  I  F  N  R  N  L  F  Q  T  I  H  I  S  I
        I  P  T  *  L  *  L  I  E  T  *  S  N  R  *  I  F  A  L  P
```

FIG. 3 CONT'D

```
11881  GAATGCAGGTGGAGCATTATCAAAACTCCGATAAAACAATTTAAATTTTGACGAACCTTA  11940
          S  V  D  V  E  Y  Y  N  Q  P  *  K  T  L  N  L  V  A  Q  F
        A  *  T  W  R  T  I  T  K  L  S  N  Q  *  I  *  F  Q  K  S
          K  R  G  G  R  L  L  K  S  A  I  K  N  F  K  F  S  S  P  I

11941  TCCACCGCACGGTCAATAACTTCAGAGGGTTTAAGTTAGTTTTAACTGACTACACTTTAC  12000
          L  H  R  A  L  *  Q  L  R  G  F  E  I  L  I  S  Q  H  S  I
         Y  T  A  H  W  N  N  F  D  G  L  N  L  *  F  Q  S  I  H  F
          P  P  T  G  T  I  S  T  E  W  I  *  D  F  N  V  S  T  F  H

12001  ACGATTACAACAAAACAATTTAACAAATGTCGTAAACGTACAACGAAGATTAAGATTCAA  12060
          H  *  H  Q  K  T  L  N  N  V  A  N  A  H  Q  K  *  N  *  T
         T  S  I  N  N  Q  *  I  T  *  L  M  Q  M  N  S  R  I  R  L
          A  L  T  T  K  N  F  Q  K  C  C  K  C  T  A  E  L  E  L  N

12061  CACCGTCATAACATCACAAAATGTATTACTTTATGATAGATGAAGTCTAAACTCACATCG  12120
          T  A  T  N  Y  H  K  V  Y  H  F  V  I  *  K  L  N  S  H  L
         Q  P  L  I  T  T  N  *  M  I  F  Y  *  R  S  *  I  Q  T  Y
          H  C  Y  Q  L  T  K  C  L  S  I  S  D  V  E  S  K  L  T  A

12121  AAAACTATTCGAACGAGTTAATAACTAACAAAATAAGCGGTTAGGACGACGTCAACTATG  12180
          K  Q  Y  A  Q  E  I  I  S  Q  K  I  R  W  D  Q  Q  L  Q  Y
         S  K  I  L  K  S  L  *  Q  N  N  *  E  G  I  R  S  C  N  I
          K  S  L  S  A  *  N  N  I  T  K  N  A  L  G  A  A  T  S  V

12181  ATTCACAGAACGTTCATATCTACTTCAATCGCTACTAATACAAGTTCTATCATGGCAAAA  12240
          *  T  D  Q  L  Y  L  H  L  *  R  H  N  H  E  L  Y  Y  R  K
         S  L  T  K  C  T  Y  I  F  N  A  I  I  I  N  L  I  T  G  N
          L  H  R  A  L  I  S  S  T  L  S  S  *  T  *  S  L  V  T  K

12241  CGTCCGAAACGTTTCACTCAAACATTTATACCGATCAAAACAACTTATACTTCAGCGTTT  12300
          A  P  K  A  F  H  T  Q  L  Y  P  *  N  Q  Q  I  H  L  R  L
         Q  L  S  Q  L  T  L  K  Y  I  H  S  T  K  N  F  I  F  D  C
          C  A  K  C  L  S  N  T  F  I  A  L  K  T  S  Y  S  T  A  F

12301  CTTTTTAAACCGACTACGATTTTTATCACCAAGACAATTAGTTGTTGTCTATTTTGTCAA  12360
          S  F  N  P  Q  H  *  F  Y  H  N  Q  *  D  V  V  S  L  V  T
         L  F  I  Q  S  I  S  F  I  T  T  R  N  I  L  L  L  Y  F  L
          F  F  K  A  S  A  L  F  L  P  E  T  L  *  C  C  I  F  C  N

12361  TCTTTTTCGTACATTATATCGATTCAGACACATACTTGCACTATTTCGACATCGAGCGTT  12420
          L  F  L  M  Y  Y  L  *  T  Q  T  H  V  H  Y  L  Q  L  E  C
         *  F  F  C  T  I  Y  S  L  R  H  I  F  T  I  F  S  Y  S  A
          S  F  A  H  L  I  A  L  D  T  Y  S  R  S  L  A  T  A  R  L
```

FIG. 3 CONT'D

```
12421  TGAACTTGCATACCGTCTGGATCGTGAATGATTGTACATATTTCTCCGAGCCTAATTACT  12480
          V  Q  V  Y  P  L  G  L  V  *  *  C  T  Y  L  P  E  S  *  H
        F  K  F  T  H  C  V  *  C  K  S  V  H  I  F  L  S  P  N  I
          S  S  R  I  A  S  R  A  S  V  L  M  Y  L  S  A  R  I  L  S

12481  ATTCTTCTCATTTCAACAAAGGCGAAACGTCTGTTACGAAAAATCGTACCAAGCATTTAA  12540
          Y  S  S  Y  L  Q  K  R  K  A  S  L  A  K  *  C  P  E  Y  I
        I  L  L  T  F  N  N  G  S  Q  L  C  H  K  K  A  H  N  T  F
          L  F  L  L  T  T  E  A  K  C  V  I  S  K  L  M  T  R  L  N

12541  CCTATTAGTCCGAAATTTAAGATAAGACCTATTACGACAATTTCCAACACATGGAAACTC  12600
          P  Y  D  P  K  L  N  *  E  P  Y  H  Q  *  L  N  H  V  K  S
        Q  I  I  L  S  *  I  R  N  Q  I  I  S  N  F  T  T  Y  R  Q
          S  L  *  A  K  F  E  I  R  S  L  A  T  L  P  Q  T  G  K  L

12601  ACGATAAGGTCGTAACCGACGATTATGAAATTGATATCATTATGGTCTATTTGTTCAAAA  12660
          H  *  E  L  M  P  Q  *  Y  K  L  *  L  L  V  L  Y  V  L  K
        T  S  N  W  C  Q  S  S  I  S  *  S  Y  Y  Y  W  I  F  L  N
          A  I  G  A  N  A  A  L  V  K  V  I  T  I  G  S  L  C  T  K

12661  ACTATTTCAACAACTATTACAAATACAATGTATACGACCATCACATACCGTATATGTCTG  12720
          Q  Y  L  Q  Q  Y  H  K  H  *  M  H  Q  Y  H  I  A  Y  V  S
        K  I  F  N  N  I  I  N  I  N  C  I  S  T  T  Y  P  M  Y  L
          S  L  T  T  S  L  T  *  T  V  Y  A  P  L  T  H  C  I  C  V

12721  ACAAGTTCTACGACTACCATAATTATTTGTCAATTGACTATAATCACAACTAAGATTAAC  12780
          Q  E  L  H  Q  H  Y  *  Y  V  T  L  Q  Y  *  H  Q  N  *  N
        S  N  L  I  S  I  T  N  I  F  L  *  S  I  N  T  N  I  R  I
          T  *  S  A  S  P  I  L  L  C  N  V  S  I  L  T  S  E  L  Q

12781  CGGAGAACAATAGTAACGCTTGTCCATATTACTTCAACGATTACGACAATACGTCTTATT  12840
          A  E  Q  *  *  Q  S  C  T  Y  H  L  Q  *  H  Q  *  A  S  Y
        P  R  K  N  D  N  R  V  P  I  I  F  N  S  I  S  N  H  L  I
          G  R  T  I  M  A  F  L  Y  L  S  T  A  L  A  T  I  C  F  L

12841  ACTCAACTACGGAGTATTTAATTTTTATGTTCAACAATTATCACCAAGACTATACTTAAC  12900
          H  T  S  A  E  Y  I  L  F  V  L  Q  *  Y  H  N  Q  Y  S  N
        I  L  Q  H  R  M  F  *  F  Y  L  N  N  I  T  T  R  I  H  I
          S  N  I  G  *  L  N  F  I  C  T  T  L  L  P  E  S  I  F  Q

12901  ATTATAAGGATGAGTTACAATAATATTATTACCATCATCACCATCTTATCAAATACGACA  12960
          Y  Y  E  *  E  I  N  N  Y  Y  H  Y  Y  H  Y  F  L  K  H  Q
        T  I  N  R  S  L  T  I  I  I  I  T  T  T  T  S  Y  N  I  S
          L  I  G  V  *  H  *  *  L  L  P  L  L  P  L  I  T  *  A  T
```

FIG. 3 CONT'D

```
12961  AGAATCACTACAACTACCAGAATTCATATGATTCTATTACTTTCTACTACCTTTAACACA  13020
          E  *  H  H  Q  H  D  *  T  Y  *  S  L  S  L  H  H  F  N  H
         N  K  T  I  N  I  T  K  L  I  S  L  Y  H  F  I  I  S  I  T
           R  L  S  T  S  P  R  L  Y  V  L  I  I  F  S  S  P  F  Q  T

13021  ACAAAATCTCGAACTAGGAGGAACATTTAAAAGATATGTTCTACAATTCCCTGAATTTTA  13080
          Q  K  L  A  Q  D  E  K  Y  I  K  *  V  L  H  *  P  V  *  F
         N  N  *  L  K  I  R  R  T  F  K  R  Y  L  I  N  L  S  K  F
           T  K  S  S  S  G  G  Q  L  N  E  I  C  S  T  L  P  S  L  I

13081  ATTCATAGAAATAAAATAATTTCCTACATTGTGAAATCGATCTCCCACCCAACAACCATG  13140
          *  T  D  K  N  *  *  L  I  Y  C  K  L  *  L  T  P  Q  Q  Y
         N  L  I  K  I  K  N  F  S  T  V  S  *  S  S  P  P  N  N  T
           L  Y  R  *  K  I  L  P  H  L  V  K  A  L  P  H  T  T  P  V

13141  AAATAGAAGTTGTTAATCTAACGTCCGACCACAACGATGACTCATACGTCGATTAAGAAG  13200
          K  I  K  L  L  *  I  A  P  Q  H  Q  *  Q  T  H  L  *  N  K
         S  *  R  *  C  N  S  Q  L  S  T  N  S  S  L  I  C  S  I  R
           K  D  E  V  I  L  N  C  A  P  T  A  V  S  Y  A  A  L  E  E

13201  ATATGAAAGTAATACACGTAAAAGACATCTAGGATTCTTTTGAATAAATCTAATATATGT  13260
          *  V  K  M  I  H  M  K  Q  L  D  *  S  F  K  N  L  N  Y  V
         R  Y  K  *  *  T  C  K  R  Y  I  R  L  F  S  I  *  I  I  Y
           I  S  E  N  H  A  N  E  T  S  G  L  F  V  *  K  S  *  I  C

13261  TGTTCCACCACATGGATATTAATTAACACAATTTTACGAGACACTAGTACGACCATGACC  13320
          V  L  H  H  V  *  L  *  N  H  *  F  A  R  H  D  H  Q  Y  Q
         L  L  T  T  Y  R  Y  N  I  T  N  F  H  E  T  I  M  S  T  S
           C  P  P  T  G  I  I  L  Q  T  L  I  S  Q  S  *  A  P  V  P

13321  ATACCGGTAATGATAATTTGGACTCCGATGATAATTGGTTCTAAGAATACCACCACGGAG  13380
          Y  P  W  *  *  *  V  Q  P  *  *  *  G  L  N  K  H  H  H  R
         T  H  G  N  S  N  F  R  L  S  S  N  V  L  I  R  I  T  T  G
           I  A  M  V  I  L  G  S  A  V  I  L  W  S  E  *  P  P  A  E

13381  TCAAACATAAATAACGGCACGTGCACATCTCGTAGGTCTACATCTACCATATACATTTAA  13440
          L  K  Y  K  N  G  H  V  H  L  A  D  L  H  L  H  Y  I  Y  I
         *  N  T  N  I  A  T  C  T  Y  L  M  W  I  Y  I  T  Y  T  F
           T  Q  I  *  Q  R  A  R  T  S  C  G  S  T  S  P  I  H  L  N

13441  TGCACCATTTAAACATGTTCAGGGAAACCCATATTTTCTAGGATAAGAAATACACAATTG  13500
          V  H  Y  I  Q  V  L  G  K  P  Y  L  L  D  *  E  K  H  T  L
         *  T  T  F  K  Y  L  D  R  Q  T  Y  F  I  R  N  K  I  H  *
           R  P  L  N  T  C  T  G  K  P  I  F  S  G  I  R  *  T  N  V
```

FIG. 3 CONT'D

```
13501  TGTACTACAAACAGTTCAGACACCAAAAACCTCTCTACCGTCAACAAGGACACATCCAAG  13560
         V  H  H  K  D  L  R  H  N  K  S  L  H  C  N  N  R  H  L  N
        C  M  I  N  T  L  D  T  T  K  P  S  I  A  T  T  G  T  Y  T
         C  S  T  Q  *  T  Q  P  K  Q  L  S  P  L  Q  E  Q  T  P  E

13561  TTCACAGCGACAAGTTAGATTTCTAAATTTAAAAAATTTGCCCAAGCCCCATGATCACAC  13620
         L  H  R  Q  E  I  *  L  N  L  N  K  L  R  T  R  P  V  L  T
         *  T  D  S  N  L  R  F  I  *  I  K  *  V  P  E  P  Y  *  H
          L  T  A  T  *  D  L  S  K  F  K  K  F  P  N  P  T  S  T  H

13621  TTACGGGCCGATCATGGGACACGATCACCAAATAGATGACTACAAGTTAATTCCCGTAAA  13680
         F  A  R  S  T  G  Q  A  L  P  K  D  V  S  T  *  N  L  A  N
         S  H  G  A  L  V  R  H  *  H  N  I  *  Q  H  E  I  L  P  M
          I  G  P  *  Y  G  T  S  T  T  *  R  S  I  N  L  *  P  C  K

13681  CTGTAAACATTATGGTTATCTCGACCATATCCAAATATAATATTTCACTTAACAACGGCA  13740
         S  M  Q  L  V  L  L  A  P  I  P  K  Y  *  L  T  F  Q  Q  R
         Q  C  K  Y  Y  W  Y  L  Q  Y  L  N  I  N  Y  L  S  N  N  G
          V  N  T  I  G  I  S  S  T  Y  T  *  I  I  F  H  I  T  A  T

13741  AAAGTCGCATATCTACTGCTGCCATTATTTAACCTATTCAAGAAACAACAGTTTTCTTGA  13800
         K  *  R  I  S  S  S  P  L  L  N  S  L  N  K  T  T  L  L  V
         N  E  A  Y  L  H  R  R  Y  Y  I  P  Y  T  R  Q  Q  *  F  F
          K  L  T  Y  I  V  V  T  I  F  Q  I  L  E  K  N  D  F  S  S

13801  TTAAATCTTCAAATATTATTTCTCTTTTGAATAATACTCAACTGATTTTCAACACCACAA  13860
         L  K  S  T  *  L  L  S  F  V  *  *  S  N  V  L  L  Q  P  T
         *  N  L  L  K  Y  Y  L  S  F  K  N  H  T  S  *  F  N  H  H
          I  *  F  N  I  I  F  L  F  S  I  I  L  Q  S  F  T  T  T  N

13861  CACCGACTTGTACTAAAGAAATGTAAACTATAACTACCATCAGCGCACGGTGTATATCAA  13920
         T  A  S  C  S  K  K  V  N  S  I  S  P  L  R  T  G  C  I  T
         Q  P  Q  V  H  N  R  *  M  Q  Y  Q  H  Y  D  R  A  V  Y  L
           H  S  F  M  I  E  K  C  K  I  N  I  T  T  A  H  W  M  Y  N

13921  GCATCCTTAGAAAGTTTCATATGATACAATCTAGAAACGATACGTAACGCAGTAAAACTA  13980
         R  L  F  R  E  F  Y  V  I  N  S  R  Q  *  A  N  R  *  K  S
         E  Y  S  D  K  L  T  Y  *  T  L  D  K  S  H  M  A  D  N  Q
          T  P  I  K  *  L  I  S  H  *  I  K  A  I  C  Q  T  M  K  I

13981  GCATTACTAACAAGTTATAACACACTTTAAGAAACACTCATACGACTAACATTTCTTAGG  14040
         R  L  S  Q  E  I  N  H  S  I  R  Q  S  Y  A  S  Q  L  S  D
         D  Y  H  N  N  L  I  T  H  F  E  K  H  T  H  Q  N  Y  L  I
          T  I  I  T  *  Y  Q  T  F  N  K  T  L  I  S  I  T  F  F  G
```

FIG. 3 CONT'D

```
14041  ATGAAAAGATTCTTTCTAACCATACTAAAACAACTTTTAGGACTATAATAATTATATATA  14100
        *  K  E  L  F  S  Q  Y  S  K  T  S  F  G  S  I  I  L  I  Y
          R  S  K  *  S  L  N  T  H  N  Q  Q  F  D  Q  Y  *  *  Y  I
            V  K  R  L  F  I  P  I  I  K  N  F  I  R  I  N  N  I  Y  I

14101  TTTTTTAATCCGGGATAAAAATTATCTCGAAATGAATTATGACAGTAAAAACGTCTGTGG  14160
        L  F  N  P  G  I  K  L  L  A  K  S  L  V  T  M  K  A  S  V
          Y  F  I  L  G  *  K  *  Y  L  K  V  *  Y  Q  *  K  Q  L  C
            F  F  *  A  R  N  K  I  S  S  *  K  I  S  D  N  K  C  V  G

14161  AATCAACTTCATCCAAATCAACCACAAAATTGAAATCTATTGGTTCTAAACATACCAGTT  14220
        K  T  S  T  P  K  T  P  T  K  V  K  S  L  W  S  K  Y  P  *
          R  L  Q  L  L  N  L  Q  H  K  L  K  L  Y  G  L  N  T  H  D
            *  N  F  Y  T  *  N  T  N  *  S  *  I  V  L  I  Q  I  T  L

14221  ACCATACTAAAACCACTAAAATATGTTTGTCGGGGTCCCAAACCACACCGTCAACGTCTA  14280
        H  Y  S  K  P  S  K  I  C  V  A  G  P  N  P  T  A  T  A  S
          I  T  H  N  Q  H  N  *  V  F  L  G  L  T  Q  H  P  L  Q  L
            P  I  I  K  T  I  K  Y  L  C  G  W  P  K  T  H  C  N  C  I

14281  AGAATGATAAGAATATACTACGGATACAACTGATACACAGTACATAATCTAACACTTAAT  14340
        E  *  *  E  *  I  I  G  I  N  V  I  H  *  T  N  S  Q  S  N
          N  K  S  N  K  Y  S  A  *  T  S  *  T  D  H  I  L  N  H  I
            R  V  I  R  I  H  H  R  H  Q  S  H  T  M  Y  *  I  T  F  *

14341  AAACAATTACTATCAATATCTGTTAAGCTAGAACATGTCATACTAAAATGACTAATGTTC  14400
        N  T  L  S  L  *  L  C  N  S  R  T  C  Y  S  K  V  S  *  L
          I  Q  *  H  Y  N  Y  V  I  R  D  Q  V  T  H  N  *  Q  N  C
            K  N  I  I  T  I  S  L  E  I  K  Y  L  I  I  K  S  I  V  L

14401  AATCTCAACAAATTATTCATAAAATTCATAACCCCATACTTCATAGTAGGATTATGACAC  14460
        N  S  N  N  L  L  Y  K  L  Y  Q  P  I  F  Y  *  G  L  V  T
          T  L  T  T  *  Y  T  N  *  T  N  P  Y  S  T  D  D  *  Y  Q
            *  L  Q  K  I  L  I  K  L  I  P  T  H  L  I  M  R  I  S  H

14461  CTAACACTATTACTATCCACATAATAAGTAACACGATTAAAATTATATGATAAATCATAC  14520
        S  Q  S  L  S  L  H  I  I  *  Q  A  L  K  L  I  S  N  L  I
          P  N  H  Y  H  Y  T  Y  *  E  N  H  *  N  *  Y  V  I  *  Y
            I  T  I  I  I  P  T  N  N  M  T  S  I  K  I  Y  *  K  T  H

14521  CAAAATGGATTATGAACAAAACCAGGGGAACAATCTGTTTAAAAACATCTACCACATGGC  14580
        T  K  G  L  *  T  K  P  G  E  Q  S  V  *  K  H  L  P  H  G
          Q  N  G  L  *  T  K  P  G  N  N  L  F  K  T  S  T  T  W
            K  W  I  M  N  K  T  R  G  T  I  C  L  K  H  L  P  H  G
```

FIG. 3 CONT'D

14581  AAACAACAAAGATAACCAATGGTAATGTTTCTCAATCCACATCAATACTTGAATCTACAA  14640
          N  T  T  E  I  P  *  W  *  L  S  N  P  T  T  I  F  K  S  T
         T  Q  Q  K  *  Q  N  G  N  C  L  T  L  H  L  *  S  S  L  H
           K  N  N  R  N  T  V  M  V  F  L  *  T  Y  N  H  V  *  I  N

14641  CTGTGTGTGGCAATAGCAAACAGAGAATTTCTAAATGAAGAAATACGTCGTCTAGGACGA  14700
          S  V  C  R  *  R  K  D  R  L  S  K  S  R  *  A  A  S  G  A
         Q  C  V  G  N  D  N  T  E  *  L  N  V  E  K  H  L  L  D  Q
           V  C  V  T  I  T  Q  R  K  F  I  *  K  K  I  C  C  I  R  S

14701  TACGTGCAACGTAGACGATCACGAGACGAACTAAATGCTTGAACAACAAAATCACATCGA  14760
          I  C  T  A  D  A  L  A  R  S  S  K  R  V  Q  Q  K  L  T  A
         *  A  R  Q  M  Q  *  H  E  A  Q  N  V  F  K  N  N  *  H  L
           H  V  N  C  R  S  T  S  Q  K  I  *  S  S  T  T  K  T  Y  S

14761  CGGTAATGTTCACCATATTTTAAAGTTTGACATTTTGGTCCATTGAAATTGGTTCTGAAA  14820
          A  M  V  L  P  I  F  N  *  V  T  F  G  P  L  K  L  W  S  K
         Q  W  *  L  H  Y  L  I  E  F  Q  L  V  L  Y  S  *  G  L  S
           G  N  C  T  T  Y  F  K  L  S  Y  F  W  T  V  K  V  L  V  K

14821  ATGCTCAAACAATTTTCATTTCCGAACAAATTTCTCCCATCATGTCAACTAAACTTTGTA  14880
          *  S  N  T  L  L  P  K  N  L  S  P  L  V  T  S  K  F  C
         K  R  T  Q  *  F  Y  L  S  T  *  L  P  Y  Y  L  Q  N  S  V
           V  L  K  N  F  T  F  A  Q  K  F  L  T  T  C  N  I  Q  F  M

14881  AAAAAGAAATGAGTTCTACCATTACGACGTTAATGACTAATATTAATAATATTCATATTA  14940
          K  K  K  V  *  S  P  L  A  A  I  V  S  *  L  *  *  L  Y  L
         N  K  R  *  E  L  H  Y  H  Q  L  *  Q  N  Y  N  N  Y  T  Y
           K  E  K  S  L  I  T  I  S  C  N  S  I  I  I  I  L  I  I

14941  AATGGATGATACCAACTATAATTCGTCAATAACAAACATAATCTTCAACAAATATTTATA  15000
          K  G  V  I  T  S  I  L  C  N  N  N  T  N  S  T  T  *  L  Y
         N  V  *  *  P  Q  Y  *  A  T  I  T  Q  I  L  L  Q  K  Y  I
           *  R  S  H  N  I  N  L  L  *  Q  K  Y  *  F  N  N  I  F  I

15001  AAACTTTAAATACTACCACCAACATATGGTCGTAGTGTTCAATAACAATTATTAATACTA  15060
          K  S  I  *  S  P  P  Q  I  G  A  D  C  T  I  T  L  L  *  S
         N  Q  F  K  H  H  H  N  Y  V  L  M  V  L  *  Q  *  Y  N  H
           K  F  N  I  I  T  T  T  Y  W  C  *  L  N  N  N  I  I  I  I

15061  TTTTCACGACCAATAGGTAAATTATTTAAACCATTTCGGTCTGAAATAATACTCCGTAAT  15120
          L  L  A  P  *  G  N  L  L  N  P  L  A  L  S  *  *  S  A  N
         Y  F  H  Q  N  D  M  *  Y  I  Q  Y  L  W  V  K  N  H  P  M
           F  T  S  T  I  W  K  I  F  K  T  F  G  S  K  I  I  L  C  *

FIG. 3 CONT'D

```
15121   AGTAAACTCCTTGTCTTACTTTAAATACGTATATGATTTGCATTACAAGACGGGTGGAAT   15180
          D  N  S  S  C  F  S  I  *  A  Y  V  L  R  L  T  R  G  V  K
         I  M  Q  P  V  S  H  F  K  H  M  Y  *  V  Y  H  E  A  W  R
           *  K  L  F  L  I  F  N  I  C  I  S  F  T  I  N  Q  G  G  *

15181   TGAGTTTACTTAAATTTTATACGATAGTCACGATTCTTATCTCGAGCGTGACATCGTCCA   15240
          V  *  I  F  K  F  Y  A  I  L  A  L  F  L  A  R  V  T  A  P
         L  E  F  S  N  L  I  H  *  *  H  *  S  Y  L  E  C  Q  L  L
           S  L  H  I  *  F  I  S  D  T  S  L  I  S  S  A  S  Y  C  T

15241   CAAAGATAAGAATCATGATACTGTCCGGCTTACAAGGTAGTTTTTACAAACTTCTCATAT   15300
          T  E  I  R  L  V  I  V  P  R  I  N  W  *  F  H  K  F  L  I
         H  K  *  E  *  Y  *  S  L  G  F  T  G  D  F  I  N  S  S  Y
           N  R  N  K  T  S  H  C  A  S  H  E  M  L  F  T  Q  L  T  Y

15301   CGTCGATGGGCTCCACAAGGACAACAATATCCTTGGTGATTTAAAATACCACCAACCCTG   15360
          A  A  V  R  P  T  G  T  T  I  P  V  V  L  N  *  P  P  Q  S
         L  L  *  G  L  H  E  Q  Q  *  L  F  W  *  I  K  H  H  N  P
           C  S  G  S  T  N  R  N  N  Y  S  G  S  F  K  I  T  T  P  V

15361   CTATACAATGCAGTAGAATATTTCCTACAACTGTTGGGACAAGAATACCCAACCCTAATA   15420
          S  I  N  R  *  R  I  F  S  T  S  L  G  T  R  I  P  Q  S  *
         R  Y  T  V  D  D  *  L  P  H  Q  C  G  Q  E  *  P  N  P  N
           I  H  *  T  M  K  Y  L  I  N  V  V  R  N  K  H  T  P  I  I

15421   GGATTTACACTAGCACGATACGGTTTATAAAACGCATAACAATCATCAAATCAAAACCGG   15480
          G  L  H  S  R  A  I  G  F  I  K  R  I  T  L  L  K  T  K
         D  *  I  H  D  H  *  A  L  Y  K  A  Y  Q  *  Y  N  L  K  P
           R  F  T  I  T  S  H  W  I  N  Q  T  N  N  T  T  *  N  Q  G

15481   GCGTTTGTACTTAAAACAACAAGTGTACCACTATCTAAAATAGCGGAACGCTTACTTACA   15540
          R  L  C  S  N  Q  Q  E  C  P  S  L  N  *  R  R  A  F  S  H
         G  C  V  H  I  K  N  N  V  H  H  Y  I  K  D  G  Q  S  H  I
           A  F  M  F  K  T  T  *  M  T  I  S  K  I  A  K  R  I  F  T

15541   CGAGTTCAAAACTCACTTTATCAATACACACCGCCAACGATAATACAATTCGGACCACCA   15600
          A  *  T  K  L  S  I  T  I  H  P  P  Q  *  *  T  L  G  P  P
         H  E  L  K  S  H  F  L  *  T  H  R  N  S  N  H  *  A  Q  H
           S  L  N  Q  T  F  Y  N  H  T  A  T  A  I  I  N  L  R  T  T

15601   TGATCGTCACCACTACGTTGATGACGAAAACGATTAAGACAAAAATTATATACAGTCCGA   15660
          V  L  L  P  S  A  V  V  A  K  A  L  E  T  K  L  I  H  *  A
         Y  *  C  H  H  H  L  *  Q  K  Q  *  N  Q  K  *  Y  I  D  P
           S  A  T  T  I  C  S  S  S  K  S  I  R  N  K  I  Y  T  L  S
```

FIG. 3 CONT'D

```
15661  CAATGACGATTACAAACAAGAGAATACCGGACATTACCGGTATTCTAACTTCTAAATTCA  15720
        T  V  A  L  T  Q  E  R  I  A  Q  L  P  W  L  I  S  S  K  L
       Q  *  Q  *  H  K  N  E  *  P  R  Y  H  G  Y  S  Q  L  N  L
         N  S  S  I  N  T  R  K  H  G  T  I  A  M  L  N  F  I  *  T

15721  TATGCGTTAAATGTTTTGCGAATATGAGATTACAAATAGCATGTCTAATACAACTAATA  15780
        I  R  L  K  C  F  R  K  Y  E  L  T  *  R  V  S  *  T  S  *
       Y  V  C  N  V  F  V  S  I  S  *  H  K  D  Y  L  N  H  Q  N
         Y  A  I  *  L  F  A  *  V  R  I  N  I  T  C  I  I  N  I  I

15781  TGTAAACAATTACTCATAATACTTAAAAATACATTCGTAAAATCATACTACTAAAACTCA  15840
        V  N  T  L  S  Y  *  S  N  K  H  L  C  K  L  I  I  I  K  L
       Y  M  Q  *  H  T  N  H  I  K  I  Y  A  N  *  Y  S  S  K  S
         C  K  N  I  L  I  I  F  K  *  T  L  M  K  T  H  H  N  Q  T

15841  CTACTACCACAACAGACAATATTGAGACTAATACGATCATTCCCAATATATCGATTATAT  15900
        S  S  P  T  T  Q  *  L  E  S  *  A  L  L  P  *  I  A  L  I
       H  H  H  H  Q  R  N  Y  S  Q  N  H  *  Y  P  N  Y  L  *  Y
         I  I  T  N  D  T  I  V  R  I  I  S  T  L  T  I  Y  S  I  Y

15901  TCACAAAAAGTTGTTCAAAACATGATAGTCTTATTACAGAAATACAGACTTAGATTTACA  15960
        L  T  K  *  C  T  K  Y  *  *  F  L  T  K  I  D  S  D  L  H
       L  H  K  E  V  L  K  T  S  D  S  Y  H  R  *  T  Q  I  *  I
         T  N  K  L  L  N  Q  V  I  L  I  I  D  K  H  R  F  R  F  T

15961  ACCCAACTTTTACTATAATGATTACCAGGAGTACTTAAAACAAGGGTTGTATGATACAAT  16020
        Q  T  S  F  S  I  V  L  P  G  *  S  N  Q  E  W  C  V  I  N
       N  P  Q  F  H  Y  *  *  H  D  E  H  I  K  N  G  V  Y  *  T
         P  N  F  I  I  N  S  I  T  R  M  F  K  T  G  L  M  S  H  *

16021  CAATTCTATCTACCACTAATACAAATAAATGGTATAGGTCTAGGAAGATCTTAAAATCCT  16080
        T  L  I  S  P  S  *  T  *  K  G  Y  G  S  G  E  L  I  K  P
       L  *  S  L  H  H  N  H  K  N  V  M  D  L  D  K  *  F  K  L
         N  L  Y  I  T  I  I  N  I  *  W  I  W  I  R  R  S  N  *  S

16081  CGACCAACAAAACAACTACTAAATAACTTCTGACTGTCACAAGAAAACTATCTCGCGAAA  16140
        A  P  Q  K  T  S  S  K  N  F  V  S  L  T  R  K  I  S  R  K
       L  Q  N  N  Q  Q  H  N  I  S  S  Q  C  H  E  K  S  L  A  S
         S  T  T  K  N  I  I  *  Q  L  S  V  T  N  K  Q  Y  L  A  K

16141  CATTCAGATCGATATCTACGAATGGGAAATCATGTAGTACTTTTACTTCTTATGGTTTTT  16200
        T  L  R  A  I  S  A  *  G  K  T  C  *  S  F  S  S  Y  W  F
       Q  L  D  L  *  L  H  K  G  K  L  V  D  H  F  H  L  I  G  F
         Y  T  *  S  Y  I  S  V  R  *  Y  M  M  F  I  F  F  V  L  F
```

FIG. 3 CONT'D

```
16201  CAGAAAGCACATATAAATCTTATATATTTTTTTGACATATTACTAGAACCATGAGTCTAG  16260
          T  K  R  T  Y  K  S  Y  I  F  F  S  Y  L  S  R  P  V  *  I
        L  R  E  H  I  N  L  I  Y  L  F  V  T  Y  H  D  Q  Y  E  S
          D  K  T  Y  I  *  F  I  Y  F  F  Q  I  I  I  K  T  S  L  D

16261  AATCTATCAATATCACAATAAAATTCATGAACACTACCAAATTTCAAATGACTTCTTAGT  16320
          K  S  L  *  L  T  I  K  L  V  Q  S  P  K  F  N  V  S  S  D
        R  L  Y  N  Y  H  *  K  L  Y  K  H  H  N  L  T  *  Q  L  I
          *  I  T  I  T  N  N  *  T  S  T  I  T  *  L  K  S  F  F  *

16321  AAAATGTTCTTATACATAAATTTTTCACGGCACTACGTCTCACATCCACGTACGCAACAA  16380
          N  *  L  F  I  Y  K  F  L  A  T  I  C  L  T  P  A  H  T  T
        M  K  C  S  Y  T  N  L  F  H  R  S  A  S  H  L  H  M  R  Q
          K  V  L  I  H  I  *  F  T  G  H  H  L  T  Y  T  C  A  N  N

16381  ACAAGTAGTGTTTGAAGAAACGCAACACCGTCAACATATGCATTCGGAAACAATACAACA  16440
          Q  E  D  C  V  E  K  R  Q  P  L  Q  I  R  L  G  K  N  H  Q
        K  N  M  V  F  K  K  A  N  H  C  N  Y  V  V  Y  A  K  T  I  N
          T  *  *  L  S  R  Q  T  T  A  T  T  Y  T  L  R  Q  *  T  T

16441  TTTACAACAATACTGGTACAATACCGTTGATTAGTATTTATACAAAACTCACAGAGTGGA  16500
          L  H  Q  *  S  W  T  I  A  V  L  *  L  Y  T  K  L  T  E  G
        Y  I  N  N  H  G  H  *  P  L  *  D  Y  I  H  K  S  H  R  V
          F  T  T  I  V  M  N  H  C  S  I  M  F  I  N  Q  T  D  *  R

16501  ATGCAAACATTACGTGGATTGACACTACACTCACTACAGTGGTTTAATATAAACCCGCCA  16560
          *  T  Q  L  A  G  L  Q  S  T  L  S  T  V  L  N  Y  K  P  P
        K  R  K  Y  H  V  *  S  H  H  S  H  H  *  W  I  I  N  P  R
          V  N  T  I  C  R  V  T  I  H  T  I  D  G  F  *  I  Q  A  T

16561  TACAGAATGATAACACTTTTGGTATTTGGGGTAATAAGTAAATTCAATCAATACTTACCA  16620
          I  D  *  *  Q  S  F  W  L  G  W  *  E  N  L  N  T  I  F  P
        Y  T  K  S  N  H  F  G  Y  V  G  N  N  M  *  T  L  *  S  H
          H  R  V  I  T  F  V  M  F  G  M  I  *  K  L  *  N  H  I  T

16621  TACCAGAAACCAAACATATTTGTTAGAACGTGCCCAAGTGGAATATATCTACTAAAATTA  16680
          I  T  K  P  K  Y  L  C  D  Q  V  P  E  G  *  I  S  S  K  L
        Y  P  R  Q  N  T  Y  V  I  K  C  P  N  V  K  Y  L  H  N  *
          H  D  K  T  Q  I  F  L  R  A  R  T  *  R  I  Y  I  I  K  I

16681  TTCTATCGATCAACATTTACCTGTCTTCAACTACTAATACAAGACCGTTTACTCACATAA  16740
          L  I  A  L  Q  L  H  V  S  T  S  S  *  T  R  A  F  S  H  I
        Y  S  L  *  N  Y  I  S  L  L  Q  H  N  H  E  P  L  H  T  Y
          L  Y  S  T  T  F  P  C  F  N  I  I  I  N  Q  C  I  L  T  N
```

FIG. 3 CONT'D

```
16741  CTTGCAAATTTCAATAAACGACGTCTTTGAGTTTTCCGTTGACTTCTCCGAAAATTTGTT  16800
         S  R  K  F  N  N  A  A  S  V  *  F  A  V  S  S  A  K  L  C
        Q  V  N  L  T  I  Q  Q  L  F  E  F  P  L  Q  L  P  K  *  V
          F  T  *  L  *  K  S  C  F  S  L  L  C  S  F  L  S  K  F  L

16801  TCGATACGAAGACGATGGTAAGTTCTCTAACAATCACTATCTCTTCAATAAAACACAACC  16860
         L  *  A  E  A  V  M  *  S  I  T  L  S  L  S  T  I  K  H  Q
        F  S  H  K  Q  *  W  E  L  S  Q  *  H  Y  L  L  *  K  T  N
          A  I  S  R  S  G  N  L  L  N  N  T  I  S  F  N  N  Q  T  P

16861  CTCTGTCCATTTCAATTTGGTGGTGAATTATTTTTAATACAAAAGTGTCCGATGGTAAAA  16920
         S  V  P  L  T  L  G  G  S  L  L  F  *  T  K  V  P  *  W  K
        P  S  L  Y  L  *  V  V  V  *  Y  F  N  H  K  *  L  S  G  N
          L  C  T  F  N  F  W  W  K  I  F  I  I  N  E  C  A  V  M  K

16921  TGATCATGACCATTCTGTCAAAATCCACTCATACAAAAACTATTTTCACTTAATTGATTG  16980
         V  L  V  P  L  V  T  K  P  S  Y  T  K  S  L  L  S  N  V  L
        *  *  Y  Q  Y  S  L  K  L  H  T  H  K  Q  Y  F  H  I  L  *
          S  T  S  T  L  C  N  *  T  L  I  N  K  I  F  T  F  *  S  V

16981  CCACACATAATGGCGCGATGTTGATGAATATTTGAAAGATATCCACTACAAAAACAAAAT  17040
         P  T  Y  *  R  A  V  V  V  *  L  S  E  I  P  S  T  K  T  K
        R  H  T  N  G  R  *  L  *  K  Y  V  K  *  L  H  H  K  Q  K
          T  H  I  V  A  S  C  S  S  I  F  K  R  Y  T  I  N  K  N  *

17041  TGTAGTGTAAGACATCGATCAAATTCACGTGGATGTGAACAGGGTGTTCTCTTGATACGA  17100
         V  D  C  E  T  A  L  K  L  A  G  V  S  T  G  C  S  F  *  A
        L  M  V  N  Q  L  *  N  L  H  V  *  V  Q  G  V  L  S  S  H
          C  *  M  R  Y  S  T  *  T  C  R  C  K  D  W  L  L  V  I  S

17101  TCATATTCTAAAAGATCACAAATATCACAAGGTAACCACAAAGTTTTATTACAACGATTA  17160
         L  I  L  N  E  L  T  *  L  T  G  N  T  N  *  F  L  T  A  L
        *  Y  L  I  K  *  H  K  Y  H  E  M  P  T  E  F  Y  H  Q  *
          T  Y  S  K  R  T  N  I  T  N  W  Q  H  K  L  I  I  N  S  I

17161  ATAGTCGTGTAACCTTACTTTGCAATAACGTGACAAGTTCCAGGGGGACCATGCCCTTTC  17220
         *  *  C  M  P  I  F  R  *  Q  V  T  *  P  G  G  P  V  P  F
        N  D  A  C  Q  F  S  V  N  N  C  Q  E  L  D  G  Q  Y  P  F
          I  L  V  N  S  H  F  T  I  A  S  N  L  T  G  R  T  R  S  L

17221  AGAGTAGAACGATATCCAGATCGACAAATAATGATGTGTCGTGCACATCAAATATGACGA  17280
         D  *  R  A  I  P  R  A  T  *  *  *  V  A  R  T  T  *  V  A
        T  E  D  Q  *  L  D  L  Q  K  N  S  C  L  V  H  L  K  Y  Q
          R  M  K  S  Y  T  *  S  N  I  V  V  C  C  T  Y  N  I  S  S
```

FIG. 3 CONT'D

```
17281  CGATCAGTACGACGACATCTACGTAACACACTTTTTCGAATATTCAAAAATTTATAATTG  17340
         A  L  *  A  A  T  S  A  N  H  S  F  A  *  L  N  K  F  I  L
        Q  *  D  H  Q  Q  L  H  M  T  H  F  L  K  Y  T  K  L  Y  *
          S  T  M  S  S  Y  I  C  Q  T  F  F  S  I  L  K  *  I  N  V

17341  CTAACATGTGCATAATAAGGACGATTTCAAGCACATCTAACAATACTATTCAAATTTTAA  17400
         S  Q  V  R  I  I  G  A  L  T  R  T  S  Q  *  S  L  N  L  I
        R  N  Y  V  V  *  E  Q  *  L  E  H  L  N  N  H  Y  T  *  F
          I  T  C  T  N  N  R  S  F  N  T  Y  I  T  I  I  L  K  F  N

17401  TTACTATGGTGAACATTCATACAAAAATGGTGTTATTTACGTAATGGTCTCAACCAATGT  17460
         L  S  V  V  Q  L  Y  T  K  V  V  I  F  A  N  G  S  N  T  V
        *  H  Y  W  K  Y  T  H  K  *  W  L  L  H  M  V  L  T  P  *
          I  I  G  S  T  L  I  N  K  G  C  Y  I  C  *  W  L  Q  N  C

17461  CTATAACAACAACAACTACTTCAATCATACGAATGATTAATACTTAACAGACAATATTTA  17520
         S  I  T  T  T  S  S  T  L  I  S  V  L  *  S  N  D  T  I  F
        L  Y  Q  Q  Q  Q  H  L  *  Y  A  *  *  N  H  I  T  Q  *  L
          I  N  N  N  I  F  N  T  H  K  S  I  I  F  Q  R  N  Y  I

17521  CGAGCATAATTTCGATTTGTAATACATATATAACCTCTAGGACGAGTTAATGGACGTGGT  17580
         A  R  I  L  A  L  C  *  T  Y  I  P  S  G  A  *  N  G  A  G
        H  E  Y  *  L  *  V  N  H  I  Y  Q  L  D  Q  E  I  V  Q  V
          S  T  N  F  S  F  M  I  Y  I  N  S  I  R  S  L  *  R  C  W

17581  GCACACGACAACTCGTTCCCAAGAAATCTTGGATCCGTGAAGTTAAGATAATGATTTTAT  17640
         R  T  S  N  L  L  P  E  K  S  G  L  C  K  L  E  I  V  L  I
        V  H  A  T  S  C  P  N  K  L  V  *  A  S  *  N  *  *  *  F
          T  H  Q  Q  A  L  T  R  *  F  R  P  V  E  I  R  N  S  F  Y

17641  TACACAACAAATCCAGGACTATAGAAAAACCCTTTAACAATATCCACAGGATTTCTTTAA  17700
         I  H  Q  K  P  G  S  I  K  K  P  F  Q  *  L  H  G  L  S  I
        L  T  N  N  L  D  Q  Y  R  K  P  F  N  N  Y  T  D  *  L  F
          H  T  T  *  T  R  I  D  K  Q  S  I  T  I  P  T  R  F  F  N

17701  CATCTTTGACAAAGTCGTAACCAAATACTATTATTTGAGTTCCGATTTTTACTATTATCA  17760
         T  S  V  T  E  A  N  T  *  S  L  L  S  L  A  L  F  S  L  L
        Q  L  F  Q  K  L  M  P  K  H  Y  Y  V  *  P  *  F  H  Y  Y
          Y  F  S  N  *  C  Q  N  I  I  I  F  E  L  S  F  I  I  I  T

17761  AGTAATACAAAATTTCATATAAAATTCCCTGTCTGTTGTGTACTCTCAAGTTCACGACAT  17820
         E  N  H  K  L  T  Y  K  L  P  C  V  V  C  S  L  E  L  A  T
        N  M  I  N  *  L  I  N  *  P  V  S  L  V  H  S  N  L  H  Q
          *  *  T  K  F  Y  I  K  L  S  L  C  C  M  L  T  *  T  S  Y
```

FIG. 3 CONT'D

```
17821  TTATAAGTTGTCTATATAGATTAATCATTTAAAAATTTTCGATTAGGTCAAACCTTATCA  17880
         F  I  *  C  I  Y  R  I  L  L  N  K  F  A  L  G  T  Q  F  L
        L  Y  E  V  S  I  D  L  *  Y  I  K  L  L  *  D  L  K  S  Y
          I  N  L  L  Y  I  *  N  T  F  K  *  F  S  I  W  N  P  I  T

17881  CGACAAAAATAATCAGGAATATTATCAGTCTTAATACAACGATTCGCACAAAATCCACAA  17940
         A  T  K  I  L  G  *  L  L  *  F  *  T  A  L  R  T  K  P  T
        H  Q  K  *  *  D  K  Y  Y  D  S  N  H  Q  *  A  H  K  L  H
          S  N  K  N  T  R  I  I  T  L  I  I  N  S  L  T  N  *  T  N

17941  GTTTGTGTTTGACATCTAAGACGAGTTCCAAGCCTTATACTAATACAATATATAAGTGTT  18000
         *  V  C  V  T  S  E  A  *  P  E  S  Y  S  *  T  I  Y  E  C
        E  F  V  F  Q  L  N  Q  E  L  N  P  I  H  N  H  *  I  N  V
          L  C  L  S  Y  I  R  S  L  T  R  F  I  I  I  N  Y  I  *  L

18001  TGTCGTCTTTGTCGGGTAAGACAATTACAATTAGCTAAATTACAACGGTATTGATCTCGG  18060
         V  A  S  V  A  W  E  T  L  T  L  R  N  L  T  A  M  V  L  A
        F  L  L  F  L  G  N  Q  *  H  *  D  I  *  H  Q  W  L  *  L
          C  C  F  C  G  M  R  N  I  N  I  S  K  I  N  G  Y  S  S  G

18061  TTCTTCCCGTAAAAAACACAATACTCATTATACGTTAATAAACTTAGAGAATTAAAATAA  18120
         L  F  P  M  K  Q  T  I  L  L  I  C  N  N  S  D  R  L  K  I
        W  S  P  C  K  K  H  *  S  Y  Y  A  I  I  Q  I  E  *  N  *
          L  L  A  N  K  T  N  H  T  I  H  L  *  K  F  R  K  I  K  N

18121  TGAGATGGAAATCTATTTTAAGTTTTAGTTTGAAATGGAGCAAACGTAACGTGTTGATTA  18180
         V  R  G  K  S  L  I  *  F  *  V  K  G  R  K  C  Q  V  V  L
        *  E  V  K  L  Y  F  E  F  D  F  K  V  E  N  A  N  C  L  *
          S  *  R  *  I  F  N  L  I  L  S  *  R  T  Q  M  A  C  S  I

18181  GAAAAATTTCTAACATCATTTTCAACGAATCCAATAGTAGGTCGCGTACGGGGGAGTAAA  18240
         R  K  L  S  Q  L  L  L  Q  K  P  *  *  G  A  C  A  G  E  N
        D  K  *  L  N  Y  Y  F  N  S  L  N  D  D  L  A  H  G  R  M
          K  K  F  I  T  T  F  T  A  *  T  I  M  W  R  M  G  G  *  K

18241  AATCGTCAACTACTATTTATATTCCAATTACTTTTAAACCGACATTTAAATTTATAAACA  18300
         K  A  T  S  S  L  Y  L  T  L  S  F  K  A  T  F  K  F  I  Q
        K  L  L  Q  H  Y  I  Y  P  *  H  F  N  P  Q  L  N  L  Y  K
          *  C  N  I  I  F  I  L  N  I  F  I  Q  S  Y  I  *  I  N  T

18301  CTTGGACAAAATTGTATAAGAGCAAATTATAGAGAATACCCAAAATTTAATCTAAACTGA  18360
         S  G  T  K  V  Y  E  R  K  I  D  R  I  P  K  L  N  S  K  V
        H  V  Q  K  L  M  N  E  N  L  I  E  *  P  N  *  I  L  N  S
          F  R  N  *  C  I  R  T  *  Y  R  K  H  T  K  F  *  I  Q  S
```

FIG. 3 CONT'D

```
18361  GAACTACCAATAAGATTTAACAAATAATGATTTCTACTTCGGTAATTTGCACAATCTCCA  18420
         R  S  P  *  E  L  N  N  I  V  L  S  S  A  M  L  R  T  L  P
        E  Q  H  N  N  *  I  T  *  *  *  L  H  L  W  *  V  H  *  L
          K  I  T  I  R  F  Q  K  N  S  F  I  F  G  N  F  T  N  S  T

18421  ACCCAACCAAAACTACAACTCCCGCGAGTACGATGAGCGCTTTTGTAACCTTGTTTGAAA  18480
         Q  T  P  K  S  T  S  P  A  *  A  V  R  S  F  M  P  V  F  K
        N  P  Q  N  Q  H  Q  P  R  E  H  *  E  R  F  C  Q  F  L  S
          P  N  T  K  I  N  L  A  S  M  S  S  A  F  V  N  S  C  V  K

18481  GGTGACGTTTATCCAAAAAGTTGACCACACCTAAAACATCAACTTCGATGACCGAATAAA  18540
         G  S  C  I  P  K  E  V  P  T  S  K  T  T  S  A  V  P  K  N
        E  V  A  F  L  N  K  L  Q  H  P  N  Q  L  Q  L  *  Q  S  I
          W  Q  L  Y  T  K  *  S  T  H  I  K  Y  N  F  S  S  A  *  K

18541  CGACTCTCTCTAACAATATGAAAATTTTTTTGACATCGATTTCGAGGAGGACCACTTTTT  18600
         A  S  L  S  Q  *  V  K  L  F  V  T  A  L  A  G  G  P  S  F
        Q  Q  S  L  N  N  Y  K  *  F  F  Q  L  *  L  E  E  Q  H  F
          S  L  S  I  T  I  S  K  F  F  S  Y  S  F  S  R  R  T  F  F

18601  AAATTTGTAAATTATGGGGAATACAGTTTTCCAGTTTTCACCCTATAACAATCTTAATCT  18660
         N  L  C  K  I  G  R  I  D  F  P  *  F  H  S  I  T  L  I  L
        I  *  V  N  L  V  G  *  T  L  L  D  F  T  P  Y  Q  *  F  *
          K  F  M  *  Y  G  K  H  *  F  T  L  L  P  I  N  N  S  N  S

18661  TAACAAGTTTACAATAGACTAATAGAAAATCTGGAAAGACTATCACATCATAAATAATGA  18720
         I  T  *  I  N  D  S  *  R  K  S  R  E  S  L  T  T  N  I  V
        F  Q  E  F  T  I  Q  N  D  K  L  G  K  Q  Y  H  L  I  *  *
          N  N  L  H  *  R  I  I  K  *  V  K  R  I  T  Y  Y  K  N  S

18721  ACCAGACGGTCAAAACTTGAATGAACAAATTCCATAAAACGATTTAATCCGTCTCTCGAA  18780
         Q  D  A  L  K  S  S  V  Q  K  L  Y  K  A  L  N  P  L  S  S
        K  T  Q  W  N  Q  V  *  K  N  L  T  N  Q  *  I  L  C  L  A
          P  R  G  T  K  F  K  S  T  *  P  I  K  S  F  *  A  S  L  K

18781  TTAACATTACACACAAGATTAGCACGATGTACGATGTTAAGATCTTGACCAATAATACCA  18840
         L  Q  L  T  H  E  L  R  A  V  H  *  L  E  L  V  P  *  *  P
        *  N  Y  H  T  N  *  D  H  *  M  S  C  N  *  F  Q  N  N  H
          I  T  I  H  T  R  I  T  S  C  A  V  I  R  S  S  T  I  I  T

18841  ACAACCGCGGTATCAATATGAACACTAATACACATATTAGGTGAATAACATCTATATGTT  18900
         Q  Q  R  W  L  *  V  Q  S  *  T  Y  L  G  S  I  T  S  I  C
        N  N  A  G  Y  N  Y  K  H  N  H  T  Y  D  V  *  Q  L  Y  V
          T  P  A  M  T  I  S  T  I  I  H  I  I  W  K  N  Y  I  Y  L
```

FIG. 3 CONT'D

| | | |
|---|---|---|
| 18901 | GTCACCCCAATATGTCCAAGAAATTGATCATTAGTGCTATATTAAACATTACATGTATTT | 18960 |
| | C H P * V P E K V L L * S I I Q L T C L | |
| | V T P N Y L N K L * Y D R Y L K Y H V Y | |
| | L P T I C T R * S T I V I Y N T I Y M F | |

| | | |
|---|---|---|
| 18961 | CCACGTGTACAACGCAGTCGACTACGTTAATACTGAGCAACAAATCGTTAGATACTAACA | 19020 |
| | P A C T A D A S A I I V R Q K A I * S Q | |
| | L H V H Q T L Q H L * S E N N L L R H N | |
| | T C M N R * S I C N H S T T * C D I I T | |

| | | |
|---|---|---|
| 19021 | AAAACATTTAGACAATTAACCTTAAATCTCATAGGTTATTAAAGATTACTCCAGTCATAT | 19080 |
| | K Q L D T L Q F K S Y G I I E L S T L I | |
| | N K Y I Q * N S N L T D L L K * H P * Y | |
| | K T F R N I P I * L I W Y N R I L D T Y | |

| | | |
|---|---|---|
| 19081 | TTATGTAGAACATCCAATAACGTCGCACAGTACGAATTTCGACGGTACGATACATTATCT | 19140 |
| | F V D Q L N N C R T M S L A A M S H L L | |
| | L Y M K Y T I A A H * A * L Q W A I Y Y | |
| | I C R T P * Q L T D H K F S G H * T I S | |

| | | |
|---|---|---|
| 19141 | ATGTTGAATACAATACTGTATCCGTTAGGATTTCCAAATCGAACACAGTTTCTAATACTT | 19200 |
| | Y L K H * S M P L G L P K A Q T L S * S | |
| | I C S I N H C L C D * L N L K H * L N H | |
| | V V * T I V Y A I R F T * S T D F I I P | |

| | | |
|---|---|---|
| 19201 | AAATTTAAAATACTACGAAAAGGACATCGGTTCAGACAATTTGTCAATAAAATACAGATA | 19260 |
| | N L N * S A K G T A L D T L C N N * T * | |
| | I * I K H H K E Q L W T Q * V T I K H R | |
| | K F K I I S K R Y G L R N F L * K I D I | |

| | | |
|---|---|---|
| 19261 | CTACACGTATTTCTATTAAAATTTCTACCAAATACATACAAAACCTTAACATTACAACTA | 19320 |
| | S T C L S L K L S P K H I N Q F Q L T S | |
| | H H A Y L Y N * L H N I Y T K S N Y H Q | |
| | I H M F I I K F I T * T H K P I T I N I | |

| | | |
|---|---|---|
| 19321 | TTTATAGGTAGATTAAGTTAACAAACATCTAAACTGTGAGCTCACAATTTATTTAATTTG | 19380 |
| | L Y G D L E I T Q L N S V R T N F L N F | |
| | Y I D M * N L Q K Y I Q C E L T L Y I L | |
| | F I W R I * N N T S K V S S H * I F * V | |

| | | |
|---|---|---|
| 19381 | GAAGGACCTACATTACCACCATCAAACATACAATTATTTGTACGTAAGGTATGATTAGGA | 19440 |
| | R G P H L P P L K Y T L L C A N W V L G | |
| | G E Q I Y H H Y N T H * Y V H M G Y * D | |
| | K R S T I T T T Q I N I F M C E M S I R | |

FIG. 3 CONT'D

```
19441  AAATGATCTTGACAAAAACTTTTAGAATTCGGATACGGAAAAAAGATAATAAGTCTATGC  19500
         K  V  L  V  T  K  S  F  R  L  G  I  G  K  K  *  *  E  S  V
        K  *  *  F  Q  K  Q  F  D  *  A  *  A  K  K  R  N  N  L  Y
          K  S  S  S  N  K  F  I  K  L  R  H  R  K  E  I  I  *  I  R

19501  GGAACACACATGCATCTACCAAATCTTAGATTTGTTCAACTAATGCAAGGAAATTCTTCG  19560
         G  Q  T  Y  T  S  P  K  S  D  L  C  T  S  *  T  G  K  L  L
        A  K  H  T  R  L  H  N  L  I  *  V  L  Q  N  R  E  K  L  F
          R  T  H  V  Y  I  T  *  F  R  F  L  N  I  V  N  R  *  S  A

19561  CGGTGAACATAGTGTGCCACATTAGATCCACCTCGACAAACAAGTTTCGTACGACTTCTT  19620
         A  V  Q  I  V  R  H  L  R  P  P  A  T  Q  E  F  C  A  S  S
        R  W  K  Y  *  V  T  Y  D  L  H  L  Q  K  N  L  A  H  Q  L
          G  S  T  D  C  P  T  I  *  T  S  S  N  T  *  L  M  S  F  F

19621  ATAACATTGATGGAACTCAGAATATTATATCAATGATGTCGTCCGAAATGAAAAACCCAA  19680
         Y  Q  L  *  R  S  D  *  L  I  T  V  V  A  P  K  V  K  Q  T
        I  N  Y  S  G  Q  T  K  Y  Y  L  *  *  L  L  S  *  K  K  P
          I  T  V  V  K  L  R  I  I  Y  N  S  C  C  A  K  S  K  P  N

19681  ATATTCTTAAAACTAAAAATATTAAATACCTTGTGAAAATGATGCAATGTCTCAAATCTT  19740
         *  L  F  K  S  K  *  L  K  H  F  V  K  V  V  N  C  L  K  S
        K  Y  S  N  Q  N  K  Y  N  I  S  C  K  *  *  T  V  S  N  L
          I  L  I  K  I  K  I  I  *  P  V  S  K  S  R  *  L  T  *  F

19741  TTGCATTATATATTGAACCAATTACAACCAGTAATACTACCTGCATGTCCACTTAATGGA  19800
         F  T  I  Y  L  K  T  L  T  P  *  *  S  P  R  V  P  S  N  G
        F  R  L  I  Y  S  P  *  H  Q  D  N  H  H  V  Y  L  H  I  V
          V  Y  Y  I  V  Q  N  I  N  T  M  I  I  S  T  C  T  F  *  R

19801  ACACGATAATACTTACTGTTTCAACAACAATTCTAATTATTACATCTATGACAATAAAAA  19860
         Q  A  I  I  F  S  L  T  T  T  L  I  L  L  T  S  V  T  I  K
        K  H  *  *  S  H  C  L  Q  Q  *  S  *  Y  H  L  Y  Q  *  K
          T  S  N  H  I  V  F  N  N  N  L  N  I  I  Y  I  S  N  N  K

19861  TTTTTATTATGTAGTAAAGGATGATTATATCGACAACTTAACAAATGTTTTGCATCATAG  19920
         L  F  L  V  D  N  G  V  L  I  A  T  S  N  N  V  F  R  L  I
        *  F  Y  Y  M  M  E  *  *  Y  L  Q  Q  I  T  *  L  V  Y  Y
          F  I  I  C  *  K  R  S  I  Y  S  N  F  Q  K  C  F  T  T  D

19921  GCCGTGGTGGGACTTGAATTCTAAGAATCTTTAAACTTGTAACTATAAACAACCTTCGTA  19980
         R  C  W  G  S  S  L  I  R  L  F  K  F  M  S  I  Q  Q  F  C
        G  A  G  G  Q  V  *  S  E  *  F  N  S  C  Q  Y  K  N  S  A
          P  V  V  R  F  K  L  N  K  S  I  Q  V  N  I  N  T  P  L  M
```

FIG. 3 CONT'D

```
19981  CAGGACACCCTAATACAATTTCTATCAAACAAAACATCAAGGTGAATACCACAAACATTT  20040
         T  R  H  S  *  T  L  S  L  K  N  Q  L  E  V  *  P  T  Q  L
          H  G  T  P  N  H  *  L  Y  N  T  K  Y  N  W  K  H  H  K  Y
           D  Q  P  I  I  N  F  I  T  Q  K  T  T  G  S  I  T  N  T  F

20041  ATGTGTCTAAACTTCAAGTAGCTTTTAAACTTATATGAAAAACTACCAGCACTGTGACCG  20100
         Y  V  S  K  F  N  M  S  F  K  F  I  S  K  S  P  R  S  V  P
          I  C  L  N  S  T  *  R  F  N  S  Y  V  K  Q  H  D  H  C  Q
           V  C  I  Q  L  E  D  F  I  Q  I  Y  K  K  I  T  T  V  S  A

20101  CGAAATCTTCGAAAATCTTTTCGTTCTTTACCACAAAAATAATCATGACTTTTTAATTCA  20160
         A  K  S  A  K  L  F  A  L  F  P  T  K  I  L  V  S  F  N  L
          R  K  L  L  K  *  F  L  L  P  H  H  K  *  *  Y  Q  F  I  L
           S  *  F  S  K  S  F  C  S  I  T  N  K  N  T  S  F  F  *  T

20161  TCCAATAGTTACTAATTTCCAGGCGTTGCTCGACTAAATTTACCACACTAACACCTATTT  20220
         L  N  D  I  I  L  P  G  C  R  A  S  K  F  P  T  I  T  S  L
          Y  T  I  L  S  *  L  D  A  V  L  Q  N  L  H  H  S  Q  P  Y
           P  *  *  H  N  F  T  R  L  S  S  I  *  I  T  H  N  H  I  F

20221  CAACCTCTTGAGTTTCAACTCAAAACCAAGCGATACTCTTTTCTACCACTGCTACAATAG  20280
         T  P  S  S  L  T  S  N  Q  N  A  I  L  F  S  P  S  S  T  I
          L  Q  L  V  *  L  Q  T  K  T  R  *  S  F  L  H  H  R  H  *
           N  S  F  E  F  N  L  K  P  E  S  H  S  F  I  T  V  I  N  D

20281  AAGTCGGCTTGTCTGTCGGATACGAGTTCGGTAATGACCTCGGGTGTTCCATTAGATCCA  20340
         K  L  R  V  S  L  R  H  E  L  W  *  Q  L  G  C  P  L  R  P
          R  *  G  F  L  C  G  I  S  L  G  N  S  S  G  V  L  Y  D  L
           E  A  S  C  V  A  *  A  *  A  M  V  P  A  W  L  T  I  *  T

20341  CCATTAACGCGCCCATTACAGTAACCATTACTACGAGATTGTGCAAAATGATAGAAATGA  20400
         P  L  Q  A  P  L  T  M  P  L  S  A  R  V  R  K  V  I  K  V
          H  Y  N  R  P  Y  H  *  Q  Y  H  H  E  L  V  N  *  *  R  *
           T  I  A  R  T  I  D  N  T  I  I  S  *  C  T  K  S  D  K  S

20401  GTCTCAGCACATAACAGTTCAAAACTTGGAGCGAGTCTAAATCTTGCCCTAAAATAACTA  20460
         *  L  R  T  N  D  L  K  S  G  R  E  S  K  S  R  S  K  I  S
          E  S  D  H  I  T  L  N  Q  V  E  S  L  N  L  V  P  N  *  Q
           L  T  T  Y  Q  *  T  K  F  R  A  *  I  *  F  P  I  K  N  I

20461  TACCTACTATTAGACAAATAACGATTTATACCAAATCTTCTGATACGTAAACTAGTATAT  20520
         I  S  S  L  R  N  I  A  L  Y  P  K  S  S  *  A  N  S  *  I
          Y  P  H  Y  D  T  *  Q  *  I  H  N  L  L  S  H  M  Q  D  Y
           H  I  I  I  Q  K  N  S  F  I  T  *  F  V  I  C  K  I  M  Y
```

FIG. 3 CONT'D

```
20521  CAAATACCATCAAAATTGGTATTTCAATATCCTCCAAACGTAAACGAATATCCGAATAAA  20580
          T  *  P  L  K  L  W  L  T  I  P  P  K  C  K  S  I  P  K  N
        L  K  H  Y  N  *  G  Y  L  *  L  L  N  A  N  A  *  L  S  I
          N  I  T  T  K  V  M  F  N  Y  S  T  Q  M  Q  K  Y  A  *  K

20581  GCATCCTTTTTTTTTAGATTAAACAATTAAGTTCTCAAAAATGTCATACTAAGATCATAA  20640
          R  L  F  F  F  D  L  K  N  I  *  S  N  K  C  Y  S  E  L  I
        E  Y  S  F  F  I  *  N  T  L  E  L  T  K  V  T  H  N  *  Y
          T  P  F  F  F  R  I  Q  *  N  L  L  K  *  L  I  I  R  T  N

20641  GTAAGTATAAAATAATGACTAGTCCTCACACCATCATCATTCTCACAAACATGTCAATAA  20700
          *  E  Y  K  I  V  S  *  S  H  P  L  L  L  L  T  Q  V  T  I
        E  N  M  N  *  *  Q  D  P  T  H  Y  Y  Y  S  H  K  Y  L  *
          M  *  I  K  N  S  I  L  L  T  T  T  T  L  T  N  T  C  N  N

20701  CTAAATAATAATCTACTAAAACAAAGATAACAATTCAGTAATTTAAACTCAACACAATCA  20760
          S  K  N  N  S  S  K  T  E  I  T  L  D  N  F  K  L  Q  T  L
        Q  N  I  I  L  H  N  Q  K  *  Q  *  T  M  L  N  S  N  H  *
          I  *  *  *  I  I  K  N  R  N  N  L  *  *  I  Q  T  T  N  T

20761  TTTCAACAATTATAATTACAACTAAAATTCCTAAAAGTTAAATACAACACCACATTACTA  20820
          L  T  T  L  I  L  T  S  K  L  S  K  *  N  I  N  H  H  L  S
        Y  L  Q  *  Y  *  H  Q  N  *  P  N  E  I  *  T  T  T  Y  H
          F  N  N  I  N  I  N  I  K  L  I  K  L  K  H  Q  P  T  I  I

20821  TTATTTTAATACTGAAAAATAGGATTTTACGTTCGGTGATTACTAACCTTTGGACCGATA  20880
          L  L  I  I  V  K  *  G  L  I  C  A  V  L  S  Q  F  G  P  *
        Y  Y  F  *  S  K  K  D  *  F  A  L  W  *  H  N  S  V  Q  S
          I  F  N  H  S  K  I  R  F  H  L  G  S  I  I  P  F  R  A  I

20881  AGATACGGACAAAACATATTCATAAACTTACAAGGTAATCTCTCTCAGAGAAATACCTTA  20940
          E  I  G  T  K  Y  L  Y  K  F  T  G  N  S  L  T  E  K  H  F
        N  *  A  Q  K  T  Y  T  N  S  H  E  M  L  S  L  R  K  I  S
          R  H  R  N  Q  I  L  I  Q  I  N  W  *  L  S  D  R  *  P  I

20941  ATACCATTTGGATAATTAAACGGATGTCCGACATACTACTTACAACGATTCATGTGAGTT  21000
          *  P  L  G  I  L  K  G  V  P  Q  I  I  F  T  A  L  Y  V  *
        N  H  Y  V  *  *  N  A  *  L  S  Y  S  S  H  Q  *  T  C  E
          I  T  F  R  N  I  Q  R  C  A  T  H  H  I  N  S  L  V  S  L

21001  AATACAGTCATAAACTTATGATGTTGTAATCGACAAGGACAATTATACGCACAAAATGTA  21060
          N  H  *  Y  K  F  V  V  V  N  A  T  G  T  L  I  R  T  K  C
        I  I  D  T  N  S  Y  *  L  M  L  Q  E  Q  *  Y  A  H  K  V
          *  T  L  I  Q  I  S  C  C  *  S  N  R  N  I  H  T  N  *  M
```

FIG. 3 CONT'D

```
21061  AATCCACGTCCCAGACTATTTCTTCATCGAGGTCCAAGACGACAAAATTCTGTCACCAAT  21120
         K  P  A  P  D  S  L  S  T  A  G  P  E  A  T  K  L  C  H  N
          N  L  H  L  T  Q  Y  L  L  L  E  L  N  Q  Q  K  L  V  T  T
           *  T  C  P  R  I  F  F  Y  S  W  T  R  S  N  *  S  L  P  *

21121  GGTAGACCATCATAAGAACATCTATTACTAAATTTGGGTAAACAATCGCTATCAAATCAA  21180
         G  D  P  L  I  R  T  S  L  S  K  F  G  N  T  L  S  L  K  T
          V  M  Q  Y  Y  E  Q  L  Y  H  N  L  G  M  Q  *  R  Y  N  L
           W  R  T  T  N  K  Y  I  I  I  *  V  W  K  N  A  I  T  *  N

21181  TGAATAAAACCTCTAACATACTGAAATGGTAAACTAACAGTAACCCTAAACTATTATAGA  21240
         V  *  K  P  S  Q  I  V  K  G  N  S  Q  *  Q  S  K  I  I  D
          *  K  N  Q  L  N  Y  S  K  V  M  Q  N  D  N  P  N  S  L  I
           S  I  K  S  I  T  H  S  *  W  K  I  T  M  P  I  Q  Y  Y  R

21241  CTATACATACTAGGAGAATGATTTTTATAACCACTAATATTACACTCATTCCTACCCAAA  21300
         S  I  Y  S  G  R  V  L  F  I  P  S  *  L  T  L  L  S  P  N
          Q  Y  T  H  D  E  *  *  F  Y  Q  H  N  Y  H  S  Y  P  H  T
           I  H  I  I  R  K  S  F  I  N  T  I  I  I  H  T  L  I  P  K

21301  AAATGAATGTAAACAGTAAATTAAGCACTATTTAATAGAAACCCACCATCACATCGATAT  21360
         K  V  *  M  Q  *  K  I  R  S  L  N  D  K  P  P  L  T  A  I
          K  *  K  C  K  D  N  L  E  H  Y  I  I  K  P  H  Y  H  L  *
           K  S  V  N  T  M  *  N  T  I  F  *  R  Q  T  T  T  Y  S  Y

21361  TTTTAATGTCTCAAAAGAACCTTACGACTAAATATATTTAATTACTCAACAAAACGTAAA  21420
         F  I  V  S  N  E  Q  F  A  S  K  Y  L  N  I  L  Q  K  A  N
          L  F  *  L  T  K  K  S  H  Q  N  I  Y  I  L  S  N  N  Q  M
           F  N  C  L  K  R  P  I  S  I  *  I  F  *  H  T  T  K  C  K

21421  ACCTGTCAAAAAACATGATTACATTTACGAAGAAGATCACTTCCCAAAAATTATCCATAT  21480
         Q  V  T  K  Q  V  L  T  F  A  E  E  L  S  P  N  K  I  P  I
          K  S  L  K  K  Y  *  H  L  H  K  K  *  H  L  T  K  L  L  Y
           P  C  N  K  T  S  I  Y  I  S  R  R  T  F  P  K  *  Y  T  Y

21481  TTAATGGACCCATTTAGAAGAAAACTTTATCTACCGTTACAATACGTACGATTGATAAAC  21540
         F  *  R  P  L  D  E  K  S  I  S  P  L  T  I  C  A  L  *  K
          L  N  G  P  Y  I  K  K  Q  F  L  H  C  H  *  A  H  *  S  N
           I  V  Q  T  F  R  R  K  F  Y  I  A  I  N  H  M  S  V  I  Q

21541  AAAACCTCTTTATCATGTTGTACCTTACCGCCACGAATATCAAATAAACTATACTGATTT  21600
         N  Q  L  F  L  V  V  H  F  P  P  A  *  L  K  N  S  I  V  L
          T  K  S  F  Y  Y  L  M  S  H  R  H  K  Y  N  I  Q  Y  S  *
           K  P  S  I  T  C  C  P  I  A  T  S  I  T  *  K  I  H  S  F
```

FIG. 3 CONT'D

```
21601  AAAAGAAACTTTAACCGACCGTGACGACAACAATTAAATTCTGGTCTAGTTAATTTACTA  21660
        N  E  K  F  N  A  P  V  A  T  T  L  K  L  G  S  *  N  F  S
       I  K  K  S  I  P  Q  C  Q  Q  Q  *  N  L  V  L  D  I  L  H
         K  R  Q  F  Q  S  A  S  S  N  N  I  *  S  W  I  L  *  I  I

21661  AATCAAATAAGAGAATAACTTTCTCCATTTAATAATCAAGCGCTATGCGCATTTCTCTAA  21720
        K  T  *  E  R  I  S  L  P  L  N  N  T  R  S  V  R  L  S  I
       N  L  K  N  E  *  Q  F  L  Y  I  I  L  E  R  Y  A  Y  L  S
         *  N  I  R  K  N  F  S  T  F  *  *  N  A  I  R  T  F  L  N

21721  AAACAACCACTATCAGAACATTTATGAACAATCTAGAGTAATTTAGATTTGATACAATTA  21780
        K  T  P  S  L  R  T  F  V  Q  *  I  E  N  F  R  F  *  T  L
       K  Q  Q  H  Y  D  Q  L  Y  K  N  S  R  M  L  D  L  S  H  *
         K  N  T  I  T  K  Y  I  S  T  L  D  *  *  I  *  V  I  N  I

21781  ATAAAAAAATAAAAAAATAAAGACAATACCAAAATTACTTGGAGAATTACAACACAGAGT  21840
        *  K  K  I  K  K  N  R  N  H  N  *  H  V  E  *  H  Q  T  E
       N  N  K  *  K  K  I  E  T  I  T  K  I  F  R  K  I  N  H  R
         I  K  K  N  K  *  K  Q  *  P  K  L  S  G  R  L  T  T  D  *

21841  AAATTTGGTACTGACCAAAAATAAACCACTATCAGCAAGACTAACATTGGTATAATTATT  21900
        N  L  G  H  S  T  K  I  Q  H  Y  D  N  Q  N  Y  G  Y  *  Y
       M  *  V  M  V  P  K  *  K  T  I  T  T  R  I  T  V  M  N  I
         K  F  W  S  Q  N  K  N  P  S  L  R  E  S  Q  L  W  I  L  L

21901  AAATTTTTAATTTTTAAAACTAATAAACCTATAAGTGGGATCAAACACGTTGTTACCATT  21960
        N  L  F  *  F  N  Q  N  N  P  Y  E  G  *  N  T  C  C  H  Y
       I  *  F  N  F  I  K  I  I  Q  I  N  V  R  T  Q  A  V  I  T
         K  F  I  L  F  K  S  *  K  S  I  *  G  L  K  H  L  L  P  L

21961  CTAAAGTAGATCACGGCCACTAAGATAAAAATTCTCAAAAGTAAAGTGAGCTAAAATATT  22020
        S  K  M  *  H  R  H  N  *  K  *  S  N  E  N  *  E  I  K  Y
       L  N  *  R  T  G  T  I  R  N  K  L  T  K  M  E  S  S  K  I
         I  E  D  L  A  P  S  E  I  K  L  L  K  *  K  V  R  N  *  L

22021  AATGTGACCGCTTCCACTAGTTTAATAAAAAATACTCCCACAATTAAAATTAGGAATAGT  22080
        N  C  Q  R  L  H  D  F  *  K  K  H  P  H  *  N  *  D  K  D
       I  V  S  A  F  T  I  L  N  N  K  I  L  T  N  I  K  I  R  I
         *  V  P  S  P  S  *  I  I  K  *  S  P  T  L  K  L  G  *  *

22081  ATCTAAATTCACAAAAGGATTACCATCATTACTACATACCGAAGAATTGTTCCATTCTAA  22140
        Y  I  *  T  N  E  *  H  Y  Y  H  H  I  A  E  *  C  P  L  I
       M  S  K  L  T  K  R  I  T  T  I  I  Y  P  K  K  V  L  Y  S
         L  N  L  H  K  G  L  P  L  L  S  T  H  S  R  L  L  T  L  N
```

FIG. 3 CONT'D

```
22141  AATAGCACGGAATATAAGATTATACCGGAAAAAAGCAATAGAATGAAAACAACTATAAGG  22200
         K  D  H  R  I  N  *  Y  P  R  K  E  N  D  *  K  Q  Q  Y  E
        K  I  T  G  *  I  R  I  H  G  K  K  T  I  K  S  K  N  I  N
          *  R  A  K  Y  E  L  I  A  K  K  R  *  R  V  K  T  S  I  G

22201  AATATTACAAAGAGAAAGATTCAAATTAAGAACATTTTCACTATAAAATAGTGAATTGTT  22260
         K  Y  H  K  E  K  *  T  *  N  K  Y  F  H  Y  K  I  V  *  C
        R  I  I  N  R  K  R  L  K  I  R  T  F  T  I  N  *  *  K  V
          *  L  T  E  R  E  L  N  L  E  Q  L  L  S  I  K  D  S  L  L

22261  AGGATAAAAATAATTAATAAGATTCCTTCAAATAAAATGAAATAATCCAACAAGAGAAAT  22320
         D  *  K  *  *  N  N  *  P  L  K  N  *  K  I  L  N  N  E  K
        I  R  N  K  N  I  I  R  L  F  N  I  K  S  *  *  T  T  R  K
          G  I  K  I  L  *  E  L  S  T  *  K  V  K  N  P  Q  E  R  *

22321  AAATCATGGCGAAACGGAAAAATTTAGATTGAAATCAGTCATGATAATATTGTATCTATG  22380
         N  L  V  A  K  G  K  *  I  *  S  *  D  T  S  N  Y  C  L  Y
        I  *  Y  R  K  A  K  K  F  R  V  K  T  L  V  I  I  V  Y  I
          K  T  G  S  Q  R  K  L  D  L  K  L  *  Y  *  *  L  M  S  V

22381  ACCGAGACAAATACCAAAAAGATTACAACAAATAGGACTAAATCTGACATAAATATAAAG  22440
         Q  S  Q  K  H  N  K  *  H  Q  K  D  Q  N  L  S  Y  K  Y  K
        S  A  R  N  I  T  K  R  I  N  N  I  R  I  *  V  T  N  I  N
          P  E  T  *  P  K  E  L  T  T  *  G  S  K  S  Q  I  *  I  E

22441  AGAATTTGGTCCAAGAATATTTCAAAGGTGGTGACGTGGAAAAAATAGGAATGGATGATT  22500
         E  *  V  L  N  K  Y  L  K  W  W  Q  V  K  K  I  R  V  *  *
        R  K  F  W  T  R  I  F  N  G  G  S  C  R  K  *  G  *  R  S
          R  L  G  P  E  *  L  T  E  V  V  A  G  K  K  D  K  G  V  L

22501  TCGAGAGACAAAACTATTTAGATTTGTTAAACATGGACATGTCCAACAACTAAGATCTAC  22560
         L  E  R  N  Q  Y  I  *  V  I  Q  V  Q  V  P  Q  Q  N  *  I
        F  S  E  T  K  I  F  R  F  L  K  Y  R  Y  L  N  N  I  R  S
          A  R  Q  K  S  L  D  L  C  N  T  G  T  C  T  T  S  E  L  H

22561  CTTGTTGCTCGCACGGAGTCTATAAAGAAATAGACAACGTACAGTTAACGGTATAACAAT  22620
         S  C  R  A  H  R  L  Y  K  K  I  Q  Q  M  D  I  A  M  N  N
        P  V  V  L  T  G  *  I  N  R  *  R  N  C  T  L  Q  W  I  T
          F  L  S  R  A  E  S  I  E  K  D  T  A  H  *  N  G  Y  Q  *

22621  AAAAGCGTTAAGAAGACGATTAATACAACCGTTCATACTATAATTGGTGCCACTATCACC  22680
         N  E  C  N  K  Q  *  N  H  Q  C  T  H  Y  *  G  R  H  Y  H
        I  K  A  I  R  R  S  I  I  N  A  L  I  I  N  V  V  T  I  T
          K  R  L  E  E  A  L  *  T  P  L  Y  S  I  L  W  P  S  L  P
```

FIG. 3 CONT'D

```
22681  AAAATAAAGATAAAATAGACCAGAAAATATATTACAAAGAACATAAAGTATAATACCACA  22740
        N * K * K I Q D K I Y H K K Y K M N H H
         T K N R N * R T K * I I N R T N * I I T
          K I E I K D P R K Y L T E Q I E Y * P T

22741  TAAAAATATACTATTAAAATGTAGGTAAACCGGGATAATAAGAAAACCATCCACAGGATG  22800
        I K I H Y N * M W K A R N N K Q Y T D *
         Y K * I I I K C G N P G I I R K T P T R
          N K Y S L K V D M Q G * * E K P L H G V

22801  TAGAAGATAATAATTTGTAGGTTAAACACAAATACTAAAAAACGGATAATAAAATGTTCC  22860
        M K * * * V D L K H K H N K A * * K V L
         C R R N N F M W N T N I I K Q R N N * L
          D E I I L C G I Q T * S K K G I I K C P

22861  ATAAAATAATACAAATCGAAATGAAAAACAACAAAAAGATAATAAAAACAATATATTGCT  22920
        Y K I I N L K V K Q Q K E I I K T I Y R
         T N * * T * S * K K N N K * * K Q * I V
          I K N H K A K S K T T K R N N K N Y L S

22921  ATTTAGAGTAATTTAGATTTGTACAATAATTAATAAAAATAAAACGGATGTTGTAATCGA  22980
        Y I E N F R F M N N I I K I K G V V N A
         I F R M L D L C T I L * K * K A * L M L
          L D * * I * V H * * N N K N Q R C C * S

22981  CAATATCCACTAAAATTAACATGATTAAAACGATAATTACTAAATTTGTGGTGTCAAGGA  23040
        T I P S K L Q V L K A I L S K F V V T G
         Q * L H N * N Y * N Q * * H N L C W L E
          N Y T I K I T S I K S N I I * V G C N R

23041  GCGTATTCACTCATACAACACCTACAAAGAATACCAAACCCATGTATAATATATGAACTA  23100
        R M L S Y T T S T E * P K P V Y * I S S
         E C L H T H Q P H K K H N P Y M N Y V Q
          A Y T L I N H I N R I T Q T C I I Y K I

23101  GCACAAATAAATTTATGATGATATAATAAATGACCAATAAAGGGATTTAGACCACGGTTA  23160
        R T * K F V V I N N V P * K G L D P A L
         D H K N L Y * * I I * Q N N G * I Q H W
          T N I * I S S Y * K S T I E R F R T G I

23161  AAATCCCTAGATAGAAATTTTCCATGATGTATAAACTCATGAGAAACCATAGTCTTTGGG  23220
        K L S R D K F P V V Y K L V R Q Y * F G
         N * P D I K L L Y * M N S Y E K T D S V
          K P I * R * F T S C I Q T S K P I L F G
```

FIG. 3 CONT'D

```
23221  AAAAATAGACTAAAATTATTACCATAAAAAGATCTCAATTCTTATGATTCAACATACAA  23280
         K  K  D  S  K  L  L  P  I  K  E  L  T  L  F  V  L  N  Y  T
         R  K  I  Q  N  *  Y  H  Y  K  K  *  L  *  S  Y  *  T  T  H
           K  *  R  I  K  I  I  T  N  K  R  S  N  L  I  S  L  Q  I  N

23281  TTATTTTGAAACATATCACTCAAATCATGATATCAATATCCATCACAAAAATAATTGTTG  23340
         L  L  V  K  Y  L  S  N  L  V  I  T  I  P  L  T  K  I  L  L
         *  Y  F  K  T  Y  H  T  *  Y  *  L  *  L  Y  H  K  *  *  C
           I  F  S  Q  I  T  L  K  T  S  Y  N  Y  T  T  N  K  N  V  V

23341  AGAATATGATAACAACAAGTTGGAGTATTACCACAAAACCTCTAATGTCGAACAGTTATG  23400
         E  *  V  I  T  T  *  G  *  L  P  T  K  S  I  V  A  Q  *  Y
         S  K  Y  *  Q  Q  E  V  E  Y  H  H  K  P  S  *  L  K  D  I
           R  I  S  N  N  N  L  R  M  I  T  N  Q  L  N  C  S  T  L  V

23401  TGATACACACTCATAGGAGTATGATAAACATTTAGATTTCCATCAAGAGCATTACTTAGA  23460
         V  I  H  S  Y  G  *  V  I  Q  L  D  L  P  L  E  R  L  S  D
         C  *  T  H  T  D  E  Y  *  K  Y  I  *  L  Y  N  E  Y  H  I
           S  H  T  L  I  R  M  S  N  T  F  R  F  T  T  R  T  I  F  R

23461  ACCGTAAAACTATTTAGACTTGGAAACACAGACAAGTTCTTTTTAAAATGAATATTACAA  23520
         Q  C  K  S  L  D  S  G  K  H  R  N  L  F  F  K  V  *  L  T
         K  A  N  Q  Y  I  Q  V  K  T  D  T  *  S  F  N  *  K  Y  H
           P  M  K  I  F  R  F  R  Q  T  Q  E  L  F  I  K  S  I  I  N

23521  AGATGTCTAACCAACATAAAAGTAAAAATAGTTCTTGCACCGTGAAAAATACGAATAATA  23580
         E  V  S  Q  N  Y  K  *  K  *  *  S  R  P  V  K  *  A  *  *
         K  *  L  N  T  T  N  E  N  K  D  L  V  H  C  K  K  H  K  N
           R  C  I  P  Q  I  K  M  K  I  L  F  T  A  S  K  I  S  I  I

23581  CGACTAAGACCGTACGGATGATGAAAAAATAAATCAAACATAGAACCATGAGAAAATAGA  23640
         A  S  E  P  M  G  V  V  K  K  N  L  K  Y  R  P  V  R  K  D
         H  Q  N  Q  C  A  *  *  K  K  I  *  N  T  D  Q  Y  E  K  I
           S  I  R  A  H  R  S  S  K  *  K  T  Q  I  K  T  S  K  *  R

23641  GTAATAATACAAAACGGAAACTGAACATTACGATATAGAAGATTATGACTATTACTCTGA  23700
         *  *  *  T  K  G  K  V  Q  L  A  I  D  E  L  V  S  L  S  V
         E  N  N  H  K  A  K  S  Y  H  *  I  K  *  Y  Q  Y  H  S
           M  I  I  N  Q  R  Q  S  T  I  S  Y  R  R  I  S  I  I  L  S

23701  AATGTTATAACCCAGTGTGGAAACAGATTTGCGGTTATAGAAGAATTTAAACTGTTGGCA  23760
         K  C  Y  Q  T  V  G  K  D  L  R  W  Y  R  R  L  N  S  L  R
         K  V  I  N  P  *  V  K  T  *  V  G  I  D  E  *  I  Q  C  G
           *  L  I  P  D  C  R  Q  R  F  A  L  I  K  K  F  K  V  V  T
```

FIG. 3 CONT'D

```
23761  CCACAATAATGATTACGACAACTAACAAGATCATCAAAGAAATCGCTCTAAGTTACATTT  23820
         P  T  I  V  L  A  T  S  Q  E  L  L  K  K  L  S  I  *  H  L
        H  H  *  *  *  H  Q  Q  N  N  *  Y  N  R  *  R  S  E  I  Y
          T  N  N  S  I  S  N  I  T  R  T  T  E  K  A  L  N  L  T  F

23821  TGATTTAGAAATAATGGATTATGACCACAAATACTGAATAGACCAAAATGACAATTCGGA  23880
         V  L  D  K  N  G  L  V  P  T  *  S  K  D  P  K  V  T  L  G
        F  *  I  K  I  V  *  Y  Q  H  K  H  S  I  Q  N  *  Q  *  A
          S  F  R  *  *  R  I  S  T  N  I  V  *  R  T  K  S  N  L  R

23881  CAACGTTGACATGTAGCAGCATAAGGACTAAATGGACTAACACTGTAACTATTTACCGAA  23940
         T  A  V  T  C  R  R  I  G  S  K  G  S  Q  S  M  S  L  H  S
        Q  Q  L  Q  V  D  D  Y  E  Q  N  V  Q  N  H  C  Q  Y  I  A
          N  C  S  Y  M  T  T  N  R  I  *  R  I  T  V  N  I  F  P  K

23941  TTGTTAAAATTACATGGGAGTGGAGAATTAACCCTTGCATTTTAAAAAAGATTAACGTTG  24000
         L  L  K  L  T  G  E  G  R  L  Q  S  R  L  I  K  E  L  Q  L
        *  C  N  *  H  V  R  V  E  *  N  P  V  Y  F  K  K  *  N  C
          V  I  K  I  Y  G  *  R  K  I  P  F  T  F  N  K  R  I  A  V

24001  AAATTAAACTCATGAAACGAAGCAAATCAAGTATGACTAAGAAAAAGAACATTATTAAAA  24060
         K  L  K  L  V  K  S  R  K  T  *  V  S  E  K  E  Q  L  L  K
        S  *  N  S  Y  K  A  E  N  L  E  Y  Q  N  K  K  K  Y  Y  N
          K  I  Q  T  S  Q  K  T  *  N  M  S  I  R  K  R  T  I  I  K

24061  CTACTTAGATTCTATATACCATCAACAAAATTCTCATAACAAAATCTATTTAAACGGTAT  24120
         S  S  D  L  I  Y  P  L  Q  K  L  L  I  T  K  S  L  N  A  M
        Q  H  I  *  S  I  H  Y  N  N  *  S  Y  Q  K  L  Y  I  Q  W
          I  F  R  L  Y  I  T  T  T  K  L  T  N  N  *  I  F  K  G  Y

24121  GGGTTGAGGTCTGCTAGACTAAACGTCAACCCGTCAAGACCAAAAGACGTTAGAAGATTA  24180
         G  L  E  L  R  D  S  K  C  N  P  L  E  P  K  R  C  D  E  L
        V  W  S  W  V  I  Q  N  A  T  P  C  N  Q  N  E  A  I  K  *
          G  V  G  S  S  R  I  Q  L  Q  A  T  R  T  K  Q  L  R  R  I

24181  ATATTTTAACTGTGATGAAGATCAAGAACAGTTAACATAATATCAAACGGACGTTAATTA  24240
         *  L  I  S  V  V  E  L  E  Q  *  N  Y  *  L  K  G  A  I  L
        N  Y  F  Q  C  *  K  *  N  K  D  I  T  N  Y  N  A  Q  L  *
          I  F  N  V  S  S  R  T  R  T  L  Q  I  I  T  Q  R  C  N  I

24241  CAATGATAATTATTAATATTAGGAAGAAGAACCTTATCTTCCATACCAAAATTATTAAAA  24300
         T  V  I  L  L  *  L  G  E  E  Q  F  L  L  Y  P  K  L  L  K
        H  *  *  *  Y  N  Y  D  K  K  K  S  Y  F  T  H  N  *  Y  N
          N  S  N  I  I  I  R  R  R  P  I  S  P  I  T  K  I  I  K
```

FIG. 3 CONT'D

24301 TTAAACTCGAGAGTATCACAACAAATGAGTGCAATAACAAAAAGACAATTATTATGAAAA 24360
        L  K  L  E  *  L  T  T  *  E  R  *  Q  K  E  T  L  L  V  K
       *  N  S  S  E  Y  H  Q  K  S  V  N  N  N  K  Q  *  Y  Y  K
         I  Q  A  R  M  T  N  N  V  *  T  I  T  K  R  N  I  I  S  K

24361 ACAGGAACACGATTTGGAAGAAAACGAAGTTCAACGTTCTCAGTATTTGGTGGAAGACGA 24420
        Q  G  Q  A  L  G  E  K  A  E  L  Q  L  L  *  L  G  G  E  A
       K  D  K  H  *  V  K  K  Q  K  L  N  C  S  D  Y  V  V  K  Q
         T  R  T  S  F  R  R  K  S  *  T  A  L  T  M  F  W  R  R  S

24421 AGGACAGGATAACCATGATTAATAGCAAGAACACTCTCATGATGACATGAGCTGGTGTGA 24480
        E  Q  G  I  P  V  L  *  R  E  Q  S  L  V  V  T  S  S  W  V
       K  R  D  *  Q  Y  *  N  D  N  K  H  S  Y  *  Q  V  R  G  C
         G  T  R  N  T  S  I  I  T  R  L  T  S  S  Y  E  V  V  S

24481 CTGACCACATCCACAAGAACAAATGGACTAGGATATTGACGAATACTGGGATCCAGAACA 24540
        S  Q  H  L  H  E  Q  K  G  S  G  I  V  A  *  S  G  L  D  Q
       Q  S  T  Y  T  N  K  N  V  Q  D  *  L  Q  K  H  G  *  T  K
         V  P  T  P  T  R  T  *  R  I  R  Y  S  S  I  V  R  P  R  T

24541 AGAGTTTTTTTCAGAGACCAACCACAACCACTTGTAACACGTCCCAAGCCACAACTACTT 24600
        E  *  F  F  D  R  T  P  T  P  S  C  Q  A  P  N  P  T  S  S
       N  E  F  F  T  E  P  Q  H  Q  H  V  N  H  L  T  R  H  Q  H
         R  L  F  L  R  Q  N  T  N  T  F  M  T  C  P  E  T  N  I  F

24601 CTTTTCACACCACATAACCTACCTAGTATATTACAAAGAACAGAAACATCATGACTACGG 24660
        S  F  H  P  T  N  S  P  D  Y  L  T  E  Q  R  Q  L  V  S  A
       L  F  T  H  H  I  P  H  I  M  Y  H  K  K  D  K  Y  Y  Q  H
         F  L  T  T  Y  Q  I  S  *  I  I  N  R  T  K  T  T  S  I  G

24661 AAAGATCCAACCAGAATACTGTGAACGCAGTCATTGTTGGCAACATTATAAAAAGATTA 24720
        K  R  P  Q  D  *  S  V  Q  T  L  L  L  R  Q  L  I  K  E  L
       R  E  L  N  T  K  H  C  K  R  *  Y  C  G  N  Y  Y  K  K  *
         K  *  T  P  R  I  V  S  A  D  T  V  V  T  T  I  N  K  R  I

24721 AAATAAAATTTACCATAGTTATCACCATGGTGAACAAGATTACTAAATAACGTCGGATTA 24780
        K  I  K  F  P  I  L  L  P  V  V  Q  E  L  S  K  N  C  G  L
       N  *  K  L  H  Y  *  Y  H  Y  W  K  N  *  H  N  I  A  A  *
         K  N  *  I  T  D  I  T  T  G  S  T  R  I  I  *  Q  L  R  I

24781 TGACTTCAAAAATGACTACAAACACAACTAATGCTGGAAATACCATAATGTCCTGTTCCA 24840
        V  S  T  K  V  S  T  Q  T  S  *  S  R  *  P  I  V  P  C  P
       Y  Q  L  K  *  Q  H  K  H  Q  N  R  G  K  H  Y  *  L  V  L
         S  F  N  K  S  I  N  T  N  I  V  V  K  I  T  N  C  S  L  T

FIG. 3 CONT'D

```
24841  TAAAAATTTCTTCAAAGACGACAAATAATATTATCAACCGTTTTAGAAAACATACTAAGA  24900
        I  K  L  S  T  E  A  T  *  *  L  L  Q  C  F  R  K  Y  S  E
       Y  K  *  L  L  K  Q  Q  K  N  Y  Y  N  A  F  D  K  T  H  N
         N  K  F  F  N  R  S  N  I  I  I  T  P  L  I  K  Q  I  I  R

24901  TTACCGTTGTAATAACCAAAATTTCTAAAACAATGATTATTTTGTATATTATAAAAGGGA  24960
        L  P  L  M  I  P  K  L  S  K  T  V  L  L  V  Y  L  I  K  G
       *  H  C  C  *  Q  N  *  L  N  Q  *  *  Y  F  M  Y  Y  K  G
         I  A  V  N  N  T  K  F  I  K  N  S  I  F  C  I  I  N  E  R

24961  ACAATACGTCCTTCTCAAAGACGACGAAAAGTAGTTTTACGAAGGAGAAACCGAAATGAA  25020
        Q  *  A  P  L  T  E  A  A  K  *  *  F  A  E  E  K  A  K  S
       K  N  H  L  F  L  K  Q  Q  K  E  D  F  H  K  R  K  P  K  V
         T  I  C  S  S  N  R  S  S  K  M  L  I  S  G  R  Q  S  *  K

25021  ATAGCATTAAATTTTACATCGATACAAAACTTATTATAAAGAAATTGATGAGTCGGTATA  25080
        *  R  L  K  F  H  L  *  T  K  F  L  I  E  K  V  V  *  G  Y
       K  D  Y  N  L  I  Y  S  H  K  S  Y  Y  K  K  L  *  E  A  M
         I  T  I  *  F  T  A  I  N  Q  I  I  N  R  *  S  S  L  W  I

25081  AAACTATCAATAGAACCAACGCAAAAATTACGACTATTAAATTGACTAATAAGACAAAGA  25140
        K  S  L  *  R  P  Q  T  K  L  A  S  L  K  V  S  *  E  T  E
       N  Q  Y  N  D  Q  N  R  K  *  H  Q  Y  N  L  Q  N  N  Q  K
         K  I  T  I  K  T  A  N  K  I  S  I  I  *  S  I  I  R  N  R

25141  AGAACACGAGAAGCGTACCCATCACCAAAAACACAACTAATATTGAGTGGAAGAAGAAGG  25200
        E  Q  A  R  R  M  P  L  P  K  Q  T  S  *  L  E  G  E  E  E
       K  K  H  E  E  C  P  Y  H  N  K  H  Q  N  Y  S  V  K  K  K
         R  T  S  K  A  H  T  T  T  K  T  N  I  I  V  *  R  R  R  G

25201  AGAAGCGCAGCATTTGCATCTTCATAAAGACGAAGAATAGCAAAACAATGAAAACTTGGG  25260
        E  E  R  R  L  R  L  L  I  E  A  E  *  R  K  T  V  K  S  G
       R  K  A  D  Y  V  V  F  Y  K  Q  K  K  D  N  Q  *  K  Q  V
         R  R  T  T  F  T  S  T  N  R  S  R  I  T  K  N  S  K  F  G

25261  AAATTACAGTCAAAACAATTACTGTCATAACTCAGACACCCACCAGAAATACTCTAGTTT  25320
        K  L  T  L  K  T  L  S  L  I  S  D  T  P  P  R  *  S  I  L
       R  *  H  *  N  Q  *  H  C  Y  Q  T  Q  P  H  D  K  H  S  *
         K  I  D  T  K  N  I  V  T  N  L  R  H  T  T  K  I  L  D  F

25321  TAAGGGTGATTGAAATGATATCAACCAGTTCTCCTTAAATAAGTTTGATTAAGAGGATTT  25380
        I  G  V  L  K  V  I  T  P  *  S  S  N  I  *  V  L  E  G  L
       F  E  W  *  S  *  *  L  Q  D  L  P  I  *  E  F  *  N  E  *
         N  G  S  V  K  S  Y  N  T  L  L  F  K  N  L  S  I  R  R  F
```

FIG. 3 CONT'D

```
25381  CAATGATAACTAACAAGAAATAAACAGACAAGATTAATACGTCGAACGGTACTGAATAAC  25440
         T V I S Q E K N T Q E L * A A Q W S K N
        L * * Q N N K I Q R N * N H L K G H S I
         N S N I T R * K D T R I I C S A M V * Q

25441  AGTCTCATACCGTGAAAAACACTATTATAATTATCATAAAATCTACTTCAATTACCAAAT  25500
         D S Y P V K Q S L I L L I K S S T L P K
         T L T H C K K H Y Y * Y Y K L H L * H N
          * L I A S K T I I N I T N * I F N I T *

25501  GAACTATGATGAGTTAACGTACATCGACTATGAGAATACGTTCCACAGTGTGAATCGAGG  25560
         S S V V * N C T A S V R I C P T V S L E
         V Q Y * E I A H L Q Y E * A L H * V * S
           K I S S L Q M Y S I S K H L T D C K A G

25561  TTAGAATTATGATTAAACGTAAAACTACAACTATTATAATTAAAATTTAGGGATCAACCT  25620
         L R L V L K C K S T S L I L K L D R T P
         W D * Y * N A N Q H Q Y Y * N * I G L Q
           I K I S I Q M K I N I I N I K F G * N S

25621  ACAAATCCAGGTGTGACGCCAAGAAGAAGAGCAAGAAAAAAACTTCTAAATAACAAACTG  25680
         H K P G C Q P E E E R E K K S S K N N S
         I N L D V S R N K K E N K K Q L N I T Q
           T * T W V A T R R R T R K K F I * Q K V

25681  TTTCAATTTGAAAGTCTACAACCAAAACAACTTCGAATATTGTTAACATGACCACCATCA  25740
         L T L S E S T P K T S A * L L Q V P P L
         C L * V K L H Q N Q Q L K Y C N Y Q H Y
           F N F K * I N T K N F S I V I T S T T T

25741  CTTTAATCTCTAGAAGAAACACATGTTAGGAAATTACCATAATTTCAAAACGGAGGATAA  25800
         S I L S R R Q T C D K L P I L T K G G I
         H F * L D E K H V I R * H Y * L K A E *
           F N S I K K T Y L G K I T N F N Q R R N

25801  AACAGACTTAGAGTTTAAAGACCAATGTGGTGTCGGCGATGACAACGACGATACAAAGGT  25860
         K D S D * I E P * V V A A V T A A I N G
         K T Q I E F K Q N C W L R * Q Q Q * T E
           Q R F R L N R T V G C G S S N S S H K W

25861  GGTACCAGTCGTCGTCGACCGTATGGTAAAAGAGAATTACATGTTATATCTTAATTACCA  25920
         G H D A A A P M G N E R L T C Y L I L P
         V M T L L L Q C V M K E * H V I Y F * H
           W P * C C S A Y W K R K I Y L I S N I T
```

FIG. 3 CONT'D

```
25921  AACCCACAATGATACCTACAAGAATTATTTTTAGTTTTCAACTATCGATGACGAAAATTA  25980
         K  P  T  V  I  S  T  R  L  L  F  *  F  N  I  A  V  A  K  L
        N  P  H  *  *  P  H  E  *  Y  F  D  F  T  S  L  *  Q  K  *
          Q  T  N  S  H  I  N  K  I  F  I  L  L  Q  Y  S  S  S  K  I

25981  TTACGAGAAGAAAGATAAGTCTTACCAAAATCACGATGGTTGAGACGTGAACGATTTTAT  26040
         L  A  R  R  E  I  *  F  P  K  L  A  V  L  E  A  S  A  L  I
        Y  H  E  E  K  *  E  S  H  N  *  H  *  W  S  Q  V  Q  *  F
          I  S  K  K  R  N  L  I  T  K  T  S  G  V  R  C  K  S  F  Y

26041  GTTTCACAACAATTAAGATTACGAGTTCGTGAATTATCAAACAATGTCGTTAATAAATTA  26100
         C  L  T  T  L  E  L  A  *  A  S  L  L  K  N  C  C  N  N  L
        V  F  H  Q  *  N  *  H  E  L  V  *  Y  N  T  V  A  I  I  *
          L  T  N  N  I  R  I  S  L  C  K  I  T  Q  *  L  L  *  K  I

26101  TTTAAACCACGTTAATCAAGAAGAAATGTTCTTTAAAATAGAGCAGAGCTACGAAATCTC  26160
         L  N  P  A  I  L  E  E  K  C  S  I  K  D  R  R  S  A  K  S
        Y  I  Q  H  L  *  N  K  K  V  L  F  K  I  E  D  R  H  K  L
          F  K  T  C  N  T  R  R  *  L  F  N  *  R  T  E  I  S  *  L

26161  CGAGTCCAAGTCTAACTATCCGAATAATTACCAGCAAATTGACGAAATTTACGAATACAG  26220
         A  *  T  *  I  S  L  S  I  L  P  R  K  V  A  K  F  A  *  T
        P  E  P  E  S  Q  Y  A  *  *  H  D  N  L  Q  K  L  H  K  H
          S  L  N  L  N  I  P  K  N  I  T  T  *  S  S  *  I  S  I  D

26221  AGAGTTGTCGAATCACTATAAAGAGAACATTTTAAACCACGACGAAATCGATACCTCTTC  26280
         E  *  C  S  L  S  I  E  R  T  F  N  P  A  A  K  A  I  S  F
        R  E  V  A  *  H  Y  K  E  Q  L  I  Q  H  Q  K  L  *  P  S
          R  L  L  K  T  I  N  R  K  Y  F  K  T  S  S  *  S  H  L  L

26281  CAATTACTCACACAATTTTCAGTTAGAGGAGCATAATTAAAAACACCATTACCATTAGTA  26340
         T  L  S  H  T  L  L  *  D  G  R  I  L  K  Q  P  L  P  L  *
        P  *  H  T  H  *  F  D  I  E  E  Y  *  N  K  H  Y  H  Y  D
          N  I  L  T  N  F  T  L  R  R  T  N  I  K  T  T  I  T  I  M

26341  TAAAACAGTAATCAAGTTTTACGAGGAATACCAAACAACAAATACGTAAAATCAATATTT  26400
         I  K  D  N  T  *  F  A  G  *  P  K  N  N  I  C  K  L  *  L
        Y  K  T  M  L  E  F  H  E  K  H  N  T  T  *  A  N  *  N  Y
          N  Q  *  *  N  L  I  S  R  I  T  Q  Q  K  H  M  K  T  I  F

26401  GGATAAAGAAAATTTTGACAAAATCATTCAGGACCAAACACATATAGTCCACTACATCCA  26460
         G  I  E  K  L  V  T  K  T  L  G  P  K  H  I  D  P  S  T  P
        V  *  K  K  *  F  Q  K  L  L  D  Q  N  T  Y  I  L  H  H  L
          R  N  R  K  F  S  N  *  Y  T  R  T  Q  T  Y  *  T  I  Y  T
```

FIG. 3 CONT'D

```
26461  TAACGTGGATTTGTTCCCATAAAATAATTTGTATTACTAGTAACCTACAAGTGACCATCA  26520
         I  A  G  L  C  P  Y  K  I  L  C  L  S  *  Q  I  N  V  P  L
        Y  Q  V  *  V  L  T  N  *  *  V  Y  H  D  N  S  T  *  Q  Y
          N  C  R  F  L  P  I  K  N  F  M  I  I  M  P  H  E  S  T  T

26521  AGAATGATAATAGGACTTGGTTAAAGTCTATTTTTACAACAAAAATACTTATGAACAAGA  26580
         E  *  *  *  G  S  G  I  E  S  L  F  T  T  K  I  F  V  Q  E
        N  K  S  N  D  Q  V  L  K  L  Y  F  H  Q  K  *  S  Y  K  N
          R  V  I  I  R  F  W  N  *  I  F  I  N  N  K  H  I  S  T  R

26581  CAATTAAAATGATTTCGCGGAGAACAAATAAACTTAGTAAGACATGGTTTTAACAGACTA  26640
         T  L  K  V  L  A  G  R  T  *  K  F  *  E  T  G  F  N  D  S
        Q  *  N  *  *  L  A  E  Q  K  N  S  D  N  Q  V  L  I  T  Q
          N  I  K  S  F  R  R  K  N  I  Q  I  M  R  Y  W  F  Q  R  I

26641  AAACTTAGACTCAATAGAGTAACCAAATTTTTAGTTTGTAGGTAACGCGGATTAAACTGA  26700
         K  S  D  S  N  D  *  Q  N  L  F  *  V  D  M  A  G  L  K  V
        N  Q  I  Q  T  I  E  N  T  *  F  D  F  M  W  Q  A  *  N  S
          K  F  R  L  *  R  M  P  K  F  I  L  C  G  N  R  R  I  Q  S

26701  AATTTAGAAGTATGATAATTACGATGAAAAAATCTAAACATAATACTCTACTTAGAATAA  26760
         K  F  R  *  V  I  L  A  V  K  K  S  K  Y  *  S  I  F  R  I
        K  L  D  E  Y  *  *  H  *  K  K  L  N  T  N  H  S  S  D  *
          *  I  K  M  S  N  I  S  S  K  *  I  Q  I  I  L  H  I  K  N

26761  GTTCTCAGATAATTCAGAAACTTATTATCAATATAGTTAGAATTTCTATATCCATGTATA  26820
         *  S  D  I  L  D  K  F  L  L  *  I  L  R  L  S  I  P  V  Y
        E  L  T  *  *  T  K  S  Y  Y  N  Y  *  D  *  L  Y  L  Y  M
          L  L  R  N  L  R  Q  I  I  T  I  D  I  K  F  I  Y  T  C  I

26821  CTTTACATACATTTTACCGGAACCATACAAACCGATGATTAAAGAAAAGTAAATATTAT  26880
         S  I  Y  T  F  H  G  Q  Y  T  Q  S  S  I  E  K  E  N  I  I
        H  F  T  H  L  I  A  K  T  H  K  A  V  L  K  K  K  M  *  L
          F  H  I  Y  F  P  R  P  I  N  P  *  *  N  R  K  *  K  Y  Y

26881  AAGGAACATAACGAGAAAAAATATACAACAACATGACCAACACCAAGACGTACAAAATCA  26940
         N  R  T  N  S  K  K  I  H  Q  Q  V  P  Q  P  E  A  H  K  L
        I  G  Q  I  A  R  K  *  I  N  N  Y  Q  N  H  N  Q  M  N  *
          E  K  Y  Q  E  K  K  Y  T  T  T  S  T  T  T  R  C  T  K  T

26941  TTTACAGTATTAACAACACTACTCATACCACCAGTAGTACTAAAACAATAGTTTTGTAGA  27000
         L  H  *  L  Q  Q  S  S  Y  P  P  *  *  S  K  T  I  L  V  D
        Y  I  D  Y  N  N  H  H  T  H  H  D  D  H  N  Q  *  *  F  M
          F  T  M  I  T  T  I  L  I  T  T  M  M  I  K  N  D  F  C  R
```

FIG. 3 CONT'D

```
27001  GTACTACTAATCTTAGAGAACAGTCTAGAGTAATTTAGATTTGAAATAAATACCTGCAAA  27060
        *  S  S  *  F  R  K  D  S  R  M  L  D  L  S  *  K  H  V  N
         E  H  H  N  S  D  R  T  L  D  *  *  I  *  V  K  N  I  S  T
          M  I  I  L  I  E  Q  *  I  E  N  F  R  F  K  I  *  P  R  K

27061  CCTCTGGATCGATGTGTGTAAGAGAACAATAATCTCTTAAACCACAATGTTTGGAACTTC  27120
          P  S  R  A  V  C  M  R  K  N  N  S  F  K  T  N  C  V  K  F
           Q  L  G  L  *  V  C  E  R  T  I  L  S  N  P  T  V  F  R  S
            S  V  *  S  C  V  N  E  Q  *  *  L  I  Q  H  *  L  G  Q  L

27121  TAAACACAGATTTCATATTAATGACAGTTGGATAACAACCAATGACATAACATGGAAATT  27180
          I  Q  T  *  L  I  I  V  T  L  R  N  N  T  V  T  N  Y  R  *
           S  K  H  R  F  Y  L  *  Q  *  G  I  T  P  *  Q  I  T  G  K
            N  T  D  L  T  Y  N  S  D  V  *  Q  Q  N  S  Y  Q  V  K  L

27181  TACAAACCACAGCGTTCAAACCGTTTAAACGAAGAGTGAAATGTAATGCATCAGTGCTAT  27240
          I  N  P  T  A  L  K  A  F  K  S  R  V  K  C  *  T  T  V  I
           F  T  Q  H  R  L  N  P  L  N  A  E  *  K  V  N  R  L  *  S
            H  K  T  D  C  T  Q  C  I  Q  K  E  S  *  M  V  Y  D  R  Y

27241  AAAGGGTATCATTATTAAAACCACAACATTGATCAAAATGATGAATACCATTATGACAAA  27300
          N  G  M  T  I  I  K  T  N  Y  S  T  K  S  S  I  T  I  S  N
           I  E  W  L  L  L  K  P  T  T  V  L  K  V  V  *  P  L  V  T
            K  G  Y  Y  Y  N  Q  H  Q  L  *  N  *  *  K  H  Y  Y  Q  K

27301  GACTCCGACACAGATCTAATCAACTTAGTCGAAGACTTAAATAACAAACCGCACGTCTCC  27360
          R  L  S  H  R  S  *  N  F  *  S  R  F  K  N  N  P  T  C  L
           E  S  A  T  D  L  N  T  S  D  A  E  S  N  I  T  Q  R  A  S
            Q  P  Q  T  *  I  L  Q  I  L  K  Q  I  *  Q  K  A  H  L  P

27361  GTGAATTATTCATACCAACTAAATAAAAAGTTACTATGACGAACCATGTATCCTGTCTAA  27420
          C  K  I  L  I  T  S  K  N  K  L  S  V  A  Q  Y  M  P  C  I
           A  S  L  L  Y  P  Q  N  I  K  *  H  Y  Q  K  T  C  L  V  S
            V  *  Y  T  H  N  I  *  K  E  I  I  S  S  P  V  Y  S  L  N

27421  AATCAAAATCAAAATAAAACAGAATAAAGAAATTAGAAACAACAACGAAAAAATCGTTGA  27480
          K  T  K  T  K  N  Q  R  I  E  K  I  K  T  T  A  K  K  A  V
           K  L  K  L  K  I  K  D  *  K  K  L  R  Q  Q  Q  K  K  L  L
            *  N  *  N  *  K  T  K  N  R  *  D  K  N  N  S  K  *  C  S

27481  TAATTCGAAACATACGTTGAAACACCAAAAACATTAAAGAAATAATAAAGTGGAAGCCGA  27540
          I  L  S  Q  I  C  S  Q  P  K  Q  L  K  K  I  I  E  G  E  A
           *  *  A  K  Y  A  V  K  H  N  K  Y  N  R  *  *  K  V  K  P
            N  L  K  T  H  L  K  T  T  K  T  I  E  K  N  N  *  R  R  S
```

FIG. 3 CONT'D

```
27541  ATGCAAATATTTTCTCCATACGTCAACATATTCAGAATATCACTTGTTCAATATGGTGGG  27600
        *  T  *  L  L  P  I  C  N  Y  L  D  *  L  S  C  T  I  G  G
        K  R  K  Y  F  L  Y  A  T  T  Y  T  K  Y  H  V  L  *  V  V
        V  N  I  F  S  T  H  L  Q  I  L  R  I  T  F  L  N  Y  W  G

27601  TGAAGTCTAATAAATTAGATTTAGATTTGTAATACTTATTTAGAAAAGAAGGAGTTAAAT  27660
        V  E  S  *  K  I  *  I  *  V  N  H  I  F  R  K  K  R  L  K
        W  K  L  N  N  L  R  F  R  F  M  I  F  L  D  K  R  G  *  N
        S  *  I  I  *  D  L  D  L  C  *  S  Y  I  K  E  E  E  I  *

27661  GAAGACTAGTTCGACAATGTAAGAATTTTCTTACCTTAAAGAGAAACCCACATTATGATG  27720
        S  R  I  L  S  N  C  E  *  F  F  P  I  E  R  Q  T  Y  Y  *
        V  E  S  *  A  T  V  N  K  F  S  H  F  K  E  K  P  T  I  S
        K  Q  D  L  Q  *  M  R  L  L  I  S  N  R  K  P  H  L  V  V

27721  AAAAATAATGATAGTATAACGTCAAGCCAATATGCTCGGCATCATACAAACAAATAGAAT  27780
        K  K  N  S  D  Y  Q  L  E  T  I  R  A  T  T  H  K  N  I  K
        S  K  I  V  I  M  N  C  N  P  *  V  L  R  L  I  N  T  *  R
        K  *  *  *  *  I  A  T  R  N  Y  S  G  Y  Y  T  Q  K  D  *

27781  AGTTCTACTAATAAGAAACCGAATACACCGGTAACTGATAGTGGAACTGATATAAATTAA  27840
        D  L  H  N  N  K  P  K  H  P  W  Q  S  D  G  Q  S  Y  K  I
        I  L  I  I  I  R  Q  S  I  H  G  N  V  I  V  K  V  I  N  L
        *  S  S  *  E  K  A  *  T  A  M  S  *  *  R  S  *  I  *  N

27841  CAAAAATACGAAACTTATTACGAAAAGAACGTAAAAGATATCACAAATGATAATAAAGAT  27900
        T  K  I  S  Q  I  I  S  K  K  C  K  R  Y  H  K  S  N  N  R
        Q  K  *  A  K  F  L  A  K  R  A  N  E  I  T  N  V  I  I  E
        N  K  H  K  S  Y  H  K  E  Q  M  K  *  L  T  *  *  *  K  *

27901  AACAATATACCTAAGAAATAAAACAATTATCATAAGCCGAAAAATAATCTTGACCGTCAA  27960
        N  N  Y  P  N  K  I  K  N  I  T  N  P  K  K  N  S  S  A  T
        I  T  I  H  I  R  *  K  T  L  L  I  R  S  K  I  L  V  P  L
        Q  *  I  S  E  K  N  Q  *  Y  Y  E  A  K  *  *  F  Q  C  N

27961  CCACCTCAAAATTAGGTCTCTGGTTATTAGAATACACATAACTATACTTTCCGTTCTACA  28020
        P  P  T  K  I  W  L  G  I  I  K  H  T  N  I  H  F  A  L  H
        Q  H  L  K  L  G  S  V  L  L  R  I  H  I  S  I  F  P  L  I
        T  S  N  *  D  L  S  W  Y  D  *  T  Y  Q  Y  S  L  C  S  T

28021  AACAATCCGGTCAATAACTCCTGATAGTGTGTAATTGACGATGACAATAAGCACCAGTAG  28080
        K  N  P  W  N  N  L  V  I  V  C  *  S  S  S  N  N  T  T  M
        N  T  L  G  T  I  S  S  *  *  V  N  V  A  V  T  I  R  P  *
        Q  *  A  L  *  Q  P  S  D  C  M  L  Q  *  Q  *  E  H  D  D
```

FIG. 3 CONT'D

```
28081  AAATATATGTCCCACAGTTTGAACCGTGACCAATATGAGAAAGTCTAAACGGGCATATAC  28140
          K  I  Y  L  T  D  F  K  A  S  T  I  S  K  *  I  Q  G  Y  I
         R  *  I  C  P  T  L  S  P  V  P  *  V  R  E  S  K  G  T  Y
        K  Y  V  P  H  *  V  Q  C  Q  N  Y  E  K  L  N  A  R  I  H

28141  AATGACATCGATTCCACGTTCATGAAACATGGATATTTGCACGGAAAAATCTATTCAATC  28200
          N  S  Y  S  L  H  Y  K  T  G  I  F  T  G  K  *  I  L  *
         T  V  T  A  L  T  C  T  S  Q  V  *  L  R  A  K  K  S  L  N
        *  Q  L  *  P  A  L  V  K  Y  R  Y  V  H  R  K  L  Y  T  L

28201  TACAATTATCACCAAAACGACAAAAACAATTCAGATTTCAACCATTGATAGCAAATGGCA  28260
          I  N  I  T  T  K  S  N  K  N  L  R  F  N  T  V  I  T  *  R
         S  T  L  L  P  K  A  T  K  T  L  D  L  T  P  L  *  R  K  G
        H  *  Y  H  Q  Q  K  Q  *  T  *  L  Q  Y  S  D  N  V  T

28261  GATCATTTGGATCACCATACCTATGACGGAACAATTCTCGAATTTAGATTTGATAATCCT  28320
          R  T  F  R  T  T  H  I  S  G  Q  *  S  S  L  D  L  S  N  P
         D  L  L  G  L  P  I  S  V  A  K  N  L  A  *  I  *  V  I  L
        *  Y  V  *  H  Y  P  Y  Q  R  T  L  L  K  F  R  F  *  *  S

28321  ACAGAATATGAGGGCCAGTAATACGACCTTCATCTTCGAGGAGACCTTTAGCAAGTCCTT  28380
          H  R  I  S  G  T  M  I  S  S  T  S  A  G  R  S  I  T  *  S
         I  D  *  V  G  P  *  *  A  P  L  L  E  E  P  F  R  E  P
        T  K  Y  E  R  D  N  H  Q  F  Y  F  S  R  Q  F  D  N  L  F

28381  AGGAGTTCTTTTGAAGAACCCGACTGGTTAGACTCGCTTTAATGGTTTGGAAATTATCTC  28440
          D  E  L  F  S  R  P  S  V  L  R  L  S  I  V  L  G  K  I  S
         I  R  L  F  V  E  Q  A  S  W  D  S  R  F  *  W  V  K  L  L
        G  *  S  F  K  K  P  Q  G  I  Q  A  F  N  G  F  R  *  Y  L

28441  CGTCTTTTTGGGTTGGATTTAAGTGACACAGATGAGTTGGTGTTCCTTTATGATAGGGTG  28500
          A  S  F  G  L  R  F  E  S  H  R  S  L  W  L  S  I  S  D  W
         P  L  F  V  W  G  L  N  V  T  D  V  *  G  C  P  F  V  I  G
        C  F  F  G  V  *  I  *  Q  T  *  E  V  V  L  F  Y  *  G  V

28501  TAATAAGGACCAAGAGGCCCTAGTGAGTTAAAGTTTTTCCATCTCTGAAATTTAAAAGTC  28560
          M  I  G  P  E  G  P  D  S  L  K  L  F  T  S  V  K  F  K  *
         C  *  E  Q  N  E  P  I  V  *  N  *  F  P  L  S  K  L  N  E
        N  N  R  T  R  R  S  *  E  I  E  F  L  Y  L  S  *  I  K  L

28561  TACCAGTTCCTCAAGGGTAACGAAAGCCTCATGGGGGAAGACTTCGTTTTCCTATAACCA  28620
          I  T  L  S  N  G  N  S  E  S  Y  G  R  R  F  C  F  S  I  P
         S  P  *  P  T  G  M  A  K  P  T  G  G  E  S  A  F  P  Y  Q
        H  D  L  L  E  W  Q  K  R  L  V  G  K  Q  L  L  I  N  T
```

FIG. 3 CONT'D

```
28621  TATCTGTGTCGGCCGCAAGAAAATTTTGTCGACTACCAGTTGTTTTCGTCAACAATGGCT  28680
         I  S  V  A  P  T  R  K  F  C  S  I  T  L  L  L  Q  *  R
        Y  L  C  R  R  E  K  L  V  A  S  P  *  C  F  C  N  N  G
          Y  V  C  G  A  N  K  *  F  L  Q  H  D  V  F  A  T  T  V  S

28681  CTACCATAAAGATGATAGAGCCATGGCCGGGTATACGGTTACGTAGGATACCACTTAGGG  28740
         S  P  I  E  V  I  E  T  G  A  W  I  G  I  C  G  I  T  F  G
        L  H  Y  K  *  *  R  P  V  P  G  Y  A  L  A  D  *  P  S  D
          I  T  N  R  S  D  R  Y  R  G  M  H  W  H  M  R  H  H  I  G

28741  AGCTTCCCCAGAAGACCCAACGATTAGTGGTTCGACTGTGAAGATGAGGGAGGCTACAAA  28800
         E  F  P  D  E  P  N  S  I  V  L  S  V  S  R  S  G  G  I  N
        R  S  P  T  K  Q  T  A  L  *  W  A  S  V  E  V  G  E  S  T
          R  L  P  R  R  P  Q  *  D  G  L  Q  C  K  *  E  R  R  H  K

28801  GCAGTTCCCTAGGATGATGAGTTCTTCGATAGGGATGATCCAAAGGCGGACCATGCTAAA  28860
         R  *  P  I  R  S  S  L  F  S  D  R  S  P  K  R  R  T  R  N
        E  D  L  S  G  V  V  *  S  A  I  G  V  L  N  G  G  P  V  I
          T  L  P  D  *  *  E  L  L  *  G  *  *  T  E  A  Q  Y  S  K

28861  ACGGAGTTCCGATAATACAACTTCCGAGTCCTTCCAGACGAAGATTATCAGCTGGTCCAA  28920
         Q  R  L  A  I  I  N  F  A  *  S  P  R  S  R  I  T  S  W  T
        K  G  *  P  *  *  T  S  P  E  P  L  D  A  E  L  L  R  G  P
          A  E  L  S  N  H  Q  L  S  L  F  T  Q  K  *  Y  D  V  L  N

28921  GTGCAAGAGTTAGTGCACCTGGGTTATTAGCAAGTAATTCATCTTCATTAAGATTAAAAT  28980
         *  T  R  L  *  T  S  G  I  I  T  *  *  T  S  T  I  R  I  K
        E  R  E  *  D  R  P  G  L  L  R  E  N  L  L  L  E  L  K
          V  N  E  I  V  H  V  W  Y  D  N  M  L  Y  F  Y  N  *  N  *

28981  CTGTAAGTCTAAGATATCATTTTGGACTATACCGACTACTCTAGCGATTAGAACAAAATC  29040
         S  M  *  I  R  Y  Y  F  R  I  H  S  I  L  D  S  I  K  N  *
        L  C  E  S  E  I  T  F  G  S  I  A  S  S  I  A  L  R  T  K
          V  N  L  N  *  L  L  V  Q  Y  P  Q  H  S  R  *  D  Q  K  L

29041  GGTTCGAACCATTTCTAAGATTTGGAGTCGTTCAGTGATTCGTTTTACGGTTCCTTTAGT  29100
         G  L  K  T  F  I  R  F  R  L  L  D  S  L  L  I  G  L  F  D
        A  L  S  P  L  S  E  L  G  *  C  T  V  L  C  F  A  L  S  I
          W  A  Q  Y  L  N  *  V  E  A  L  *  *  A  F  H  W  P  F  *

29101  CCGTATTTTAAAATTGTTTTGGAGCGGTTTTCGCTTGAGGATTATTTGTAACATTACAAG  29160
         P  M  F  N  *  C  F  R  A  L  L  S  S  R  I  F  M  T  I  N
        L  C  L  I  K  V  F  G  R  W  F  R  V  G  L  L  C  Q  L  T
          A  Y  F  K  L  L  V  E  G  F  A  F  E  *  Y  V  N  Y  H  E
```

FIG. 3 CONT'D

```
29161  TTGTCACAAAACCATTTTCTCCTGGAAGAGTTTTAAAACCATTACGACTTTACAATTTCG  29220
         L  L  T  K  T  F  S  S  R  R  L  I  K  T  I  S  F  H  *  L
       *  C  H  K  P  L  L  P  G  E  *  F  K  P  L  A  S  I  N  F
          V  T  N  Q  Y  F  L  V  K  E  F  N  Q  Y  H  Q  F  T  L  A

29221  AACCATGATTACTAGGAGTCAAAGGATAAGAACGTCTTAATCGAGGATGTGGTCCACGAA  29280
         K  T  S  I  I  R  L  K  R  N  K  C  F  *  S  R  C  W  T  S
         S  P  V  L  S  G  *  N  G  I  R  A  S  N  A  G  V  G  P  A
          Q  Y  *  H  D  E  T  E  *  E  Q  L  I  L  E  *  V  L  H  K

29281  AAAGAAACCAAGATTTAATCTGAACCAATTTTCTCTAAGGCTCCGACTGAGTGGACAAT  29340
         K  E  K  T  R  F  *  V  Q  N  F  S  I  G  L  S  V  *  R  N
         K  K  K  P  E  L  N  S  K  T  L  L  S  E  S  A  S  E  G  T
          K  R  Q  N  *  I  L  S  P  *  F  L  N  R  P  Q  S  V  Q  *

29341  TTCTACAAAAACTTGAAGTAATAAGACCAAGATAATCCAAACTATCATGAAATGGTCCGA  29400
         F  I  N  K  F  K  M  I  R  T  R  N  P  K  I  T  S  *  W  A
         L  S  T  K  S  S  *  *  E  P  E  I  L  N  S  L  V  K  G  P
          L  H  K  Q  V  E  N  N  Q  N  *  *  T  Q  Y  Y  K  V  L  S

29401  AACTCTGTTAATACTTTCAAGAACTTCTCTTAAATTTACGAATGCAATTAAGATTAGTCT  29460
         K  L  C  N  H  F  N  K  F  L  I  *  I  S  V  N  I  R  I  L
         K  S  V  I  I  F  T  R  S  S  F  K  F  A  *  T  L  E  L  *
          Q  S  L  *  S  L  E  Q  L  S  N  L  H  K  R  *  N  *  D  S

29461  TGTGACTAAGACTAAGCAACTCAAGATTTGGAGTCGCATTTTCTCCACAATTTGTTAATG  29520
         V  S  I  R  I  R  Q  T  R  F  R  L  T  F  S  T  N  F  L  *
         F  V  S  E  S  E  N  L  E  L  G  *  R  L  L  P  T  L  C  N
          C  Q  N  Q  N  T  S  N  *  V  E  A  Y  F  L  H  *  V  I  V

29521  GTCTTGTCAAACTGAGAGAATTAAATTCACGACCATGAGTCGTGTAAAGTTTACTAAAAT  29580
         W  F  L  K  V  R  K  I  *  T  S  T  S  L  V  N  *  I  I  K
         G  S  C  N  S  E  R  L  K  L  A  P  V  *  C  M  E  F  S  K
          L  V  T  Q  S  E  *  N  L  H  Q  Y  E  A  C  K  L  H  N  *

29581  GAGGACTCCTAGTATCAAATGAACGATGAGAACTACTAGGAATACATCTTCTGAGACAAC  29640
         S  R  L  I  M  T  *  K  S  S  K  I  I  R  I  Y  F  V  R  N
         V  G  S  S  *  L  K  S  A  V  R  S  S  G  *  T  S  S  E  T
          E  Q  P  D  Y  N  V  Q  *  E  Q  H  D  K  H  L  L  S  Q  Q

29641  GAATTACTCTTACTTAGGATTAAGCTGTGATCCACCATTGGGGAGCGATAATAAGCCTTA  29700
         S  L  S  F  S  D  *  N  S  V  L  H  Y  G  R  A  I  I  R  F
         A  *  H  S  H  I  R  I  R  C  *  T  T  V  G  R  *  *  E  S
          K  I  L  I  F  G  L  E  V  S  P  P  L  G  E  S  N  N  P  I
```

FIG. 3 CONT'D

```
29701  TCCTGTGAGAGATAGTCTTACTTAAGAACGACATTATTGTCTATCTCATCCAACAATGTC  29760
         L  V  S  E  I  L  I  F  E  Q  Q  L  L  L  Y  L  L  N  N  C
        Y  S  V  R  *  *  F  S  N  K  S  Y  Y  C  I  S  Y  T  T  V
          P  C  E  R  D  S  H  I  R  A  T  I  V  S  L  T  P  Q  *  L

29761  TGATATATAATTAATCATCTTTAAAATATAAATCTGTAAACTAACAATCTCATCAATATT  29820
         V  I  Y  *  N  T  S  I  K  Y  K  S  M  Q  N  N  S  Y  N  Y
        S  *  I  N  I  L  L  F  K  I  N  L  C  K  I  T  L  T  T  I
          S  Y  I  L  *  Y  F  N  *  I  *  V  N  S  Q  *  L  L  *  L

29821  CCAAATCGACATCATATTTGCGGAGGCCCTTCTCGATAGTTAACATCACAAATTATATAT  29880
         P  K  A  T  T  Y  V  G  G  P  L  A  I  L  Q  L  T  *  Y  I
        L  N  L  Q  L  I  F  A  E  P  F  L  *  *  N  Y  H  K  I  Y
          T  *  S  Y  Y  L  R  R  R  S  S  S  D  I  T  T  N  L  I  Y

29881  ATAATCATATACTAACTTTAATTAATATCGGAAAACCTCCTTAATGTTTTTTTTTTTTTT  29940
         Y  *  Y  I  I  S  I  L  *  L  R  K  S  S  N  C  F  F  F  F
        I  N  T  Y  S  Q  F  *  N  Y  G  K  P  P  I  V  F  F  F  F
          I  L  I  H  N  F  N  I  I  A  K  Q  L  F  *  L  F  F  F  F

29941  TT                                                            29942
         F
        F
```

FIG. 3 CONT'D

HUMAN VIRUS CAUSING RESPIRATORY TRACT INFECTION AND USES THEREOF

CROSS-REFERENCE TO RELATED APPLICATION

This application is a continuation of U.S. application Ser. No. 10/895,064, filed Jul. 21, 2004, now U.S. Pat. No. 7,553,944, which is hereby incorporated by reference in its entirety.

SEQUENCE LISTING

The Sequence listing for this application is labeled "seqlist.txt", which was created on Jul. 21, 2004, and is 1,548 KB. The entire contents is incorporated herein by reference in its entirety.

1. INTRODUCTION

The present invention relates to a novel virus causing respiratory tract infection in humans ["coronavirus-HKU1 (CoV-HKU1)"]. The CoV-HKU1 is identified to be phylogenetically similar to known members of Coronaviridae. The present invention relates to a nucleotide sequence comprising the complete genomic sequence or the CoVHKU1. The invention further relates to nucleotide sequences comprising a portion of the genomic sequence of the CoV-HKU1. The invention also relates to the deduced amino acid sequences of the complete genome of the CoV-HKU1. The invention further relates to the nucleic acids and peptides encoded by and/or derived from these sequences and their use in diagnostic methods and therapeutic methods, such as for immunogens. The invention further encompasses chimeric or recombinant viruses encoded by said nucleotide sequences and antibodies directed against polypeptides encoded by the nucleotide sequence. Furthermore, the invention relates to vaccine preparations comprising the CoV-HKU1 recombinant and chimeric forms of said virus as well as protein extracts and subunits of said virus.

2. BACKGROUND OF THE INVENTION

In January, 2004, a 71-year-old Chinese man was admitted to hospital because of fever and chills for two days associated with sore throat, rhinorrhoea, productive cough with purulent sputum, headache and nausea. He had history of pulmonary tuberculosis more than 40 years ago complicated by cicatrization of right upper lobe and bronchiectasis with chronic *Pseudomonas aeruginosa* colonization of airways. He was a chronic smoker and also had chronic obstructive airway disease, hyperlipidemia, and asymptomatic abdominal aortic aneurysm. He had just returned from Shenzhen of China three days before admission. During his three-day trip to Shenzhen, he had no history of contact with or consumption of wild animals. On admission, his oral temperature was 37.6° C. Physical examination showed tracheal deviation to the right and inspiratory crackles over the anterior left lower zone. His haemoglobin level was 14.7 g/dL, total white cell count 12.1× $10^9$/L, with neutrophil 9.7× $10^9$/L, lymphocyte 1.6× $10^9$/L and monocyte 0.5× $10^9$/L, and plate count 303× $10^9$/L. His liver and renal function tests were within normal limits. Chest radiograph showed right upper lobe collapse and new patchy infiltrates over the left lower zone. Blood culture was performed. Empirical oral amoxicillin/clavulanate and azithromycin were commenced. Nasopharyngeal aspirates for direct antigen detection for respiratory viruses, RT-PCR for influenza A virus, human metapneumovirus and SARS-CoV, and viral cultures were negative. Sputum for bacterial culture only recovered *P. aeruginosa*. Sputum for mycobacterial culture was negative. Blood culture was negative. Paired sera for antibodies against *Mycoplasma, Chlamydia, Legionella*, and SARS-CoV did not show any rise in antibody titres. His fever subsided two days after admission. His cough improved and he was discharged after five days of hospitalization. Amoxicillin/clavulanate and azithromycin were continued for a total of seven days. The present inventors were the group involved in the investigation of this patient. All tests for identifying commonly recognized viruses and bacteria were negative in these patients. The etiologic agent responsible for this disease was not known until the complete genome of CoV-HKU1 from this patient by the present inventors as disclosed herein. Namely, the present invention discloses a novel human virus that has been identified from a patient suffering from pneumonia. The invention is useful in both clinical and scientific research applications.

3. SUMMARY OF INVENTION

The present invention is based upon the inventor's complete genome sequencing of a novel virus ("CoV-HKU1") causing pneumonia in humans. The virus was discovered from a patient suffering from pneumonia in Hong Kong. The virus is a single-stranded RNA virus of positive polarity which belongs to the order, Nidovirales, of the family, Coronaviridae. Accordingly, the invention relates to CoV-HKU1 that phylogenetically relates to known members of Coronaviridae. In a specific embodiment, the invention provides complete genomic sequence of CoV-HKU1. In a preferred embodiment, the virus comprises a nucleotide sequence of SEQ ID NO:1 and/or 3. In another specific embodiment, the invention provides nucleic acids isolated from the virus. The virus preferably comprises a nucleotide sequence of SEQ ID NO:1 and/or 3 in its genome. In a specific embodiment, the present invention provides isolated nucleic acid molecules comprising or, alternatively, consisting of the nucleotide sequence of SEQ ID NO:1, a complement thereof or a portion thereof, preferably at least 5, 10, 15, 20, 25, 30, 35, 40, 45, 100, 150, 200, 300, 350, or more contiguous nucleotides of the nucleotide sequence of SEQ ID NO: 1, or a complement thereof. In another specific embodiment, the present invention provides isolated nucleic acid molecules comprising or, alternatively, consisting of the nucleotide sequence of SEQ ID NO:3, a complement thereof or a portion thereof, preferably at least 5, 10, 15, 20, 25, 30, 35, 40, 45, 100, 150, 200, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or more contiguous nucleotides of the nucleotide sequence of SEQ ID NO:3, or a complement thereof. Furthermore, in another specific embodiment, the invention provides isolated nucleic acid molecules which hybridize under stringent conditions, as defined herein, to a nucleic acid molecule having the sequence of SEQ ID NO:1 or 3, or a complement thereof. In preferred embodiments, such nucleic acid molecules encode amino acid sequences that have biological activities exhibited by the polypeptides encoded by the nucleotide sequence of SEQ ID NO:1 or 3. In another specific embodiment, the invention provides isolated polypeptides or proteins that are encoded by a nucleic acid molecule comprising or, alternatively consisting of a nucleotide sequence that is at least 5, 10, 15, 20, 25, 30, 35, 40, 45, 100, 150, 200, 300, 350, or more contiguous nucleotides of the nucleotide sequence of SEQ ID NO:1, or a complement thereof. In yet another specific embodiment, the invention provides isolated polypeptides or proteins that are encoded by a nucleic acid molecule comprising or, alternatively consisting of a nucleotide sequence that is at least 5, 10, 15, 20, 25, 30, 35, 40, 45, 100, 150, 200, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or more contiguous nucleotides of the nucleotide sequence of SEQ ID NO:3, or a complement thereof. The polypeptides or proteins include those having the amino acid sequences of SEQ ID NO:2 and SEQ ID NOS:34-2918 shown in FIGS. 2 and 3, respectively. The invention further provides proteins or polypeptides that are isolated from the CoV-HKU1, including viral proteins isolated from cells infected with the virus but not present in comparable uninfected cells. The polypeptides or the proteins of the present invention preferably have a biological activity of the protein (including antigenicity and/or immunogenicity) encoded by the nucleotide sequence that is at least 5, 10, 15, 20, 25, 30, 35, 40, 45, 100, 150, 200, 300, 350, or more contiguous nucleotides of the nucleotide sequence of SEQ ID NO:1. In other embodiments, the polypeptides or the proteins of the present invention have a biological activity of the protein (including antigenicity and/or immunogenicity) encoded by a nucleotide sequence that is at least 5, 10, 15, 20, 25, 30, 35, 40, 45, 100, 150, 200, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or more contiguous nucleotides of the nucleotide sequence of SEQ ID NO:3, or a complement thereof.

In one aspect, the invention relates to the use of CoV-HKU1 for diagnostic methods. In a specific embodiment, the invention provides a method of detecting in a biological sample an antibody that immunospecifically binds to the CoV-HKU1, or any proteins or polypeptides thereof. In another specific embodiment, the invention provides a method of detecting in a biological sample an antibody that immunospecifically binds to the CoV-HKU1-infected cells. In yet another specific embodiment, the invention provides a method of screening for an antibody that immunospecifically binds and neutralizes CoV-HKU1. Such an antibody is useful for a passive immunization or immunotherapy of a subject infected with CoV-HKU1.

The invention further relates to the use of the sequence information of the isolated virus for diagnostic methods. In a specific embodiment, the invention provides nucleic acid molecules which are suitable for use as primers consisting of or comprising the nucleotide sequence of SEQ ID NO:1 or 3, a complement thereof, or at least a portion of the nucleotide sequence thereof. In another specific embodiment, the invention provides nucleic acid molecules which are suitable for hybridization to CoV-HKU1 nucleic acid, including, but not limited to, as PCR primers, Reverse Transcriptase primers, probes for Southern or Northern analysis or other nucleic acid hybridization analysis for the detection of CoV-HKU1 nucleic acids, e.g., consisting of or comprising the nucleotide sequence of SEQ ID NO:1 or 3, a complement thereof, or a portion thereof.

The invention further provides antibodies that specifically bind a polypeptide of the invention encoded by the nucleotide sequence of SEQ ID NO:1 or 3 or a fragment thereof, including the polypeptide having the amino acid sequence of SEQ ID NO:2 or SEQ ID NOS:34-2918 shown in FIGS. 2 and 3, or encoded by a nucleic acid comprising a nucleotide sequence that hybridizes under stringent conditions to the nucleotide sequence of SEQ ID NO:1 or 3 and/or any CoV-HKU1 epitope, having one or more biological activities of a polypeptide of the invention. The invention further provides antibodies that specifically bind cells or tissues that are infected by CoV-HKU1. Such antibodies include, but are not limited to, polyclonal, monoclonal, bi-specific, multi-specific, human, humanized, chimeric antibodies, single chain antibodies, Fab fragments, F(ab')$_2$ fragments, disulfide-linked Fvs, intrabodies and fragments containing either a VL or VH domain or even a complementary determining region (CDR) that specifically binds to a polypeptide of the invention.

In one embodiment, the invention provides methods for detecting the presence, activity or expression of the CoV-HKU1 of the invention in a biological material, such as cells, blood, saliva, urine, and so forth. The increased or decreased activity or expression of the CoV-HKU1 in a sample relative to a control sample can be determined by contacting the biological material with an agent which can detect directly or indirectly the presence, activity or expression of the CoV-HKU1. In a specific embodiment, the detecting agents are the antibodies or nucleic acid molecules of the present invention. Antibodies of the invention may also be used to detect and/or treat other coronaviruses, such as Severe Acute Respiratory Syndrome ("SARS") viruses.

In another embodiment, the invention provides vaccine preparations, comprising the CoV-HKU1 recombinant and chimeric forms of said virus, or protein subunits of the virus. In a specific embodiment, the present invention provides methods of preparing recombinant or chimeric forms of CoV-HKU1. In another specific invention, the vaccine preparations of the present invention comprise a nucleic acid or fragment of the CoV-HKU1, or nucleic acid molecules having the sequence of SEQ ID NO:1 or 3, or a fragment thereof. In another embodiment, the invention provides vaccine preparations comprising one or more polypeptides isolated from or produced from nucleic acid of CoV-HKU1. In a specific embodiment, the vaccine preparations comprise a polypeptide of the invention encoded by the nucleotide sequence of SEQ ID NO:1 or 3, or a fragment thereof, including the polypeptides having the amino acid sequences of SEQ ID NO:2 or SEQ ID NOS:34-2918 shown in FIGS. 2 and 3, respectively. Furthermore, the present invention provides methods for treating, ameliorating, managing or preventing respiratory tract infections caused by CoV-HKU1 by administering to a subject in need thereof the anti-viral agents of the present invention, alone or in combination with various anti-viral agents as well as adjuvants, and/or other pharmaceutically acceptable excipients.

In another aspect, the present invention provides methods for preventing or inhibiting, under a physiological condition, binding to a host cell, or infection of a host cell, or replication in a host cell, of CoV-HKU1 or a virus comprising a nucleic acid molecule comprising the nucleotide sequence of SEQ ID NO:1 or 3 or a complement thereof, by administering to the host cell the anti-viral agents of the present invention, alone or in combination with other anti-viral agents. In a specific embodiment, the anti-viral agent of the invention includes the immunogenic preparations of the invention or an antibody that immunospecifically binds CoV-HKU1 or any CoV-HKU1 epitope and/or neutralizes CoV-HKU1. In another specific embodiment, the anti-viral agent is a polypeptide or protein of the present invention or a nucleic acid molecule of the invention. In a specific embodiment, the host cell is a mammalian cell, including a cell of human, primates, cows, horses, sheep, pigs, fowl (e.g., chickens), goats, cats, dogs, hamsters, mice and rats. Preferably a host cell is a primate cell, and most preferably a human cell. Furthermore, the present invention provides pharmaceutical compositions comprising anti-viral agents of the present invention and a pharmaceutically acceptable carrier. The invention also provides kits containing a pharmaceutical composition of the present invention.

3.1 Definitions

The term "an antibody or an antibody fragment that immunospecifically binds a polypeptide of the invention" as used herein refers to an antibody or a fragment thereof that immunospecifically binds to the polypeptide encoded by the nucleotide sequence of SEQ ID NO:1 or 3, or a fragment thereof, and does not non-specifically bind to other polypeptides. An antibody or a fragment thereof that immunospecifically binds to the polypeptide of the invention may cross-react with other antigens. Preferably, an antibody or a fragment thereof that immunospecifically binds to a polypeptide of the invention does not cross-react with other antigens. An antibody or a fragment thereof that immunospecifically binds to the polypeptide of the invention, can be identified by, for example, immunoassays or other techniques known to those skilled in the art.

An "isolated" or "purified" peptide or protein is substantially free of cellular material or other contaminating proteins from the cell or tissue source from which the protein is derived, or substantially free of chemical precursors or other chemicals when chemically synthesized. The language "substantially free of cellular material" includes preparations of a polypeptide/protein in which the polypeptide/protein is separated from cellular components of the cells from which it is isolated or recombinantly produced. Thus, a polypeptide/protein that is substantially free of cellular material includes preparations of the polypeptide/protein having less than about 30%, 20%, 10%, 5%, 2.5%, or 1%, (by dry weight) of contaminating protein. When the polypeptide/protein is recombinantly produced, it is also preferably substantially free of culture medium, i.e., culture medium represents less than about 20%, 10%, or 5% of the volume of the protein preparation. When polypeptide/protein is produced by chemical synthesis, it is preferably substantially free of chemical precursors or other chemicals, i.e., it is separated from chemical precursors or other chemicals which are involved in the synthesis of the protein. Accordingly, such preparations of the polypeptide/protein have less than about 30%, 20%, 10%, 5% (by dry weight) of chemical precursors or compounds other than polypeptide/protein fragment of interest. In a preferred embodiment of the present invention, polypeptides/proteins are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a preferred embodiment of the invention, nucleic acid molecules encoding polypeptides/proteins of the invention are isolated or purified. The term "isolated" nucleic acid molecule does not include a nucleic acid that is a member of a library that has not been purified away from other library clones containing other nucleic acid molecules.

The term "portion" or "fragment" as used herein refers to a fragment of a nucleic acid molecule containing at least about 10, 15, 25, 30, 35, 40, 45, 100, 150, 200, 250, 300, 350, 400, 450, 500, 550, 600, 650, 700, 750, 800, 850, 900, 950, 1000, 1050, 1100, 1150, 1200, 1250, 1300, 1350, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, or more contiguous nucleic acids in length of the relevant nucleic acid molecule and having at least one functional feature of the nucleic acid molecule (or the encoded protein has one functional feature of the protein encoded by the nucleic acid molecule); or a fragment of a protein or a polypeptide containing at least 5, 10, 15, 20, 25, 30, 35, 40, 45, 50, 55, 60, 65, 70, 75, 80, 90, 100, 120, 140, 160, 180, 200, 220, 240, 260, 280, 300, 320, 340, 360, 380, 400, 500, 600, 700, 800, 900, 1,000, 1,500, 2,000, 2,500, 3,000, 3,500, 4,000, 4,100, 4,200, 4,300, 4,350, 4,360, 4,370, 4,380 amino acid residues in length of the relevant protein or polypeptide and having at least one functional feature of the protein or polypeptide.

The term "having a biological activity of the protein" or "having biological activities of the polypeptides of the invention" refers to the characteristics of the polypeptides or proteins having a common biological activity similar or identical structural domain and/or having sufficient amino acid identity to the polypeptide encoded by the nucleotide sequence of SEQ ID NO:1 or 3, or the polypeptide having the amino acid sequence of SEQ ID NO:2, or a complement thereof. Such common biological activities of the polypeptides of the invention include antigenicity and immunogenicity.

The term "under stringent condition" refers to hybridization and washing conditions under which nucleotide sequences having at least 70%, at least 75%, at least 80%, at least 85%, at least 90%, or at least 95% identity to each other remain hybridized to each other. Such hybridization conditions are described in, for example but not limited to, Current Protocols in Molecular Biology, John Wiley & Sons, N.Y. (1989), 6.3.1-6.3.6.; Basic Methods in Molecular Biology, Elsevier Science Publishing Co., Inc., N.Y. (1986), pp. 75-78, and 84-87; and Molecular Cloning, Cold Spring Harbor Laboratory, N.Y. (1982), pp. 387-389, and are well known to those skilled in the art. A preferred, non-limiting example of stringent hybridization conditions is hybridization in 6× sodium chloride/sodium citrate (SSC), 0.5% SDS at about 68° C. followed by one or more washes (e.g., about 5 to 30 min each) in 2×SSC, 0.5% SDS at room temperature. Another preferred, non-limiting example of stringent hybridization conditions is hybridization in 6×SSC at about 45° C. followed by one or more washes (e.g., about 5 to 30 min each) in 0.2×SSC, 0.1% SDS at about 45-65° C.

The term "variant" as used herein refers either to a naturally occurring genetic mutant of CoV-HKU1 or a recombinantly prepared variation of CoV-HKU1 each of which contain one or more mutations in its genome compared to CoV-HKU1. The term "variant" may also refers either to a naturally occurring variation of a given peptide or a recombinantly prepared variation of a given peptide or protein in which one or more amino acid residues have been modified by amino acid substitution, addition, or deletion.

4. DESCRIPTION OF FIGURES

FIG. 1 shows a partial DNA sequence (SEQ ID NO:1) and its deduced amino acid sequence (SEQ ID NO:2) obtained from CoV-HKU1 that has 91% amino acid identity to the RNA-dependent RNA polymerase protein of known Coronaviruses.

FIG. 2 shows the entire genomic DNA sequence (SEQ ID NO:3) of CoV-HKU1 and its deduced amino acid sequences therefrom in three frames. An asterisk (*) indicates a stop codon which marks the end of a peptide. The first-frame translation and amino acid sequences: SEQ ID NOS:34-456; the second-frame translation and amino acid sequences: SEQ ID NOS:457-723; and the third-frame translation and amino acid sequences: SEQ ID NOS:724-1318.

FIG. 3 shows the complement (SEQ ID NO: 1319) of the entire genomic DNA sequence (SEQ ID NO:3) of CoV-HKU1 in 3'→5' orientation and its deduced amino acid sequences therefrom in three frames. An asterisk (*) indicates a stop codon which marks the end of a peptide. The first-frame translation and amino acid sequences: SEQ ID NOS:1319-1907; the second-frame translation and amino acid sequences: SEQ ID NO:1908-2453; and the third-frame translation and amino acid sequences: SEQ ID NOS:2454-2918.

FIG. 4 shows the genome organization of CoV-HKU1. Arrows indicate the putative cleavage sites of the polyprotein encoded by ORF 1a and ORF 1b. The peptides are shown in SEQ ID NOS:15-17, respectively, in order of appearance.

Figure 5A:
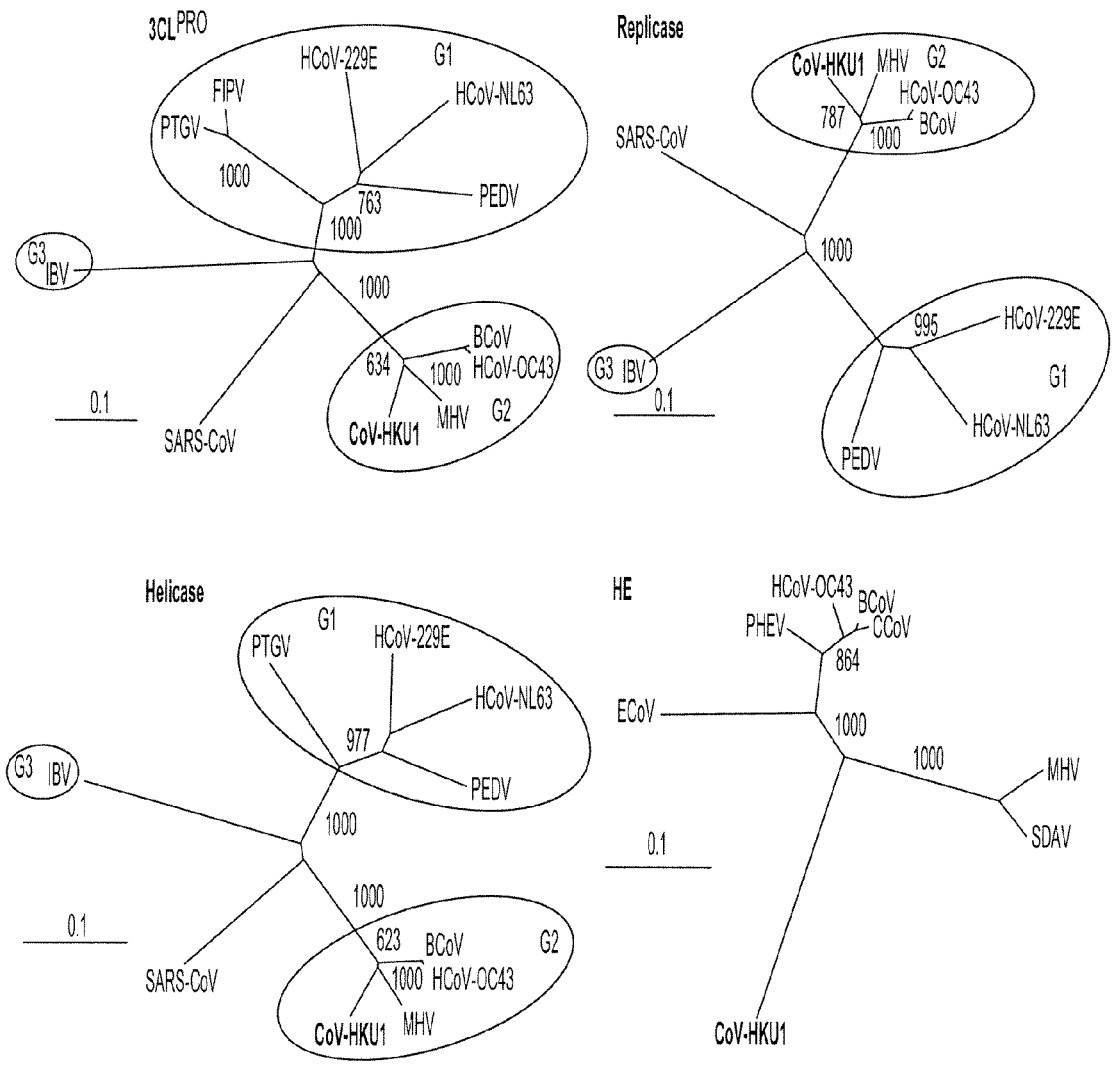
Figure 5B:
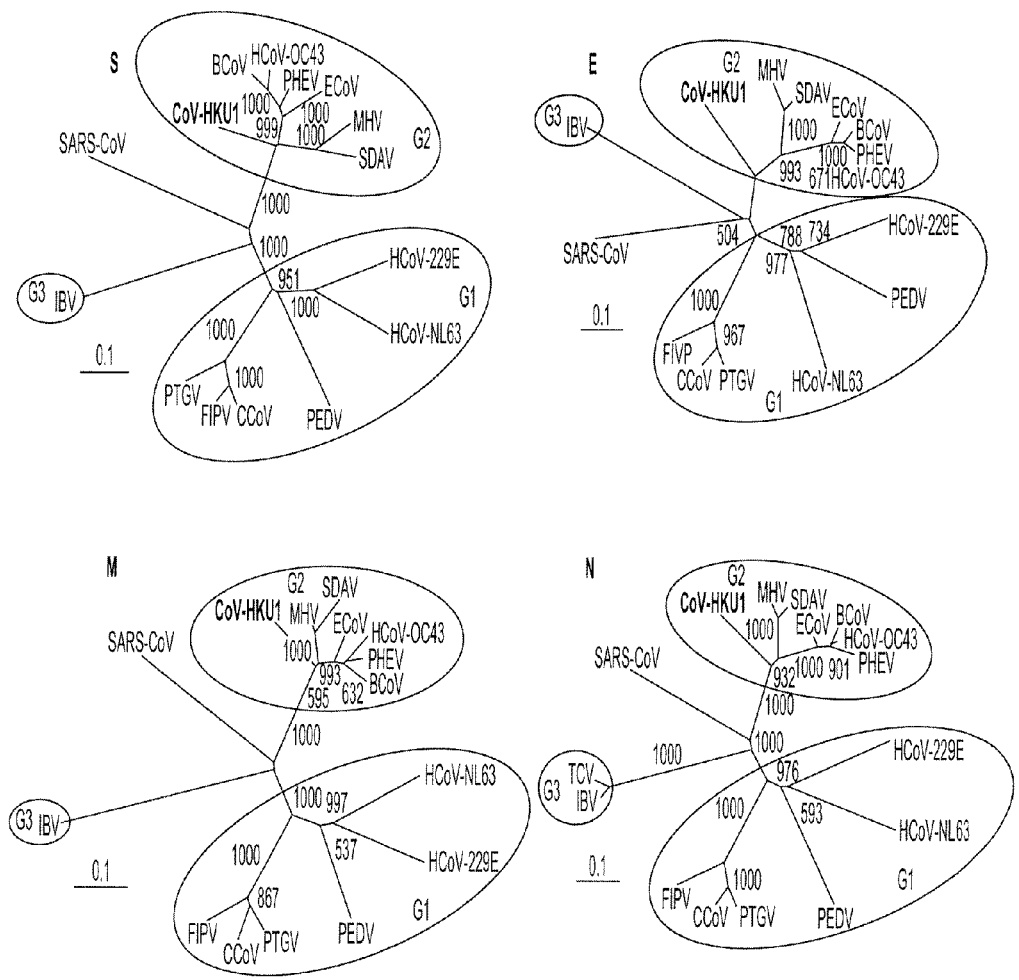

FIG. 5A shows the phylogenetic analysis of the chymotrypsin like protease ($3CL^{pro}$), replicase (Rep), helicase (Hel), and hemagglutinin esterase (HE); and FIG. 5B shows that of the spike (S), envelope (E), membrane (M), and nucleocapsid (N) proteins of CoV-HKU1. The trees were constructed by the neighbor joining method using the Jukes-Cantor correction and bootstrap values were calculated from 1000 trees. A total of 303, 928, 603, 386, 1356, 82, 223 and 441 amino acid positions in $3CL^{pro}$, Rep, Hel, HE, S, E, M, and N respectively were included in the analysis. The scale bar indicates the estimated number of substitutions per 10 amino acids.

Figure 6:
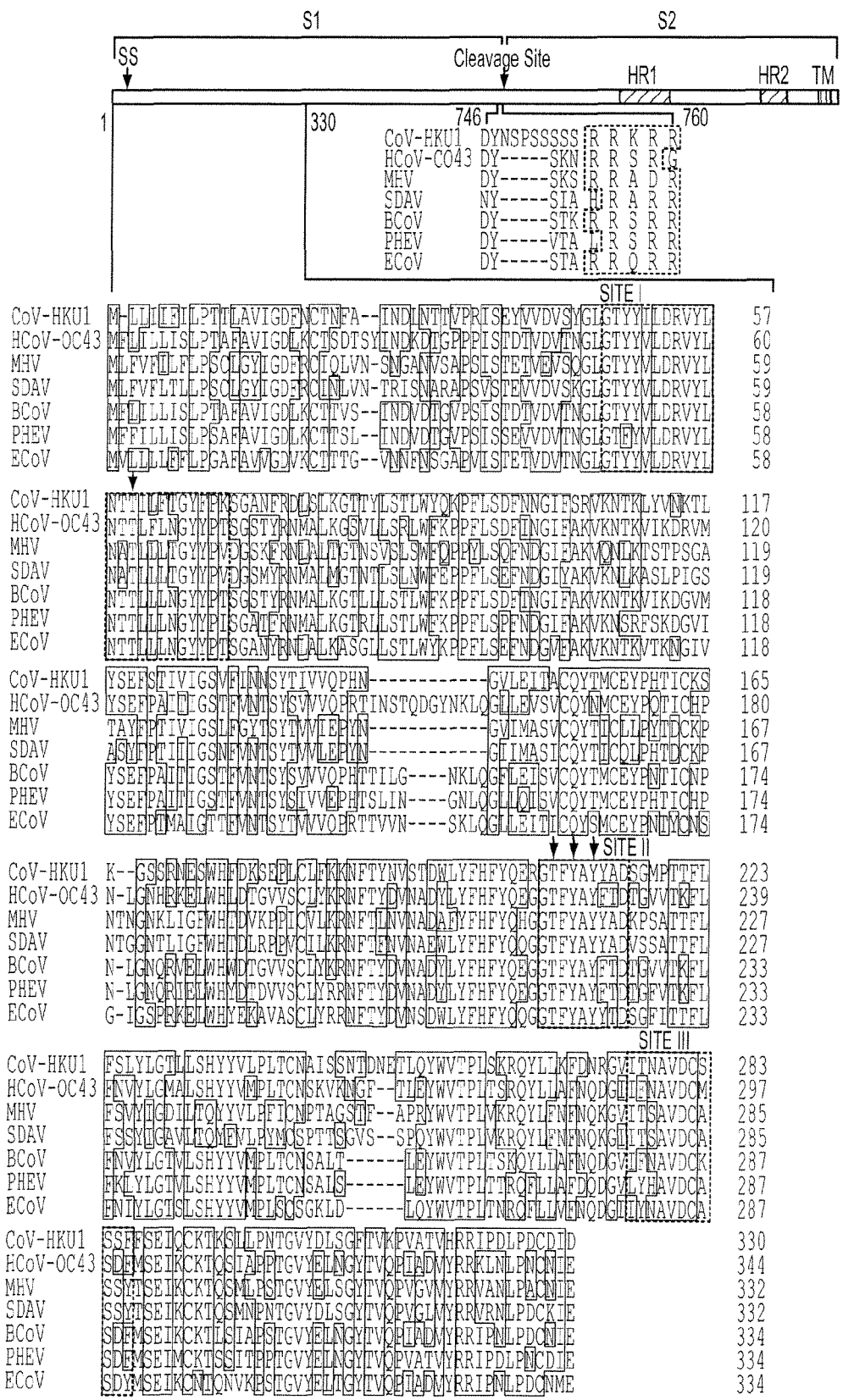

FIG. 6 shows the important features of the S protein of CoV-HKU1 (residues 7-336 of SEQ ID NO:420) in comparison with those of other viruses, i.e., HCoV-OC43 (human coronavirus OC43; SEQ ID NO:21), MHV (murine hepatitis virus; SEQ ID NO:22), SDAV (rat sialodacryoadenitis encephalomyelitis virus; SEQ ID NO:23), BCoV (bovine coronavirus; SEQ ID NO:24), PHEV (porcine hemagglutinating encephalomyelitis virus; SEQ ID NO:25), and ECoV (equine coronavirus; SEQ ID NO:26). The cleavage site peptides are shown in residues 752-766 of SEQ ID NO:420 and SEQ ID NOS:28-33, respectively, in order of appearance.

Figure 7:
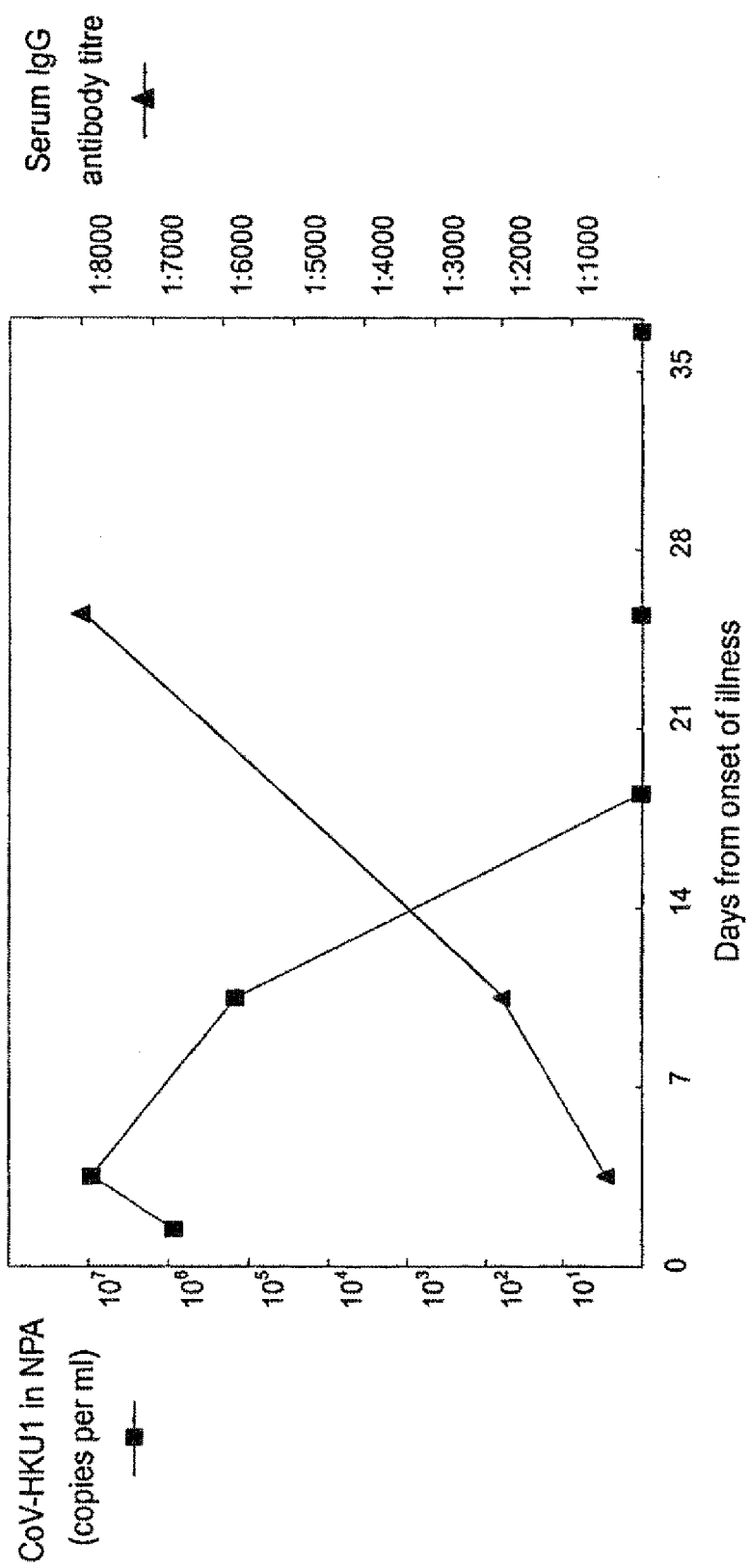

FIG. 7 shows the sequential quantitative RT-PCR (closed squares; copies/ml) for CoV-HKU1 in nasopharyngeal aspirates; and serum IgG antibody titers against N protein of CoV-HKU1 (closed triangles).

Figure 8:
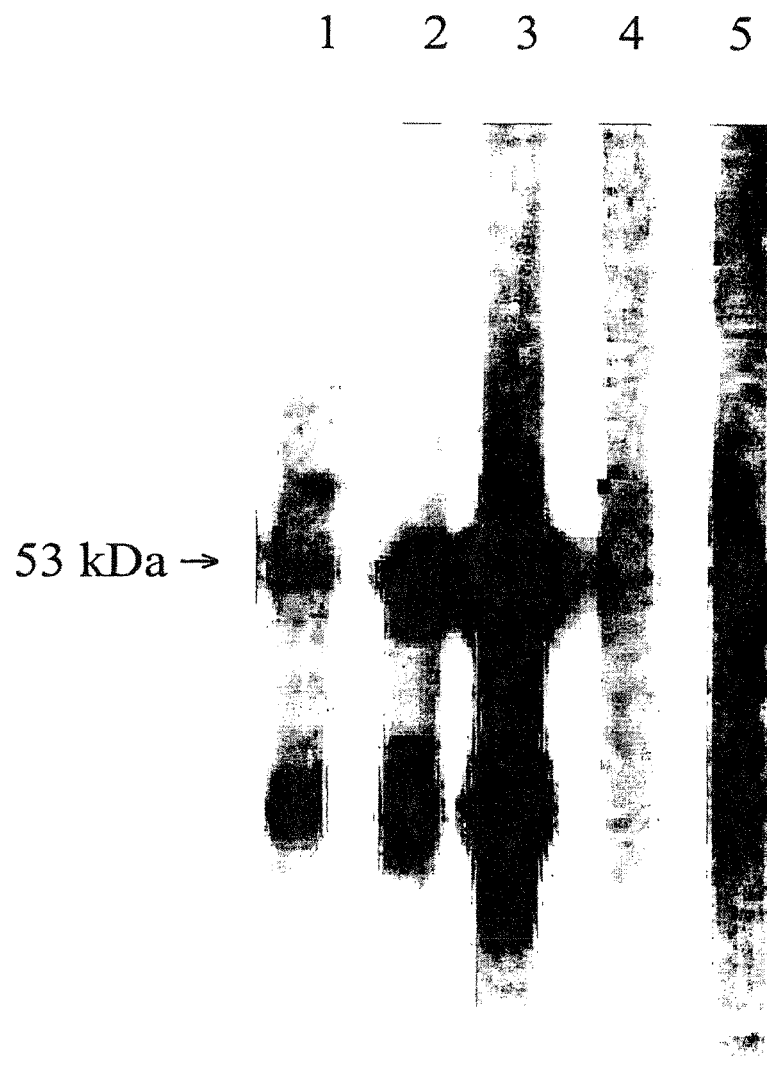

FIG. 8 shows the Western blot analysis of purified recombinant CoV-HKU1 N protein antigen. Prominent immunoreactive protein bands of about 53 kDa were detected by the Western blot using the patient's sera obtained during the second and fourth weeks of the illness (lanes 2 and 3). Only very faint bands were observed with the serum samples obtained from the patient during the first week of the illness (lane 1) and two healthy blood donors (lane 4 and 5), respectively.

5. DETAILED DESCRIPTION OF THE INVENTION

The present invention relates to the CoV-HKU1 that phylogenetically relates to known Coronaviruses. In a specific embodiment, CoV-HKU1 comprises a nucleotide sequence of SEQ ID NO:1 and/or 3. In a specific embodiment, the present invention provides isolated nucleic acid molecules of the CoV-HKU1, comprising, or, alternatively, consisting of the nucleotide sequence of SEQ ID NO:1 and/or 3, a complement thereof or a portion thereof. In another specific embodiment, the invention provides isolated nucleic acid molecules which hybridize under stringent conditions, as defined herein, to a nucleic acid molecule having the sequence of SEQ ID NO:1 or 3, or specific genes of known member of Coronaviridae, or a complement thereof. In another specific embodiment, the invention provides isolated polypeptides or proteins that are encoded by a nucleic acid molecule comprising a nucleotide sequence that is at least about 5, 10, 15, 20, 25, 30, 35, 40, 45, 100, 150, 200, 300, 350, or more contiguous nucleotides of the nucleotide sequence of SEQ ID NO:1, or a complement thereof. In yet another specific embodiment, the invention provides isolated polypeptides or proteins that are encoded by a nucleic acid molecule comprising or, alternatively consisting of a nucleotide sequence that is at least 5, 10, 15, 20, 25, 30, 35, 40, 45, 100, 150, 200, 300, 350, 400, 450, 500, 550, 600, 650, 700, 750, 800, 850, 900, 950, 1,000, 1,050, 1,100, 1,150, 1,200, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or more contiguous nucleotides of the nucleotide sequence of SEQ ID NO:3, or a complement thereof. The polypeptides or the proteins of the present invention preferably have one or more biological activities of the proteins encoded by the sequence of SEQ ID NO:1, 3, or the native viral proteins containing the amino acid sequences encoded by the sequence of SEQ ID NO:1 or 3.

The invention further relates to the use of the sequence information of the isolated virus for diagnostic and therapeutic methods. In a specific embodiment, the invention provides the entire nucleotide sequence of CoV-HKU1 (SEQ ID NO:3), or fragments, or complement thereof. Furthermore, the present invention relates to a nucleic acid molecule that hybridizes any portion of the genome of the CoV-HKU1 (SEQ ID NO:3) under the stringent conditions. In a specific embodiment, the invention provides nucleic acid molecules which are suitable for use as primers consisting of or comprising the nucleotide sequence of SEQ ID NO:1 or 3, or a complement thereof, or a portion thereof. In another specific embodiment, the invention provides nucleic acid molecules which are suitable for use as hybridization probes for the detection of nucleic acids encoding a polypeptide of the invention, consisting of or comprising the nucleotide sequence of SEQ ID NO:1 or 3, a complement thereof, or a portion thereof. The invention further encompasses chimeric or recombinant viruses or viral proteins encoded by said nucleotide sequences.

The invention further provides antibodies that specifically bind a polypeptide of the invention encoded by the nucleotide sequence of SEQ ID NO:1 or 3, or a fragment thereof, or any CoV-HKU1 epitope as well as the polypeptides having the amino acid sequences of SEQ ID NO:2 and SEQ ID NOS: 34-2918, respectively, shown in FIGS. 2 and 3. Such antibodies include, but are not limited to polyclonal, monoclonal, bi-specific, multi-specific, human, humanized, chimeric antibodies, single chain antibodies, Fab fragments, F(ab')$_2$ fragments, disulfide-linked Fvs, intrabodies and fragments containing either a VL or VH domain or even a complementary determining region (CDR) that specifically binds to a polypeptide of the invention.

In one embodiment, the invention provides methods for detecting the presence, activity or expression of the CoV- HKU1 of the invention in a biological material, such as cells, blood, saliva, urine, sputum, nasopharyngeal aspirates, and so forth. The presence of the CoV-HKU1 in a sample can be determined by contacting the biological material with an agent which can detect directly or indirectly the presence, activity or expression of the CoV-HKU1. In a specific embodiment, the detection agents are the antibodies of the present invention. In another embodiment, the detection agent is a nucleic acid of the present invention.

In another embodiment, the invention provides vaccine preparations comprising the CoV-HKU1 recombinant and chimeric forms of said virus, or subunits of the virus.

The present invention further provides methods of preparing recombinant or chimeric forms of CoV-HKU1. In another specific embodiment, the vaccine preparations of the present invention comprise one or more nucleic acid molecules comprising or consisting of the sequence of SEQ ID NO:1 and/or 3, or a fragment thereof. In another embodiment, the invention provides vaccine preparations comprising one or more polypeptides of the invention encoded by a nucleotide sequence comprising or consisting of the nucleotide sequence of SEQ ID NO:1 and/or 3, or a fragment thereof, including the polypeptides having the amino acid sequences of SEQ ID NO:2 or SEQ ID NOS:34-2918 shown in FIGS. 2 and 8. Furthermore, the present invention provides methods for treating, ameliorating, managing, or preventing respiratory tract infections by administering to a subject in need thereof the anti-viral agents of the present invention, alone or in combination with other antivirals [e.g., amantadine, rimantadine, gancyclovir, acyclovir, ribavirin, penciclovir, oseltamivir, foscarnet zidovudine (AZT), didanosine (ddI), lamivudine (3TC), zalcitabine (ddC), stavudine (d4T), nevirapine, delavirdine, indinavir, ritonavir, vidarabine, nelfinavir, saquinavir, relenza, tamiflu, pleconaril, interferons, etc.], steroids and corticosteroids such as prednisone, cortisone, fluticasone and glucocorticoid, antibiotics, analgesics, bronchodialaters, or other treatments for respiratory and/or viral infections. In one aspect, the anti-viral agent of the present invention prevents or inhibit the binding of the virus or viral proteins to a host cell under a physiological condition, thereby preventing or inhibiting the infection of the host cell by the virus. In another aspect, the anti-viral agent of the invention prevents or inhibits replication of the viral nucleic acid molecules in the host cell under a physiological condition by interacting with the viral nucleic acid molecules or its transcription mechanisms. In a specific embodiment, the antiviral agent of the invention includes the vaccine or immunogenic preparations of the invention or an antibody that immunospecifically binds CoV-HKU1 or any CoV-HKU1 epitope and may neutralizes CoV-HKU1. In another specific embodiment, the anti-viral agent is a polypeptide or protein of the invention or a nucleic acid molecule of the invention. In addition, the present invention provides a method of preventing or inhibiting replication in a host cell of a nucleic acid molecule having the nucleotide sequence of SEQ ID NO:1 and/or 3, or inhibiting the activities of the polypeptides encoded by the nucleotide sequence of SEQ ID NO:1 and/or 3, a complement thereof, or a portion thereof, including the polypeptides having the amino acid sequence of SEQ ID NO:2 or SEQ ID NO:34-2918 shown in FIGS. 2 and 8, by administering to said host cell the anti-viral agent of the invention. In a specific embodiment the host cell is a mammalian cell, such as a cell of humans, primates, horses, cows, sheep, pigs, goats, dogs, cats, arivan species and rodents. Preferably, the cell is a primate cell and most preferably a human cell.

Furthermore, the present invention provides pharmaceutical compositions comprising anti-viral agents of the present invention and a pharmaceutically acceptable carrier. The present invention also provides kits comprising pharmaceutical compositions of the present invention.

5.1 Recombinant and Chimeric CoV-HKU1

The present invention encompasses recombinant or chimeric viruses encoded by viral vectors derived from the genome of CoV-HKU1 or natural variants thereof. In a specific embodiment, a recombinant virus is one derived from the CoV-HKU1. In a specific embodiment, the virus has a nucleotide sequence of SEQ ID NO:3. In another specific embodiment, a recombinant virus is one derived from a natural variant of CoV-HKU1. A natural variant of CoV-HKU1 has a sequence that is different from the genomic sequence (SEQ ID NO:3) of CoV-HKU1, due to one or more naturally occurred mutations, including, but not limited to, point mutations, rearrangements, insertions, deletions etc., to the genomic sequence that may or may not result in a phenotypic change. In accordance with the present invention, a viral vector which is derived from the genome of the CoV-HKU, is one that contains a nucleic acid sequence that encodes at least a part of one ORF of the CoV-HKU1. In a specific embodiment, the ORF comprises or consists of a nucleotide sequence of SEQ ID NO:1 or a fragment thereof. In a specific embodiment, there are more than one ORF within the nucleotide sequence of SEQ ID NO:3, or a fragment thereof. In another embodiment, the polypeptides encoded by the ORF comprises or consists of amino acid sequences of SEQ ID NO:34-2918 shown in FIGS. 2 and 8, or SEQ ID NO:2, or a fragment thereof. In accordance with the present invention these viral vectors may or may not include nucleic acids that are non-native to the viral genome.

In another specific embodiment, a chimeric virus of the invention is a recombinant CoV-HKU1 which further comprises a heterologous nucleotide sequence. In accordance with the invention, a chimeric virus may be encoded by a nucleotide sequence in which heterologous nucleotide sequences have been added to the genome or in which endogenous or native nucleotide sequences have been replaced with heterologous nucleotide sequences.

According to the present invention, the chimeric viruses are encoded by the viral vectors of the invention which further comprise a heterologous nucleotide sequence. In accordance with the present invention a chimeric virus is encoded by a viral vector that may or may not include nucleic acids that are non-native to the viral genome. In accordance with the invention a chimeric virus is encoded by a viral vector to which heterologous nucleotide sequences have been added, inserted or substituted for native or non-native sequences. In accordance with the present invention, the chimeric virus may be encoded by nucleotide sequences derived from different strains or variants of CoV-HKU1. In particular, the chimeric virus is encoded by nucleotide sequences that encode antigenic polypeptides derived from different strains or variants of CoV-HKU1.

A chimeric virus may be of particular use for the generation of recombinant vaccines protecting against two or more viruses (Tao et al., J. Virol. 72, 2955-2961; Durbin et al., 2000, J. Virol. 74, 6821-6831; Skiadopoulos et al., 1998, J. Virol. 72, 1762-1768 (1998); Teng et al., 2000, J. Virol. 74, 9317-9321). For example, it can be envisaged that a virus vector derived from the CoV-HKU1 expressing one or more proteins of variants of CoV-HKU1, or vice versa, will protect a subject vaccinated with such vector against infections by both the native CoV-HKU1 and the variant. Attenuated and replication-defective viruses may be of use for vaccination purposes with live vaccines as has been suggested for other viruses.

In accordance with the present invention the heterologous sequence to be incorporated into the viral vectors encoding the recombinant or chimeric viruses of the invention include sequences obtained or derived from different strains or variants of CoV-HKU1.

In certain embodiments, the chimeric or recombinant viruses of the invention are encoded by viral vectors derived from viral genomes wherein one or more sequences, intergenic regions, termini sequences, or portions or entire ORE have been substituted with a heterologous or non-native sequence. In certain embodiments of the invention, the chimeric viruses of the invention are encoded by viral vectors derived from viral genomes wherein one or more heterologous sequences have been inserted or added to the vector.

The selection of the viral vector may depend on the species of the subject that is to be treated or protected from a viral infection.

In accordance with the present invention, the viral vectors can be engineered to provide antigenic sequences which confer protection against infection by the CoV-HKU1 and natural variants thereof. The viral vectors may be engineered to provide one, two, three or more antigenic sequences. In accordance with the present invention the antigenic sequences may be derived from the same virus, from different strains or variants of the same type of virus, or from different viruses.

The expression products and/or recombinant or chimeric virions obtained in accordance with the invention may advantageously be utilized in vaccine formulations. The expression products and chimeric virions of the present invention may be engineered to create vaccines against a broad range of pathogens, including viral and bacterial antigens, tumor antigens, allergen antigens, and auto antigens involved in autoimmune disorders. In particular, the chimeric virions of the present invention may be engineered to create vaccines for the protection of a subject from infections with CoV-HKU1 and variants thereof.

In certain embodiments, the expression products and recombinant or chimeric virions of the present invention may be engineered to create vaccines against a broad range of pathogens, including viral antigens, tumor antigens and autoantigens involved in autoimmune disorders. One way to achieve this goal involves modifying existing CoV-HKU1 genes to contain foreign sequences in their respective external domains. Where the heterologous sequences are epitopes or antigens of pathogens, these chimeric viruses may be used to induce a protective immune response against the disease agent from which these determinants are derived.

Thus, the present invention relates to the use of viral vectors and recombinant or chimeric viruses to formulate vaccines against a broad range of viruses and/or antigens. The present invention also encompasses recombinant viruses comprising a viral vector derived from the CoV-HKU1 or variants thereof which contains sequences which result in a virus having a phenotype more suitable for use in vaccine formulations. The mutations and modifications can be in coding regions, in intergenic regions and in the leader and trailer sequences of the virus.

The invention provides a host cell comprising a nucleic acid or a vector according to the invention. Plasmid or viral vectors containing the polymerase components of CoV-HKU1 are generated in prokaryotic cells for the expression of the components in relevant cell types (bacteria, insect cells, eukaryotic cells). Plasmid or viral vectors containing full-length or partial copies of the CoV-HKU1 genome will be generated in prokaryotic cells for the expression of viral nucleic acids in-vitro or in-vivo. The latter vectors may contain other viral sequences for the generation of chimeric viruses or chimeric virus proteins, may lack parts of the viral genome for the generation of replication defective virus, and may contain mutations, deletions or insertions for the generation of attenuated viruses.

In addition, eukaryotic cells, transiently or stably expressing one or more full-length or partial CoV-HKU1 proteins can be used. Such cells can be made by transfection (proteins or nucleic acid vectors), infection (viral vectors) or transduction (viral vectors) and may be useful for complementation of mentioned wild type, attenuated, replication-defective or chimeric viruses.

The viral vectors and chimeric viruses of the present invention may be used to modulate a subject's immune system by stimulating a humoral immune response, a cellular immune response or by stimulating tolerance to an antigen. As used herein, a subject means: humans, primates, horses, cows, sheep, pigs, goats, dogs, cats, avian species and rodents.

5.2 Formulation of Vaccines and Antivirals

In a preferred embodiment, the invention provides a proteinaceous molecule or CoV-HKU1 specific viral protein or functional fragment thereof encoded by a nucleic acid according to the invention. Useful proteinaceous molecules are for example derived from any of the genes or genomic fragments derivable from the virus according to the invention, including envelop protein (E protein), integral membrane protein (M protein), spike protein (S protein), nucleocapsid protein (N protein), hemagglutinin esterase (HE protein), and RNA-dependent RNA polymerase. Such molecules, or antigenic fragments thereof, as provided herein, are for example useful in diagnostic methods or kits and in pharmaceutical compositions such as subunit vaccines. Particularly useful are polypeptides encoded by the nucleotide sequence of SEQ ID NO:1 or 3, including the polypeptides having the amino acid sequences of SEQ ID NOS:34-2918 in FIGS. 2 and 8, or SEQ ID NO:2, or antigenic fragments thereof for inclusion as antigen or subunit immunogen, but inactivated whole virus can also be used. Particularly useful are also those proteinaceous substances that are encoded by recombinant nucleic acid fragments of the CoV-HKU1 genome; of course preferred are those that are within the preferred bounds and metes of ORFs, in particular, for eliciting CoV-HKU1 specific antibody or T cell responses, whether in vivo (e.g. for protective or therapeutic purposes or for providing diagnostic antibodies) or in vitro (e.g. by phage display technology or another technique useful for generating synthetic antibodies).

The invention provides vaccine formulations for the prevention and treatment of infections with CoV-HKU1. In certain embodiments, the vaccine of the invention comprises recombinant and chimeric viruses of the CoV-HKU1.

In another aspect, the present invention also provides DNA vaccine formulations comprising a nucleic acid or fragment of the CoV-HKU1, or nucleic acid molecules having the sequence of SEQ ID NO:1 or 3, or a fragment thereof. In another specific embodiment, the DNA vaccine formulations of the present invention comprises a nucleic acid or fragment thereof encoding the antibodies which immunospecifically binds CoV-HKU1. In DNA vaccine formulations, a vaccine DNA comprises a viral vector, such as that derived from the CoV-HKU1, bacterial plasmid, or other expression vector, bearing an insert comprising a nucleic acid molecule of the present invention operably linked to one or more control elements, thereby allowing expression of the vaccinating proteins encoded by said nucleic acid molecule in a vaccinated subject. Such vectors can be prepared by recombinant DNA technology as recombinant or chimeric viral vectors carrying a nucleic acid molecule of the present invention.

Various heterologous vectors are described for DNA vaccinations against viral infections. For example, the vectors described in the following references may be used to express CoV-HKU1 sequences instead of the sequences of the viruses or other pathogens described; in particular, vectors described for hepatitis B virus (Michel, M. L. et al., 1995, DAN-mediated immunization to the hepatitis B surface antigen in mice: Aspects of the humoral response mimic hepatitis B viral infection in humans, *Proc. Natl. Aca. Sci. USA* 92:5307-5311; Davis, H. L. et al., 1993, DNA-based immunization induces continuous seretion of hepatitis B surface antigen and high levels of circulating antibody, *Human Molec. Genetics* 2:1847-1851), HIV virus (Wang, B. et al., 1993, Gene inoculation generates immune responses against human immunodeficiency virus type 1, *Proc. Natl. Acad. Sci. USA* 90:4156-4160; Lu, S. et al., 1996, Simian immunodeficiency virus DNA vaccine trial in macques, *J. Virol.* 70:3978-3991; Letvin, N. L. et al., 1997, Potent, protective anti-HIV immune responses generated by bimodal HIV envelope DNA plus protein vaccination, *Proc Natl Acad Sci USA.* 94(17):9378-83), and influenza viruses (Robinson, H L et al., 1993, Protection against a lethal influenza virus challenge by immunization with a haemagglutinin-expressing plasmid DNA, *Vaccine* 11:957-960; Ulmer, J. B. et al., Heterologous protection against influenza by injection of DNA encoding a viral protein, *Science* 259:1745-1749), as well as bacterial infections, such as tuberculosis (Tascon, R. E. et al., 1996, Vaccination against tuberculosis by DNA injection, *Nature Med.* 2:888-892; Huygen, K. et al., 1996, Immunogenicity and protective efficacy of a tuberculosis DNA vaccine, *Nature Med.,* 2:893-898), and parasitic infection, such as malaria (Sedegah, M., 1994, Protection against malaria by immunization with plasmid DNA encoding circumsporozoite protein, *Proc. Natl. Acad. Sci. USA* 91:9866-9870; Doolan, D. L. et al., 1996, Circumventing genetic restriction of protection against malaria with multigene DNA immunization: CD8+ T cell-interferon δ, and nitric oxide-dependent immunity, *J. Exper. Med.,* 1183:1739-1746).

Many methods may be used to introduce the vaccine formulations described above. These include, but are not limited to, oral, intradermal, intramuscular, intraperitoneal, intravenous, subcutaneous, and intranasal routes. Alternatively, it may be preferable to introduce the chimeric virus vaccine formulation via the natural route of infection of the pathogen for which the vaccine is designed. The DNA vaccines of the present invention may be administered in saline solutions by injections into muscle or skin using a syringe and needle (Wolff J. A. et al., 1990, Direct gene transfer into mouse muscle in vivo, Science 247:1465-1468; Raz, E., 1994, Intradermal gene immunization: The possible role of DNA uptake in the induction of cellular immunity to viruses, *Proc. Natl. Acad. Sci. USA* 91:9519-9523). Another way to administer DNA vaccines is called "gene gun" method, whereby microscopic gold beads coated with the DNA molecules of interest is fired into the cells (Tang, D. et al., 1992, Genetic immunization is a simple method for eliciting an immune response, *Nature* 356:152-154). For general reviews of the methods for DNA vaccines, see Robinson, H. L., 1999, DNA vaccines: basic mechanism and immune responses (Review), *Int. J. Mol. Med.* 4(5):549-555; Barber, B., 1997, Introduction: Emerging vaccine strategies, *Seminars in Immunology* 9(5): 269-270; and Robinson, H. L. et al., 1997, DNA vaccines, *Seminars in Immunology* 9(5):271-283.

5.3 Adjuvants and Carrier Molecules

CoV-HKU1-associated antigens are administered with one or more adjuvants. In one embodiment, the CoV-HKU1-associated antigen is administered together with a mineral salt adjuvants or mineral salt gel adjuvant. Such mineral salt and mineral salt gel adjuvants include, but are not limited to, aluminum hydroxide (ALHYDROGEL, REHYDIRAGEL), aluminum phosphate gel, aluminum hydroxyphosphate (ADJU-PHOS), and calcium phosphate.

In another embodiment, CoV-HKU1-associated antigen is administered with an immunostimulatory adjuvant. Such class of adjuvants, include, but are not limited to, cytokines (e.g., interleukin-2, interleukin-7, interleukin-12, granulocyte-macrophage colony stimulating factor (GM-CSF), interferon-γ interleukin-1β (IL-1β), and IL-1β peptide or Sclavo Peptide), cytokine-containing liposomes, triterpenoid glycosides or saponins (e.g., QuilA and QS-21, also sold under the trademark STIMULON, ISCOPREP), Muramyl Dipeptide (MDP) derivatives, such as N-acetyl-muramyl-L-threonyl-D-isoglutamine (Threonyl-MDP, sold under the trademark TERMURTIDE), GMDP, N-acetyl-nor-muramyl-L-alanyl-D-isoglutamine, N-acetylmuramyl-L-alanyl-D-isoglutaminyl-L-alanine-2-(1'-2'-dipaimitoyl-sn-glycero-3-hydroxy phosphoryloxy)-ethylamine, muramyl tripeptide phosphatidylethanolamine (MTP-PE), unmethylated CpG dinucleotides and oligonucleotides, such as bacterial DNA and fragments thereof, LPS, monophosphoryl Lipid A (3D-MLA sold under the trademark MPL), and polyphosphazenes.

In another embodiment, the adjuvant used is a particular adjuvant, including, but not limited to, emulsions, e.g., Freund's Complete Adjuvant, Freund's Incomplete Adjuvant, squalene or squalane oil-in-water adjuvant formulations, such as SAF and MF59, e.g., prepared with block-copolymers, such as L-121 (polyoxypropylene/polyoxyetheylene) sold under the trademark PLURONIC L-121, Liposomes, Virosomes, cochleates, and immune stimulating complex, which is sold under the trademark ISCOM.

In another embodiment, a microparticular adjuvant is used. Microparticulare adjuvants include, but are not limited to biodegradable and biocompatible polyesters, homo- and copolymers of lactic acid (PLA) and glycolic acid (PGA), poly(lactide-co-glycolides) (PLGA) microparticles, polymers that self-associate into particulates (poloxamer particles), soluble polymers (polyphosphazenes), and virus-like particles (VLPs) such as recombinant protein particulates, e.g., hepatitis B surface antigen (HbsAg).

Yet another class of adjuvants that may be used include mucosal adjuvants, including but not limited to heat-labile enterotoxin from *Escherichia coli* (LT), cholera holotoxin (CT) and cholera Toxin B Subunit (CTB) from *Vibrio cholerae*, mutant toxins (e.g., LTK63 and LTR72), microparticles, and polymerized liposomes.

In other embodiments, any of the above classes of adjuvants may be used in combination with each other or with other adjuvants. For example, non-limiting examples of combination adjuvant preparations that can be used to administer the CoV-HKU1-associated antigens of the invention include liposomes containing immunostimulatory protein, cytokines, or T-cell and/or B-cell peptides, or microbes with or without entrapped IL-2 or microparticles containing enterotoxin. Other adjuvants known in the art are also included within the scope of the invention (see *Vaccine Design: The Subunit and Adjuvant Approach*, Chap. 7, Michael F. Powell and Mark J.

Newman (eds.), Plenum Press, New York, 1995, which is incorporated herein in its entirety).

The effectiveness of an adjuvant may be determined by measuring the induction of antibodies directed against an immunogenic polypeptide containing a CoV-HKU1 polypeptide epitope, the antibodies resulting from administration of this polypeptide in vaccines which are also comprised of the various adjuvants.

The polypeptides may be formulated into the vaccine as neutral or salt forms. Pharmaceutically acceptable salts include the acid additional salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trimethylamine, 2-ethylamino ethanol, histidine, procaine and the like.

The vaccines of the invention may be multivalent or univalent. Multivalent vaccines are made from recombinant viruses that direct the expression of more than one antigen.

Many methods may be used to introduce the vaccine formulations of the invention; these include but are not limited to oral, intradermal, intramuscular, intraperitoneal, intravenous, subcutaneous, intranasal routes, and via scarification (scratching through the top layers of skin, e.g., using a bifurcated needle).

The patient to which the vaccine is administered is preferably a mammal, most preferably a human, but can also be a non-human animal including but not limited to cows, horses, sheep, pigs, fowl (e.g., chickens), goats, cats, dogs, hamsters, mice and rats.

5.4 Preparation of Antibodies

Antibodies which specifically recognize a polypeptide of the invention, such as, but not limited to, polypeptides comprising the sequence of SEQ ID NO:2 or any of SEQ ID NOS: 34-2918 or CoV-HKU1 epitope, or antigen-binding fragments thereof, can be used for detecting, screening, and isolating the polypeptide of the invention or fragments thereof, or similar sequences that might encode similar enzymes from the other organisms. For example, in one specific embodiment, an antibody which immunospecifically binds CoV-HKU 1 epitope, or a fragment thereof, can be used for various in vitro detection assays, including enzyme-linked immunosorbent assays (ELISA), radioimmunoassays, Western blot, etc., for the detection of a polypeptide of the invention or, preferably, CoV-HKU1, in samples, for example, a biological material, including cells, cell culture media (e.g., bacterial cell culture media, mammalian cell culture media, insect cell culture media, yeast cell culture media, etc.), blood, plasma, serum, tissues, sputum, naseopharyngeal aspirates, etc.

Antibodies specific for a polypeptide of the invention or any epitope of CoV-HKU1 may be generated by any suitable method known in the art. Polyclonal antibodies to an antigen-of-interest, for example, the CoV-HKU1 epitopes or polypeptides encoded by a nucleotide sequence of SEQ ID NO:1 or 3, including the polypeptides shown in FIG. 2 (SEQ ID NOS: 34-1318), FIG. 8 (SEQ ID NOS:1319-2918), as well as SEQ ID NO:2, can be produced by various procedures well known in the art. For example, an antigen can be administered to various host animals including, but not limited to, rabbits, mice, rats, etc., to induce the production of antisera containing polyclonal antibodies specific for the antigen. Various adjuvants may be used to increase the immunological response, depending on the host species, and include but are not limited to, Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (Bacille Calmette-Guerin) and *Corynebacterium parvum*. Such adjuvants are also well known in the art (see Section 5.4, supra).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563-681 (Elsevier, N.Y., 1981) (both of which are incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments which recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain.

The antibodies of the invention or fragments thereof can be also produced by any method known in the art for the synthesis of antibodies, in particular, by chemical synthesis or preferably, by recombinant expression techniques.

The nucleotide sequence encoding an antibody may be obtained from any information available to those skilled in the art (i.e., from Genbank, the literature, or by routine cloning and sequence analysis). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., supra; and Ausubel et al., eds., 1998, Current Protocols in Molecular Biology, John Wiley & Sons, NY, which are both incorporated by reference herein in their entireties), to generate antibodies having a different amino acid sequence by, for example, introducing amino acid substitutions, deletions, and/or insertions into the epitope-binding domain regions of the antibodies or any portion of antibodies which may enhance or reduce biological activities of the antibodies.

Recombinant expression of an antibody requires construction of an expression vector containing a nucleotide sequence that encodes the antibody. Once a nucleotide sequence encoding an antibody molecule or a heavy or light chain of an antibody, or portion thereof has been obtained, the vector for the production of the antibody molecule may be produced by recombinant DNA technology using techniques well known in the art as discussed in the previous sections. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody may be cloned into such a vector for expression. Thus-prepared expression vector can be then introduced into appropriate host cells for the expression of the antibody. Accordingly, the invention includes host cells containing a polynucleotide encoding an antibody specific for the polypeptides of the invention or fragments thereof.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature, 322:52, 1986; and Kohler, Proc. Natl. Acad. Sci. USA, 77:2 197, 1980). The coding sequences for the heavy and light chains may comprise cDNA or genomic DNA.

In another embodiment, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., J. Immunol. Methods, 182:41-50, 1995; Ames et al., J. Immunol. Methods, 184:177-186, 1995; Kettleborough et al., Eur. J. Immunol., 24:952-958, 1994; Persic et al., Gene, 187:9-18, 1997; Burton et al., Advances in Immunology, 57:191-280, 1994; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab)$_2$ fragments can also be employed using methods known in the art such as those disclosed in PCT publication WO 92/22324; Mullinax et al., BioTechniques, 12(6):864-869, 1992; and Sawai et al., AJRI, 34:26-34, 1995; and Better et al., Science, 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., Methods in Enzymology, 203:46-88, 1991; Shu et al., PNAS, 90:7995-7999, 1993; and Skerra et al., Science, 240:1038-1040, 1988.

Once an antibody molecule of the invention has been produced by any methods described above, it may then be purified by any method known in the art for purification of an immunoglobulin molecule, for example, by chromatography (e.g., ion exchange, affinity, particularly by affinity for the specific antigen after Protein A or Protein G purification, and sizing column chromatography), centrifugation, differential solubility, or by any other standard techniques for the purification of proteins. Further, the antibodies of the present invention or fragments thereof may be fused to heterologous polypeptide sequences described herein or otherwise known in the art to facilitate purification.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, Science, 229:1202, 1985; Oi et al., BioTechniques, 4:214 1986; Gillies et al., J. Immunol. Methods, 125:191-202, 1989; U.S. Pat. Nos. 5,807,715; 4,816,567; and 4,816,397, which are incorporated herein by reference in their entireties. Humanized antibodies are antibody molecules from non-human species that bind the desired antigen having one or more complementarity determining regions (CDRs) from the non-human species and framework regions from a human immunoglobutin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Riechmann et al., Nature, 332:323, 1988, which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, Molecular Immunology, 28(4/5):489-498, 1991; Studnicka et al., Protein Engineering, 7(6):805-814, 1994; Roguska et al., Proc Natl. Acad. Sci. USA, 91:969-973, 1994), and chain shuffling (U.S. Pat. No. 5,565,332), all of which are hereby incorporated by reference in their entireties.

Completely human antibodies are particularly desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies can also be produced using transgenic mice which are incapable of expressing functional endogenous immunoglobulins, but which can express human immunoglobulin genes. For an overview of this technology for producing human antibodies, see Lonberg and Huszar, Int. Rev. Immunol., 13:65-93, 1995. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Abgenix, Inc. (Fremont, Calif.), Medarex (NJ) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology, 12:899-903, 1988).

Antibodies filsed or conjugated to heterologous polypeptides may be used in in vitro immunoassays and in purification methods (e.g., affinity chromatography) well known in the art. See e.g., PCT publication Number WO 93/21232; EP 439,095; Naramura et al., Immunol. Lett., 39:91-99, 1994; U.S. Pat. No. 5,474,981; Gillies et al., PNAS, 89:1428-1432, 1992; and Fell et al., J. Immunol., 146:2446-2452, 1991, which are incorporated herein by reference in their entireties.

Antibodies may also be attached to solid supports, which are particularly useful for immunoassays or purification of the polypeptides of the invention or fragments, derivatives, analogs, or variants thereof, or similar molecules having the similar enzymatic activities as the polypeptide of the invention. Such solid supports include, but are not limited to, glass, cellulose, polyacrylamide, nylon, polystyrene, polyvinyl chloride or polypropylene.

5.5 Pharmaceutical Compositions and Kits

The present invention encompasses pharmaceutical compositions comprising anti-viral agents of the present invention. In a specific embodiment, the anti-viral agent is an antibody which immunospecifically binds CoV-HKU1 or variants thereof, or any proteins derived therefrom. In another specific embodiment, the anti-viral agent is a polypeptide or nucleic acid molecule of the invention. The pharmaceutical compositions have utility as an anti-viral prophylactic agent and may be administered to a subject where the subject has been exposed or is expected to be exposed to a virus.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu and Wu, 1987, J. Biol. Chem. 262:4429 4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In a preferred embodiment, it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, by means of nasal spray, or by means of an implant, said implant being of a porous, non porous, or gelatinous material, including membranes, such as sialastic membranes, or fibers. In one embodiment, administration can be by direct injection at the site (or former site) infected tissues.

In another embodiment, the pharmaceutical composition can be delivered in a vesicle, in particular a liposome (see Langer, 1990, Science 249:1527-1533; Treat et al., in Liposomes in the Therapy of Infectious Disease and Cancer, Lopez Berestein and Fidler (eds.), Liss, New York, pp. 353-365 (1989); Lopez-Berestein, ibid., pp. 317-327; see generally ibid.).

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

The pharmaceutical compositions of the present invention comprise a therapeutically effective amount of recombinant or chimeric CoV-HKU1, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2 ethylamino ethanol, histidine, procaine, etc.

The amount of the pharmaceutical composition of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a preferred embodiment, the kit contains an anti-viral agent of the invention, e.g., an antibody specific for the polypeptides encoded by a nucleotide sequence of SEQ ID NO:1 or 3, or any CoV-HKU1 epitope, or a polypeptide or protein of the present invention, including those shown in FIG. 2 (SEQ ID NOS:34-1318), FIG. 8 (SEQ ID NOS:1319-2918), and SEQ ID NO:2, or a nucleic acid molecule of the invention, alone or in combination with adjuvants, antivirals, antibiotics, analgesic, bronchodialaters, or other pharmaceutically acceptable excipients.

The present invention further encompasses kits comprising a container containing a pharmaceutical composition of the present invention and instructions for use.

5.6 Detection Assays

The present invention provides a method for detecting an antibody, which immunospecifically binds to the CoV-HKU1, in a biological sample, for example blood, serum, plasma, saliva, urine, etc., from a patient suffering from respiratory tract infection. In a specific embodiment, the method comprising contacting the sample with the polypeptides or protein encoded by the nucleotide sequence of SEQ ID NO:1 and/or 3, including the polypeptides having the amino acid sequences of SEQ ID NOS:34-1318 shown in FIG. 2, SEQ ID NOS:1319-2918 shown in FIG. 8, or SEQ ID NO:2, directly immobilized on a substrate and detecting the virus-bound antibody directly or indirectly by a labeled heterologous anti-isotype antibody. In another specific embodiment, the sample is contacted with a host cell comprising a nucleic acid molecule having the nucleotide sequence of SEQ ID NO:1 or 3 and expressing the polypeptides encoded thereby, and the bound antibody can be detected by immunofluorescent assay.

An exemplary method for detecting the presence or absence of a polypeptide or nucleic acid of the invention in a biological sample involves obtaining a biological sample from various sources and contacting the sample with a compound or an agent capable of detecting an epitope or nucleic acid (e.g., mRNA, genomic RNA) of CoV-HKL1 such that the presence of CoV-HKU1 is detected in the sample. A preferred agent for detecting CoV-HKU1 mRNA or genomic RNA of the invention is a labeled nucleic acid probe capable of hybridizing to mRNA or genomic RNA encoding a polypeptide of the invention. The nucleic acid probe can be, for example, a nucleic acid molecule comprising or consisting of the nucleotide sequence of SEQ ID NO:1 or 3, or a portion thereof, or a complement thereof, such as an oligonucleotide of at least 15, 20, 25, 30, 50, 100, 250, 500, 750, 1,000 or more contiguous nucleotides in length and sufficient to specifically hybridize under stringent conditions to a CoV-HKU1 mRNA or genomic RNA.

In another preferred specific embodiment, the presence of CoV-HKU1 is detected in the sample by an reverse transcription polymerase chain reaction (RT-PCR) using the primers that are constructed based on a partial nucleotide sequence of the genome of CoV-HKU1 or a genomic nucleic acid sequence of SEQ ID NO:3, or based on a nucleotide sequence of SEQ ID NO: 1. In a non-limiting specific embodiment, preferred primers to be used in a RT-PCR method are: 5'-GGTTGGGACTATCCTAAGTGTGA-3'(SEQ ID NO:4) and 5'-CCATCATCAGATAGAATCATCATA-3' (SEQ ID NO:5), in the presence of 3 mM $MgCl_2$ and the thermal cycles are, for example, but not limited to, 94° C. for 8 min followed by 40 cycles of 94° C. for 1 min, 50° C. for 1 min, 72° C. for 1 min. In more preferred specific embodiment, the present invention provides a real-time quantitative PCR assay to detect the presence of CoV-HKU1 in a biological sample by subjecting the cDNA obtained by reverse transcription of the extracted total RNA from the sample to PCR reactions using the specific primers, such as those having nucleotide sequences of SEQ ID NOS:4 and 5, and a fluorescence dye, such as SYBR® Green I, which fluoresces when bound non-specifically to double-stranded DNA. The fluorescence signals from these reactions are captured at the end of extension steps as PCR product is generated over a range of the thermal cycles, thereby allowing the quantitative determination of the viral load in the sample based on an amplification plot.

A preferred agent for detecting CoV-HKU1 is an antibody that specifically binds a polypeptide of the invention or any CoV-HKU1 epitope, preferably an antibody with a detectable label. Antibodies can be polyclonal, or more preferably, monoclonal. An intact antibody, or a fragment thereof (e.g., Fab or $F(ab')_2$) can be used.

The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The detection method of the invention can be used to detect mRNA, protein (or any epitope), or genomic RNA in a sample in vitro as well as in vivo. For example, in vitro techniques for detection of mRNA include northern hybridizations, in situ hybridizations, RT-PCR, and RNase protection. In vitro techniques for detection of an epitope of CoV-HKU1 include enzyme linked immunosorbent assays (ELISAs), Western blots, immunoprecipitations and immunofluorescence. In vitro techniques for detection of genomic RNTA include northern hybridizations, RT-PCR, and RNase protection. Furthermore, in vivo techniques for detection of CoV-HKU1 include introducing into a subject organism a labeled antibody directed against the polypeptide. For example, the antibody can be labeled with a radioactive marker whose presence and location in the subject organism can be detected by standard imaging techniques, including autoradiography.

In a specific embodiment, the methods further involve obtaining a control sample from a control subject, contacting the control sample with a compound or agent capable of detecting CoV-HKU1, e.g., a polypeptide of the invention or mRNA or genomic RNA encoding a polypeptide of the invention, such that the presence of CoV-HKU1 or the polypeptide or mRNA or genomic RNA encoding the polypeptide is detected in the sample, and comparing the absence of CoV-HKU1 or the polypeptide or mRNA or genomic RNA encoding the polypeptide in the control sample with the presence of CoV-HKU1, or the polypeptide or mRNA or genomic DNA encoding the polypeptide in the test sample.

The invention also encompasses kits for detecting the presence of CoV-HKU1 or a polypeptide or nucleic acid of the invention in a test sample. The kit, for example, can comprise a labeled compound or agent capable of detecting CoV-HKU1 or the polypeptide or a nucleic acid molecule encoding the polypeptide in a test sample and, in certain embodiments, a means for determining the amount of the polypeptide or mRNA in the sample (e.g., an antibody which binds the polypeptide or an oligonucleotide probe which binds to DNA or mRNA encoding the polypeptide). Kits can also include instructions for use.

For antibody-based kits, the kit can comprise, for example: (1) a first antibody (e.g., attached to a solid support) which binds to a polypeptide of the invention or CoV-HKU1 epitope; and, optionally, (2) a second, different antibody which binds to either the polypeptide or the first antibody and is conjugated to a detectable agent.

For oligonucleotide-based kits, the kit can comprise, for example: (1) an oligonucleotide, e.g., a detectably labeled oligonucleotide, which hybridizes to a nucleic acid sequence encoding a polypeptide of the invention or to a sequence within the CoV-HKU1 genome or (2) a pair of primers useful for amplifying a nucleic acid molecule containing an CoV-HKU1 sequence. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for use.

6. EXAMPLES

The following examples illustrate the identification of the novel CoV-HKU1. These examples should not be construed as limiting.

Methods and Results

As a general reference, Wiedbrauk DL & Johnston SLG. (Manual of Clinical Virology, Raven Press, New York, 1993) was used.

6.1 Clinical Subject

The patient is an in-patient of the United Christian Hospital in Hong Kong. Nasopharyngeal aspirates were collected from the patient weekly from the first till the fifth week of the illness, stool and urine in the first and second week of the illness, and sera in the first, second, and fourth weeks of the illness.

6.2 Antibody Detection

To produce a fusion plasmid for protein purification, primers, 5'-TTTTCCTTTTGCGGCCGCTTAAGCAACA-GAGTCTTCTA-3' (SEQ ID NO:6) and 5'-CGGAATTC-GATGTCTTATACTCCCGGT-3'(SEQ ID NO:7) were used to amplify the gene encoding the N protein of the CoV-HKU1 by RT-PCR. The sequence coding for amino acid residues 1 to 441 of the N protein was amplified and cloned into the EcoRI and NotI sites of expression vector pET-28b(+) (Novagen, Madison, Wis., USA) in frame and downstream of the series of six histidine residues. The $(His)_6$-tagged (SEQ ID NO:27) recombinant N protein was expressed in *E. coli* and purified using the $Ni^{2+}$-loaded HiTrap Chelating System (Amersham Pharmacia, USA) according to the manufacturer's instructions.

Western blot analysis was performed as follows: Two-hundred ng of purified $(His)_6$-tagged (SEQ ID NO:27) recombinant N protein of CoV-HKU1 were loaded into each well of a sodium dodecyl sulfate (SDS-10% polyacrylamide gel and subsequently electroblotted onto a nitrocellulose membrane (Bio-Rad, Hercules, Calif., USA). The blot was cut into strips and the strips were incubated separately with 1:2000 dilution of serum samples obtained during the first, second, and fourth weeks of the patient's illness. Serum samples of two healthy blood donors were used as controls. Antigen-antibody interaction was detected with an ECL fluorescence system (Amersham Life Science, Buckinghamshire, UK).

Several prominent immunoreactive bands were visible for serum samples collected during the second and fourth weeks of the patient's illness (FIG. 7, lanes 2 and 3). The sizes of the largest bands were about 53 kDa, consistent with the expected size of 52.8 kDa for the full-length $(His)_6$-tagged (SEQ ID NO:27) N protein, whereas the other bands were consistent with the degradation products of the $(His)_6$-tagged (SEQ ID NO:27) N protein. Only very faint bands were observed for serum samples obtained from the patient during the first week of the illness (FIG. 7, lane 1) and two healthy blood donors (FIG. 7, lanes 4 and 5).

ELISA was performed using the recombinant N protein of CoV-HKU1 prepared as described above. Each well of a Nunc immunoplate (Roskilde, Denmark) was coated with 20 ng of purified $(His)_6$-tagged (SEQ ID NO:27) recombinant N protein for 12 h and then blocked in phosphate-buffered saline with 2% bovine serum albumin. The serum samples obtained from the patient during the first, second, and fourth weeks of the illness were serially diluted and were added to the wells of the $(His)_6$-tagged (SEQ ID NO:27) recombinant N protein-coated plates in a total volume of 100 μl per well and incubated at 37° C. for 2 h. After washing with washing buffer five times, 100 μl per well of 1:4000 diluted horse radish peroxidase-conjugated goat anti-human IgG antibody (Zymed Laboratories Inc., South San Francisco, Calif., USA) were added to the wells and incubated at 37° C. for 1 h. After washing with washing buffer five times, 100 μl of diluted 3,3',5,5'-tetramethylbenzidine (Zymed Laboratories Inc.) were added to each well and incubated at room temperature for 15 min. One hundred microliters of 0.3 M $H_2SO_4$ were added and the absorbance at 450 nm of each well was measured. Each sample was tested in duplicate and the mean absorbance for each serum was calculated.

Box titration was carried out with different dilutions of $(His)_6$-tagged (SEQ ID NO:27) recombinant N protein coating antigen and serum obtained from the fourth week of the patient's illness. The results identified 20 ng and 80 ng of purified $(His)_6$-tagged recombinant N protein per ELISA well as the ideal amount for plate coating and 1:1000 and 1:20 as the most optimal serum dilution for IgG and IgM detection, respectively.

To establish the baseline for the tests, serum samples (diluted at 1:1000 and 1:20 for IgG and IgM, respectively) from 100 healthy blood donors were tested in the CoV-HKU1 antibody ELISA. For the 100 sera from healthy blood donors, the mean ELISA $OD_{450}$ values for IgG and IgM detection were 0.178 and 0.224, with standard deviations of 0.070 and 0.117. Absorbance values of 0.387 and 0.576 were selected as the cutoff values (that equal the sum of the mean value from the healthy control and three times the standard deviation) for IgG and IgM, respectively. Using these cutoff values, the titers for IgG of the patient's serum samples obtained during the first, second, and fourth weeks of the illness were <1:1000, 1:2000, and 1:8000, respectively (FIG. 6), and those for IgM were 1:20, 1:40, and 1:80, respectively (data not shown).

6.3 RT-PCR and Real Time Quantitative PCR

RT-PCR Assay

An RT-PCR was developed to detect the CoV-HKU1 sequence from NPA samples. Total RNA from clinical samples was reverse transcribed using random hexamers and cDNA was amplified using primers 5'-GGTTGGGACTATC-CTAAGTGTGA-3'(SEQ ID NO:4) and 5'-CCATCATCA-GATAGAATCATCATA-3'(SEQ ID NO:5), which were constructed based on the RNA-dependent RNA polymerase-encoding sequence (SEQ ID NO: 1) of the CoV-HKU1 in the presence of 2.5 mM $MgCl_2$ (94° C. for 8 min followed by 40 cycles of 94° C. for 1 min, 50° C. for 1 min, 72° C. for 1 min).

The summary of a typical RT-PCR protocol is as follows:

1. RNA Extraction

RNA from 140 μl of NPA samples was extracted by QIAquick® viral RNA extraction kit and was eluted in 50 μl of elution buffer.

2. Reverse Transcription

| | |
|---|---|
| RNA | 11.5 μl |
| 0.1 M DTT | 2 μl |
| 5x buffer | 4 μl |
| 10 mM dNTP | 1 μl |
| Superscript II, 200 U/μl (Invitrogen) | 1 μl |
| Random hexamers, 0.3 μg/μl | 0.5 μl |
| Reaction condition | 42° C., 50 min |
| | 94° C., 3 min |
| | 4° C. |

3. PCR cDNA generated by random primers was amplified in a 50 µl reaction as follows:

| cDNA | 2 µl |
|---|---|
| 10 mM dNTP | 0.5 µl |
| 10x buffer | 5 µl |
| 25 mM MgCl$_2$ | 5 µl |
| 25 µM Forward primer | 0.5 µl |
| 25 µM Reverse primer | 0.5 µl |
| AmpliTaq Gold ® polymerase, 5 U/µl (Applied Biosystems) | 0.25 µl |
| Water | 36.25 µl |

Thermal-cycle condition: 95° C., 10 min, followed by 40 cycles of 95° C., 1 min; 50° C. 1 min; 72° C., 1 min.

4. Primer Sequences

Primers were designed based on the RNA-dependent RNA polymerase encoding sequence (SEQ ID NO:1) of the CoV-HKU1.

```
Forward primer:
                                     (SEQ ID NO: 4)
5'-GGTTGGGACTATCCTAAGTGTGA-3'

Reverse primer:
                                     (SEQ ID NO: 5)
and 5'-CCATCATCAGATAGAATCATCATA-3'
Product size: 440 bps
```

Real-Time Quantitative PCR Assay

Total RNA from 140 µl of nasopharyngeal aspirate (NPA) was extracted by QIAamp® virus RNA mini kit (Qiagen) as instructed by the manufacturer. Ten µl of eluted RNA samples were reverse transcribed by 200 U of Superscript® II reverse transcriptase (Invitrogen) in a 20 µl reaction mixture containing 0.15 µg of random hexamers, 10 mmol/L DTT, and 0.5 mmol/L dNTP, as instructed. Complementary DNA was then amplified in a SYBR® Green I fluorescence reaction (Roche, Ind.) mixtures. Briefly, 20 µl reaction mixtures containing 2 µl of cDNA, 3.5 mmol/L MgCl$_2$, 0.25 µmol/L of forward primer [5'-GGTTGGGACTATCCTAAGTGTGA-3' (SEQ ID NO:4)] and 0.25 tµmol/L reverse primer [5'-CCATCATCA-GATAGAATCATCATA-3' (SEQ ID NO:5)] were thermal-cycled by a LightCycler® (Roche) with the PCR program, [95° C., 10 min followed by 50 cycles of 95° C., 10 min; 57° C., 5 sec; 72° C. 9 sec]. Plasmids containing the target sequence were used as positive controls. Fluorescence signals from these reactions were captured at the end of extension step in each cycle. To determine the specificity of the assay, PCR products (440 base pairs) were subjected to a melting curve analysis at the end of the assay (65° C. to 95° C., 0.1° C. per second) (data not shown).

The amount of CoV-HKU1 RNA in the nasopharyngeal aspirates was followed weekly. Quantitative RT-PCR showed that the amounts of CoV-HKU1 RNA were 8.5×10$^5$ and 9.6×10$^6$ copies per ml in two nasopharyngeal aspirates collected in the first week of the illness, 1.5×10$^5$ copies per ml of NPA, respectively, at two time points collected in the second week of the illness, but CoV-HKU1 RNA was undetectable in the NPA collected in the third, fourth and fifth weeks of the illness (FIG. 6). CoV-HKU1 RNA was also undetectable in the urine and stool of the patient collected in the first and second weeks of the illness.

Discussion

The genome of CoV-HKU1 is a 29942-nucleotide long, polyadenylated RNA. The G+C content is 32%, which is the lowest among all known coronaviruses with genome sequences available, with a GC skew of 0.19. Table 1 shows the comparison of genomic features of CoV-HKU1 and other corona viruses.

TABLE 1

| Coronaviruses | Genome features | | |
|---|---|---|---|
| | Size (bases) | G + C content | GC skew |
| Group 1 | | | |
| HCoV-229E | 27317 | 0.38 | 0.13 |
| PEDV | 28033 | 0.42 | 0.09 |
| HCoV-NL63 | 27553 | 0.34 | 0.16 |
| Group 2 | | | |
| CoV-HKU1 | 29942 | 0.32 | 0.19 |
| HCoV-OC43 | 30738 | 0.37 | 0.18 |
| BcoV | 31028 | 0.37 | 0.17 |
| MHV | 31357 | 0.42 | 0.14 |
| Group 3 | | | |
| IBV | 27608 | 0.38 | 0.14 |
| SARS-CoV | 29751 | 0.41 | 0.02 |

HCoV-229E = human coronavirus 229E;
PEDV = porcine epidemic diarrhea virus;
HCoV-NL63 = human coronavirus NL63;
HCoV-OC43 = human coronavirus OC43;
MHV = murine hepatitis virus;
BCoV = bovine coronavirus;
IBV = infectious bronchitis virus;
SARS-CoV = SARS coronavirus;
GC skew = (G − C)/(G + C)

The genome organization is the same as other coronaviruses, with the characteristic gene order 5'-replicase, S, E, M, N-3'. Both 5' and 3' ends contain short untranslated regions. The 5' end of the genome consists of a putative 5' leader sequence. A putative transcription regulatory sequences (TRS) motif, 5'-CUAAAC-3', was found at the 3' end of the leader sequence and precedes each translated ORF except ORF4 and ORF6 which encodes the putative E protein. Table 2 shows the putative transcription regulatory sequences in the genome of CoV-HKU1.

TABLE 2

| Number of base upstream of AUG | ORF | TRS sequence | SEQ ID NO. |
|---|---|---|---|
| −140 | Leader | UUAAAU<u>CUAAAC</u>UUUUUAA (127) AUG | 8 |
| −7 | Hemagglutinin esterase | UUAAAU<u>CUAAAC</u>UAUG | 9 |
| −6 | Spike | UUAAAU<u>CUAAAC</u>AUG | 10 |
| −13 | ORF 5 | UUAAAU<u>CUAAAC</u>UUUAUUUAUG | 11 |
| −9 | Membrane | <u>CUAAAU</u><u>CUAAAC</u>AUUAUG | 12 |
| −13 | Nucleocapsid | UUAAAU<u>CUAAAC</u>UAUUAGGAUG | 13 |
| −35 | ORF 9 | UUAAAU<u>CUAAAC</u>UAUUAGGAUGUCU UAUACUCCCGGUCAUUAUG | 14 |

As in SDAV (Sialodacryoadenitis virus) and MHV (mouse hepatitis virus), ORF6 may share the same TRS with ORF 5, suggesting that the translation of the E protein is cap-independent, possibly via an internal ribosomal entry site. The 3' untranslated region contains a predicted pseudoknot structure 59-119 bp downstream of N gene. This pseudoknot structure is highly conserved among coronaviruses and plays a role in coronavirus RNA replication.

The coding potential of the CoV-HKU1 genome is shown in FIG. 3 and Table 3 and the phylogenetic analyses of the chymotrypsin-like protease (3CL$^{pro}$), replicase, helicase, haemagglutinin-esterase (HE), S, E, M and N, are shown in FIGS. 4A and 4B.

TABLE 3

| ORFs | Start-end (base) | No. of bases | No. of amino acids | Frame | Candidate TRS |
|---|---|---|---|---|---|
| ORF 1a | 206-13600 | 13395 | 4465 | +2 | — |
| ORF 1b | 13600-21753 | 8154 | 2717 | +1 | — |
| HE (ORF 2) | 21773-22933 | 1161 | 386 | +2 | Strong |
| S (ORF 3) | 22942-27012 | 4071 | 1356 | +1 | Strong |
| ORF 4 | 26960-27070 | 111 | 36 | +2 | None |
| ORF 5 | 27051-27380 | 330 | 109 | +3 | Strong |
| E (ORF 6) | 27373-27621 | 249 | 82 | +1 | None |
| M (ORF 7) | 27633-28304 | 672 | 223 | +3 | Strong |
| N (ORF 8) | 28320-29645 | 1326 | 441 | +3 | Strong |
| ORF 9 | 28342-28959 | 618 | 205 | +1 | Strong |

The replicase 1a ORF (bases 206-13600) and replicase 1b ORF (bases 13600-21753) occupy 21.5 kb of the CoV-HKU1 genome. Similar to other coronaviruses, a frame shift interrupts the protein-coding regions and separates the 1a and 1b ORFs. This ORF encodes a number of putative proteins, including papain-like protease (PLP) with two copies of the PLP domain, PLP1$^{pro}$ and PLP2$^{pro}$, 3CL$^{pro}$, replicase, helicase, and other proteins of unknown functions. These proteins are produced by proteolytic cleavages of a large polyprotein (FIG. 3). The sequence of the resulting putative proteins is the same as that in the MHV genome. This polyprotein is synthesized by a −1 ribosomal frameshift at a conserved site (UUUAAAC) upstream of a pseudoknot structure at the junction of ORF 1a and ORF 1b. This ribosomal frameshift would result in a polyprotein of 7182 amino acids, which has 75-77% amino acid identities with the polyprotein in other Group 2 coronaviruses and 43-47% amino acid identities with the polyprotein in other non-Group 2 coronaviruses. The replicase gene of CoV-HKU1, which encodes 928 amino acids, has 87-89% amino acid identities with the replicase of other Group 2 coronaviruses and 54-65% amino acid identities with the replicase of other non-Group 2 coronaviruses (Table 4 and FIG. 4A). Table 4 shows amino acid identities between the predicted chymotrypsin-like protease (3CL$^{pro}$), replicase (Rep), helicase (Hel), hemagglutinin-esterase (HE), spike (S), envelope (E), membrane (M), and nucleocapsid (N) proteins of CoV-HKU1 and the corresponding proteins of other coronaviruses.

TABLE 4

| | | Pairwise amino acid identity (%) | | | | | | | |
|---|---|---|---|---|---|---|---|---|---|
| Group | Virus | 3CL$^{pro}$ | Rep | Hel | HE | S | E | M | N |
| 1 | HCoV-229E | 45 | 54 | 55 | — | 31 | 26 | 35 | 28 |
| | PEDV | 44 | 56 | 55 | — | 30 | 34 | 37 | 37 |
| | PTGV | 45 | 57 | 57 | — | 32 | 34 | 37 | 27 |
| | CCoV | — | — | — | — | 31 | 32 | 36 | 27 |
| | HCoV-NL63 | 43 | 54 | 54 | — | 30 | 28 | 32 | 28 |
| 2 | HCoV-OC43 | 82 | 87 | 88 | 57 | 60 | 54 | 76 | 58 |
| | MHV | 85 | 89 | 87 | 50 | 58 | 55 | 78 | 60 |
| | BCoV | 84 | 88 | 88 | 56 | 61 | 55 | 76 | 57 |
| | SDAV | — | — | — | 50 | 61 | 60 | 77 | 62 |
| | ECoV | — | — | — | 53 | 61 | 56 | 78 | 59 |
| | PHEV | — | — | — | 54 | 61 | 54 | 77 | 57 |
| 3 | IBV | 41 | 60 | 57 | — | 32 | 28 | 38 | 27 |
| SARS-CoV | SARS-CoV | 48 | 65 | 63 | — | 33 | 27 | 34 | 31 |

HCoV-229E = human coronavirus 229E;
PEDV = porcine epidemic diarrhea virus;
PTGV = porcine transmissible gastroenteritis virus;
CCoV = canine enteric coronavirus;
HCoV-NL63 = human coronavirus NL63;
HCoV-OC43 = human coronavirus OC43;
MHV = murine hepatitis virus;
BCoV = bovine coronavirus;
SDAV = rat sialodacryoadenitis coronavirus;
ECoV = equine coronavirus NC99;
PHEV = porcine hemagglutinating encephalomyelitis virus;
IBV = infectious bronchitis virus;
SARS-CoV = SARS coronavirus The catalytic histidine and cysteine amino acid residues, conserved among the 3CL$^{pro}$ in all coronaviruses, are present in the predicted 3CL$^{pro}$ of CoV-HKU1 (amino acids His$^{3375}$ and Cys$^{3479}$ of ORF 1a). In the N-terminal of the putative PLP (amino acid residues 945 to 1104 of ORF 1a), there are 14 tandem copies of a 30-base repeat, which encode NDDEDV-VTGD (SEQ ID NO: 15), followed by two 30-base regions that encode NNDEEIVTGD (SEQ ID NO:16) and NDDQIV-VTGD (SEQ ID NO:17), located upstream to the first copy of PLP domain, PLP1$^{pro}$. This repeat is not observed in other coronaviruses.

ORF 2 (bases 21773-22933) encodes the predicted HE glycoprotein with 386 amino acids. The HE protein of CoV-HKU1 has 50-57% amino acid identities with the HE proteins of other Group 2 coronaviruses (Table 4 and FIG. 4A). PFAM and InterProScan analyses of the ORF show that amino acid residues 1 to 349 of the predicted protein is a member of the haemagglutinin esterase family (PFAM accession no.: PF03996 and INTERPRO accession no. IPR007142). This family contains membrane glycoproteins that are present on viral surface and are involved with the cell infection process. It contains haemagglutinin chain 1 (HE1) and haemagglutinin chain 2 (HE2), and forms a homotrimer with each monomer being formed by two chains linked by a disulphide bond. Furthermore, PFAM and InterProScan analyses of the ORF show that amino acid residues 122 to 236 of the predicted protein are the haemagglutinin domain of HE-fusion glycoprotein family (PFAM accession no.: PF02710 and INTERPRO accession no. IPRO03860). HE is also present in other Group 2 coronaviruses and influenza C virus. SignalP analysis reveals a signal peptide probability of 0.738, with a cleavage site between residues 13 and 14. Although TMpred and TMHMM analyses of the ORF show four and three transmembrane domains, respectively, PHDhtm analysis of the ORF shows only one transmembrane domain at positions 354 to 376. This concurs with only one transmembrane region reported in the C terminal of the HE of BCoV (bovine coronavirus) and puffinosis virus. PrositeScan analysis of the HE protein of CoV-HKU1 reveals eight potential N-linked glycosylation (six NXS and two NXT) sites. These are located at positions 83 (NYT), 110, (NGS), 145 (NVS), 168 (NYS), 193 (NFS), 286 (NSS), 314 (NVS, and 328 (NFT). The putative active site for neuraminate O-acetyl-esterase activity, FGDS (SEQ ID NO:18), is located at positions 31-34.

ORF 3 (bases 22942-27012) encodes the predicted S glycoprotein (PFAM accession no. PF01601) with 1356 amino acids. The S protein of CoV-HKU1 has 58-61% amino acid identities with the S proteins of other Group 2 coronaviruses, but has fewer than 35% amino acid identities with the S proteins of Group 1, Group 3, and SARS-CoV (Table 4 and FIG. 4B). InterProScan analysis predicts it as a type I membrane glycoprotein. Important features of the S protein of CoV-HKU1 are depicted in FIG. 5. PrositeScan of the S protein of CoV-HKU1 reveals 28 potential N-linked glycosylation (12 NXS and 16 NXT) sites. SignalP analysis reveals a signal peptide probability of 0.909, with a cleavage site between residues 13 and 14. By multiple alignments with the S proteins of other Group 2 coronaviruses, a potential cleavage site located after RRKRR (SEQ ID NO: 19), between residues 760 and 761, where S will be cleaved into S1 and S2, is identified. Immediately upstream to RRKRR (SEQ ID NO: 19), there is a series of five serine residues that are not present in any other known coronaviruses (FIG. 5). Most of the S protein (residues 15 to 1300) is exposed on the outside of the virus, with a transmembrane domain at the C terminus (TMHMM analysis of the ORF shows one transmembrane domain at positions 1301 to 1356), followed by a cytoplasmic tail rich in cysteine residues. Two heptad repeats (HR), located at residues 982 to 1083 (HR1) and 1250 to 1297 (HR2), identified by multiple alignments with other coronaviruses, are present. In MHV, it has been confirmed that the receptor for its S protein binding is CEACAM1, a member of the carcinoembryonic antigen (CEA) family of glycoproteins in the immunoglobulin superfamily. Furthermore, it has been shown by site-directed mutage-tesis, that three conserved regions (sites T, II, and III) and some amino acid residues (Thr$^{62}$, Thr$^{212}$, Tyr$^{214}$, and Tyr$^{216}$ in MHV) in the N-terminal of the S protein are particularly important for its receptor-binding activity. By multiple alignments with the N-terminal 330 amino acids of the S protein of MHV and other group 2 coronaviruses, it is observed that these conserved regions and amino acids are present in CoV-HKU1 (FIG. 5). This infers that the receptor for CoV-HKU1 could be a member of the CEA family on the surface of the cells in the respiratory tract. On the other hand, for HCoV-OC43, it has been shown in vitro that the receptor for the S protein is a sialic acid. However, the amino acid residues on the S protein of HCoV-OC43 that are important for receptor binding are not well defined.

ORF 4 (bases 26960-27070) encodes a predicted protein with 36 amino acids. This ORF overlaps with the ORF that encodes the S protein. This ORF is not present in other coronaviruses and BlastP analysis of the ORF does not show any hits.

ORF 5 (bases 27051-27380) encodes a predicted protein with 109 amino acids. This ORF overlaps with the ORF that encodes the E protein. PFAM analysis of the ORF shows that the predicted protein is a member of the coronavirus non-structural protein NS2 family (PFAM accession no.: PF04753). TMpred and TMHMM analysis do not reveal any transmembrane helix. This predicted protein of CoV-HKU1 has 44-51% amino acid identities with the corresponding proteins of other Group 2 coronaviruses.

ORF 6 (bases 27373-27621) encodes the predicted E protein with 82 amino acids. The E protein of CoV-HKU1 has 54-60% amino acid identities with the E proteins of other Group 2 coronaviruses, but has fewer than 35% amino acid identities with the E proteins of Group 1, Group 3, and SARS-CoV (Table 4 and FIG. 4B). PFAM and InterProScan analyses of the ORF show that the predicted E protein is a member of the non-structural protein NS3/Small envelope protein E (NS3_envE) family (PFAM accession no.: PF02723). SignalP analysis predicts the presence of a transmembrane anchor (probability 0.995). TMpred analysis of the ORF shows two transmembrane domains at positions 16 to 34 and 39 to 59, and TMHMM analysis of the ORF shows two transmembrane domains at positions 10 to 32 and 39 to 58, consistent with the anticipated association of the E protein with the viral envelope. Both programs predict that both the N and C termini are located on the surface of the virus.

ORF 7 (bases 27633-28304) encodes the predicted M protein with 223 amino acids. The M protein of CoV-HKU1 has 76-78% amino acid identities with the M proteins of other Group 2 coronavirus, but has fewer than 40% amino acid identities with the M proteins of Group 1, Group 3, and SARS-CoV (Table 4 and FIG. 4B). PFAM analysis of the ORF shows that the predicted M protein is a member of the coronavirus matrix glycoprotein (Corona_M) family (PFAM accession no.: PF01635). SignalP analysis predicts the presence of a transmembrane anchor (probability 0.926). TMpred analysis of the ORF shows three transmembrane domains at positions 21 to 42, 53 to 74, and 77 to 98. TMHMM analysis of the ORF shows three transmembrane domains at positions 20 to 39, 46 to 68, and 78 to 100. The N terminal 19-20 amino acids are located on the outside and the C terminal 123-125-amino acid hydrophilic domain on the inside of the virus.

ORF 8 (bases 28320-29645) encodes the predicted N protein (PFAM accession no.: PF00937) with 441 amino acids. The N protein of CoV-HKU1 has 57-62% amino acid identities with the N proteins of other Group 2 coronaviruses, but has fewer than 40% amino acid identities with the N proteins of Group 1, Group 3, and SARS-CoV (Table 4 and FIG. 4B).

ORF 9 (bases 28342-28959) encodes a hypothetical protein (N2) of 205 amino acids within the ORF that encodes the predicted N protein. PFAM analysis of the ORF shows that the predicted protein is a member of the coronavirus nucleocapsid I protein (Corona_I) family (PFAM accession no.: PF03187). This hypothetical N2 protein of CoV-HKU1 has 32-39% amino acid identities with the N2 proteins of other Group 2 coronaviruses.

We report the characterization and complete genome sequence of a novel coronavirus detected in the nasopharyngeal aspirates of patients with pneumonia. The clinical significance of the virus in the first patient was evident by the high viral loads in the patient's nasopharyngeal aspirates during the first week of his illness, which coincided with the acute symptoms developed in the patient. The viral load decreased during the second week of the illness and was undetectable in the third week of the illness. In addition, the fall in viral load was accompanied by the recovery from the illness and development of specific antibody response to the recombinant N protein of the virus. Similar to other recently discovered viruses, such as hepatitis C virus, GB virus C, transfusion transmitted virus, and SEN virus, the present virus could not be recovered from cell cultures using the standard cell lines. This could be related to the inherently low recovery rate of coronaviruses. Human coronaviruses are particularly difficult to culture in vitro. Many decades after the recognition of HCoV-229E and HCoV-OC43, there are still only a handful of primary virus isolates available and organ culture is required for primary isolation of HCoV-OC43. In our experience, SARS-CoV can only be recovered from less than 20% of patients with serologically and RT-PCR documented SARS-CoV pneumonia. Therefore, it is not surprising that the new coronavirus CoV-HKU1 has been so far proven difficult to culture in vitro. After the discovery of CoV-HKU1 in the first patient, we conducted a preliminary study on 400 nasopharyngeal aspirates that were collected last year during the SARS epidemic period. Among these 400 nasopharyngeal aspirates, CoV-HKU1 was detected in one specimen, with a viral load comparable to that of the first patient. These results have suggested that CoV-HKU1 is not only incidentally found in one patient, but a previously unrecognized coronavirus associated with pneumoma.

Genomic analysis has reveals that CoV-HKU1 is a Group 2 coronavirus. The genome organization of CoV-HKU1 concurs with those of other coronaviruses, with the characteristic gene order, i.e., 5'-repticase, S, E, M, N-3', short untranslated regions in both 5' and 3' ends, 5' conserved coronavirus core leader sequence, putative TRS upstream to multiple ORFs, and conserved pseudoknot in the 3' untranslated region. In contrast to coronaviruses of other groups, CoV-HKU1 contains certain features that are characteristics of Group 2 coronaviruses, including the presence of HE, ORF 5, and N2. Phylogenetic analysis of the $3CL^{Pro}$, replicase, helicase, S, E, M, and N proteins showed that these genes of CoV-HKU1 were clustered with the corresponding genes in other Group 2 coronaviruses. However, the proteins of CoV-HKU1 formed distinct branches in the phylogenetic trees, indicating that CoV-HKU1 is a distinct member of the group, and is not very closely related to any other known members of Group 2 coronaviruses (FIGS. 4A and 4B).

In addition to phylogenetic analysis of the putative proteins, CoV-HKU1 exhibits certain features that are distinct from other Group 2 coronaviruses. Compared to other Group 2 coronaviruses, there is a deletion of about 800 bps between the replicase ORF 1b and the HE ORF 2 in CoV-HKU1. In other Group 2 coronaviruses, including MHV, SDAV, HCoV-OC43 and BCoV, an ORF of 798-837 bp (273-278 amino acids) is present between the replicase 1b ORF and the HE ORF 2. This ORF encodes a protein of the coronavirus non-structural protein NS2a family (PFAM accession no.: PF05213). The absence of this ORF in CoV-HKU1 indicates that this is probably a non-essential gene of coronavirus. In addition to the deletion, the N-terminal of the putative PLP in ORF 1a contains 14 tandem copies of a 30-bp repeat that codes for a highly acidic domain. Similar repeats, with different amino acid compositions, have been found in the genomes of human, rat and parasites, but have not been found in other coronaviruses. The function of these repeats is not well understood, although some authors have suggested that the repeats could be important antigens, and their biological role may be related to their special three-dimensional structures. The vitellaria antigenic protein of Clonorchis sinensis contains 23 tandem copies of a 30-bp repeat that codes for DGGAQPPKSG (SEQ ID NO:20). In the case of Plasmodium falciparum, it has been shown that the antigenicity of the circumsporozoite protein is due to its repeating epitope structure. It has also been suggested that the tandemly repeated peptide may induce strong humoral immune response in the infected host and thus may also be useful in serological diagnosis. Further experiments should be performed to delineate the antigenic properties, biological role, and possible clinical usefulness of the repeat in the PLP of CoV-HKU1.

The geographical, political, and economic location of Hong Kong makes it a unique place for the study of emerging infectious disease. Hong Kong, as the gateway of southern China, with thousands of people crossing the border on surface and by air every day, has a high potential of importing and exporting infectious diseases to and from China, countries in Southeast Asia and from the rest of the world. In 1997, the first 18 human cases of avian influenza A H5N1 virus infection were reported in Hong Kong. In early 2003, two cases of human infection caused by avian influenza A (H5N1) that was acquired in Fujian, were diagnosed in Hong Kong, which provided an early warning of the impending disease threat for humans and poultry in Southeast Asia that followed in 2004. For the SARS epidemic, although both epidemiological and genomic evidence revealed that the disease had first occurred in southern China in November 2002, it did not receive as much international attention until the disease was spread to Hong Kong and through Hong Kong to Singapore, Toronto, Vietnem, and the United States of America. As for emerging bacterial infections, 50% of the patients with gastroenteritis associated with the recovery of *Laribacter hongkongensis* had recent history of travel to southern China. In this report, one of the patients also had recent history of travel to Shenzhen of China prior to the development of the respiratory illness. We speculate that he might have contacted the virus in Shenzhen. More intensive surveillance of emerging infectious pathogens in this locality is warranted.

7. MARKET POTENTIAL

The genome of CoV-HKU1 is completely sequenced. This allows the development of various diagnostic tests as described hereinabove. In addition, this virus contains genetic information which is extremely important and valuable for clinical and scientific research applications.

8. EQUIVALENTS

Those skilled in the art will recognize, or be able to ascertain many equivalents to the specific embodiments of the invention described herein using no more than routine experimentation. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08092994B2). An electronic copy of the "Sequence Listing" will also be available from the USPTO upon request and payment of the fee set forth in 37 CFR 1.19(b)(3).

What is claimed:

1. A method for detecting the presence of a first nucleic acid molecule comprising the nucleotide sequence of SEQ ID NO: 1 or a fragment thereof or a full length complement thereof in a biological sample, said method comprising:
    (a) contacting the biological sample with a second nucleic acid molecule that selectively binds to said first nucleic acid molecule, wherein the second nucleic acid molecule comprises at least 45 contiguous nucleotides of SEQ ID NO: 1 or of a full length complement of a sequence comprising at least 45 contiguous nucleotides of SEQ ID NO: 1; and
    (b) detecting whether the second nucleic acid binds to a nucleic acid molecule in the sample under conditions of strict hybridization.

2. The method of claim 1, wherein the second nucleic acid molecule that binds to said first nucleic acid molecule comprises the nucleotide sequence of SEQ ID NO: 1 or a full length complement of a sequence comprising at least 45 contiguous nucleotides of SEQ ID NO: 1.

3. The method of claim 1, wherein the second nucleic acid molecule comprises at least 100, 150, 200, 300, or 350 contiguous nucleotides of the nucleotide sequence of SEQ ID NO: 1 or of a full length complement of a sequence comprising at least 100, 150, 200, 300, or 350 contiguous nucleotides of SEQ ID NO: 1.

4. A method for detecting the presence of a first nucleic acid molecule comprising the nucleotide sequence of SEQ ID NO: 3 or a fragment thereof or a full length complement thereof in a biological sample, said method comprising:
    (a) contacting the biological sample with a second nucleic acid molecule that selectively binds to said first nucleic acid molecule, wherein the second nucleic acid molecule comprises at least 45 contiguous nucleotides of SEQ ID NO: 1 or 3 or of a full length complement of a sequence comprising at least 45 contiguous nucleotides of SEQ ID NO:1 or 3; and
    (b) detecting whether the second nucleic acid molecule binds to a nucleic acid molecule in the sample under conditions of strict hybridization.

5. The method of claim 4, wherein the compound that binds to said second nucleic acid molecule comprises the nucleotide sequence of SEQ ID NO: 1 or 3, or a full length complement of a sequence comprising at least 45 contiguous nucleotides of SEQ ID NO:1 or 3.

6. The method of claim 4, wherein the second nucleic acid molecule comprises at least 100, 150, 200, 300, or 350 contiguous nucleotides of the nucleotide sequence of SEQ ID NO: 1 or of a full length complement of a sequence comprising at least 100, 150, 200, 300, or 350 contiguous nucleotides of SEQ ID NO: 1.

7. The method of claim 4, wherein the second nucleic acid molecule comprises at least 100, 150, 200, 300, 350, 400, 450, 500, 550, 600, 650, 700, 750, 800, 850, 900, 950, 1000, 1050, 1100, 1150, 1200, 2000, 3000, 4000, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, or 29000 contiguous nucleotides of the nucleotide sequence of SEQ ID NO: 3 or of a full length complement of a sequence comprising at least 100, 150, 200, 300, 350, 400, 450, 500, 550, 600, 650, 700, 750 800, 850, 900, 950, 1000, 1050, 1100, 1150, 1200, 2000, 3000, 4000, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, or 29000 contiguous nucleotides of SEQ ID NO: 3.

8. A method for identifying a subject infected with CoV-HKU1, comprising:
    (a) obtaining total RNA from a biological sample obtained from the subject;
    (b) reverse transcribing the total RNA to obtain cDNA; and
    (c) amplifying the cDNA using a set of primers derived from the nucleotide sequence of SEQ ID NO: 1 or 3, or from a full length complement of SEQ ID NO:1 or 3.

9. The method of claim 8, wherein the set of primers comprises first and second primers, said first and second primers comprising the nucleotide sequences of SEQ ID NOS: 4 and 5, respectively.

10. The method of claim 8, wherein the set of primers comprises first and second primers, said first and second primers comprising the nucleotide sequences of SEQ ID NOS: 6 and 7, respectively.

* * * * *

UNITED STATES PATENT AND TRADEMARK OFFICE
CERTIFICATE OF CORRECTION

PATENT NO.       : 8,092,994 B2
APPLICATION NO.  : 12/476019
DATED            : January 10, 2012
INVENTOR(S)      : Kwok-Yung Yuen et al.

It is certified that error appears in the above-identified patent and that said Letters Patent is hereby corrected as shown below:

Column 1,
Line 25, "CoVHKU1" should read --CoV-HKU1--.

Column 2,
Line 12, "in these patients" should read --in this patient--.

Column 6,
Line 58, "may also refers" should read --may also refer--.

Column 9,
Line 40, "prevents or inhibit" should read --prevents or inhibits--.
Line 51, "may neutralizes" should read --may neutralize--.
Line 65, "arivan species" should read --avian species--.

Column 11,
Line 13, "entire ORE" should read --entire ORF--.

Column 12,
Line 31, "envelop protein" should read --envelope protein--.

Column 14,
Line 9, "adjuvants or" should read --adjuvant or--.
Line 11, "REHYDIRAGEL" should read --REHYDRAGEL--.
Line 27, "1'-2'-dipaimitoyl" should read --1'-2'-dipalmitoyl--.

Column 18,
Line 29, "and F(ab)₂" should read --and F(ab)2--.
Line 61, "4:214 1986;" should read --4:214, 1986;--.

Signed and Sealed this
Tenth Day of April, 2012

David J. Kappos
*Director of the United States Patent and Trademark Office*

Column 19,
Line 1, "human immunoglobutin" should read --human immunoglobulin--.

Column 20,
Line 25, "262:4429 4432" should read --262:4429-4432--.
Line 49, "site (or former site)" should read --site (or former site) of--.

Column 23,
Line 6, "CoV-HKL1" should read --CoV-HKU1--.

Column 24,
Line 2, "RNTA include" should read --RNA include--.

Column 27,
Line 43, "0.25 tµmol/L" should read --0.25 µmol/L--.

Column 28,
Line 4, "corona viruses" should read --coronaviruses--.

Column 30,
Line 62, "(NVS, and" should read --(NVS), and--.

Column 31,
Line 28, "mutage-tesis" should read --mutagenesis--.
Line 29, "(sites T, II, and III)" should read --(sites I, II, and III)--.

Column 33,
Line 6, "5'-repticase," should read --5'-replicase,--.

Column 34,
Line 20, "Vietnem," should read --Vietnam,--.

Column 35,
Lines 41-42, "wherein the compound that binds to said second" should read --wherein the second--.